US012670970B2

(12) United States Patent
Fisher et al.

(10) Patent No.: US 12,670,970 B2
(45) Date of Patent: Jun. 30, 2026

(54) VARIANT DETECTION

(71) Applicant: Cancer Research Technology Limited, London (GB)

(72) Inventors: Eyal Fisher, London (GB); Katrin Heider, London (GB); Charles Massie, London (GB); Florent Mouliere, London (GB); Nitzan Rosenfeld, London (GB); Christopher G. Smith, London (GB); Jonathan C. M. Wan, London (GB)

(73) Assignee: Cancer Research Technology Limited, London (GB)

( * ) Notice: Subject to any disclaimer, the term of this patent is extended or adjusted under 35 U.S.C. 154(b) by 1472 days.

(21) Appl. No.: 16/978,518

(22) PCT Filed: Mar. 6, 2019

(86) PCT No.: PCT/EP2019/055610
§ 371 (c)(1),
(2) Date: Sep. 4, 2020

(87) PCT Pub. No.: WO2019/170773
PCT Pub. Date: Sep. 12, 2019

(65) Prior Publication Data
US 2020/0402613 A1 Dec. 24, 2020

(30) Foreign Application Priority Data

Mar. 6, 2018 (GB) ...................................... 1803596
Nov. 23, 2018 (GB) ..................................... 1819134

(51) Int. Cl.
| | |
|---|---|
| *G16B 20/20* | (2019.01) |
| *C12Q 1/6869* | (2018.01) |
| *G16B 30/00* | (2019.01) |
| *G16B 40/00* | (2019.01) |

(52) U.S. Cl.
CPC ........... *G16B 20/20* (2019.02); *C12Q 1/6869* (2013.01); *G16B 30/00* (2019.02); *G16B 40/00* (2019.02)

(58) Field of Classification Search
None
See application file for complete search history.

(56) References Cited

U.S. PATENT DOCUMENTS

| | | |
|---|---|---|
| 2014/0274740 A1 | 9/2014 | Srinivasan et al. |
| 2018/0208999 A1 | 7/2018 | Lo et al. |
| 2018/0371453 A1 | 12/2018 | Lv et al. |
| 2022/0017891 A1 | 1/2022 | Heider et al. |

FOREIGN PATENT DOCUMENTS

| | | |
|---|---|---|
| CN | 105063208 A | 11/2015 |
| CN | 105518151 A | 4/2016 |
| CN | 107075730 A | 8/2017 |
| CN | 107406885 A | 11/2017 |
| CN | 108473932 A | 8/2018 |
| WO | WO 2013/138510 A1 | 9/2013 |
| WO | WO 2014/039556 A1 | 3/2014 |
| WO | WO 2015/164432 A1 | 10/2015 |
| WO | WO 2016/009224 A1 | 1/2016 |
| WO | WO 2016/040901 A1 | 3/2016 |
| WO | WO 2017/024784 A1 | 2/2017 |
| WO | WO 2017/027835 A1 | 2/2017 |
| WO | WO 2017/127742 A1 | 7/2017 |
| WO | WO 2019/170773 A1 | 9/2019 |

OTHER PUBLICATIONS

Phallen et al. (Sci. Translational Medicine (2017), vol. 9, August: 12 pages).*
Gates et al. (Aug. 26, 2016 release; CON-69 document from https://github.com/umich-brcf-bioinf/Connor/commits/master/doc/METHODS.rst; 9 pages).*
Casadio et al. (Journal of Visualized Experiments (2017) Issue 119:6 pages).*
English translation of the First Office Action for Chinese Application No. 201980026704.7 issued Aug. 21, 2023.
International Search Report and Written Opinion for International Application No. PCT/EP2019/055610 mailed Jun. 6, 2019.
Search Report for United Kingdom Application No. GB 1803596.4 dated Nov. 22, 2018.
Ahn et al., Asymmetrical barcode adapter-assisted recovery of duplicate reads and error correction strategy to detect rare mutations in circulating tumor DNA. Scientific reports. May 2, 2017;7:46678, 9 pages.
Kockan et al., SiNVICT: ultra-sensitive detection of single nucleotide variants and indels in circulating tumour DNA. Bioinformatics. Jan. 1, 2017;33(1):26-34.

(Continued)

*Primary Examiner* — Lori A. Clow
(74) *Attorney, Agent, or Firm* — Wolf, Greenfield & Sacks, P.C.

(57) ABSTRACT

The present invention provides a computer-implemented method for detecting cell-free DNA (cfDNA), such as circulating tumour DNA, in a DNA-containing sample obtained from a patient, the method comprising: (a) providing loci of interest comprising at least 2 mutation-containing loci representative of a tumour of the patient ("patient-specific loci"); (b) providing sequence data comprising sequence reads of a plurality of polynucleotide fragments from a DNA-containing sample from the patient, wherein said sequence reads span said at least 2 mutation-containing loci of step (a); (c) optionally, performing reads collapsing to group the sequence reads into read families; (d) calculating the mutant allele fraction across some or all of said at least 2 patient-specific loci, optionally wherein the mutant allele fraction is calculated by aggregating mutant reads and total reads; (e) classifying the sample as containing or not containing the target cfDNA based on the calculated mutant allele fraction. Also provided a related methods and systems.

19 Claims, 72 Drawing Sheets

(56) References Cited

OTHER PUBLICATIONS

Pecuchet et al., Analysis of base-position error rate of next-generation sequencing to detect tumor mutations in circulating DNA. Clinical chemistry. Nov. 1, 2016;62(11):1492-503.

Communication pursuant to Article 94(3) EPC for European Application No. 19709043.4 dated Jun. 19, 2023.

Jongen-Lavrencic et al., Prospective molecular MRD detection by NGS: a powerful independent predictor for relapse and survival in adults with newly diagnosed AML. Blood. Dec. 8, 2017;130:LBA-5. 3 pages.

Preston et al., High-specificity detection of rare alleles with paired-end low error sequencing (PELE-Seq). BMC genomics. Dec. 2016;17:1-21.

Notice of Reason for Rejection for Japanese Application No. 2020-546469 dated Jan. 30, 2023.

[No Author Listed], Targeted Capture of ThruPLEX® Libraries with Agilent SureSelect®XT Target Enrichment System. Rubicon Genomics. 2016. 2 pages. rubicongenomics.com/wp-/content/uploads/2016/11/RDM-152-002-SureSelectXT.pdf.

[No Author Listed], ThruPLEX® Tag-seq Kit User Manual. Takara Bio USA, Inc. 2016. 33 pages. https://www.takarabio.com/documents/User%20Manual/ThruPLEX_Tag/ThruPLEX_Tag-seq_Kit_User_Manual_030520.pdf.

[No Author Listed], Simple vcf parser, based on PyVCF. GitHub. Dec. 6, 2018. 7 pages. https://github.com/moonso/vcf_parser [Last accessed Apr. 28, 2023].

Abbosh et al., Phylogenetic ctDNA analysis depicts early-stage lung cancer evolution. Nature Accelerated Article Preview. 2017. 25 pages.

Alexandrov et al., Clock-like mutational processes in human somatic cells. Europe PMC Funders Group. Author Manuscript. Jun. 2016. 19 pages.

Bettegowda et al., Detection of Circulating Tumor DNA in Early- and Late-Stage Human Malignancies. NIH Public Access. Sci Transl Med Author manuscript. May 2014. 25 pages.

Brash, UV signature mutations. Photochemistry and photobiology. Author Manuscript. Jan. 1, 2016. 24 pages.

Chan et al., Size distributions of maternal and fetal DNA in maternal plasma. Clinical chemistry. Jan. 1, 2004;50(1):88-92.

Diehl et al., Detection and quantification of mutations in the plasma of patients with colorectal tumors. Proceedings of the National Academy of Sciences. Nov. 8, 2005;102(45):16368-73.

Eisenhauer et al., New response evaluation criteria in solid tumours: revised RECIST guideline (version 1.1). European journal of cancer. Jan. 1, 2009;45(2):228-47.

Fan et al., Analysis of the size distributions of fetal and maternal cell-free DNA by paired-end sequencing. Clinical chemistry. Aug. 1, 2010;56(8):1279-86.

Forbes et al., COSMIC: exploring the world's knowledge of somatic mutations in human cancer. Nucleic acids research. Jan. 28, 2015;43(D1):D805-11.

Forshew et al., Noninvasive identification and monitoring of cancer mutations by targeted deep sequencing of plasma DNA. Science translational medicine. May 30, 2012;4(136):136ra68. 13 pages.

Gates et al., Deduplication based on custom inline DNA barcodes. Aug. 2018. 3 pages. https://github.com/umich-brcf-bioinf/Connor [Last accessed Mar. 24, 2023].

Gerber et al., Circulating tumor DNA as a liquid biopsy in plasma cell dyscrasias. Haematologica. Jun. 2018;103(6):e245, 4 pages.

Hoang et al., Genome-wide quantification of rare somatic mutations in normal human tissues using massively parallel sequencing. Proceedings of the National Academy of Sciences. Aug. 30, 2016;113(35):9846-51.

Hodis et al., A landscape of driver mutations in melanoma. Cell. Jul. 20, 2012;150(2):251-63.

Jamal-Hanjani et al., Detection of ubiquitous and heterogeneous mutations in cell-free DNA from patients with early-stage non-small-cell lung cancer. Annals of Oncology Advance Access. Jan. 2016. 19 pages.

Jiang et al., Lengthening and shortening of plasma DNA in hepatocellular carcinoma patients. Proceedings of the National Academy of Sciences. Mar. 17, 2015;112(11):E1317-25.

Jiang et al., The long and short of circulating cell-free DNA and the ins and outs of molecular diagnostics. Trends in Genetics. Jun. 1, 2016;32(6):360-71.

Johnson et al., Targeted Next Generation Sequencing Identifies Markers of Response to PD-1 BlockadeHybrid Capture-Based NGS and Response to Anti-PD-1. Cancer immunology research. Nov. 1, 2016;4(11):959-67.

Kinde et al., Detection and quantification of rare mutations with massively parallel sequencing. Proceedings of the National Academy of Sciences. Jun. 7, 2011;108(23):9530-5.

Manson-Bahr et al., Mutation detection in formalin-fixed prostate cancer biopsies taken at the time of diagnosis using next-generation DNA sequencing. Journal of Clinical Pathology. Mar. 2015. 7 pages.

Mouliere et al., Circulating tumor-derived DNA is shorter than somatic DNA in plasma. Proceedings of the National Academy of Sciences. Mar. 17, 2015;112(11):3178-9.

Mouliere et al., Selecting short DNA fragments in plasma improves detection of circulating tumour DNA. BioRxiv. May 5, 2017:134437. 12 pages.

Murtaza et al., Non-invasive analysis of acquired resistance to cancer therapy by sequencing of plasma DNA. Nature. May 2, 2013;497(7447):108-12.

Newman et al., An ultrasensitive method for quantitating circulating tumor DNA with broad patient coverage. Nature medicine. Apr. 2014. 9 pages.

Newman et al., Integrated digital error suppression for improved detection of circulating tumor DNA. Nature biotechnology. Mar. 2016. 14 pages.

Nioche et a., A freeware for tumor heterogeneity characterization in PET, SPECT, CT, MRI and US to accelerate advances in radiomics. Journal of Nuclear Medicine abstract. May 2017. 4 pages. https://jnm.snmjournals.org/content/58/supplement_1/1316.abstract [Last accessed Mar. 24, 2023], 4 pages.

Poole et al., Combining dependent P-values with an empirical adaptation of Brown's method. Bioinformatics. Sep. 1, 2016;32(17):1430-6.

Shyr et al., FLAGS, frequently mutated genes in public exomes. BMC medical genomics. Dec. 2014;7:1-4.

Siravegna et al., Integrating liquid biopsies into the management of cancer. Nature reviews Clinical oncology. Sep. 2017;14(9):531-48.

Thierry et al., Origin and quantification of circulating DNA in mice with human colorectal cancer xenografts. Nucleic acids research. Oct. 1, 2010;38(18):6159-75.

Underhill et al., Fragment length of circulating tumor DNA. PLoS genetics. Jul. 18, 2016;12(7):e1006162. 24 pages.

Varela et al., Exome sequencing identifies frequent mutation of the SWI/SNF complex gene PBRM1 in renal carcinoma. Nature. Europe PMC Funders Group Author Manuscript. 2011. 10 pages.

Wan et al., Liquid biopsies come of age: towards implementation of circulating tumour DNA. Nature Reviews Cancer. Feb. 2017. 16 pages.

International Search Report and Written Opinion for International Application No. PCT/EP2019/082268 mailed Feb. 24, 2020.

International Preliminary Report on Patentability for International Application No. PCT/EP2019/082268 mailed Jun. 3, 2021.

English translation of the First Office Action for Chinese Application No. 201980085671.3 issued Jul. 29, 2023.

Canadian Office Action for Canadian Application No. CA 3,119,078 dated Dec. 24, 2024.

[No Author Listed], Beckman Coulter (SPRIselect User Guide) SPRI Based Size Selection. Oct. 2012. 30 pages.

[No Author Listed], QIAamp DNA Mini and Blood Mini Handbook. Sample & Assay Technologies. Qiagen. Apr. 2010. Third Edition. 72 pages.

[No Author Listed], QIAseq cfDNA All-in-One Kit Handbook. Qiagen. Jul. 2016. 51 pages.

[No Author Listed], QIAmp DNA Mini and Blood Mini Handbook. Sample & Assay Technologies. Qiagen. Nov. 2007. Second Edition. 72 pages.

(56)             References Cited

OTHER PUBLICATIONS

Bischoff et al., Detecting fetal DNA from dried maternal blood spots: another step towards broad scale non-invasive prenatal genetic screening and feasible testing. Reproductive biomedicine online. Jan. 1, 2003;6(3):349-51.

Brash, UV signature mutations. Photochemistry and photobiology. Jan. 2015;91(1):15-26.

Hodis et al., A Landscape of Driver Mutations in Melanoma. Cell. NIH Public Access Author Manuscript. Jul. 2013. 24 pages.

Kurihara et al., Circulating free DNA as non-invasive diagnostic biomarker for childhood solid tumors. Journal of Pediatric Surgery. Dec. 1, 2015;50(12):2094-7.

Li et al., Size fractionation of cell-free DNA in maternal plasma and its application in noninvasive detection of fetal single gene point mutations. Methods in Molecular Biology. Prenatal Diagnosis. 2008;44:239-251.

Li et al., Size separation of circulatory DNA in maternal plasma permits ready detection of fetal DNA polymorphisms. Clinical chemistry. Jun. 1, 2004;50(6):1002-11.

Maggi et al., Development of a method to implement whole-genome bisulfite sequencing of cfDNA from cancer patients and a mouse tumor model. Frontiers in genetics. Jan. 23, 2018;9:1-12.

Mouliere et al., Enhanced detection of circulating tumor DNA by fragment size analysis. Sci Transl Med. Author Manuscript. Nov. 7, 2018;10(466). 28 pages.

Raymond et al., Collection of cell-free DNA for genomic analysis of solid tumors in a clinical laboratory setting. PloS one. Apr. 27, 2017;12(4):e0176241. 11 pages.

Seitz, Can I use Agencourt Ampure XP to get a higher concentration for my cfDNA sample? ResearchGate. Feb. 2, 2017. https://www.researchgate.net/post/Can-I-use-Agencourt-Ampure-XP-to-get-a-higher-concentration-for-my-cfDNA-sample [last accessed Feb. 6, 2020]. 6 pages.

* cited by examiner b

| number of mutations | specificity |
|---|---|
| 50 | 1.0000 |
| 100 | 1.0000 |
| 500 | 0.9999 |
| 1000 | 0.9990 |
| 2500 | 0.9960 |
| 5000 | 0.9931 |

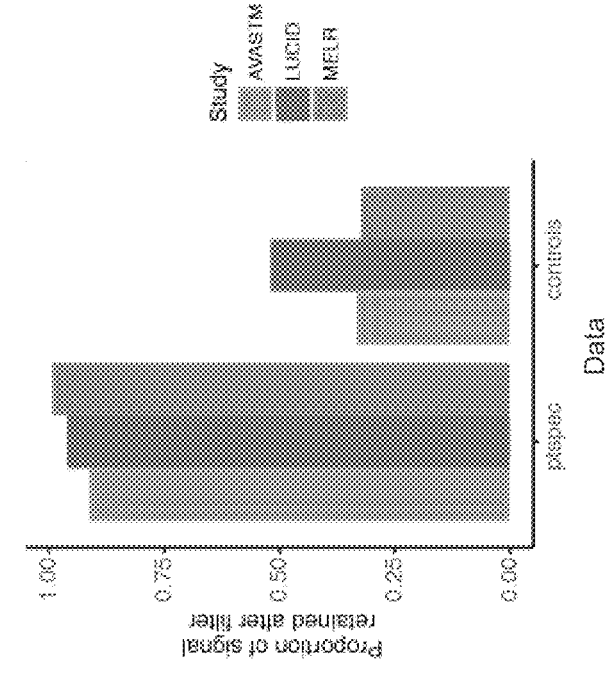
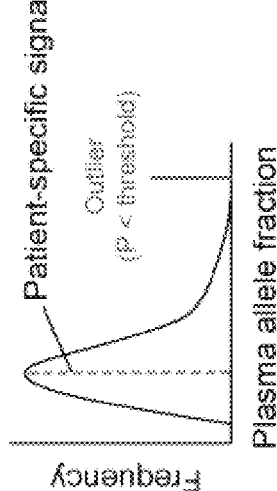
Fig. 34a, b

| Cohort | Patient control | Healthy control |
|---|---|---|
| Stage IV melanoma | 95.4% | 98.7% |
| Stage I-IIIA NSCLC | 98% | 97.4% |
| Stage II-III melanoma | 98.4% | N/A |
| WES plasma | 96.1% | 95.8% |
| sWGS plasma | 100% | 97.6% |

VARIANT DETECTION

RELATED APPLICATIONS

This application is a national stage filing under § 371 of international application number PCT/EP2019/055610, filed Mar. 6, 2019, which claims priority from British application number GB1803596.4 filed Mar. 6, 2018 and from GB1819134.6 filed Nov. 23, 2018, the entire contents of each of which are incorporated herein by reference.

This application claims priority from GB1803596.4 filed 6 Mar. 2018 and from GB1819134.6 filed 23 Nov. 2018, the contents and elements of which are herein incorporated by reference for all purposes.

FIELD OF THE INVENTION

The present invention relates in part to methods for detecting the presence of variant DNA, such as circulating tumour DNA (ctDNA) from, e.g., a cell-free DNA (cfDNA) source, such as blood plasma, or for detecting variant DNA in forensic applications, in pathogen identification, in agricultural and environmental monitoring of species contamination. In particular, the methods of the invention find use in the diagnosis, treatment and especially monitoring of cancer, including monitoring that is done following tumour resection.

The work leading to this invention has received funding from the European Union Seventh Framework Programme (FP7/2007-2013) under grant agreement no 337905.

BACKGROUND TO THE INVENTION

Cell-free DNA (cfDNA), such as circulating tumour DNA (ctDNA) is increasingly being used as a non-invasive tool to monitor disease burden, response to treatment, and risk of relapse[1,2]. Following treatment, patients may have low ctDNA levels and even in advanced disease, concentrations can be lower than a few copies per sample volume[3]. In such cases, an individual sample may contain less than one detectable copy of a given mutation due to sampling statistics, resulting in undetected ctDNA even if its average concentration is non-zero: i.e. a false-negative underestimate of the ctDNA level[1,3,4].

Next-generation sequencing (NGS) offers the possibility to analyse a large number of mutations in plasma in a single reaction. This has been demonstrated through amplicon-based[5,6] and hybrid-capture methods for targeted sequencing[7-9], using either standardised panels[5,9] or bespoke panels covering regions that are specific to each patient[5]-7. These approaches have generally been applied to screen or monitor individual mutations. Despite targeting ~20 patient-specific loci, a recent study detected ctDNA in <50% of patients with early-stage NSCLC and did not detect ctDNA immediately post-surgery in most patients who later relapsed[6]; this suggests that greater sensitivity would be required to effectively achieve this important clinical goal. The use of highly multiplexed capture panels that cover thousands of mutations has been suggested[1,7], but this has not so far been demonstrated for analysis of ctDNA. These approaches for ctDNA analysis relied on identification of individual mutations across panels of variable sizes.

The detection of individual mutations is limited by both sampling error and sequencing background noise; when signals do not reach a pre-specified threshold for mutation calling, the information in these signals is lost.

Pécuchet et al., *Clin. Chem.*, 2016, Vol. 62, No. 11, pp. 1492-1503, describes analysis of base-position error rate of next-generation sequencing to detect tumour mutations in circulating DNA. WO2016/009224 describes a method for detecting a genetic variant. WO2015/164432 describes a method for detecting mutations and ploidy in chromosomal segments. WO2013/138510 describes measurement of nucleic acid variants using highly-multiplexed error-suppressed deep sequencing. Ahn et al., Scientific Reports, 2017, 7:46678|DOI: 10.1038/srep46678 describes asymmetrical barcode adapter-assisted recovery of duplicate reads and error correction strategy to detect rare mutations in circulating tumor DNA. Kockan et al., *Bioinformatics*, 2017, Vol. 33, No. 1, pp. 26-34, describes ultra-sensitive detection of single nucleotide variants and indels in circulating tumour DNA. WO2014/039556 describes systems and method to detect rare mutations and copy number variation. These references generally concern methods for reducing background noise rates of sequencing, including by use of Unique molecular identifiers (UMIs).

Newman et al., 2016 describe improvements to the CAPP-Seq method for detecting ctDNA in which integrated digital error suppression is employed (iDES CAPP-Seq)[7]. However, the iDES CAPP-Seq method involves the use of position-specific error rate for error correction. This requires determination of the error rate for each locus, which in turn requires a least 1/(position-specific error rate) molecules to be targeted at every locus to be interrogated. There remains an unmet need for methods of ctDNA detection that reduce the number of samples required to be analysed in order to carry out error suppression.

While detection of ctDNA shows promise in the field of cancer care, there remains an unmet need for methods and systems that maximise signal-to-noise ratio in the context of low ctDNA fraction. The present invention seeks to provide solutions to these needs and provides further related advantages.

BRIEF DESCRIPTION OF THE INVENTION

The present inventors hypothesised that by integrating signals across a large number of mutation loci, it would be possible to mitigate the effects of sampling noise and obtain a more sensitive and accurate estimate of ctDNA levels, even when ctDNA was present at very low concentrations (FIG. 1a).

To use ctDNA information more efficiently, the present inventors circumvented the "calling" of individual mutations, and aimed to combine the information from mutant reads across multiple, e.g., all, the tumour-mutated loci. The present inventors found that by generating and combining a large number of sequencing reads from plasma DNA covering multiple loci that are mutated in a patient's tumour, it is possible to achieve detection that surpasses the sensitivity of previous methods. The inventors developed an algorithm, called INtegration of VAriant Reads (INVAR), that aggregates mutant signal across hundreds or thousands of mutation loci, to assess whether overall genome-wide signal is significantly above background, or non-distinguishable from background (FIG. 1b). To generate for each patient ~$10^6$ reads covering tumour-mutated loci, in a sequencing-efficient manner, the inventors employed TAilored PAnel Sequencing (TAPAS; FIG. 1c). The inventors first identified mutations from tumour tissue sequencing for 10 stage IV melanoma patients receiving systemic anticancer therapy. These mutations were used to design a panel of hybridisation capture baits, targeting a median of 673 mutations per patient (inter-quartile range "IQR" 250-1, 209), which was applied to longitudinal plasma samples. As detailed herein, using TAPAS data and INVAR analysis, the present inventors were able to detect residual ctDNA down to levels of individual parts per million and below.

In a further optimisation of the INVAR approach, integration may be targeted to focus on the integration of residual disease signal. In particular, a focused INVAR approach, described herein, aggregates minimal residual disease (MRD) 'MRD-like signal' by selecting signal from loci with up to 2 mutant molecules only. Secondly, only molecules with a mutation supported by the forward and reverse (F+R) read are considered for contributing to signal, which constitutes both an error-suppression and size-selection step. Thirdly, mutant reads per locus are weighted based on their tumour allele fraction to up-weight the mutations that are more prevalent in the tumour. Fourthly, the signal is then aggregated—in some cases by trinucleotide context. Fifthly, P-values are integrated using a suitable method (e.g. Fisher's method or Brown's method), but only across the top N classes in order to focus on MRD-like signal The end result is a focused INVAR algorithm that is optimised for detection of residual disease.

Accordingly, in a first aspect the present invention provides a method (optionally a computer-implemented method) for detecting and/or quantifying cell-free DNA (cfDNA), such as circulating tumour DNA (ctDNA), in a DNA-containing sample obtained from a patient, the method comprising:

- (a) providing loci of interest comprising at least 2, 3, 4, 5, 6, 7, 8, 9, 10, 50, 100, 500, 1000, 2500 or at least 5000 mutation-containing loci representative of a tumour of the patient ("patient-specific loci");
- (b) obtaining sequence data comprising sequence reads of a plurality of polynucleotide fragments from a DNA-containing sample from the patient, wherein said sequence reads span said at least 2, 3, 4, 5, 6, 7, 8, 9, 10, 50, 100, 500, 1000, 2500 or 5000 mutation-containing loci of step (a);
- (c) optionally, performing sequencing noise reduction, such as performing reads collapsing to group the sequence reads into read families;
- (d) calculating the mutant allele fraction across some or all of said at least 2, 3, 4, 5, 6, 7, 8, 9, 10, 50, 100, 500, 1000, 2500 or 5000 patient-specific loci, optionally by aggregating mutant reads and total reads. In particular, calculating mutant allele fraction may comprise aggregating mutant reads and total reads according to the formula:

$$\frac{\sum_{loci}(\text{mutant reads})_{patient\text{-}specific}}{\sum_{loci}(\text{total reads})_{patient\text{-}specific}}.$$

In certain cases, calculating mutant allele fraction may comprise calculating the weighted mean of the allele fractions at each of the patient-specific loci. In certain cases, calculating mutant allele fraction may comprise counting the number of mutant reads and comparing this to a pre-determined threshold. The pre-determined threshold may in some cases be a function of sequencing depth, but need not be a simple sum. In particular, a threshold model on the number of mutant reads may be applied.

Step (c) may be considered optional because its function is to reduce noise which may not be necessary in certain cases. In some embodiments a noise reduction step may be employed, which may for example comprise reads collapsing. In certain embodiments a noise reduction step may be omitted. In particular, where confidence arises from other mechanisms (such as replicates, use of classes, etc.), or as a result of improvements in sequencing quality, which may arise in the future. In particular, where step (c) is performed, reads collapsing may be as defined further herein. As used herein there terms "reads collapsing" and "read collapsing" are intended to be interchangeable.

Step (d) may be considered optional and/or may be carried out in different ways in different embodiments. In particular, in some embodiments step (d) is performed in order to compare the mutant fraction to background. This need not include the step of calculating the sum of mutant divided by the sum of total reads. Some key statistical tests which do not use that calculation, but instead use only the number of mutant reads and the number of total reads, without dividing them. In some embodiments the method comprises interrogation of the individual at each mutant read and assess the background rate of that individual to compare with it. In this embodiment it is not necessary to calculate the sum of the mutant reads across all loci.

In some embodiments, the method further comprises:
- (e) classifying the sample
  - (i) as containing cfDNA (e.g. ctDNA) when the mutant allele fraction is found to be greater than a pre-determined threshold (e.g. the background sequencing error rate), or
  - (ii) as not containing cfDNA (e.g. ctDNA) or having unknown cfDNA (e.g. ctDNA) status when the mutant allele fraction is not found to be greater or not found to be statistically significantly greater than the predetermined threshold (e.g. the background sequencing error rate).

In some embodiments, the method comprises quantifying the concentration or amount of cfDNA (e.g., ctDNA) in the sample obtained from the patient, wherein quantifying the concentration or amount of cfDNA (e.g., ctDNA) comprises subtracting the background sequencing error rate from the mutant allele fraction calculated in step (d). In some embodiments, the calculation of Fisher's exact test may be independent of said step (d).

As described herein, differences were observed in the background sequencing error rate per class of mutation, i.e. the error rate of different single nucleotide substitutions differs (e.g. see FIG. 2b showing a higher error rate for G>A than for T>G). Indeed, a nearly 40-fold difference in error rate between the "noisiest" (greatest error) and least "noisy" (least error) mutation classes was seen. The present inventors realised that it would be possible to consider splitting the mutations by class (which may be considered splitting or grouping mutations into groups by class), while still integrating across all variant reads in a class, to overcome technical noise, i.e. error, and improve sensitivity for low levels of cfDNA (e.g. ctDNA) (see, in particular, FIGS. 3a and 3b, wherein "splitting data" into mutation classes (i.e. grouping the mutations into groups based on the mutation class) led to around a 10-fold improvement in the lowest detected allele fraction to 0.3 ppm). Accordingly, in some embodiments, the mutant allele fraction is determined per class of mutation taking into account the background sequencing error rate for each class of mutation.

In some embodiments, the background sequencing error rate is or has been determined for each class of mutation (e.g., each class of base substitution) ("mutation class") represented in said at least 2, 3, 4, 5, 6, 7, 8, 9, 10 or more patient-specific loci, and the mutant allele fraction calculation in step (d) is performed for each mutation class, taking into account the background sequencing error rate of that mutation class; the mutant allele fraction of each class is combined to provide a measure of the global mutant allele fraction of the sample. In particular, the global mutant allele fraction may be calculated as the mean of all of the individual per-class background-subtracted mutant allele fractions, weighted by the total number of read families observed in that class. In certain embodiments, particularly where the number of mutant and non-mutant reads is used to determine the presence of cfDNA without determining the mutant allele fraction, the calculation step (d) may be omitted.

In some embodiments, the method comprises making a determination of the statistical significance or otherwise of the calculated mutant allele fraction, taking into account the background sequencing error rate. In cases where the mutant allele fraction is calculated per mutation class and then combined into a global mutant allele fraction, the determination of statistical significance of the calculated global mutant allele fraction, may comprise determining the individual statistical significance of the mutant allele fraction of each mutation class and then combining the individual statistical significance determinations into a global statistical significance determination for the global mutant allele fraction. Various statistical methods may be suitable for the determination of statistical significance of the mutant allele fraction. In particular cases, the determination of the statistical significance of the mutant allele fraction may comprise carrying out a one-sided Fisher's exact test, given a contingency table comprising: the number of mutant reads from the sample, the total number of reads from the sample, and the number of mutant reads expected from the background sequencing error rate. In certain embodiments where mutant allele fraction is calculated on a per mutation class basis, the determination of mutant allele statistical significance may comprise carrying out multiple one-sided Fisher's exact tests to determine the statistical significance of the number of mutant reads observed given the background sequencing error rate for that mutation class, thereby generating a p-value for each mutation class, and combining the p-values using the Empirical Brown's method to provide a global measure of statistical significance for the mutant allele fraction of the sample.

When mutant allele fraction is calculated on a per mutation class basis, the number of mutation classes will generally be governed by the mutations found to be present in the at least 2, 3, 4, 5, 6, 7, 8, 9, 10, 100, 1000 or at least 5000 mutation-containing loci representative of a tumour of the patient ("patient-specific loci"). For many cases, the mutation classes may comprise at least 2, 3, 4, 5, 6, 7, 8, 9, 10, 11 or all 12 of the following mutation classes: C>G, G>C, T>G, A>C, C>A, G>T, T>C, A>G, T>A, A>T, C>T and T>C. Preferably, the tumour-specific mutations at the patient-specific loci include mutations belonging to at least 2, 3, 4, 5, 6, 7, 8, 9, 10, 11 or 12 different mutation classes. Further mutation classes are contemplated herein. For example, mutations may be split based on a greater number of sequence subsets such as by di-nucleotide context, tri-nucleotide context or by individual locus, which may further improve resolution of error rates.

As described herein (see Example 8 and FIGS. 11 and 13), in some cases the error rate per mutation class was assessed by trinucleotide context. Trinucleotide context may be one or more (e.g. all) of the following trinucleotide contexts: CGC, GGC, TCG, ACG, GCG, TGC, CCG, GCA, CGA, GCC, CGG, CGT, AGC, GCT, TCA, TGA, AGT, ACC, CCC, CCA, CTT, GGG, CCT, GAG, CTG, AGG, CAG, CTC, AGA, TCC, GGT, TGG, CTA, ACA, TCT, TAG, AAG, TGT, ACT, GTC, GGA, TAC, TTG, CAA, TTC, TTA, ATC, ATG, TAA, TAT, CAT, GTT, ATT, ATA, GAA, GAC, GAT, CAC, GTG, TTT, GTA, AAT, AAA and AAC. The mutation classes may comprise at least 2, 3, 4, 5, 6, 7, 8, 9, 10, 11 or all 12 of the following mutation classes: C>G, G>C, T>G, A>C, C>A, G>T, T>C, A>G, T>A, A>T, C>T and T>C. In particular, the method may employ only a subset of the total mutation classes and/or trinucleotide contexts. For example, the method may comprise combining P-values from the 2, 3, 4, 5, 6, 7, 8, 10 or 12 most significant trinucleotide contexts per sample. In particular cases, the method of the present invention may comprise combining the 6 most significant trinucleotide contexts per sample. In certain cases, the p-value per trinucleotide context may be determined using a Fisher's test to compare the number of mutant reads for a trinucleotide context given the background error rate for that context. The background error rate for each mutation class and trinucleotide context may be determined through the use of sequencing data within 10 b.p. of the target base, but not including the targeted base. The present inventors found that when performing error correction by mutation class from trinucleotide contexts, it was preferable that not every single trinucleotide context should be used because it is thought that signal will only be expected in a small number of contexts from any one sample. In the context of minimal residual disease (MRD), the expectation is that ctDNA levels will be low; therefore, one expects few trinucleotide contexts to show true signal. Thus, it may be warranted to restrict analysis to a smaller number of trinucleotide contexts during analysis (e.g. the 2, 3, 4, 5, 6, 7, 8, 10 or 12 most significant trinucleotide contexts as defined above). This may have utility for reducing background noise, for example, if a control sample were to randomly show a high level of signal: such a result would be inconsistent with MRD.

In some embodiments, the sequence data comprising sequence reads obtained in step (b) represent Tailored Panel Sequencing (TAPAS) sequence reads, focused-exome sequence reads, whole-exome sequence reads or whole-genome sequence reads. The choice of sequence reads may reflect, inter alia, the mutation rate of the cancer being studied. Tumour-derived mutations can be identified using exome sequencing as demonstrated herein, but also across smaller focused panels or larger scales such as whole genome. In examples described herein where the patients had melanoma, exome sequencing was sufficient to identify hundreds to thousands of mutations per patient. Based on known mutation rates of cancer types, exome sequencing would also suffice for many cancer types with relatively high mutation rates, for example: lung, bladder, oesophageal, or colorectal cancers. For cancers with a mutation rate of ~1 per megabase or less, whole-genome sequencing of tumours for mutation profiling may be desirable. For ovarian and brain cancers, this would result in thousands of mutations identified per patient. Moreover, the sequence data comprising sequence reads may cover a sufficient portion of the exome or genome of the sequence tumour to identify at least 2, 3, 4, 5, 6, 7, 8, 9, 10, 50, 100, 500, 1000, 2500 or at least 5000 mutation-containing loci. Additionally or alternatively, the sequence data comprising sequence reads may cover a sufficient portion of the exome or genome of the sequence tumour to ensure that the tumour-specific mutations at the patient-specific loci include mutations belonging to at least 2, 3, 4, 5, 6, 7, 8, 9, 10, 11 or 12 different mutation classes.

Additionally or alternatively, the sequence data comprising sequence reads may cover a sufficient portion of the exome or genome of the tumour to ensure that the tumour-specific mutations at the patient-specific loci include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 or at least 64 trinucleotide contexts, in particular, trinucleotide contexts selected from the group consisting of: CGC, GGC, TCG, ACG, GCG, TGC, CCG, GCA, CGA, GCC, CGG, CGT, AGC, GCT, TCA, TGA, AGT, ACC, CCC, CCA, CTT, GGG, CCT, GAG, CTG, AGG, CAG, CTC, AGA, TCC, GGT, TGG, CTA, ACA, TCT, TAG, AAG, TGT, ACT, GTC, GGA, TAC, TTG, CAA, TTC, TTA, ATC, ATG, TAA, TAT, CAT, GTT, ATT, ATA, GAA, GAC, GAT, CAC, GTG, TTT, GTA, AAT, AAA and AAC.

In some embodiments, the 2, 3, 4, 5, 6, 7, 8, 9, 10, 50, 100, 500, 1000, 2500 or at least 5000 mutation-containing loci representative of the tumour of the patient are obtained by sequencing DNA obtained directly from a tumour sample from the patient or sequencing DNA obtained from a plasma sample from the patient at a time of high tumour disease burden (e.g. prior to the start of therapeutic treatment or prior to surgical resection). In this way the determination of the tumour sequence, e.g., tumour exome or portion thereof or tumour genome or portion thereof, can be made using a relatively more abundant source of tumour-derived DNA and then the information about which loci contain tumour-specific mutations (step (a)) can be employed in the methods of the present invention practiced on sequence reads (step (b) obtained at a time when tumour-derived DNA is more scarce (e.g. after the patient has received at least one course of treatment and/or after surgical tumour resection)). For example, the method may be used to monitor recurrence of the tumour by detecting low levels of ctDNA. The determination of loci of interest comprising the 2, 3, 4, 5, 6, 7, 8, 9, 10, 50, 100, 500, 1000, 2500 or at least 5000 mutation-containing loci representative of the tumour of the patient will generally involve comparison with germline DNA sequencing of the patient so as to identify which loci contain mutations that are specific to the tumour relative to, or compared with, the patient's germline genomic sequence. For example, DNA extracted from buffy coat or any other suitable source of germline DNA (e.g. saliva, hair follicles, skin, cheek swab, white blood cells).

In some embodiments, the loci of interest are filtered by removing loci known to be single nucleotide polymorphisms (SNPs), e.g., by removing those positions found in common SNP databases (such as 1000 Genomes ALL or EUR). This filtering focuses on signal, i.e. tumour mutated loci, by excluding those loci that may be SNPs (see Example 10 herein).

In some embodiments, the sequence data comprising sequence reads provided in step (b) represent sequence reads of a plurality of DNA fragments from a substantially cell-free plasma sample from the patient. In some embodiments, the sequence data comprising sequence reads provided in step (b) represent sequence reads of a plurality of DNA fragments from any of the sample types as defined herein. The use of cell-free DNA (cfDNA) as a sample source provides a relatively non-invasive method for obtaining sample (so called "liquid biopsy"). The sequence reads obtained from cfDNA will comprise sequence reads of both that fraction of circulating DNA fragments that has its origins from the tumour or tumours of the patient (ctDNA fraction), if present, and that fraction of circulating DNA fragments that has its origins from non-tumour tissue or cells.

In some embodiments, the sequence data comprising sequence reads obtained in step (b) represent sequence reads of a plurality of polynucleotide fragments from a sample obtained from the patient after the patient has begun a course of treatment of the tumour and/or after the patient has had surgical resection of the tumour, and wherein the method is for monitoring the presence, growth, treatment response, or recurrence of the tumour. In particular embodiments, the method is for monitoring the presence and/or recurrence of minimal residual disease (MRD).

In accordance with this and other aspects of the present invention, the patient may be a patient who has, or has had, a cancer selected from melanoma, lung cancer, bladder cancer, oesophageal cancer, colorectal cancers, ovarian cancer brain cancer, and/or breast cancer. In particular, the patient may have been diagnosed as having melanoma, including advanced and/or invasive melanoma with or without metastases.

In some embodiments, the reads collapsing step (c) comprises the grouping of duplicate sequencing reads into read families based on fragment start and end positions and at least one molecular barcode, which uniquely label individual starting cfDNA molecules. As defined further herein, "barcode" or "molecular barcode" as used herein means a unique string of bases, generally of length <20, such as <10 bp, that may be ligated to DNA molecules as the first step during library preparation. As a result, read families may be uniquely identified, and thus linked to their starting molecule. This allows error-suppression via "reads collapsing". Therefore, duplicate reads with the same start and end positions and molecular barcode can be identified computationally as having originated from the same starting cfDNA molecule, termed as a 'read family'. In particular, a minimum 60%, 70%, 75%, 80%, 85%, 90% or even a 95% consensus ('consensus threshold') may be required between all family members for a read to be included in a read family. Thus, for example, where there are three reads in a read family and two of those reads show consensus while one shows, e.g., an alternative base a given nucleotide position, the read family would have a resulting consensus of 2/3 or 66%. In the case where there is a mutation, but the mutant base is not supported by a consensus greater than, or equal to, the consensus threshold for inclusion in a read family may be discarded (i.e. not used further in the analysis). In particular cases, a minimum family size of 2, 3, 4 or 5 reads may be required. In some cases, read families not satisfying this minimum family size may be disregarded in the analysis. The greater the family size, the greater the extent of error-suppression, because the consensus across the read family is supported by a larger number of independent reads. Therefore, in order to set a limit for the error-suppression step, it may be advantageous to specify a particular minimum family size threshold.

As described herein, the present inventors found that an in silico size selection, even with relaxed settings, was able to enrich for mutant signal (i.e. ctDNA) while minimising loss of rare mutant alleles. The enrichment was in some cases greater for lower initial allele fractions (see FIG. 4c). Accordingly, in some embodiments, the sequence reads may be size selected to favour or enrich for mutant reads relative to non-mutant reads. In certain embodiments, the sequence reads are size selected in silico for reads within the size ranges 115-160 bp, 115-190 bp, 250-400 bp and/or 440-460 bp in order to enrich for those reads representing ctDNA. In general, it is advantageous to use size ranges where ctDNA is enriched and not depleted. These size ranges may vary by cancer type and stage.

Non-tumour DNA has been observed to peak at 166 bp, thus in some aspects size-selection windows may be adjusted to exclude or minimise non-tumour DNAs of length proximal to this maxima. Also contemplated herein are one or more narrower size windows for the size selection that would be expected to result in greater enrichment. For example, size ranges of 120-155 bp, 120-180 bp, 260-390 bp and/or 445-455 may be employed. Alternatively, the size selection may be less stringent with wider size selection windows such as 110-200 bp, 240-410 bp and/or 430-470 bp. In some embodiments, the in silico size selection may size select to one or more (e.g. 2 or 3) size windows that have been predetermined based on experimentally-determined size windows that enrich for ctDNA in the sample(s) in question. For example, the sequence reads from one or more samples may be combined, the size distribution of fragments determined, and the ratio between the proportion of mutant, and wild-type (i.e. germline sequence) reads determined. The size windows for the methods of the present invention may be those that display enrichment in the proportion of mutant reads relative to wild-type reads.

In certain embodiments, one or more filters are applied to the read families in order to focus on those families more likely to be tumour-derived. In some cases, the one or more filters may be minimal residual disease (MRD) filters, such as those described in Example 10 herein. In particular, a filter step may comprise excluding those loci with >2 mutant molecules. Alternatively or additionally, a filter step may comprise selecting (i.e. including) only those fragments which have been sequence in both forward (F) and reverse (R) direction. As described in Example 10, the requirement that mutant reads only be considered as contributing to signal at a locus if there is at least one F and at least one R read at the locus serves a dual purpose of suppressing sequencing artifacts, and selecting for mutant reads from short cfDNA fragments (supported by reads in both directions), which are slightly enriched in ctDNA (FIG. 4 (*a*)). Having applied the MRD filters, such as one or both of the exclusion of those loci with >2 mutant molecules and the selection of only those reads having at least one F and at least one R read at the locus, the resulting filtered loci may be termed "MRD-like loci".

In certain embodiments, a tumour allele fraction weighting is applied in order to increase the weighting (up-weight) the signal applied from mutations that are more prevalent in the tumour. As described in Example 11 herein, the present inventors found that the likelihood of observing a given mutation in cfDNA from plasma is proportional to the tumour allele fraction for the given mutation in the tumour (see FIG. 16). The present inventors therefore reasoned that patient-specific tumour sequencing provides an opportunity to advantageously weight signal per locus by the tumour allele fraction prior to aggregation of signal by mutation context. In some embodiments, the mutant allele fraction per locus is weighted by tumour allele fraction. In some embodiments, the number of mutant alleles per locus is weighted by tumour fraction. Preferably, tumour allele fraction weighting is applied per locus by dividing the number of mutant read families that include the locus by (1 minus the tumour allele fraction at that locus) and by dividing the total number of read families that include the locus also by (1 minus the tumour allele fraction at that locus). This may be expressed using the formula:

$$AF_{context} = \frac{\Sigma_{MRD\text{-}like\ loci}\text{mutant families} \div (1 - \text{tumour } AF)}{\Sigma_{MRD\text{-}like\ loci}\text{total families} \div (1 - \text{tumour } AF)}$$

wherein:

$AF_{context}$ is the allele frequency of a given (e.g. trinucleotide) context; tumourAF is the allele frequency of the locus as determined by analysis of the tumour (e.g by sequencing DNA obtained directly from the tumour); and MRD-like loci are the mutation-containing loci determined from the tumour of the patient and which have been filtered to select for minimal residual disease signal. The effect of weighting by tumour allele fraction can be seen in Example 11, particularly comparing FIGS. 15 and 18. Weighting by tumour allele fraction according to the above formula, which was done in FIG. 18, but not in FIG. 15, results in differential enrichment of mutant signal.

In certain embodiments, the p-value for each trinucleotide context is determined by comparing samples against background error rates. The top (i.e. most significant) n p-values from trinucleotide contexts are then combined using a suitable technique, such as Fisher's method or Brown's method. In some cases n may be 2, 3, 4, 5, 6, 7, 8, 10, 12 or more. For example, where n=6 p-values from the top 6 trinucleotide contexts may be combined according to the formula:

$$\text{Combined } p\text{-value} = -2\sum_{i=1}^{6} \ln(p_i)$$

In certain embodiments, the global allele fraction, $AF_{global}$, is calculated based on all signal in all contexts, taking into account the background error, E. Preferably, $AF_{global}$ is determined according to the formula:

$$AF_{global} = \frac{\sum \max(AF_{context} - E_{context}, 0) \times \text{total } familes_{context}}{\sum \text{total families}}.$$

In a second aspect, the present invention provides a method for monitoring the presence of, growth of, prognosis of, regression of, treatment response of, or recurrence of a cancer in a patient, the method comprising:

(i) sequencing a polynucleotide-containing sample that has been obtained from the patient in order to obtain sequence data comprising sequence reads of a plurality of polynucleotide fragments from the sample, wherein said sequence reads span at least 2, 3, 4, 5, 6, 7, 8, 9, 10, 50, 100, 500, 1000, 2500 or at least 5000 loci that have been determined to be mutation-carrying loci in cancer cells of the patient;

(ii) carrying out the method of the first aspect of the invention using the sequence data obtained in step (i);

(iii) determining the presence of, growth of, prognosis of, regression of, treatment response of, or recurrence of the cancer in the patient based on at least the classification of the sample as containing ctDNA, not containing ctDNA or based on the calculated allele fraction taking into account the background error, optionally wherein the method is for monitoring recurrence of a cancer following tumour resection.

In some cases, the sequencing step (i) may comprise Next-generation Sequencing (NGS), including Illumina® sequencing, or Sanger sequencing. NGS offers the speed and accuracy required to detect mutations, either through whole-genome sequencing (WGS) or by focusing on specific regions or genes using whole-exome sequencing (WES) or targeted gene sequencing. Examples of NGS techniques include methods employing sequencing by synthesis, sequencing by hybridisation, sequencing by ligation, pyro-sequencing, nanopore sequencing, or electrochemical sequencing.

In some cases, the method of this aspect of the present invention further comprises a step, prior to sequencing, of preparing a DNA library from a sample (e.g. a plasma sample) obtained from the patient or from more than one patient. Optionally, the library may be barcoded.

In some cases, the method of this aspect of the present invention further comprises a step prior to sequencing of obtaining a sample from the patient. For example, a blood sample may be collected from a patient who has been diagnosed as having, or being likely to have, a cancer. The sample may be subjected to one or more extraction or purification steps, such as centrifugation, in order to obtain substantially cell-free DNA source (e.g. to obtain a plasma sample). The method may further comprise determining the cfDNA concentration of the sample. It is specifically con-templated that the sample may be transported and/or stored (optionally after freezing). The sample collection may take place at a location remote from the sequencing location and/or the computer-implemented method steps may take place at a location remote from the sample collection location and/or remote from the sequencing location (e.g. the computer-implemented method steps may be performed by means of a networked computer, such as by means of a "cloud" provider). Nevertheless, the entire method may in some cases be performed at single location, which may be advantageous for "on-site" determination or monitoring of cancer.

In some cases, the method of this aspect of the invention may further comprise obtaining tumour imaging data and/or measuring or detecting one or more tumour biomarkers to assist with the determination of presence of, growth of, treatment response of, or recurrence of the cancer. In par-ticular, the tumour imaging data may comprise computed tomography (CT) data, e.g. to measure tumour volume. In particular, cases, the biomarker may comprise lactate dehy-drogenase (LDH) concentration. Such additional means of tumour detection and/or quantification may corroborate a determination made by the methods of the present invention and/or may assist with resolving ambiguous determinations.

In some cases, the method of this aspect may further comprise a step of recommending or selecting the patient for anti-cancer treatment, including follow-on or continuing treatment(s). For example, where the sample is determined to contain ctDNA (e.g. where the mutant allele fraction is found to be greater, including statistically significantly greater, than the background sequencing error rate), the patient may be determined to have, or to have a recurrence of, a cancer which may benefit from anti-cancer treatment, including chemotherapy, immunotherapy, radiotherapy, sur-gery or a combination thereof. Likewise, where the sample is determined not to contain ctDNA or to have a ctDNA level below the limit of detection of the method of the present invention (e.g. where the mutant allele fraction is found to be not greater, or not statistically significantly greater, than the background sequencing error rate), the patient may be determined not to have, or to be in remission from, a cancer.

The patient may therefore benefit from the avoidance of unnecessary anti-cancer treatment which could be associ-ated with unwanted side effects.

In a third aspect, the present invention provides a method of treatment of a patient who has or has had a cancer, the method comprising:

a) carrying out the method of the first or the second aspect of the present invention; and
b) (i) where the sample is determined to contain cfDNA (e.g., ctDNA) (e.g. where the mutant allele fraction is found to be greater, including statistically significantly greater, than the background sequencing error rate), administering an anti-cancer treatment to the patient; or
(ii) where the sample is determined not to contain cfDNA (e.g., ctDNA) or to have a cfDNA (e.g., ctDNA) level below the limit of detection of the method of the present invention (e.g., where the mutant allele fraction is found to be not greater, or not statistically signifi-cantly greater, than the background sequencing error rate), the patient may be determined not to have, or to be in remission from, a cancer and anti-cancer therapy may be curtailed.

In some cases, the anti-cancer treatment may be selected from chemotherapy, immunotherapy, radiotherapy and sur-gery. In particular, the anti-cancer treatment may comprise one or more of: vemurafenib, ipilimumab, pazopanib, dab-rafenib and trametinib. In particular, where the patient has or has had melanoma, and the sample is determined to contain cfDNA (e.g., ctDNA), the aforementioned anti-cancer treat-ments may be suitable.

Without wishing to be bound by any particular theory, the present inventors believe that the methods of the present invention may find application beyond the field of cancer monitoring and cf DNA e.g., ctDNA detection. In particular, the INVAR algorithm may find use in forensic science (e.g. detecting trace amounts of a suspected perpetrator's (or victim's) DNA in a sample containing a larger fraction of another person's DNA, such as a suspected victim (or perpetrator, as the context directs), agriculture and food (e.g. to detect contamination), lineage tracing, clinical genetics, and transplant medicine. The ability of the INVAR method to improve signal-to-noise ratio by aggregating across many, e.g., all, mutant reads and optionally splitting (further analy-sing) by mutation class, makes this method attractive in applications where a sample is suspected of containing a minor fraction of a target DNA or other polynucleotide (e.g. RNA), including fragments thereof, that may differ in sequence at a number of loci from the DNA or other polynucleotide (e.g. RNA), including fragments thereof, making up the larger fraction of the sample.

Accordingly, in a fourth aspect the present invention provides a method for detecting a target polynucleotide in a sample in which the target polynucleotide is a minor fraction of the total polynucleotide in the sample, wherein the target polynucleotide and the non-target polynucleotide differ in sequence at a plurality of loci, the method comprising:

(a) obtaining sequence information comprising at least 2, 3, 4, 5, 6, 7, 8, 9, 10, 50, 100, 500, 1000, 2500 or at least 5000 loci, wherein at least one base at each of said loci differs between the target and non-target polynucle-otide sequences ("target-specific loci");
(b) obtaining sequence data comprising sequence reads of multiple polynucleotide fragments from the sample, wherein said sequence reads span said at least 2, 3, 4, 5, 6, 7, 8, 9, 10, 50, 100, 500, 1000, 2500 or 5000 target-specific loci of step (a);

(c) optionally, performing reads collapsing to group the sequence reads into read families;

(d) calculating the target polynucleotide fraction across some or all of said at least 2, 3, 4, 5, 6, 7, 8, 9, 10, 50, 100, 500, 1000, 2500 or 5000 or more target-specific loci, optionally wherein the target polynucleotide fraction is calculated by aggregating mutant reads and total reads according to the formula:

$$\frac{\sum_{loci}(\text{mutant reads})_{target\text{-}specific}}{\sum_{loci}(\text{total reads})_{target\text{-}specific}};$$

(e) classifying the sample (i) as containing the target polynucleotide when the target polynucleotide fraction is found to be statistically significantly greater than the fraction that would be expected based on the background sequencing error rate, or (ii) as not containing the target polynucleotide or having unknown target polynucleotide status when the target polynucleotide fraction is not found to be statistically significantly greater than the fraction that would be expected based on the background sequencing error rate.

In some cases, the background sequencing error rate is or has been determined for each class of base substitution represented in said at least 2, 3, 4, 5, 6, 7, 8, 9, 10, 50, 100, 500, 1000, 2500 or 5000 loci, wherein the target polynucleotide fraction calculation in step (d) is performed for each base substitution class, and wherein the target polynucleotide fraction statistical significance determination comprises computing the statistical significance for each base substitution class taking into account the background sequencing error rate of that base substitution class and combining the computed statistical significance of each base substitution class to provide a measure of statistical significance for the global target polynucleotide fraction of the sample.

The target polynucleotide may be DNA or RNA.

In accordance with any aspect of the present invention, the patient is a mammal, preferably a human. The patient may have been diagnosed as having a cancer. In some cases, the patient may have had a course of treatment for the cancer and/or had surgery to excise a cancer.

In accordance with any aspect of the present invention, the method may comprise analysing a given sample in a plurality of (e.g. 2, 3, 4, 5, 6, or more) replicates, and using the signal in the replicates to improve confidence in the determination of presence or absence of cfDNA in the sample. In such cases, it is possible to relax other constraints of the methods of the present invention. For example, by using sample replicates it may be possible to omit the reads collapsing step. Nevertheless, the use of sample replicates and reads collapsing are not mutually exclusive, and so both sample replicates and reads collapsing may, in certain embodiments, both be employed in methods of the present invention.

In accordance with any aspect of the present invention, in some embodiments the analysis of the sample includes a size-selection step which separates out different fragment sizes of DNA.

In some embodiments the sample obtained from the patient is a limited volume sample comprising less than one tumour-derived haploid genome. In some embodiments the sequencing data from the sample represents sequencing coverage or depth of less than 1, 2, 3, 4, 10 or 12 haploid genomes.

In some embodiments the sample obtained from the patient is a limited volume sample selected from the group consisting of:

(i) a blood, serum or plasma sample of less than 500 μl, less than 400, less than 200, less than 100 μl or less than 75 μl (e.g. a blood or plasma sample of about 50 μl);

(ii) a fine needle aspirate (FNA);

(iii) a lymph node biopsy;

(iv) a urine, cerebrospinal fluid, sputum, bronchial lavage, cervical smear or a cytological sample;

(v) a sample that has been stored for more than 1 year, 2 years, 3 years, 5 years or 10 years from the time of collection from the patient; and (vi) a sample that has been previously processed and failed quality metrics for DNA or sequencing quality, or a sample that belongs to a set of samples from which other samples have been previously processed and failed quality metrics for DNA or sequencing quality.

In some embodiments the sample obtained from the patient is:

a dried blood spot sample;

a pin-prick blood sample;

an archival blood, serum or plasma sample that has been of less than 500 μl that has been stored for greater than 1 day (e.g. at least one month) or at least 1 year or at least 10 years after collection from the patient.

In some embodiments the patient is healthy or has a disease (e.g. a cancer) and/or wherein the patient is human or a non-human animal (e.g. a rodent).

In some embodiments the animal has xenografted or xenotransplanted human tumour tissue.

In some embodiments the sample being analysed (e.g. the sample obtained from the patient) is subjected to a size-selection step in which genomic DNA (gDNA) fragments of >200 bp, >300 bp, >500 bp, >700 bp, >1000 bp, >1200 bp, >1500 bp or >2000 bp are filtered-out, depleted or removed from the sample prior to analysis, e.g. prior to DNA sequencing, to generate a size-selected sample.

In some embodiments the size selection step is carried out prior to sequencing library preparation or after sequencing library preparation.

In some embodiments the size selection step is a right-sided size selection employing bead-based capture of gDNA fragments.

In some embodiments the method comprises a step of suppressing outlier noise at a locus that is not consistent with the remaining distribution of patient-specific mutant signal in that sample ("outlier suppression").

In some embodiments the likelihood of ctDNA presence in the sample is determined by the generalized likelihood ratio:

$$\lambda(p_0) = \frac{L(p_0; M, L, AF, e)}{L(\hat{p}; M, L, AF, e)}$$

wherein the terms of the generalized likelihood ratio are as defined in the Supplementary Methods for Example 14.

In a fifth aspect the present invention provides a method for detecting variant cell-free DNA (cfDNA) in a sample obtained from a patient, where analysis of the sample includes a size-selection step which separates out different fragment sizes of DNA.

In some embodiments the sample obtained is a limited volume sample selected from the group consisting of:

(i) a blood, serum or plasma sample of less than 500 µl, less than 400, less than 200, less than 100 µl or less than 75 µl (e.g. a blood or plasma sample of about 50 µl);

(ii) a fine needle aspirate (FNA);

(iii) a lymph node biopsy;

(iv) a urine, cerebrospinal fluid, sputum, bronchial lavage, cervical smear or a cytological sample;

(v) a sample that has been stored for more than 1 year, 2 years, 3 years, 5 years or 10 years from the time of collection from the patient; and (vi) a sample that has been previously processed and failed quality metrics for DNA or sequencing quality, or a sample that belongs to a set of samples from which other samples have been previously processed and failed quality metrics for DNA or sequencing quality.

In some embodiments said size-selection step comprises filtering-out, depleting or removing genomic DNA (gDNA) fragments of >200 bp, >300 bp, >500 bp, >700 bp, >1000 bp, >1200 bp, >1500 bp, or >2000 bp prior to analysis, e.g. prior to DNA sequencing.

In some embodiments the method comprises:

(i) DNA sequencing the size-selected sample or a library generated from the size-selected sample to generate a plurality of sequence reads and analysing the sequence reads to detect the presence of ctDNA; or (ii) analysing DNA modifications, such as methylation.

In some embodiments the sample obtained from the patient is:

a dried blood spot sample;

a pin-prick blood sample;

an archival blood, serum or plasma sample that has been of less than 500 µl that has been stored for greater than 1 day (e.g. at least one month), at least 1 year or at least 10 years after collection from the patient.

In some embodiments the patient is healthy or has a disease (e.g. a cancer) and/or wherein the patient is human or a non-human animal (e.g. a rodent).

In some embodiments the animal model has xenografted or xenotransplanted human tumour tissue.

In some embodiments said analysis comprises next-generation sequencing (NGS) of the size-selected sample or a library generated from the size-selected sample.

In some embodiments said analysis comprises sequencing the size-selected sample or a library generated from the size-selected sample to generate sequence reads and further comprises analysis of the sequence reads selected from:

performing a method of any of the first to fourth aspects of the invention;

performing copy number analysis;

processing the sequence reads to determine a trimmed Median Absolute Deviation from copy number neutrality (t-MAD) score or an ichorCNA score; and/or aligning the sequence reads to at least two different reference genomes, e.g. a human reference genome and a rodent reference genome.

In some embodiments the t-MAD score is determined by trimming regions of genome that exhibit high copy number variability in whole genome datasets derived from healthy subjects and then calculating the median absolute deviation from $\log_2 R=0$ of the non-trimmed regions of the genome.

In some embodiments the size selection step is carried out prior to, or after, a sequencing library preparation step.

In some embodiments the size selection step is a right-sided size selection employing bead-based capture of gDNA fragments.

In some embodiments the variant cell-free DNA is circulating tumour DNA (ctDNA).

In some embodiments the method is for early detection of cancer, monitoring of cancer treatment, detection of residual disease, is used to guide treatment decisions, to assess the status of a cancer in the patient or cancer progression or cancer response to treatment, or the need for or the type of further treatment for the patient.

In some embodiments the patient is a human or an animal model of a cancer (e.g. a rodent).

In some embodiments the variant cell-free DNA comprises:

cfDNA from a donor tissue or organ that has been transplanted into the patient;

foetal cfDNA from a foetus in gestation in the patient; or abnormally methylated cfDNA.

In some embodiments the method is used to provide information to guide medical treatment, changes in diet, or physical training, or is used for forensic analysis or to identify individuals whose biological material is present in the sample or to identify organisms whose biological material is present in the sample.

In some embodiments the patient is a human child having or suspected of having a paediatric cancer. Paediatric cancers are often associated with difficulties in sample collection, e.g. due to the age of the patient, and samples may be of small volume and/or contain low levels of ctDNA. Paediatric cancers include: various brain tumours, lymphomas, leukaemia, neuroblastoma, Wilms tumour, Non-Hodgkin lymphoma, Childhood rhabdomyosarcoma, Retinoblastoma, Osteosarcoma, Ewing sarcoma, Germ cell tumors, Pleuropulmonary blastoma, Hepatoblastoma and hepatocellular carcinoma.

In a sixth aspect, the present invention provides a system for detecting target cell-free DNA (cfDNA) in a DNA-containing sample obtained from a patient, comprising:

at least one processor; and at least one non-transitory computer readable medium containing instructions that, when executed by the at least one processor, cause the at least one processor to perform operations comprising:

(a) receiving sequence data comprising sequence reads of a plurality of polynucleotide fragments from a DNA-containing sample from the patient, wherein said sequence reads span at least 2, 3, 4, 5, 6, 7, 8, 9, 10, 50, 100, 500, 1000, 2500 or 5000 mutation-containing loci;

(b) optionally, performing sequencing noise reduction, e.g. performing reads collapsing to group the sequence reads into read families;

(c) calculating the mutant allele fraction across some or all of said at least 2, 3, 4, 5, 6, 7, 8, 9, 10, 50, 100, 500, 1000, 2500 or 5000 patient-specific loci, optionally wherein the mutant allele fraction is calculated by aggregating mutant reads and total reads according to the formula:

$$\frac{\sum_{loci} (\text{mutant reads})_{patient\text{-}specific}}{\sum_{loci} (\text{total reads})_{patient\text{-}specific}};$$

(d) classifying the sample as containing or not containing the target cfDNA based on the calculated mutant allele fraction.

In some embodiments the system is for use in a method of the present invention.

In a seventh aspect, the present invention provides a non-transitory computer readable medium for detecting target cell-free DNA (cfDNA) in a DNA-containing sample obtained from a patient, comprising instructions that, when executed by at least one processor, cause the at least one processor to perform operations comprising:

(a) receiving sequence data comprising sequence reads of a plurality of polynucleotide fragments from a DNA-containing sample from the patient, wherein said sequence reads span said at least 2, 3, 4, 5, 6, 7, 8, 9, 10, 50, 100, 500, 1000, 2500 or 5000 mutation-containing loci;

(b) optionally performing sequencing noise reductions, e.g. performing reads collapsing to group the sequence reads into read families;

(c) calculating the mutant allele fraction across some or all of said at least 2, 3, 4, 5, 6, 7, 8, 9, 10, 50, 100, 500, 1000, 2500 or 5000 patient-specific loci, optionally wherein the mutant allele fraction is calculated by aggregating mutant reads and total reads according to the formula:

$$\frac{\sum_{loci} (\text{mutant reads})_{patient\text{-}specific}}{\sum_{loci} (\text{total reads})_{patient\text{-}specific}};$$

(d) classifying the sample as containing or not containing the target cfDNA based on the calculated mutant allele fraction.

In some embodiments the medium is for use in a method of the present invention.

Embodiments of the present invention will now be described by way of examples and not limited thereby, with reference to the accompanying figures. However, various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

Mutant reads from test samples are shown in blue, and controls are shown in red. The absolute number of mutant reads for tests and controls were downsampled to be equal for this plot. The dashed lines represent the lines y=x and y=2x for reference.

Figure 20:
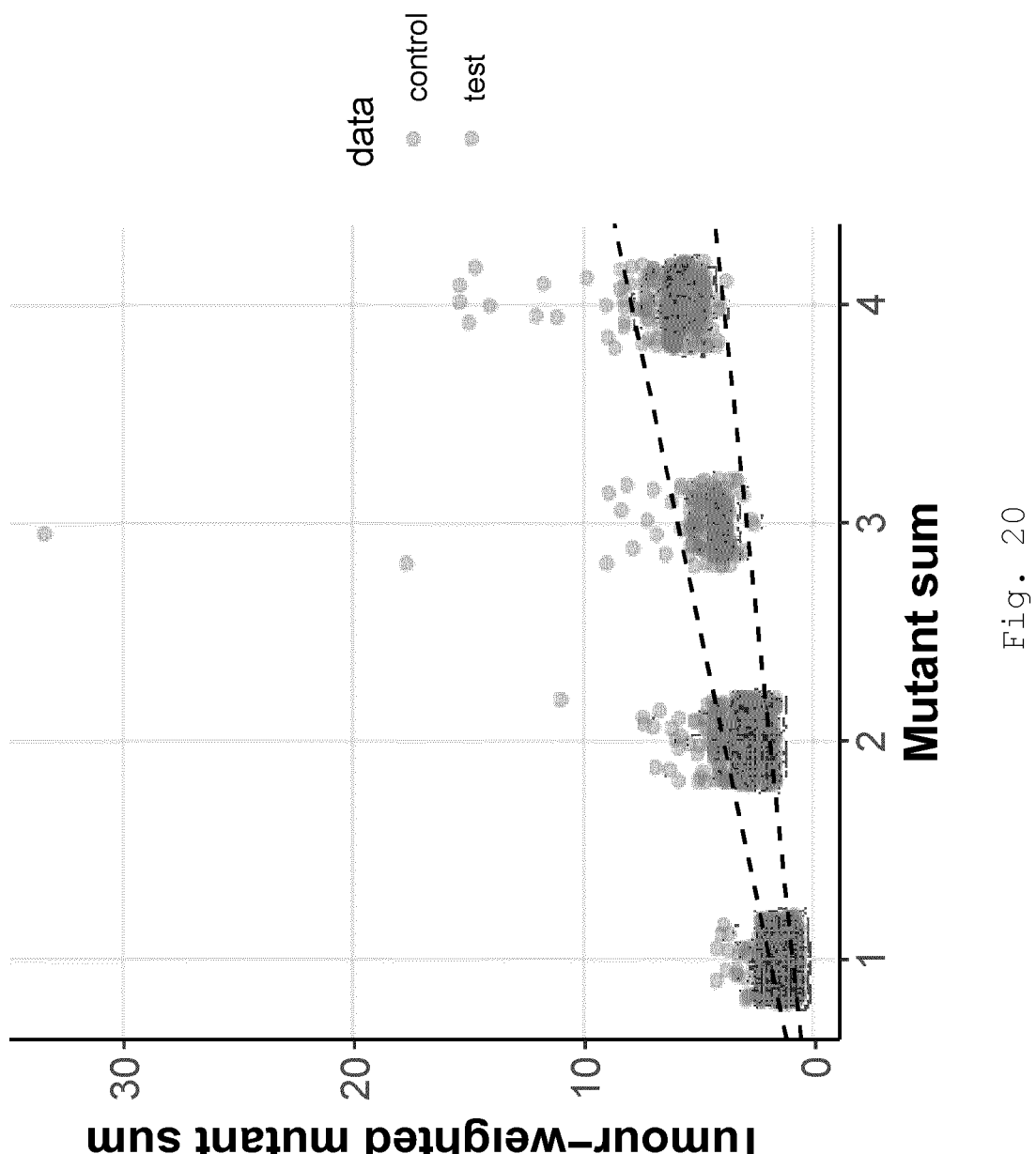

FIG. 20 shows mutant sum before and after tumour AF weighting for test and control samples using exome sequencing. Only loci with a mutant sum <=4 are shown. Mutant reads from test samples are shown in blue, and controls are shown in red. No downsampling of read families was performed. The dashed lines represent the lines y=x and y=2x for reference.

Figure 21:
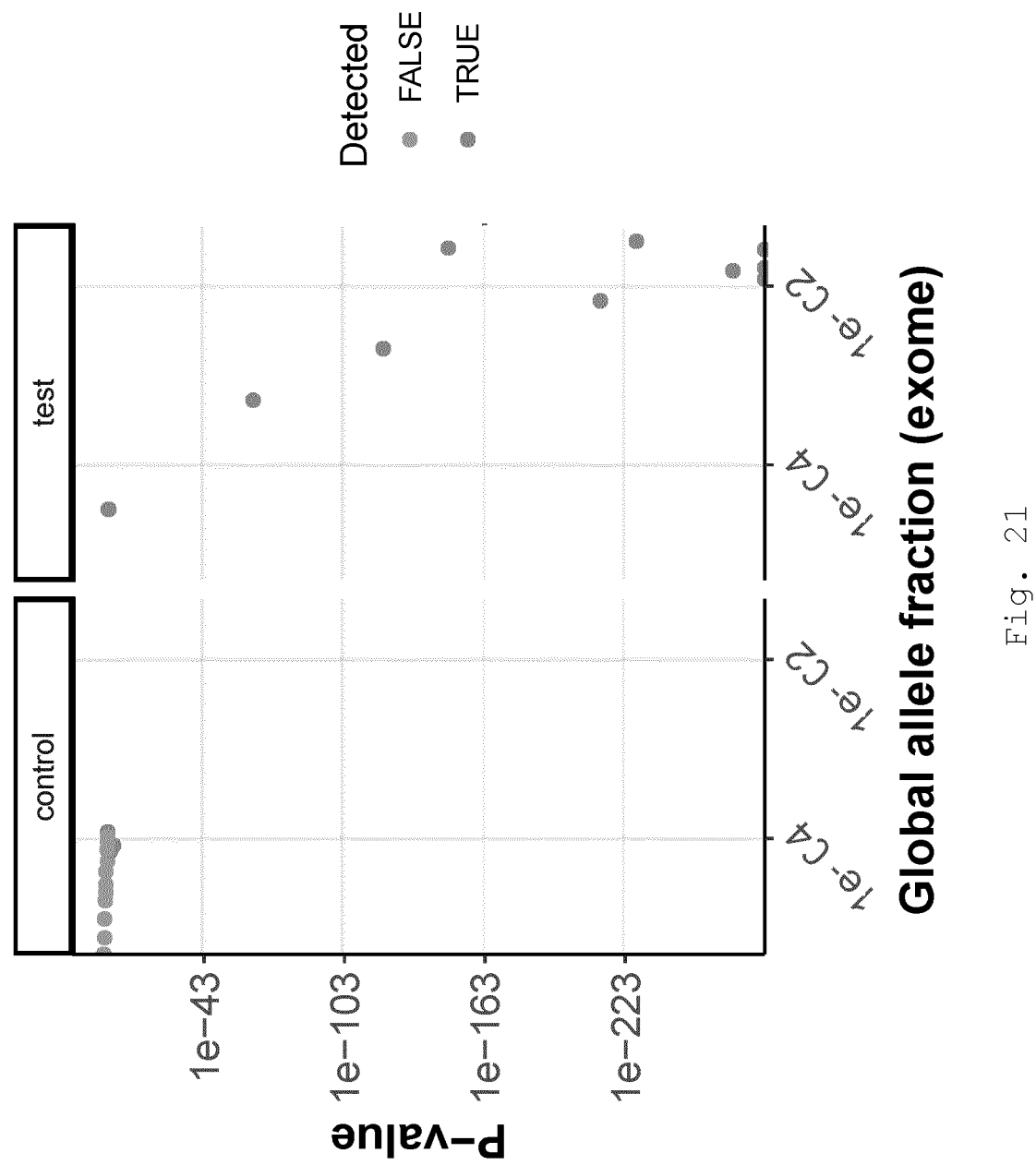

FIG. 21 shows detection of $5 \times 10^{-5}$ mutant allele fraction using plasma exome sequencing without molecular barcodes. The P-values for test and control samples are shown, and are plotted against their global allele fractions from INVAR. Each point represents one sample. Detected samples are shown in blue, and non-detected in red. The P-value threshold was set empirically using control samples with a specificity of 97.5%.

Figure 22:
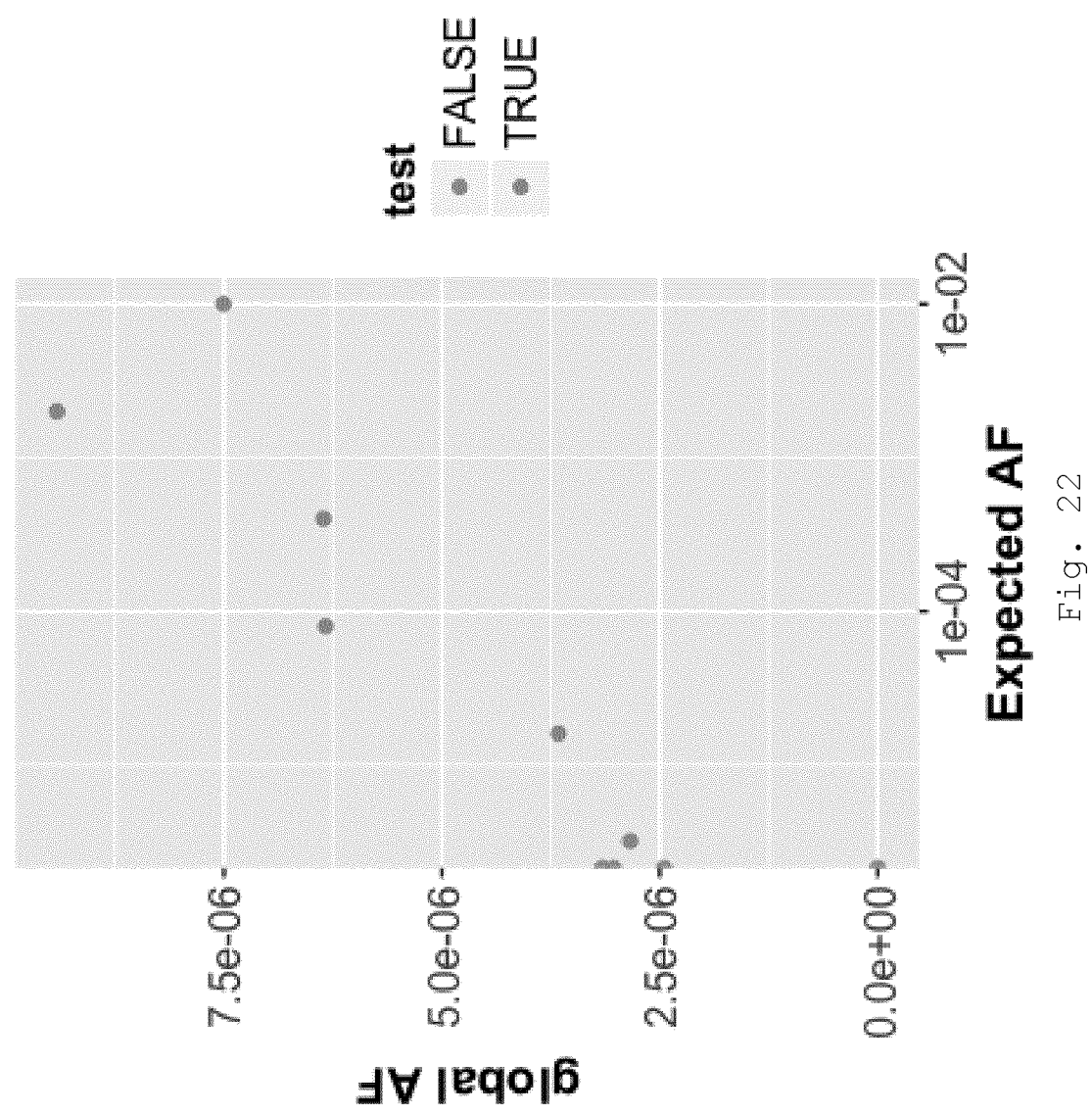

FIG. 22 shows application of untargeted INVAR on TAPAS data. The expected allele fraction (AF) of this spike-in dilution experiment is plotted against the global allele fraction (AF) as determined by INVAR. Test samples are shown in blue, and controls in red.

Figure 23:
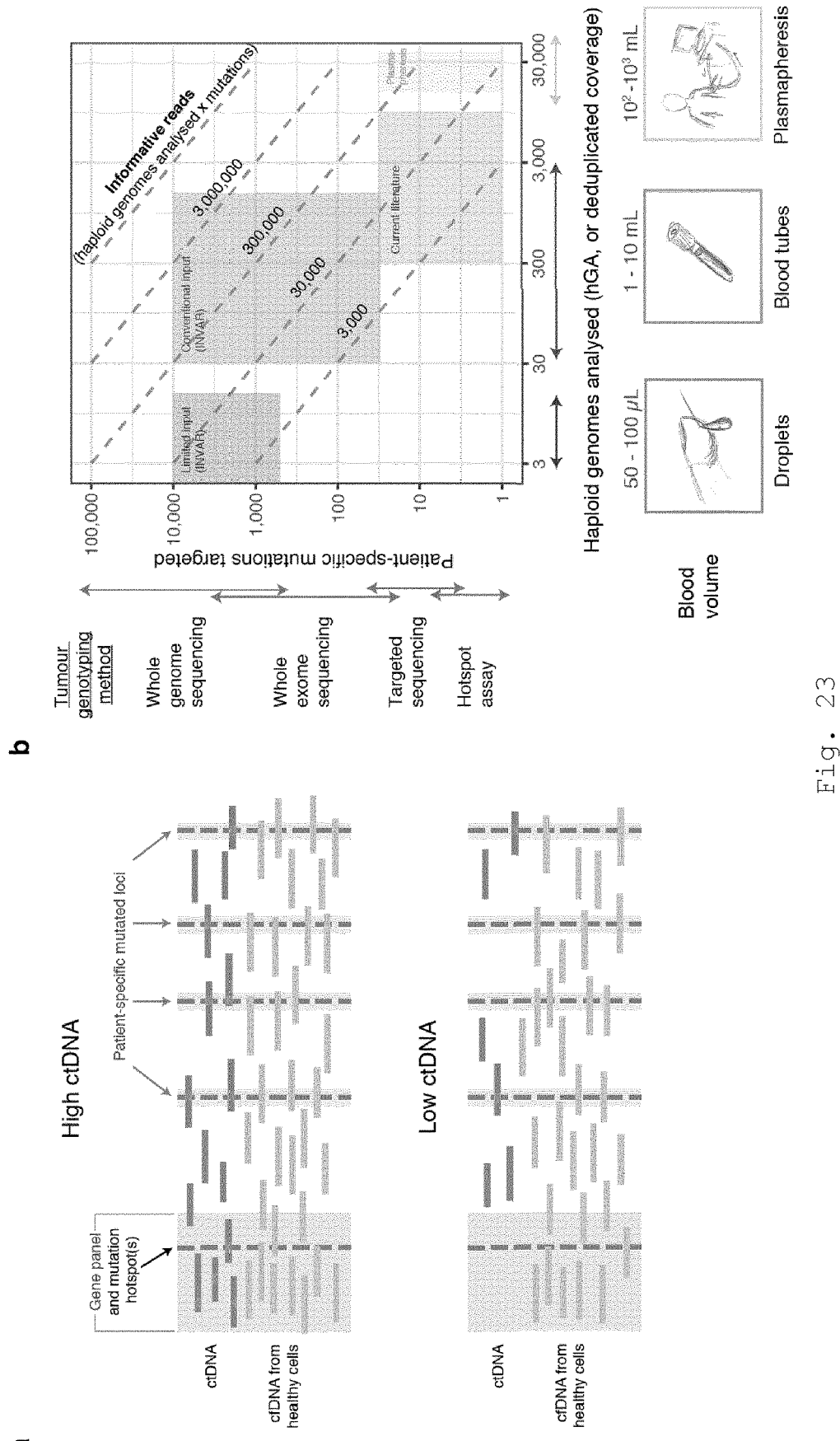
Figure 23:
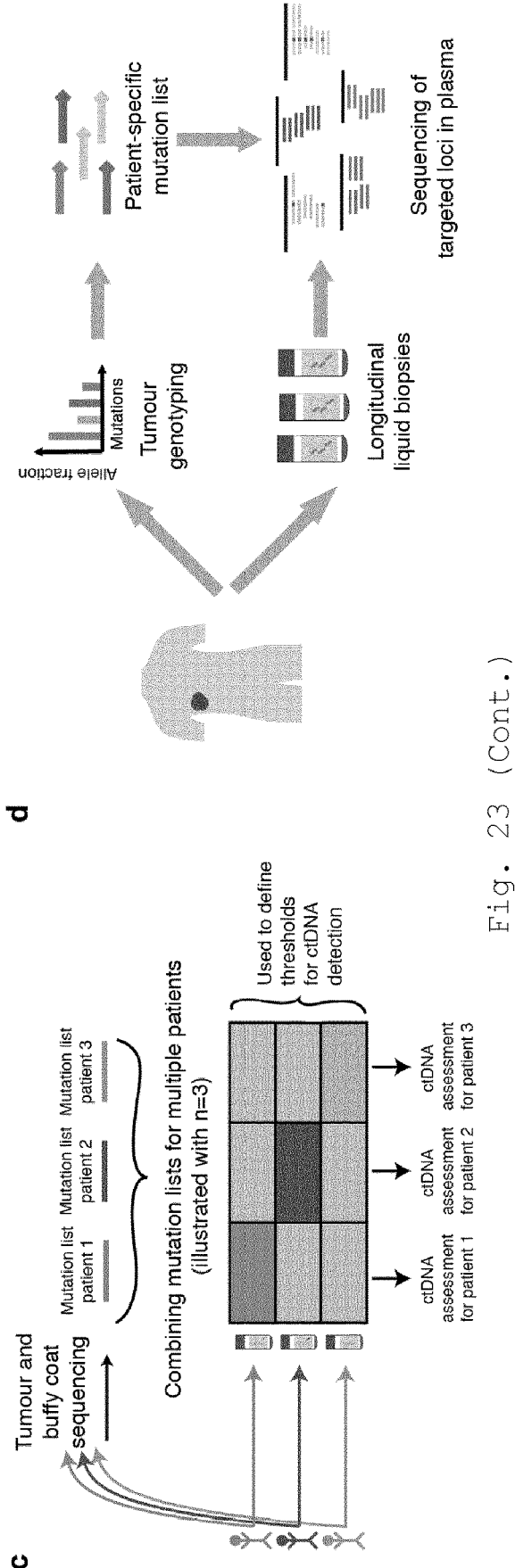
Figure 25:
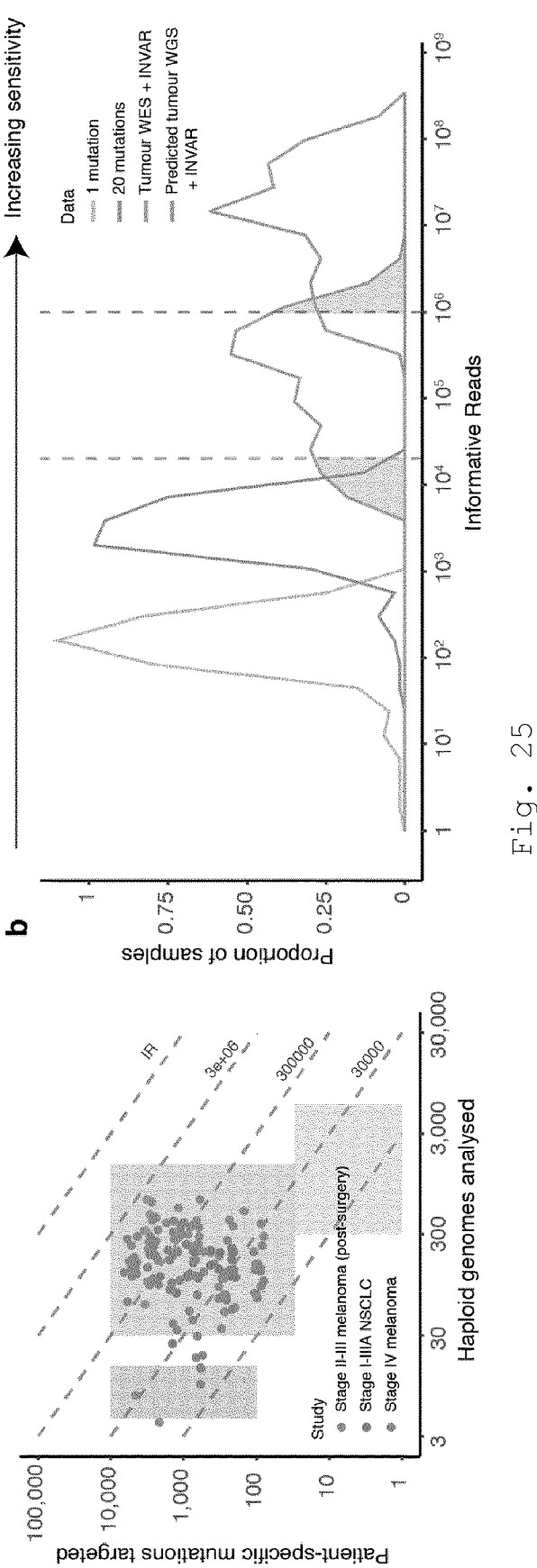
Figure 25:
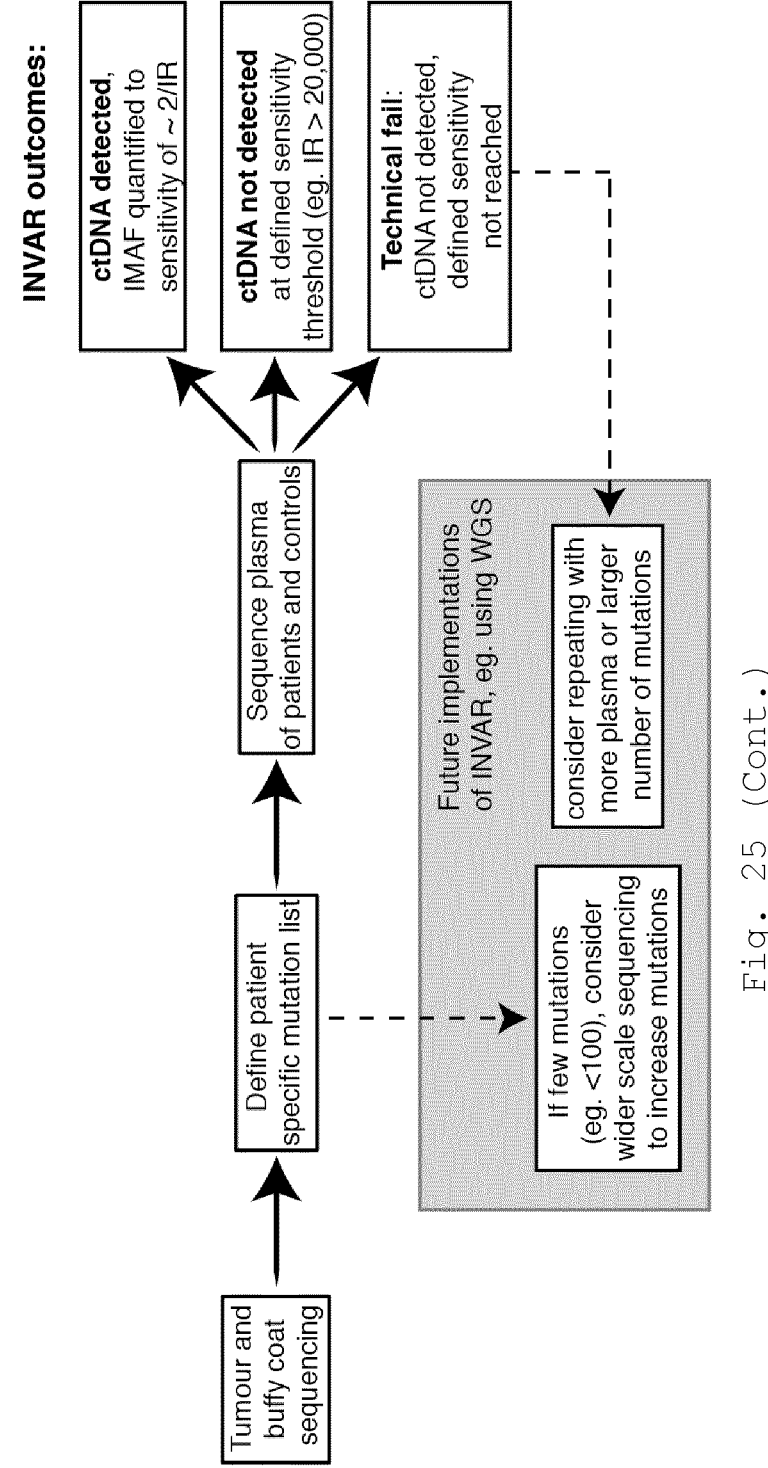
Figure 25:
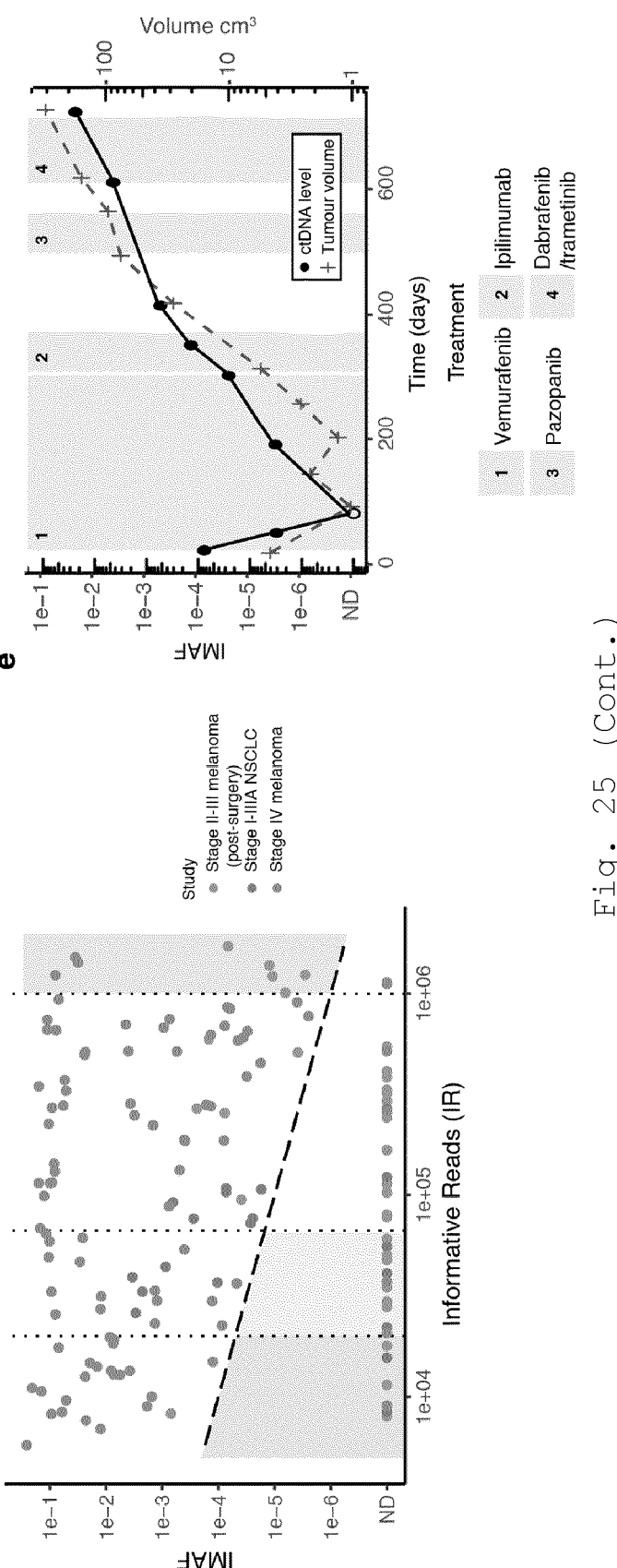
Figure 26:
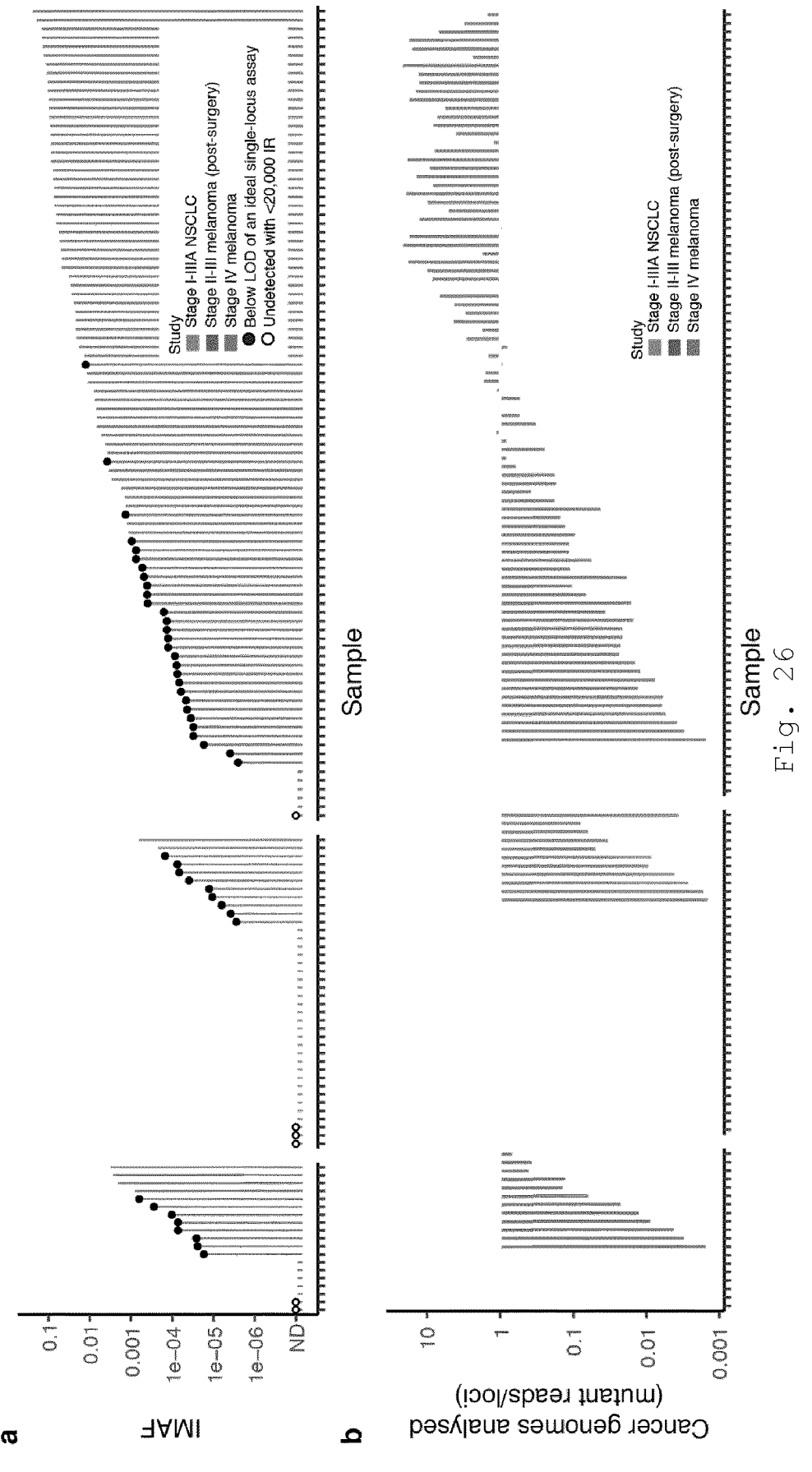
Figure 26:
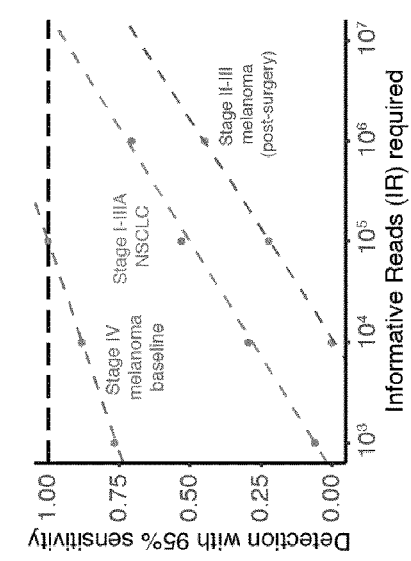
Figure 26:
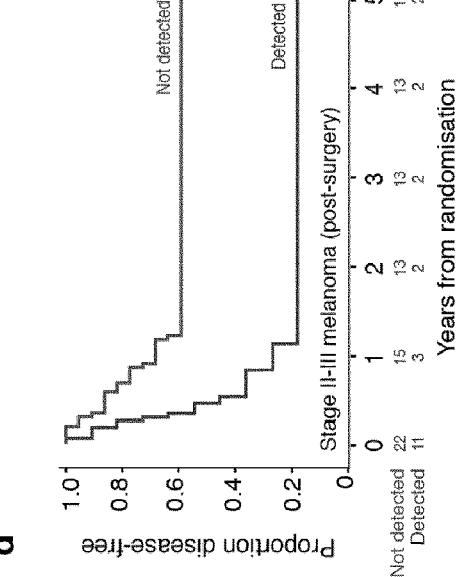
Figure 26:
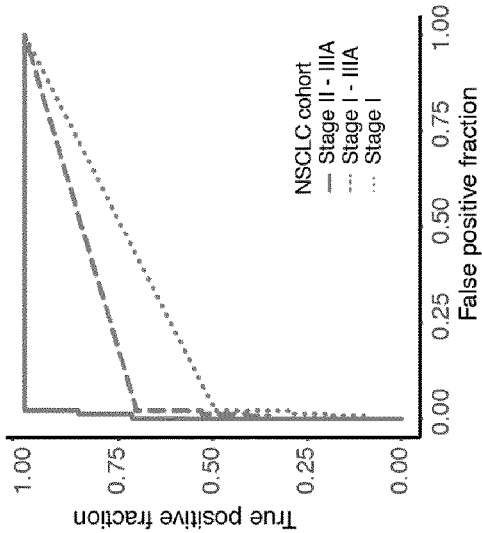

FIG. 23—Study outline and rationale for integration of variant reads. (a) In samples with high levels of ctDNA (shown in blue, top panel), multiple DNA fragments carrying mutations (in orange) may be found in plasma across loci covered by hot-spot assays or limited gene panels (shaded pink). These can be discriminated from the background non-mutant reads from healthy cells (grey) using a variety of assays. In samples with very low abundance of ctDNA (bottom panel), assays with limited breadth of coverage may not detect any mutant fragments, while these are more likely to be detected by spanning a large number of loci that are mutated in the tumour (green vertical dotted lines). Sporadic mutations may also occur at low proportions, but were not represented in this diagram. (b) Illustration of the range of possible working points for ctDNA analysis using INVAR, plotting the haploid genomes analysed vs. the number of mutations. Diagonal lines indicate multiple ways to generate the same number of informative reads (IR, equivalent to hGA×targeted loci). Current methods often focus on analysis of ~10 ng of DNA (300-10,000 haploid copies of the genome) across 1 to 30 mutations per patient. This typically results in ~10,000 IR, leading to frequently encountered detection limits of 0.01%-0.1%[6,10]. In this study we developed an analytical framework, INVAR (FIG. 24), that utilises information from larger numbers of targeted mutations. Using patient-specific hybrid-capture panels we obtained $10^4$-$10^6$ IR for most samples (see FIG. 25 and FIG. 26). We used WES and WGS of cfDNA to together INVAR to detect ctDNA from limited input (FIG. 27 and FIG. 28). ng, nanogram; mL, millilitre. (c) Overview of the usage of sequencing data by the INVAR method. Individual mutation lists are generated for each patient by analysis of their tumour samples and non-cancerous material. In this study, WES was used to analyse tumour and buffy coat DNA. Data is collected for each locus of interest in the matched patient (shown in coloured boxes), and in additional patients from the same cohort for whom this locus was not found to be mutated in the tumour or buffy coat analysis (shown by grey boxes). Such data can be generated by applying a standardised sequencing panel (such as WES/WGS) to all samples (FIG. 27 and FIG. 28) or by combining multiple patient-specific mutation lists into a custom panel that is sequenced across multiple patients (FIG. 25 and FIG. 26). For each patient, INVAR aggregates the sequencing information across the loci of the patient-specific mutation list. Data from other patients in those loci ('non-matched mutations') are used to determine background mutation rates and a ctDNA detection cut-off. (d) To generate sequencing data across large patient-specific mutations lists at high depth, patient-specific mutation lists generated by tumour genotyping were used to define hybrid-capture panels that were applied to DNA extracted from plasma samples.

Figure 24:
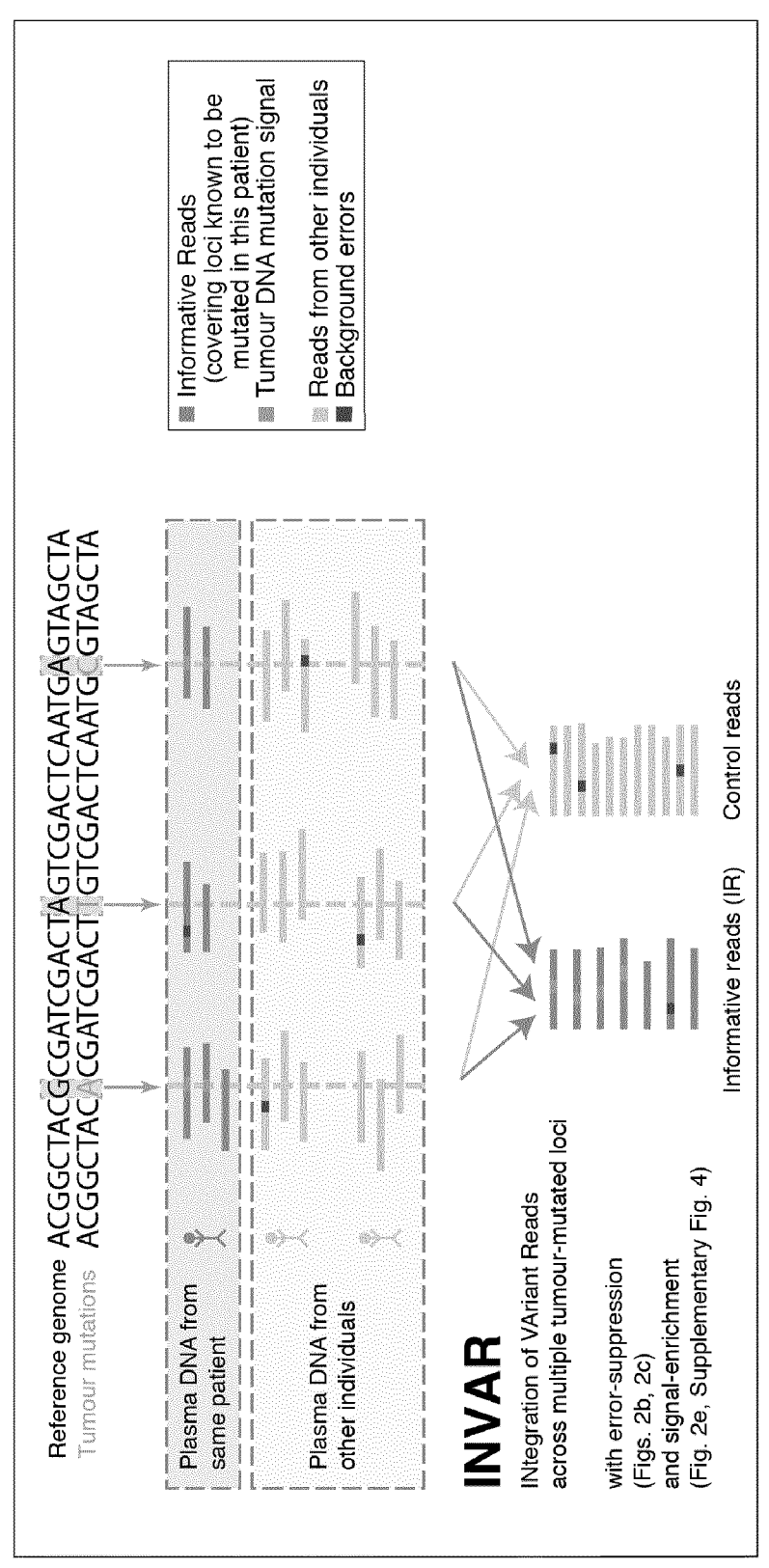
Figure 24:
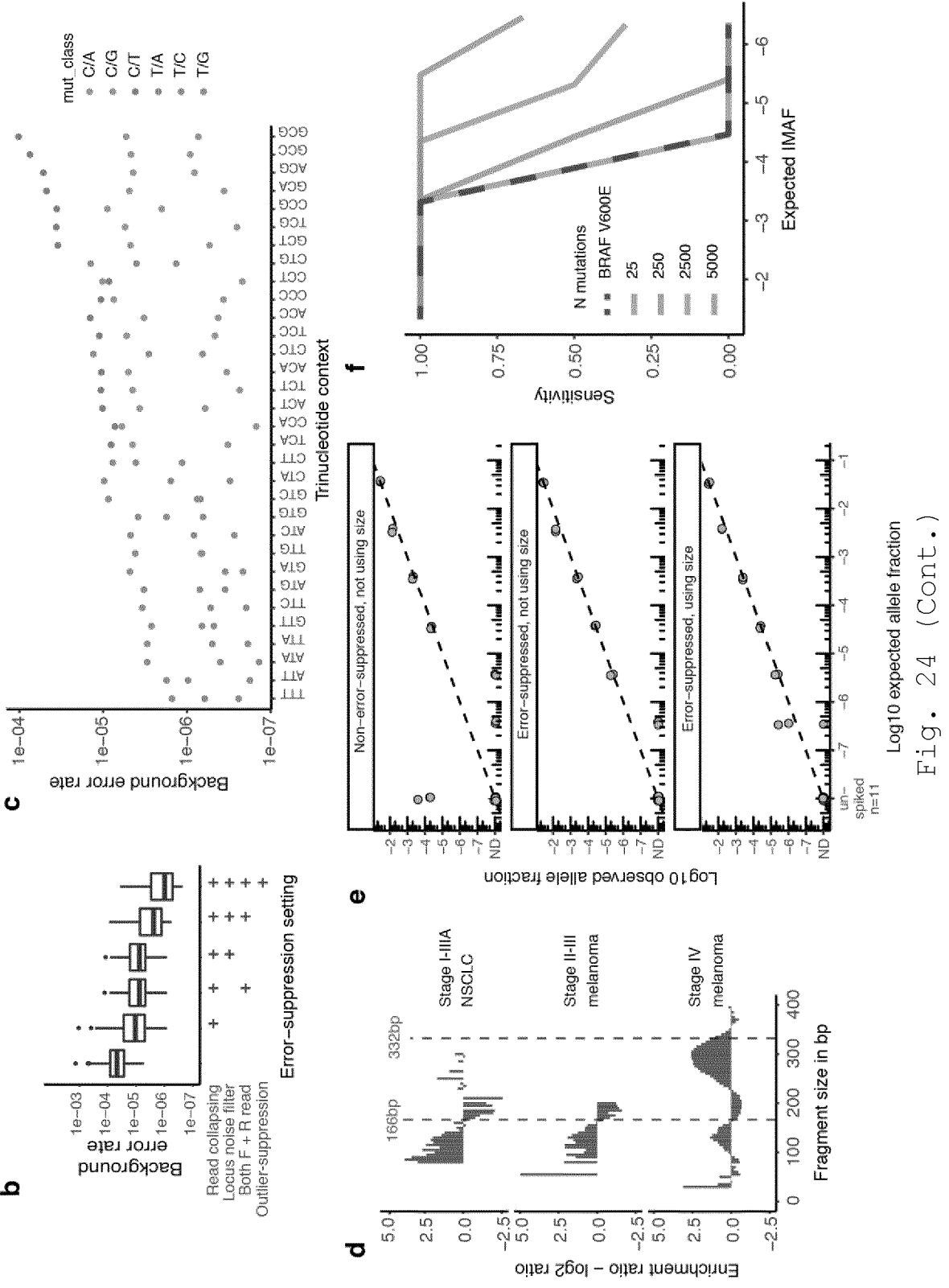

FIG. 24—Development and analytical performance of the INVAR method. (a) Integration of variant reads. To overcome sampling error, signal was aggregated across hundreds to thousands of mutations. Here we classify samples (rather than individual mutations) as significantly containing ctDNA, or not detected. 'Informative Reads' (IR, shown in blue) are reads generated from a patient's sample that overlap loci in the same patient's mutation list. Some of these may carry mutations in the loci of interest (shown in orange). Reads from plasma samples of other patients at the same loci ('non-patient-specific') are used as control data to calculate the rates of background error rates (shown in purple) that can occur due to sequencing errors, PCR artifacts, or biological background signal. INVAR incorporates additional sequencing information on fragment length and tumour allelic fraction to enhance detection. (b) Reduction of error rates following different error-suppression settings (Supplementary Methods). (c) Error rates by trinucleotide context and mutation class following data filtering. Error rates can vary by more than an order of magnitude within the same mutation class, highlighting the need to assess loci with respect to their trinucleotide context. (d) $\text{Log}_2$ enrichment ratios for mutant fragments from three different cohorts of patients. Size ranges enriched for ctDNA are assigned more weight by the INVAR algorithm. (e) Spike-in dilution experiment to assess the sensitivity of INVAR. Using error-suppressed data with INVAR, ctDNA was detected in replicates for all dilutions to 3.6 ppm, and in 2 of 3 replicates at an expected ctDNA allele fraction of $3.6\times10^{-7}$ (Supplementary Methods). Using error-suppressed data of 11 replicates from the same healthy individuals without spiked-in DNA from the cancer patient, no mutant reads were observed in an aggregated $6.3\times10^6$ informative reads across the patient-specific mutation list. (f) The sensitivity in the spike-in dilution series was assessed after the number of loci analysed was downsampled in silico to between 1 to 5,000 mutations (Supplementary Methods).

FIG. 25—Integration of variant reads across patient-specific capture panels. (a) Number of haploid genomes analysed (hGA; calculated as the average depth of unique reads) and the number of mutations targeted, in 144 plasma samples from 66 cancer patients across three cohorts. These were sequenced using custom hybrid-capture panels covering patient-specific mutation lists (FIG. 23d) to achieve a median unique depth after read collapsing (hGA) of 185 (Methods) across a median of 628 mutated loci. Each hybrid-capture panel combined mutation lists from multiple patients from the same cohort and was applied to plasma samples from multiple patients to generate both patient-matched reads and control data (FIG. 23c). Dashed diagonal lines indicate the number of targeted loci hGA that yield the indicated IR. (b) The number of informative reads that would be obtainable with different numbers of mutations analysed, across the cases in these three cohorts. Increasing sensitivity is directly correlated to IR, with the minimal detected ctDNA fraction being 2/IR in the current implementation of INVAR (Methods). The red line shows the distribution of IR obtained with the custom panels covering all mutations identified by tumour WES. Light/dark green lines show the IR generated if 1 or 20 mutations were analysed for each sample (calculated based on the mean IR per locus). IR could be increased further by using whole genome sequencing (WGS) to guide the design of custom panels (orange curve, extrapolated based on our observed mutation rates in WES). Using mutation lists from WES, samples exceeding $10^6$ IR are shaded in orange, and samples with fewer than $2\times10^4$ IR are shaded in blue. (c) Schematic showing the design process, analysis, and possible outcomes: ctDNA may be detected, undetected despite high IR, or in some cases low IR is obtained due to few mutations or low unique depth of sequencing. This latter case should be defined as a technical fail, since analysis sensitivity is limited. In routine implementation, such cases can be re-analysed with additional sequencing to increase depth, analysis of additional material, or by generating an expanded mutation list using broader sequencing of the tumour (e.g. by WGS) that can be used to design a revised capture panel. (d) Two-dimensional representation of ctDNA fractions detected plotted against the IR for each sample. ctDNA could be detected if its fractional concentration (IMAF) was higher than 2/IR (falling above the dashed line, which is plotted at 1/IR). In some samples, >$10^6$ IR were obtained, and ctDNA was detected down to fractions of few ppm (orange shaded region). In some samples, few IR were obtained resulting in limited sensitivity. In our study we used a threshold of 20,000 IR (left-most dotted line), such that samples with undetected ctDNA with fewer than 20,000 IR were excluded as technical failures (total of 6 of 144 samples; dark blue shaded region). Samples outside this region had detected ctDNA, or had estimated ctDNA levels below 0.01% (undetected with >20,000 IR; confidence ranges for this value vary for each sample depending on IR). Excluding those samples as technical fails, the overall detection rate of ctDNA across increased from 73.6% to 76.2% for the combined 3 cohorts. An alternative threshold could be used, for example 66, 666 IR, resulting in detection level of 0.003% or 30 ppm (indicated by the second dotted line and the light blue shaded region). Excluding the samples where detection sensitivity of 0.003% was not reached (11 samples), the ctDNA detection rate across the cohorts increased to 82.6%. (e) ctDNA IMAF and tumour volume are plotted over time for one patient with metastatic melanoma over the course of several treatment lines (indicated by shaded boxes). ctDNA was detected to 2.5 ppm during treatment with anti-BRAF targeted therapy, when disease volume was approximately 1.3 cm$^3$.

FIG. 26—ctDNA detection by INVAR in early and advanced disease. (a) ctDNA fractional levels (IMAF) detected in the samples in this study, shown in ascending order for each of the three cohorts. Filled circles indicate samples where the number of haploid genomes analysed would fall below the 95% limit of detection for a perfect single-locus assay given the measured IMAF (Supplementary Methods). Empty circles indicate technical fails, i.e. samples for whom ctDNA was not detected (ND) with IR<20,000. (b) The number of copies of the cancer genome detected for each of the samples in the same order as above in part (a), calculated as the number of mutant fragments divided by the number of loci queried. (c) ROC analysis for detection of ctDNA in plasma of stage I-IIIA NSCLC patients at diagnosis, compared to samples from healthy volunteers. At a specificity of 97.4%, ctDNA was detected in 50% of stage I patients (20% of 5 with stage IA and 80% of 5 with stage IB; 9 of the 10 cases were adenocarcinomas). (d) The proportion of disease-free individuals after surgical resection in patients with stage II-III melanoma, for samples where ctDNA was detected in the first 6 months after surgery (blue line) or not detected (red line). Disease-free interval was significantly poorer in patients with ctDNA detected within 6 months following surgery (P=0.007), which included half of the patients who recurred within the 5-year period. (e) Detection rates of ctDNA for different numbers of IR sequenced were estimated. There was a linear relationship between IR and detection (R$^2$=0.95) in the baseline samples of the stage IV melanoma cohort (blue). In stage I-IIIA NSCLC at diagnosis (green) and stage II-III melanoma post-surgery (red), linear relationships were observed between IR and detection rates, and the predicted rates of detection of ctDNA were extrapolated. ND, not detected.

Figure 27:
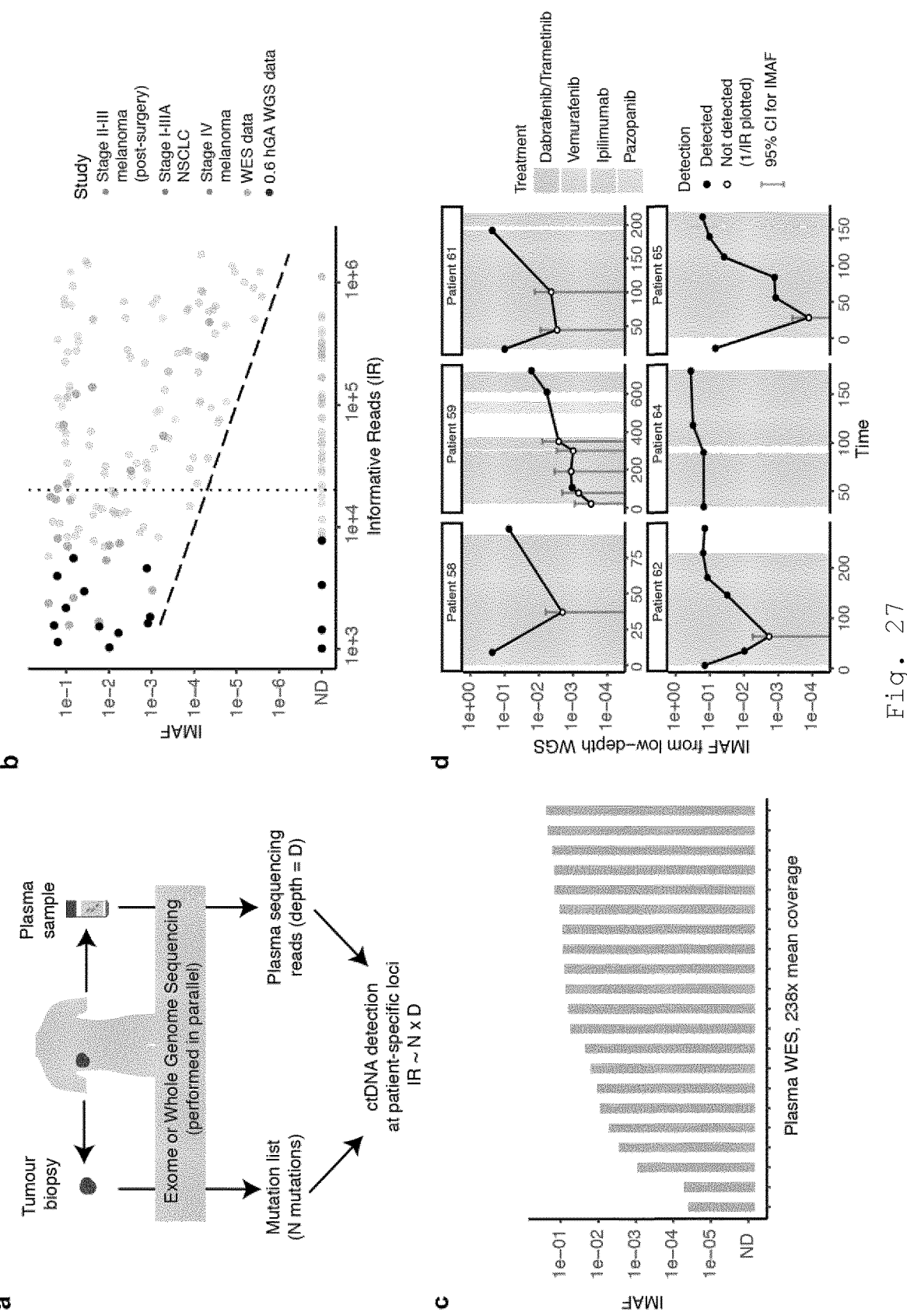

FIG. 27—Sensitive detection of ctDNA from WES/WGS data using INVAR. (a) schematic overview of a generalised INVAR approach. Tumour (and buffy coat), and plasma samples are sequenced in parallel using whole exome or genome sequencing, and INVAR can be applied to the plasma WES/WGS data using mutation lists inferred from the tumour (and buffy coat) sequencing. (b) INVAR was applied to WES data from 21 plasma samples with an average sequencing depth of 238× (before read collapsing), and to WGS data from 33 plasma samples with an average sequencing depth of 0.6× (prior to read collapsing). IMAF values are plotted vs. the number of unique IR for every sample. WES at this depth yielded lower IR compared to the custom capture panel, yet in some cases IR exceeded 10$^5$. WGS at low depth yielded <10,000 IR, because mutation lists only spanned the exome based on the extent of tumour sequencing for these cases. The dotted vertical line indicates the 20,000 IR threshold, and the dashed diagonal line indicates 1/IR. (c) IMAF observed for the 21 samples analysed with WES ordered from low to high. ND, not detected. (d) Longitudinal monitoring of ctDNA levels in plasma of six patients with stage IV melanoma using sWGS data with an average depth of 0.6×, analysed using INVAR with patient-specific mutation lists (including >500 mutations for each patient, based on WES tumour profiling). Filled circles indicate detection at a specificity level of >0.99 by ROC analysis of the INVAR likelihood (Methods, FIG. 36). For other samples, the 95% confidence intervals of the ctDNA level are shown, based on the number of informative reads for each sample (empty circles and bars). ND, not detected.

Figure 28:
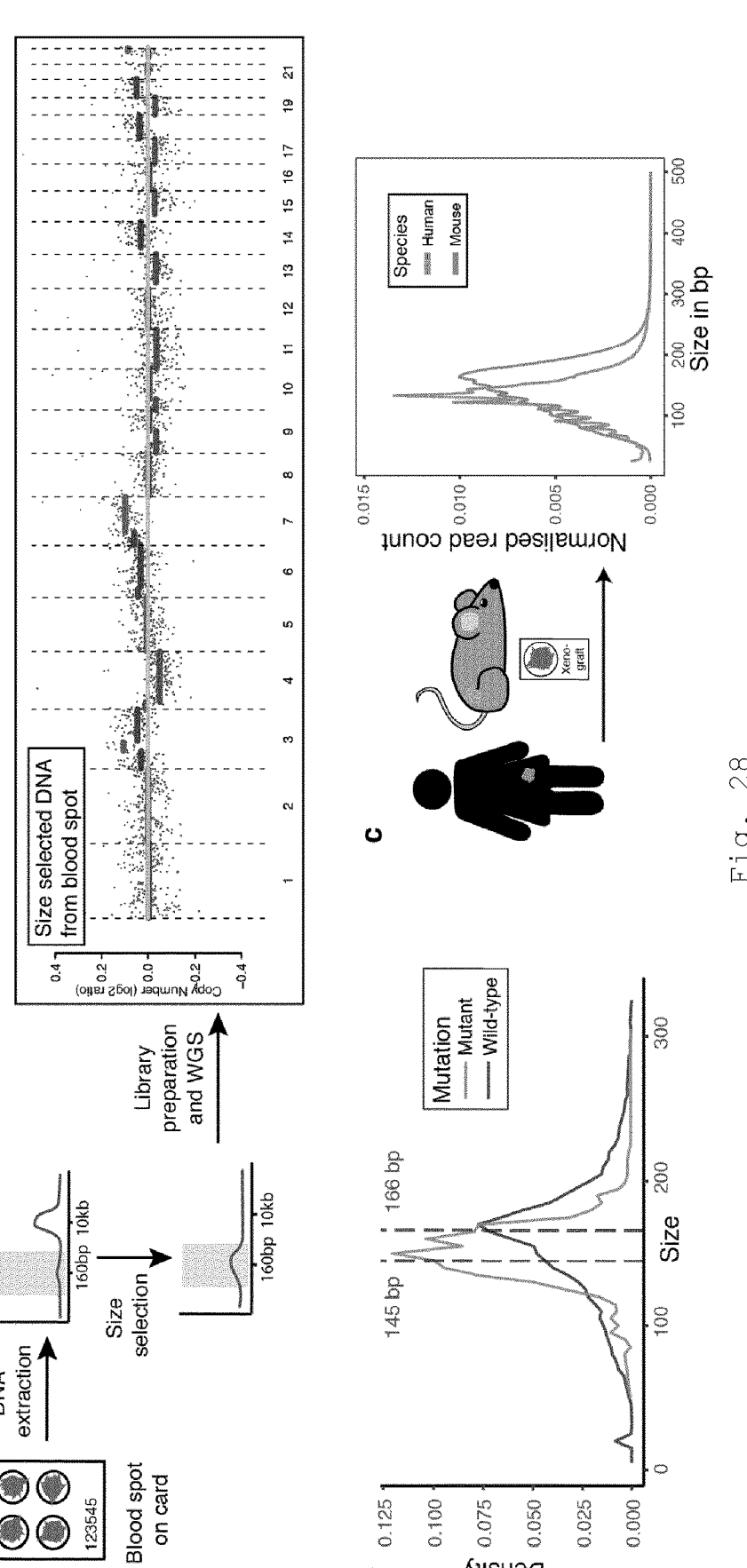
Figure 28:
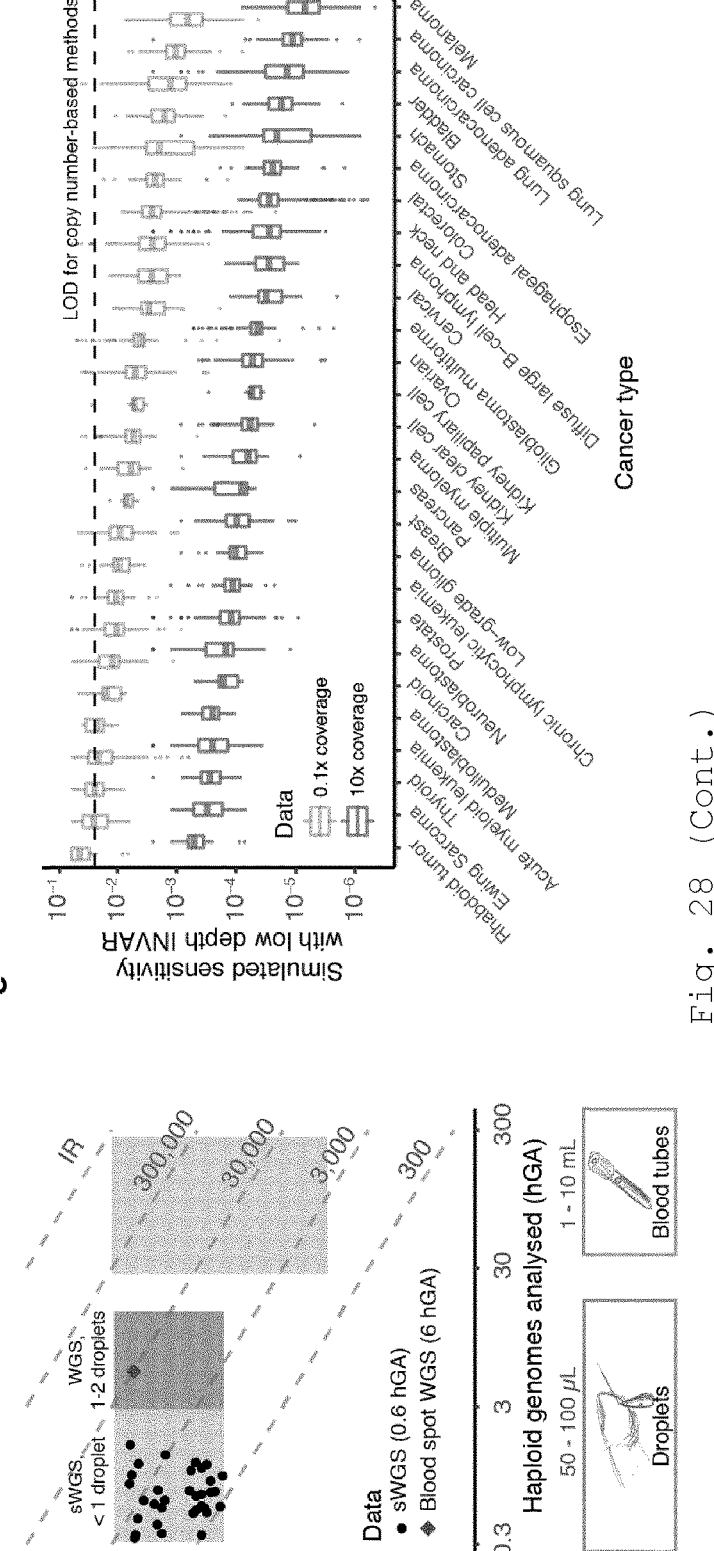

FIG. 28—Detection of ctDNA in individual blood droplets. (a) Overview for analysis of dried blood spots by DNA extraction, followed by size selection, and low-depth WGS. Reads are collapsed using unique molecular identifies (UMIs) before applying INVAR or analysis of copy number abnormalities. The plot on the right shows the read density across the genome. (b) Fragment length of reads carrying the tumour mutated alleles (light blue) and the reference alleles (dark blue) from sequencing of DNA extracted from a dried blood spot collected from a cancer patient. (c) We analysed DNA extracted from a blood spot collected from a xenograft model of ovarian cancer (illustrated in the left panel) by shallow whole genome sequencing. The fragment lengths of reads aligning to the human genome (red) were shorter than those aligning to the mouse genome (blue). (d) Number of hGA and mutations analysed for samples analysed by WGS, from a whole blood spot (red diamond) or from libraries sequenced at an average depth of 0.6× WGS, equivalent to 0.6× hGA (black circles, data shown in FIG. 27*d*). The dark blue shaded box indicates the working point achieved when using WGS data from 1-2 droplets of blood, which can reach IR of ~10$^5$ and sensitivity below 10$^{-4}$. The light blue shaded box indicates the working point when using sWGS data. (e) Predicted sensitivities for WGS analysis of a dried blood spot in patients with different cancer types, using an average of 0.1× or 10× coverage (equivalent to 0.1 and 10 hGA). Based on known mutation rates per Mbp of the genome for different cancer types[24], the number of informative reads obtainable per droplet can be estimated. The limit of detection for ctDNA based on copy number alterations is shown as a guide to the eye at 3%[28].

Figure 29:
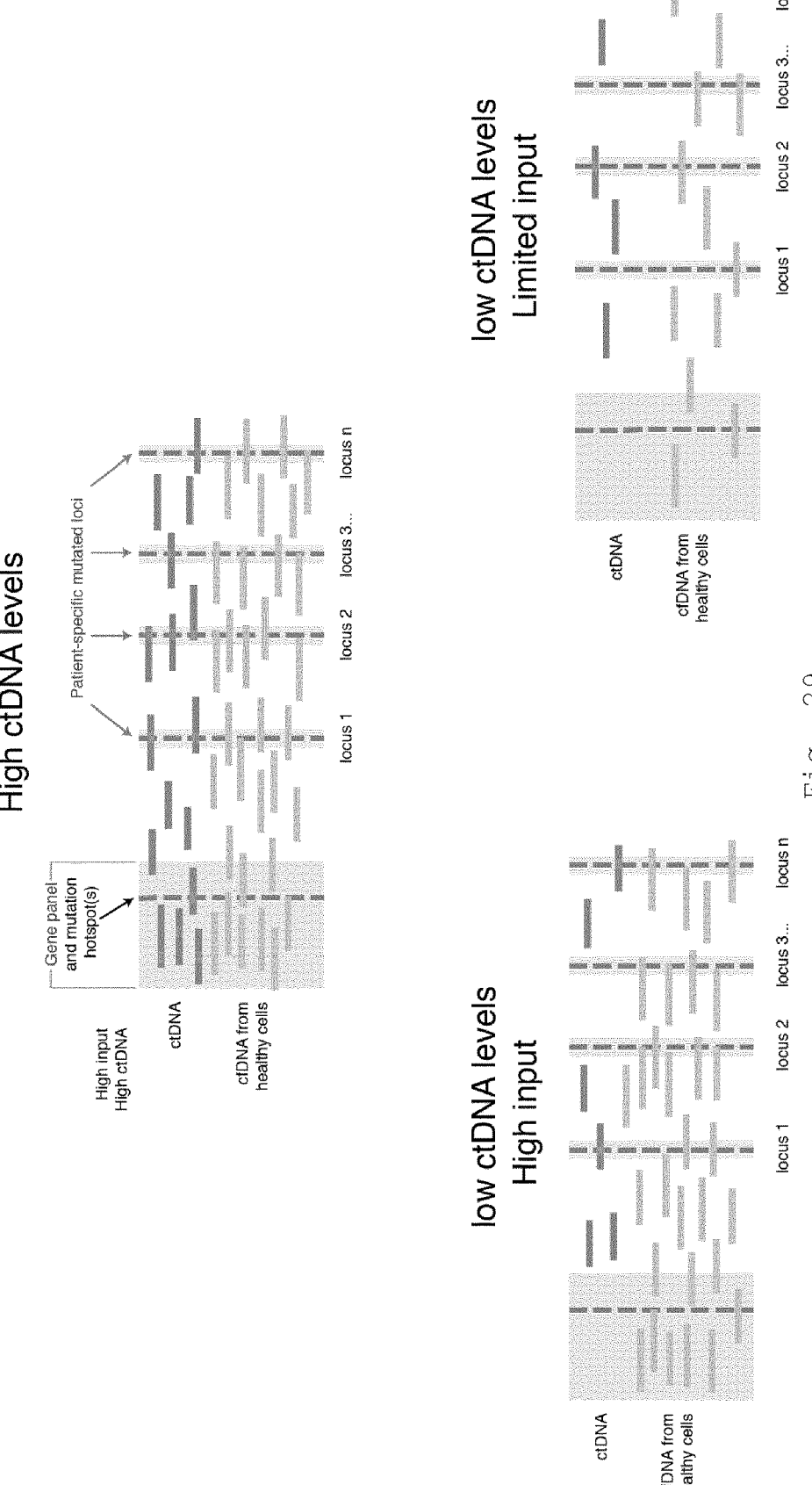

FIG. 29—Patient-specific analysis overcomes sampling error in conventional and limited input scenarios. When high levels of ctDNA are present, gene panels and hotspot analysis are sufficient to detect ctDNA. However, if ctDNA concentrations are low (due to low ctDNA concentration in the patient, or limited material availability) these generic assays are at high risk of false negative results due to sampling noise. Utilising a large list of patient specific mutations allows sampling of mutant reads at multiple loci, enabling detection of ctDNA when there are few mutant reads due to either ultra-low ctDNA levels, or limited starting material.

Figure 30:
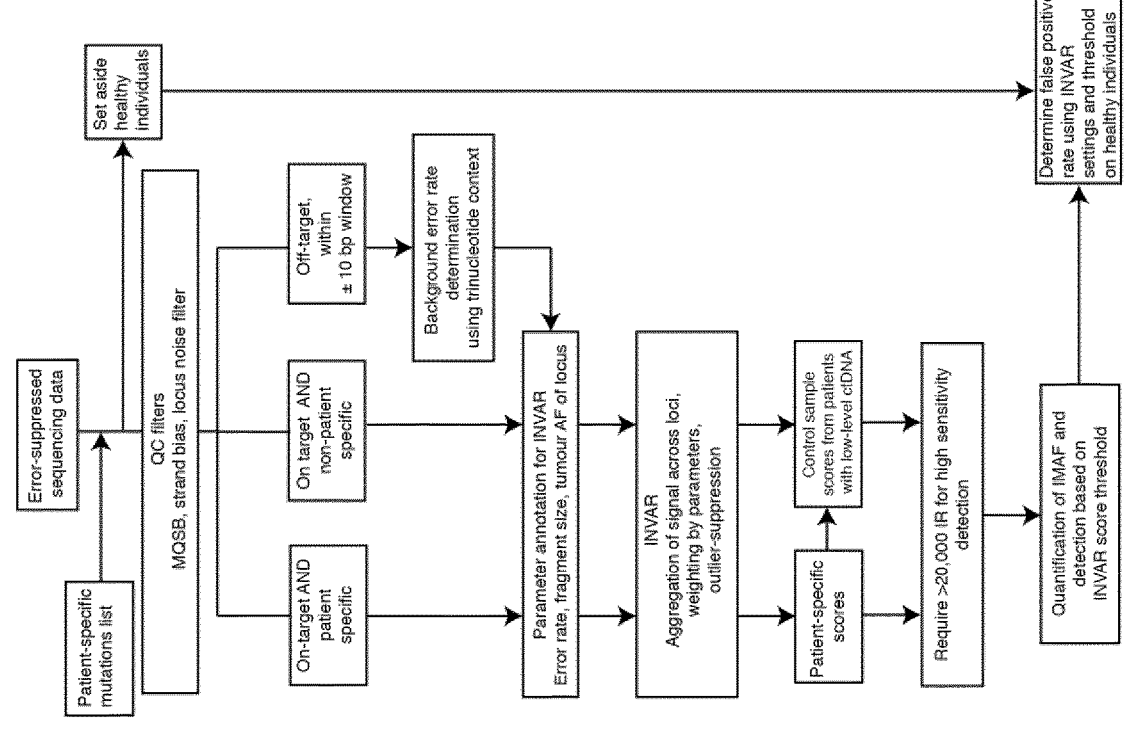
Figure 30:
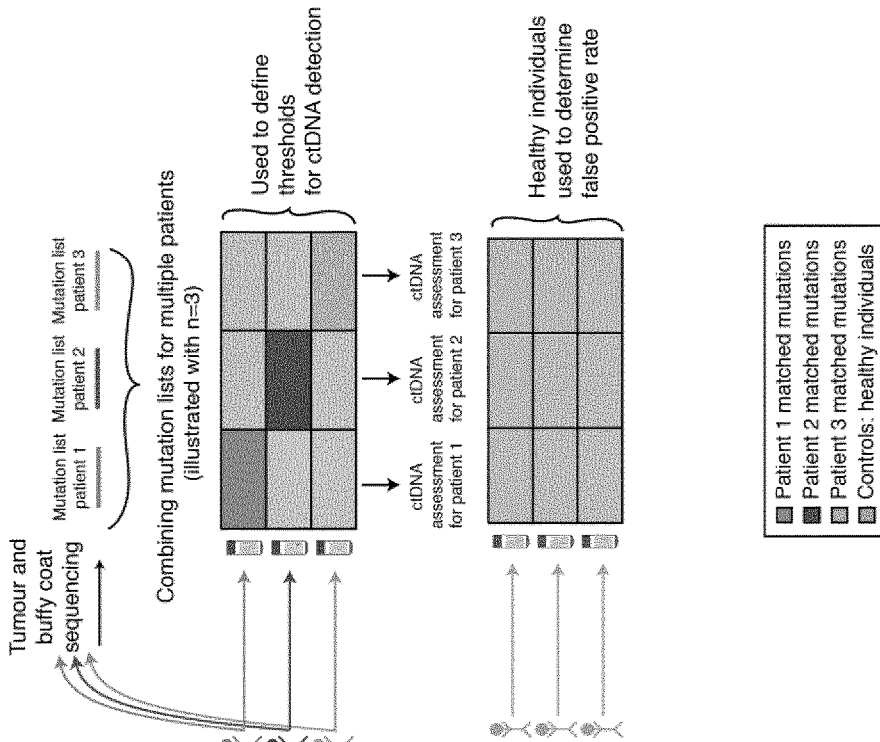

FIG. 30—Overview of the INVAR algorithm. (a) INVAR leverages patients to control for one another, and uses separate healthy controls. In this study, individual mutation lists are generated from tumour and buffy coat sequencing. Each locus of interest is sequenced in the matched patient, and in additional patients from the same cohort for whom this locus was not found to be mutated in the tumour or buffy coat analysis. This can be done by applying a generic panel to all samples (such as WES/WGS, FIG. 27), or by combining multiple patient-specific mutation lists into a combined custom panel that is sequenced across multiple patients (FIG. 25 and FIG. 26). For each patient, INVAR aggregates the sequencing information across the loci of the patient-specific mutation list.

Data from other patients in those loci ('non-matched mutations') are used to determine background mutation rates and detection cut-offs (Supplementary Methods). Additional samples from healthy individuals are analysed by the same panels, this data was not used in the INVAR algorithm to determine detection of ctDNA in patient samples, but was used to assess the false positive rates in healthy individuals. (b) Integration of variant reads workflow. INVAR utilises plasma sequencing data and requires a list of patient-specific mutations, which may be derived from tumour or plasma sequencing. Filters are applied to sequencing data, then the data is split into: patient-specific (locus belonging to that patient), non-patient-specific (locus not belonging to that patient), and near-target (bases within 10 bp of all patient-specific loci). Patient-specific and non-patient-specific data are annotated with features that influence the probability of observing a real mutation. Outlier-suppression is applied to identify mutant signal inconsistent with the overall level of patient-specific signal. Next, signal is aggregated across all loci, taking into account annotated features, to generate an INVAR score per sample. Based on non-patient-specific samples, an INVAR score threshold is determined using ROC analysis for each cohort. Healthy control samples separately undergo the same steps to establish a specificity value for each cohort.

Figure 31:
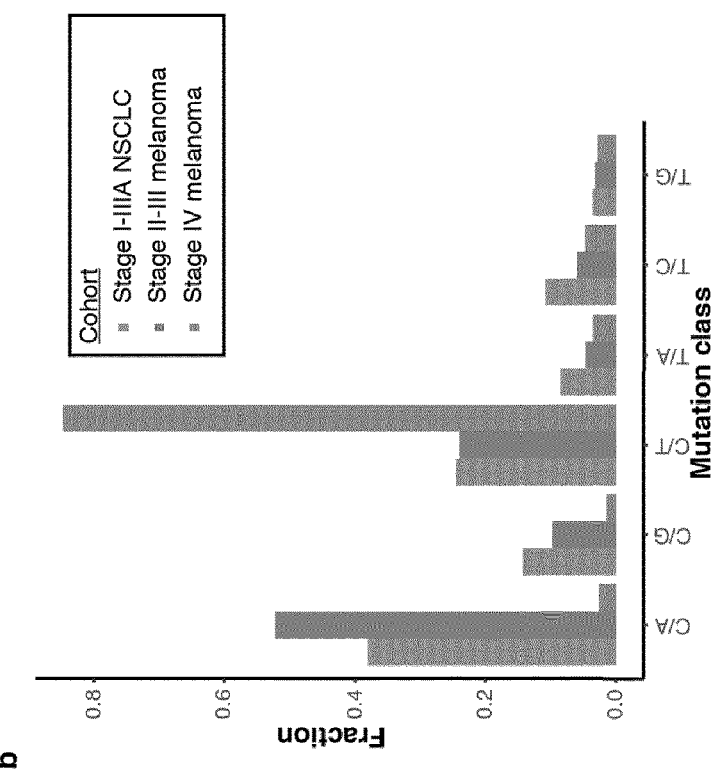
Figure 31:
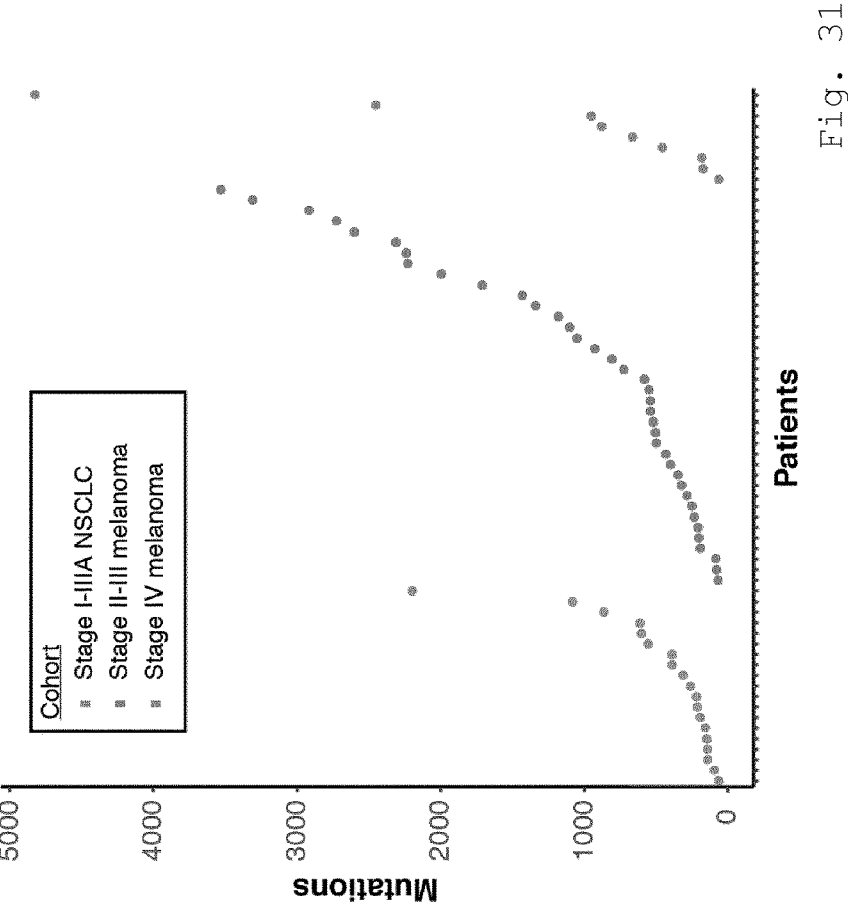
Figure 31:
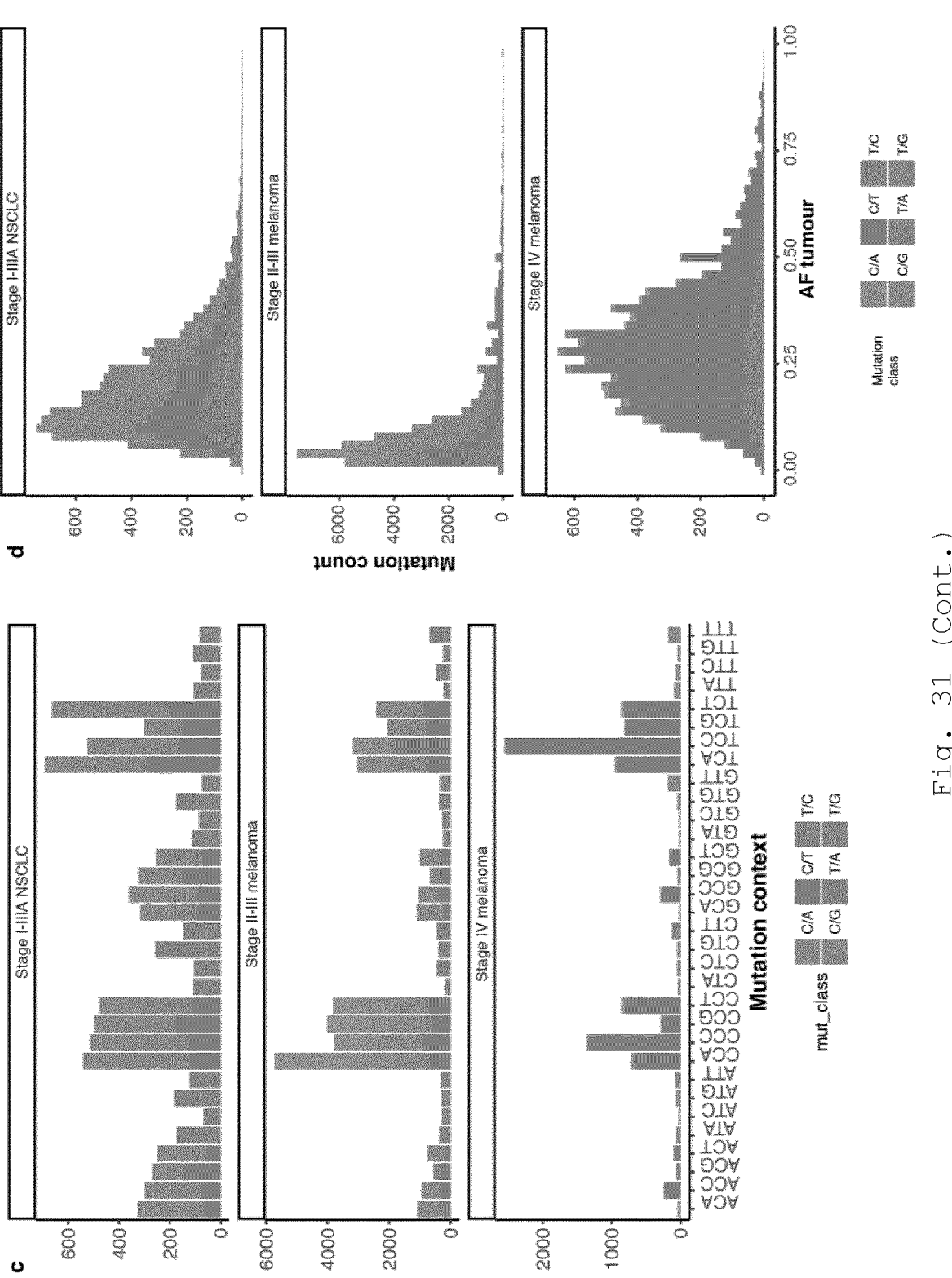

FIG. 31—Tumour mutation list characterisation for INVAR. (a) Number of somatic mutations per patient, ordered by cancer type and cohort. (b) Frequency of each mutation class included in each panel design. (c) Mutation counts by trinucleotide context, coloured by mutation class. (d) Distribution of tumour mutation allele fractions in tumour samples per cancer type coloured by mutation class.

Figure 32:
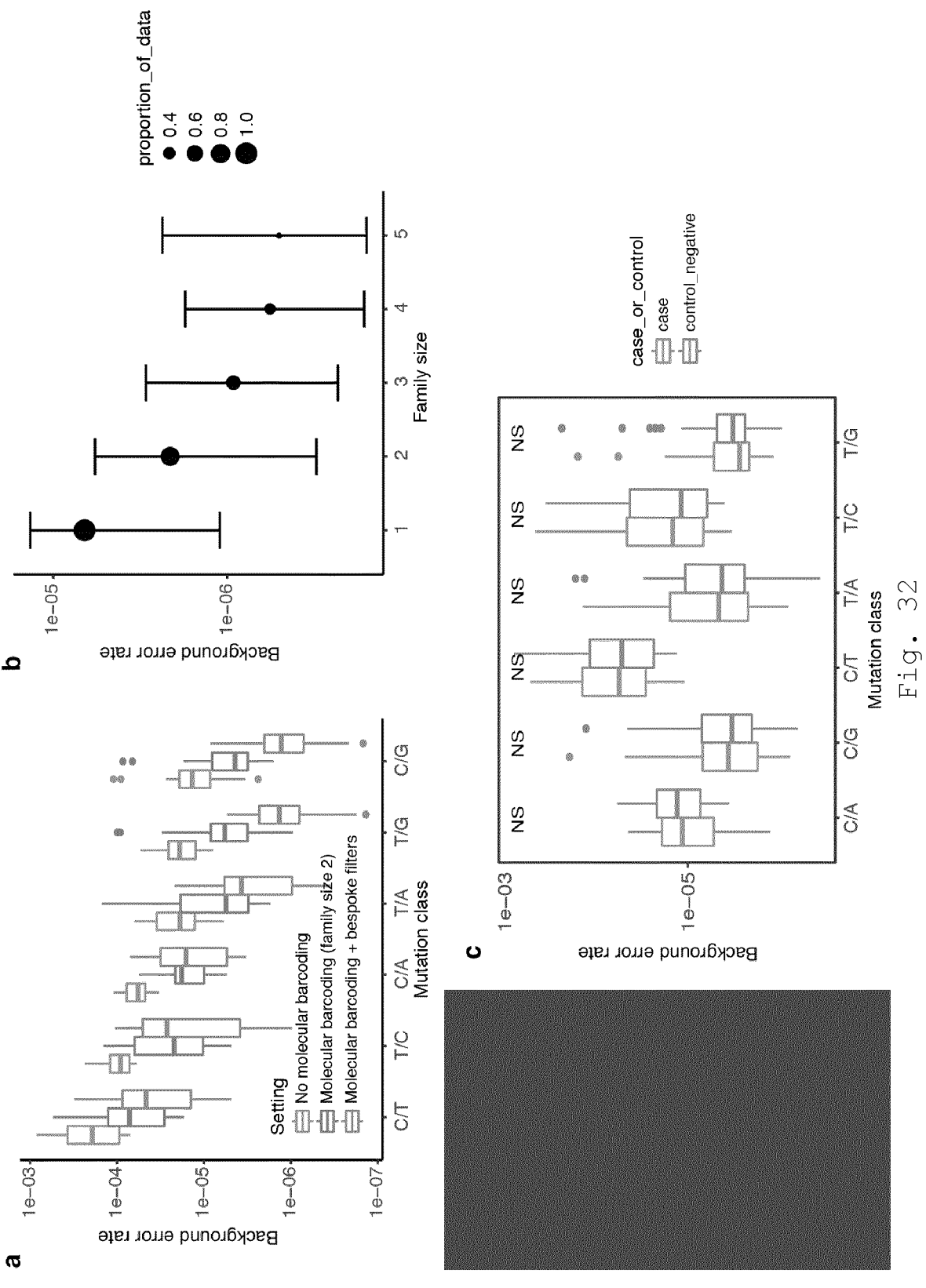

FIG. 32—Characterisation of background error rates. (a) Error suppressed (family size 2) and non-error suppressed background error rates, with and without bespoke INVAR filters. Background error rates were calculated by aggregating all non-reference bases across all bases considered. To assess background error rate, 10 bp either side of patient-specific loci were used, excluding the patient-specific locus itself ('near-target', Supplementary Methods). (b) Overall background error rates resulting from different minimum family size requirements, and the proportion of read families retained with each setting. (c) Background error rates were calculated by mutation class for healthy control individuals (blue) and patient samples (red) after equalising the number of read families per group. Complementary mutation classes were combined. t-tests were performed between healthy and patient samples. NS, not significant.

Figure 33:
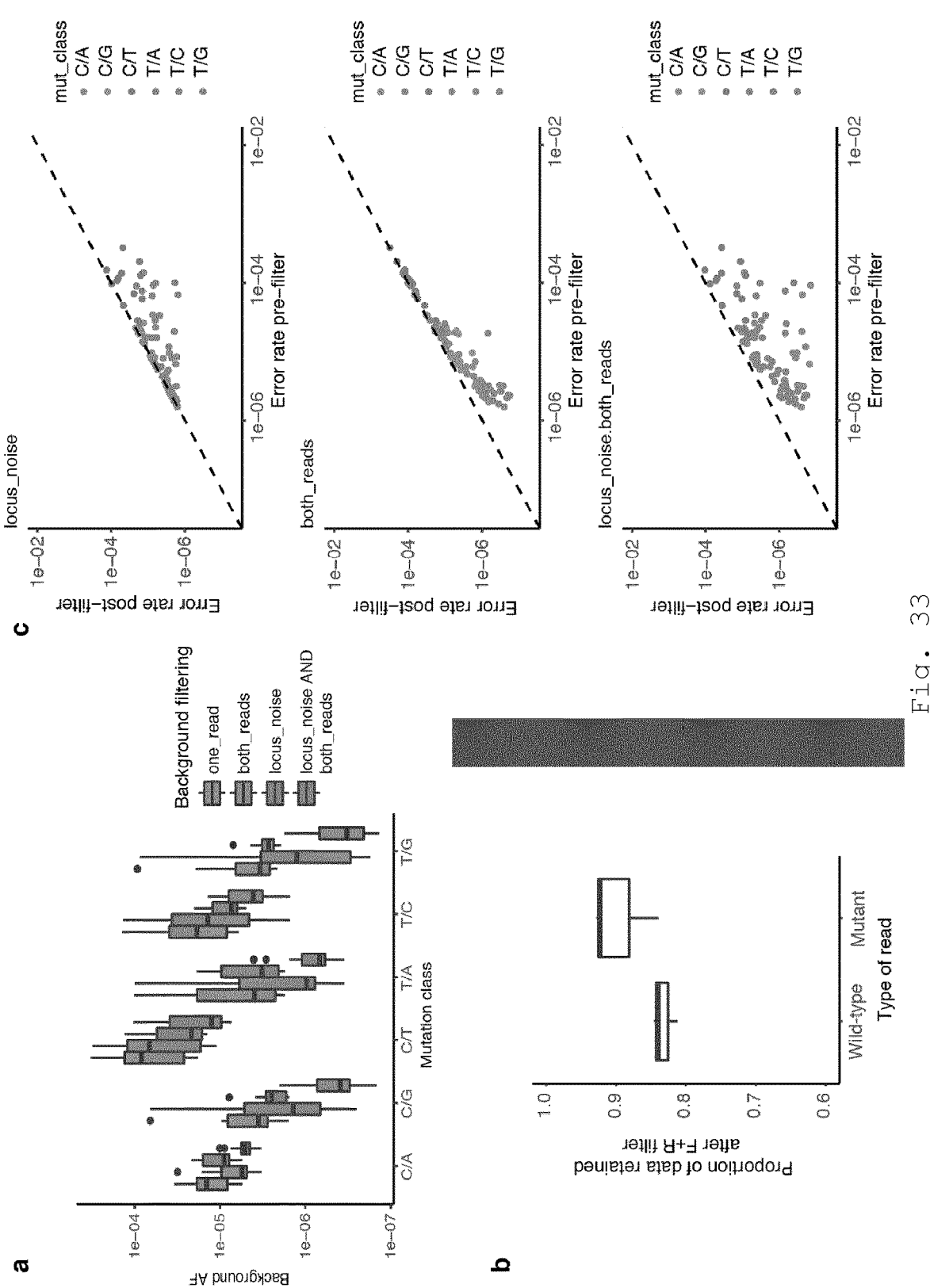
Figure 33:
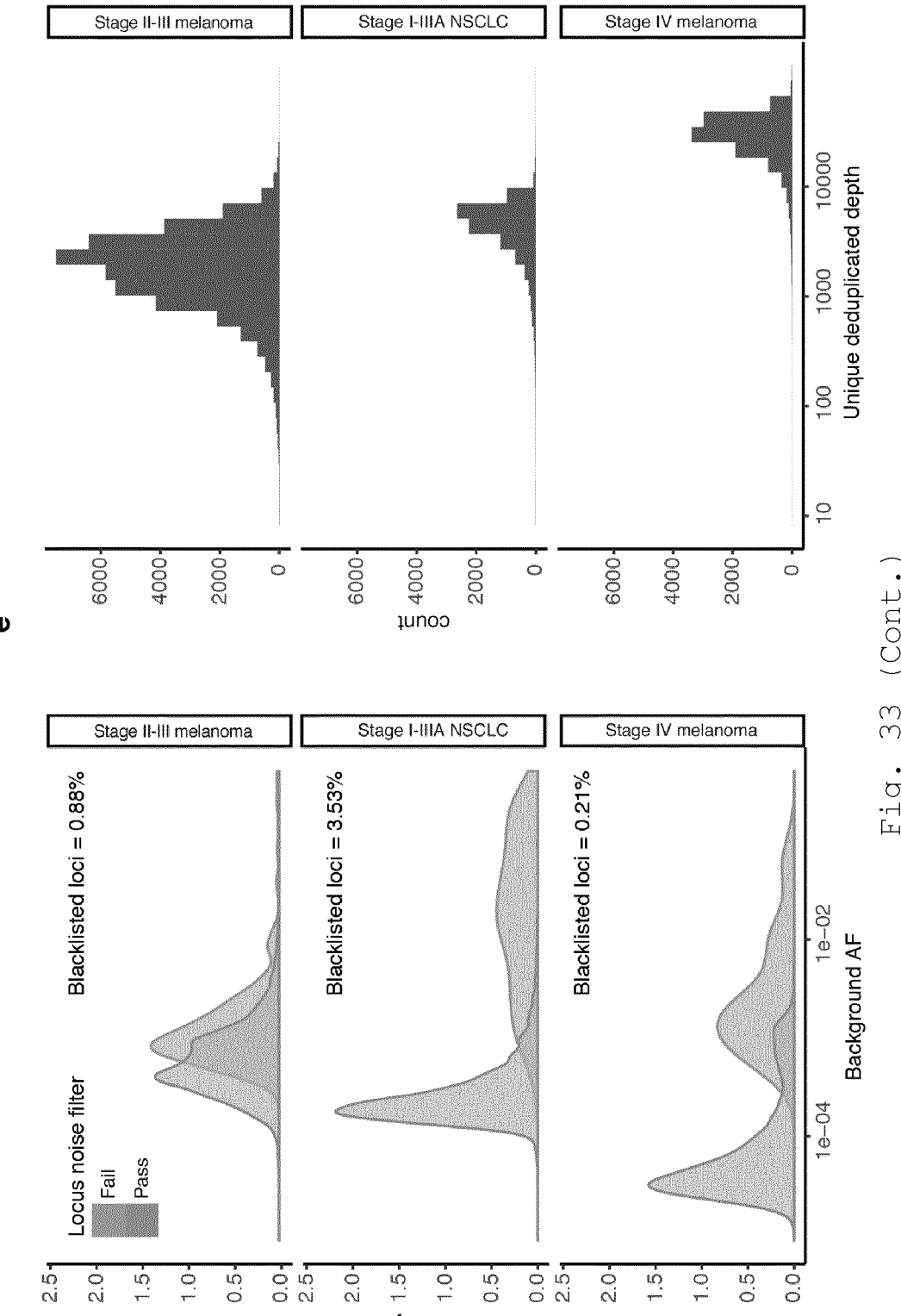

FIG. 33—Application of error rate filters and locus noise filter. (a) Summary of error rates by class with different filters developed for INVAR data (Supplementary Methods). (b) Effect of requiring forward and reverse reads at a locus; a median of 84.0% of the wild-type reads and a median of 92.4% of the mutant reads were retained with this filter. (c) For each trinucleotide context, background error rates (per trinucleotide) are plotted before and after each background error filter, highlighting the additive benefit of each of the error filters. (d) Background error rates were characterised per locus based on all reads generated from control samples, split by cohort. The loci that passed the locus noise filter are shown in blue, loci that did not pass the filter are shown in red. The proportions of loci blacklisted by this filter are indicated at the top right. (e) Histogram of the unique deduplicated depth per each locus (separated into the three cohorts). This is in the range of $10^3$~$10^4$, and would limit the quantification or background error rates for each individual locus to 0.1%~0.01%. To estimate background noise rates with greater depth, loci were grouped according to trinucleotide context (FIG. 24c).

Figure 34C:
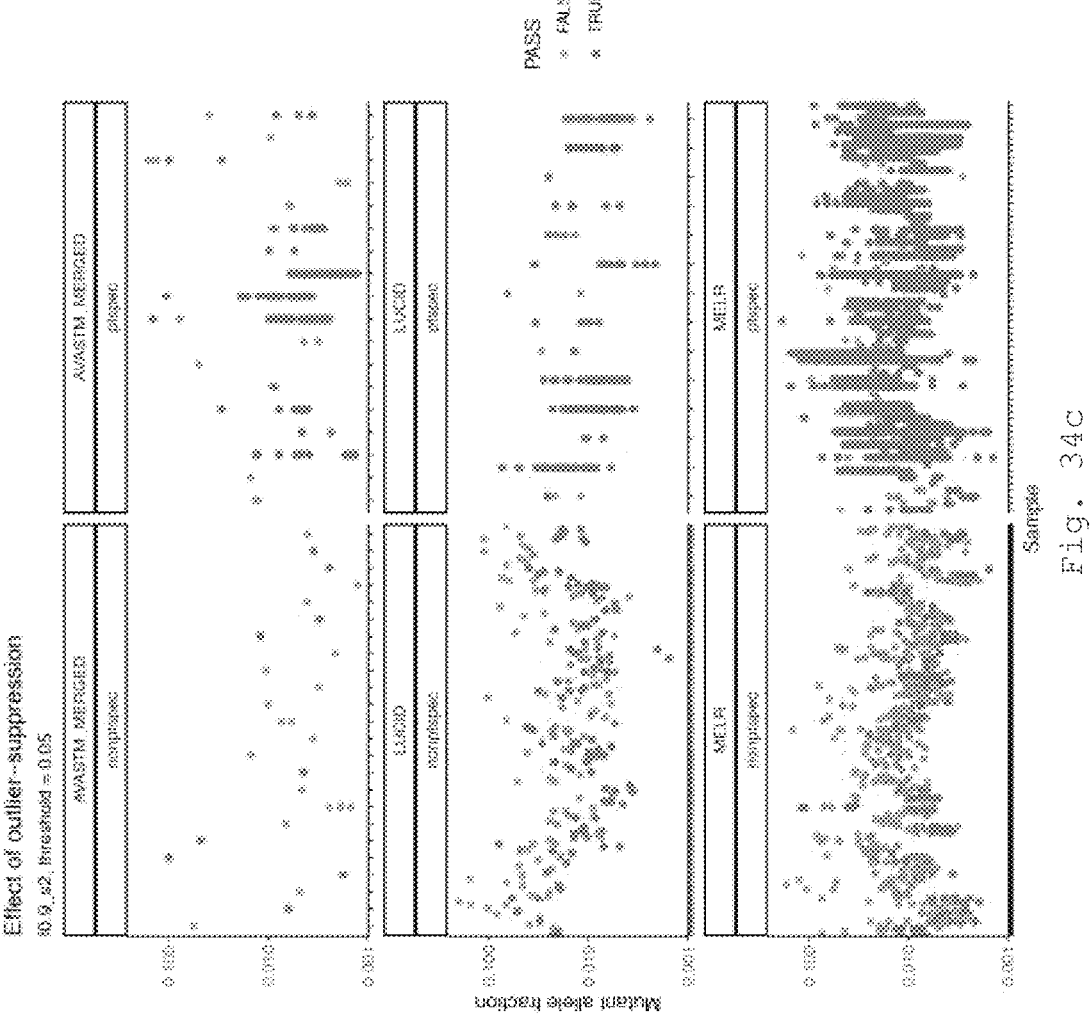

FIG. 34—Patient-specific outlier suppression filter. (a) Loci observed with significantly greater signal than the remainder of the loci of that patient might be due to noise at that locus, contamination, or a mis-genotyped SNP locus (in red, see Methods). (b) Summary of effect of outlier suppression on all cohorts. Mutant signal was reduced 3-fold in control samples, while retaining 96.1% of mutant signal in patient samples. (c) Raw data-points for all cohorts (patient and control samples), with the outlier-suppressed data points indicated in red.

Figure 35:
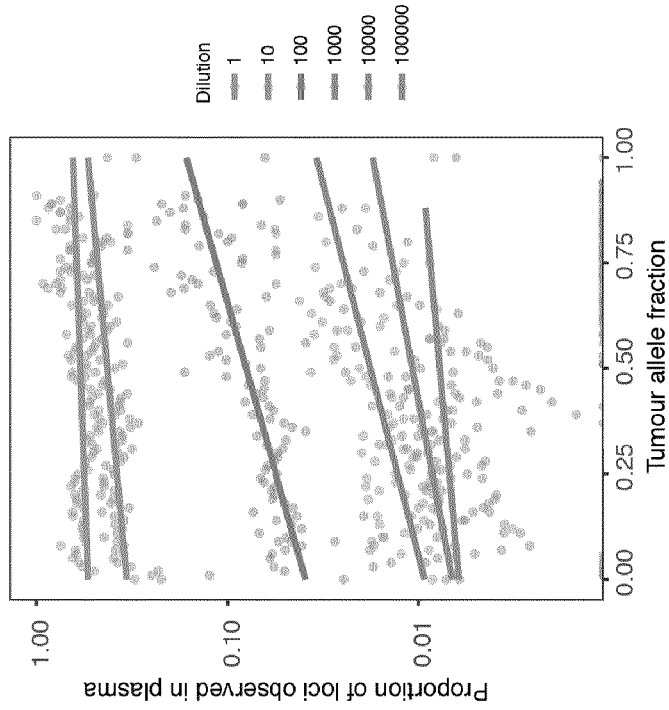
Figure 35:
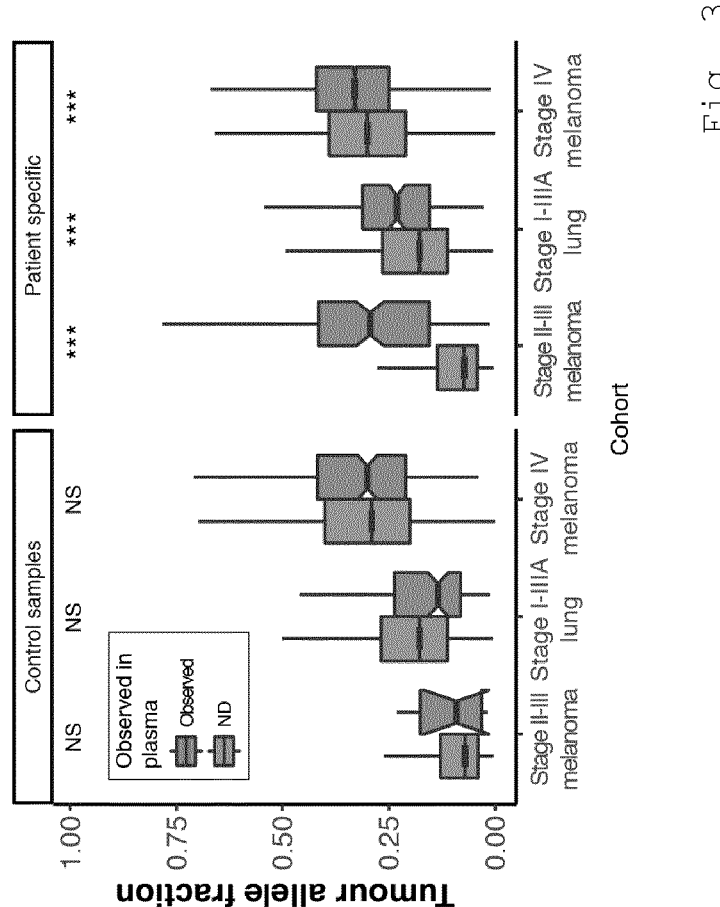
Figure 35:
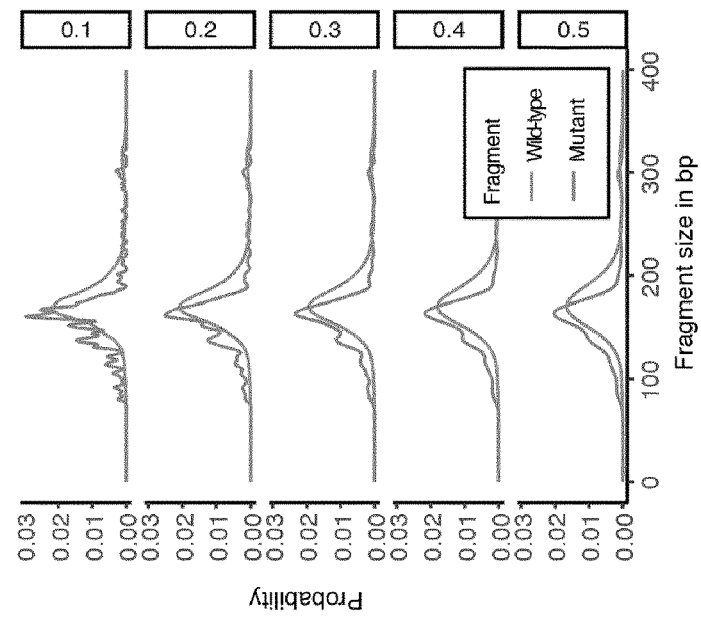
Figure 35:
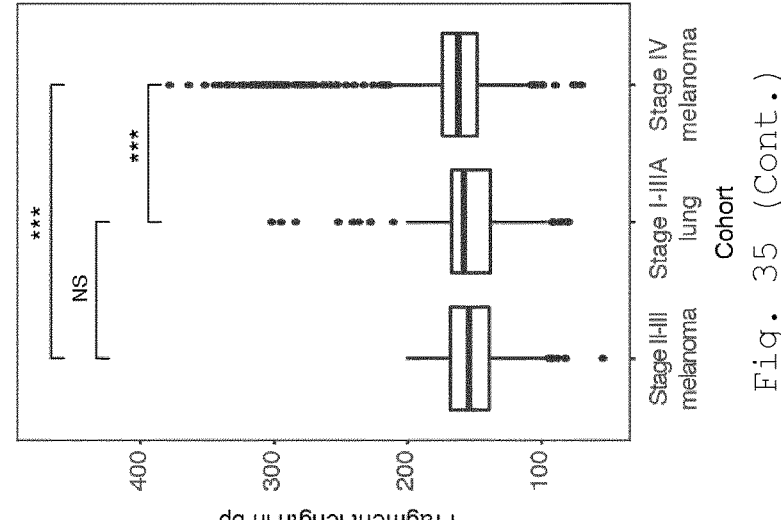

FIG. 35—Utilising tumour allelic fraction information and plasma DNA fragment length to enhance ctDNA signal. (a) Tumour allele fractions were compared between loci with and without detected signal in plasma. Loci with signal in plasma had significantly higher tumour allele fractions in patient samples. There was no significant increase in tumour allele fraction when performing this analysis on non-patient-specific samples (Student's t-test, NS, not significant; ***=P<0.0001). (b) Comparison of tumour and plasma mutant allele fractions. Using error-suppressed data, tumour loci were grouped into bins of 0.01 mutant allele fraction, and the proportion of loci observed in plasma was determined for different levels of a dilution series. The dilution level of the spike-in dilution series is indicated by each colour. At each dilution level, there is a positive correlation between the tumour allele fraction and proportion of loci observed in plasma. (c) For each cohort, size profiles were generated for mutant and wild-type fragments. (d) Comparison of mutant fragment distributions between cohorts. These were compared using a two-sided Wilcoxon rank test after downsampling the number of mutant reads to match for all cohorts. (e) The distributions of fragment sizes for different levels of smoothening, used to assign weights to fragment sizes (Supplementary Methods).

Figure 36:
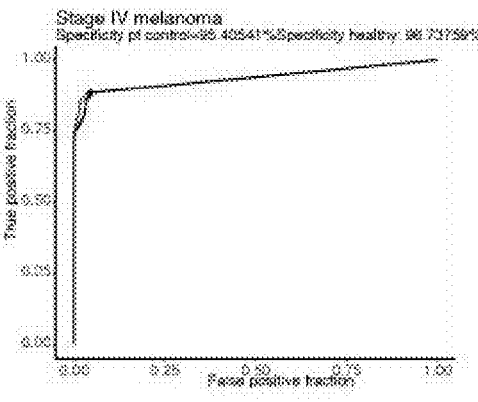
Figure 36:
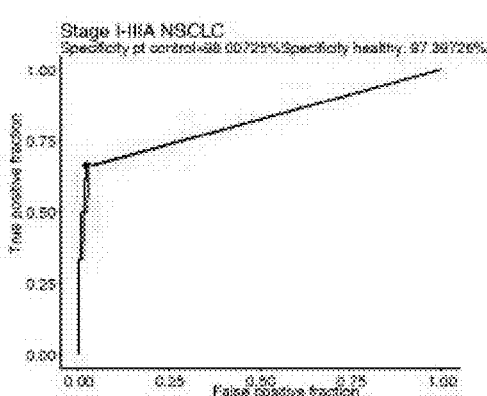
Figure 36:
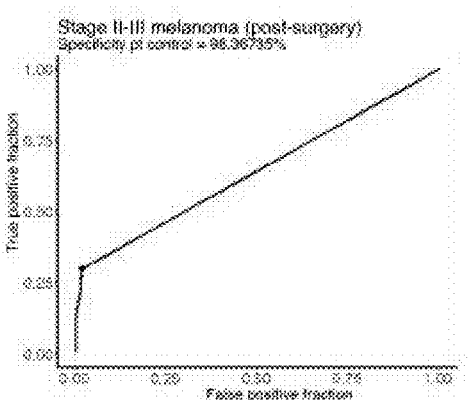
Figure 36:
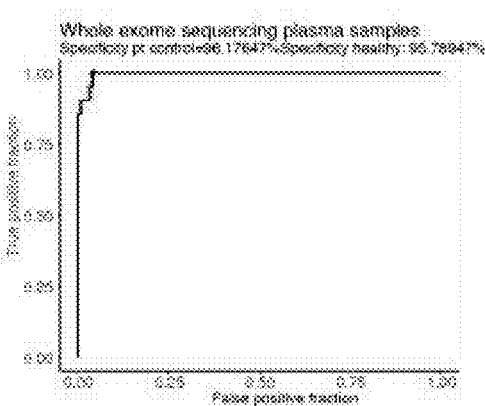
Figure 36:
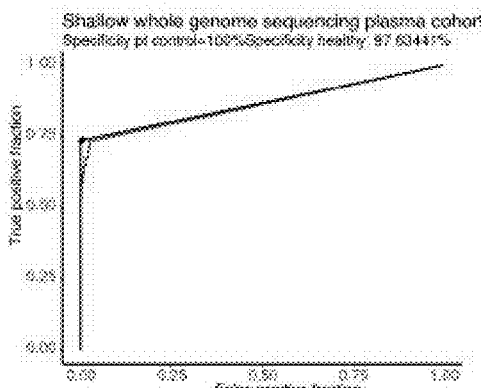
Figure 36:
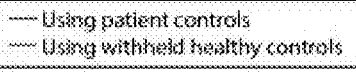

FIG. 36—ROC curves and specificity for all cohorts and data types. Specificity was determined as both analytical specificity (based on control data from other patients; black line), and clinical specificity (based on healthy individual data; red line). For the stage II-III melanoma (post-surgery) cohort, analysis was blinded to outcome, and patients who did not relapse within 5 years were also included in the ROC analysis; thus the maximal possible "sensitivity" for this cohort (as defined) was the fraction of relapsing patients (18/33=54.5%). INVAR detected 9 out of 18 patients who relapsed (ROC showing sensitivity at 9/33=27.3%). No healthy controls were run on this panel. The table shows the specificity at the selected threshold values.

Figure 37:
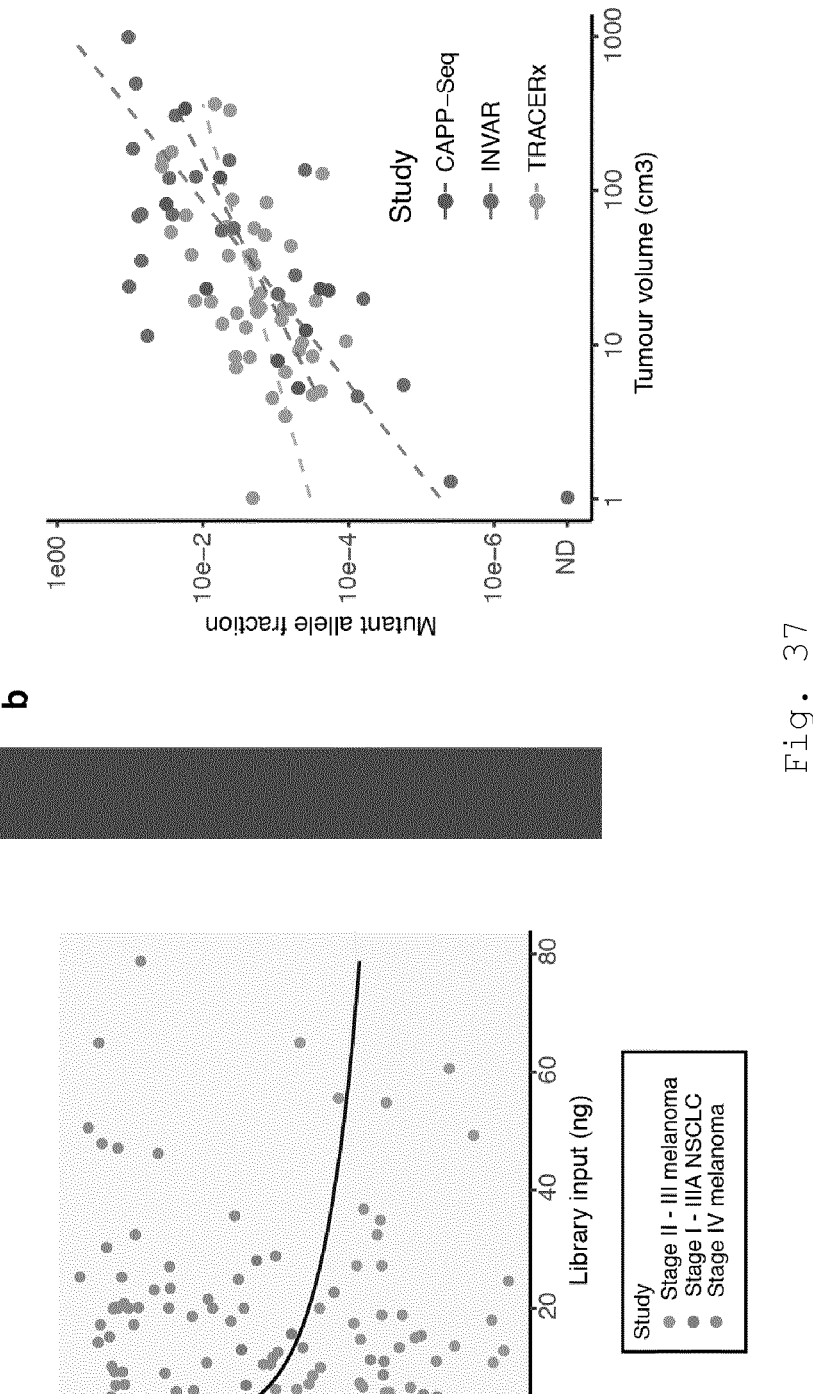
Figure 37:
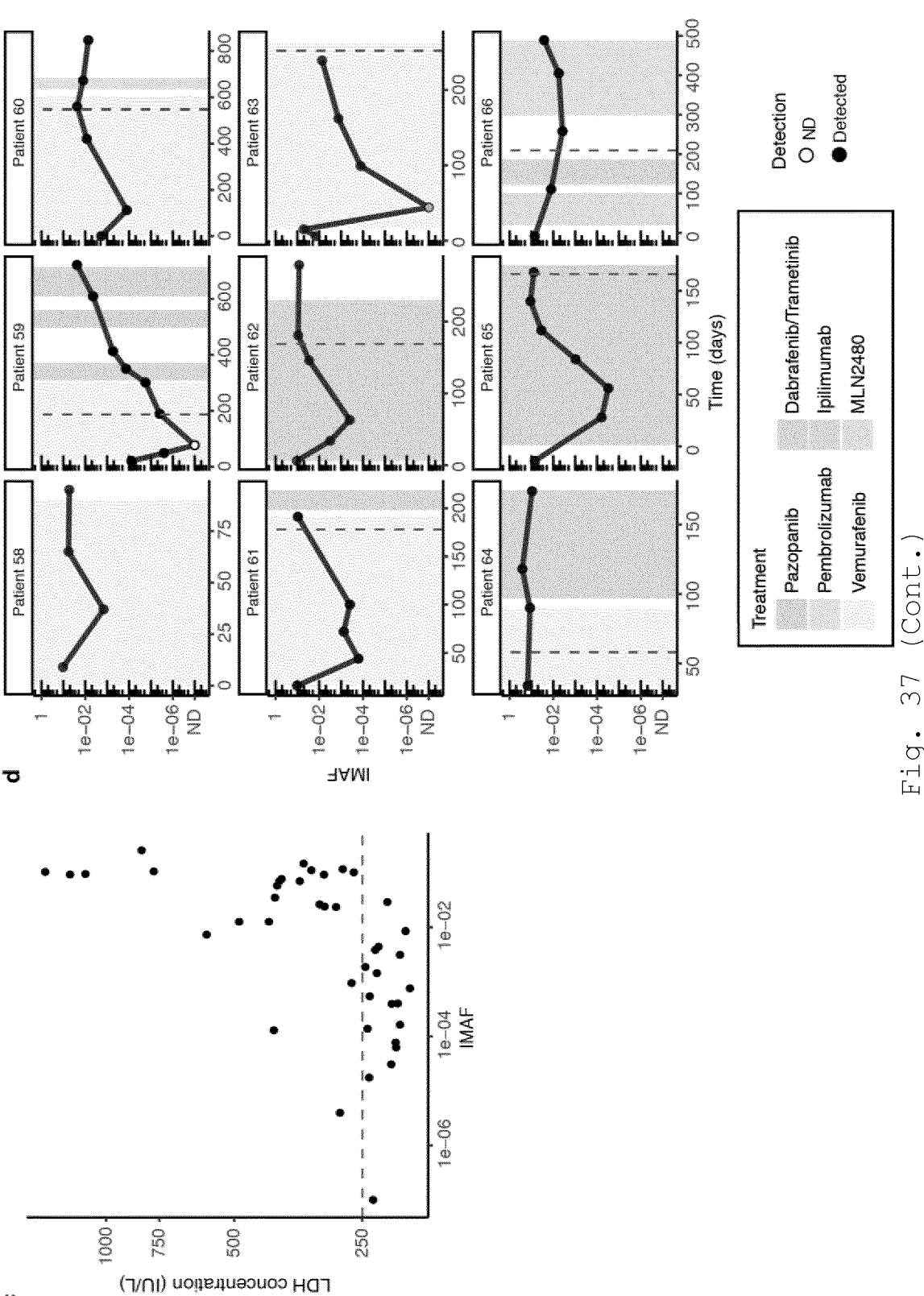

FIG. 37—Characterisation of ctDNA levels in advanced melanoma. (a) Comparison of input mass and IMAF observed. For each library with detected ctDNA, the DNA input mass for library preparation is plotted against the IMAF determined by INVAR. The black line indicates the threshold below which a perfect single-locus assay would have <95% sensitivity, based on the likelihood that no mutant copies would be sampled given the expected number of mutant copies in the sample. In this study, 48% of samples would not be detectable using a perfect single-locus assay with the plasma DNA input amounts used. (b) Comparison between ctDNA and tumour volume in our study (Pearson's r=0.67, P=0.0002) and in previous publications measuring multiple mutations per patient in NSCLC, using CAPP- Seq[6], and using multiplexed PCR in the TRACERx cohort[7]. The relationship between tumour volume and ctDNA level was steeper in this study than in previous analyses. This may be due to detection of ctDNA at lower concentrations using INVAR, which may have been missed or over-estimated by other assays. (c) Relationship between serum lactate dehydrogenase with IMAF in advanced stage melanoma patients. A Pearson correlation score of 0.46 was observed (P=0.0058). A dashed line is drawn at 2501 U/L, the upper limit of normal for LDH. (d) Longitudinal ctDNA profiles for advanced melanoma patients. IMAF values are plotted over time per patient, using error-suppressed individualised sequencing data. Vertical dashed lines indicate time of radiological progression.

Figure 38:
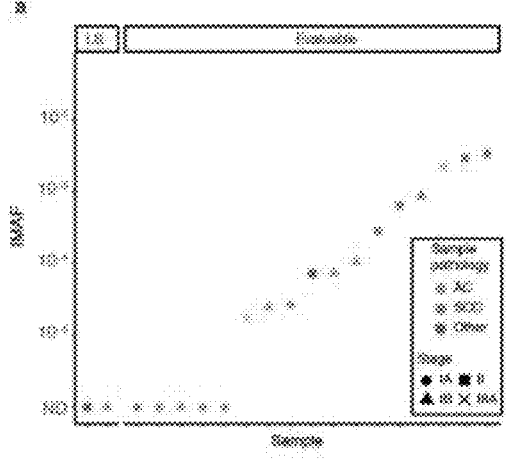
Figure 38:
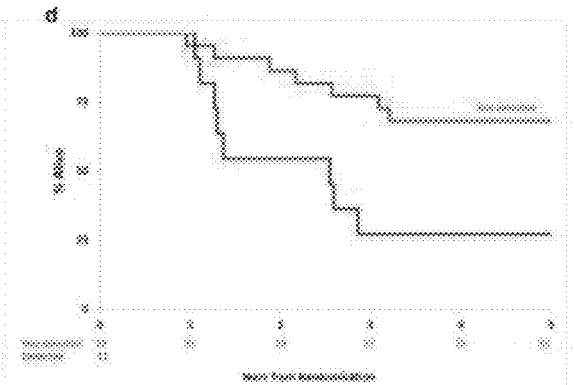
Figure 38:
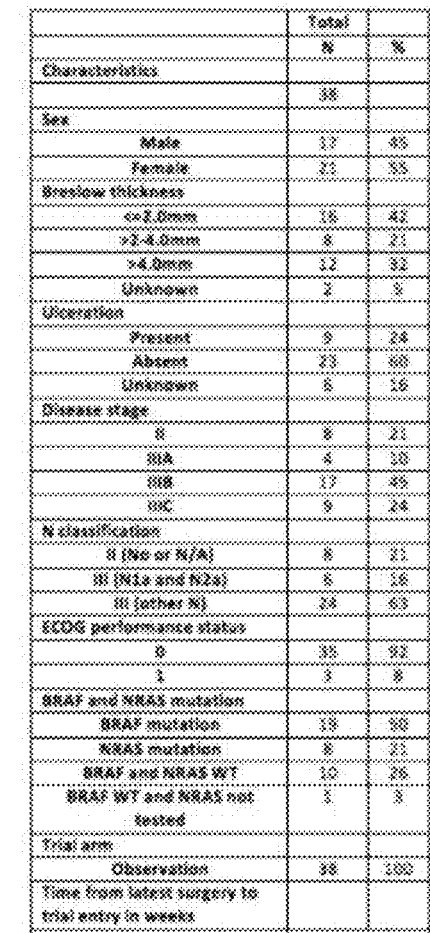
Figure 38:
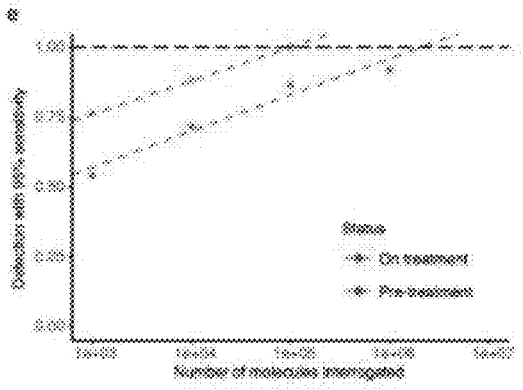

FIG. 38—Characterisation of IMAF values in early-stage cohorts. (a) IMAF values in the early-stage NSCLC cohort. Sample pathology and stage are indicated for each sample. Low sensitivity samples (LS) indicate those where fewer than 20,000 unique molecules (IR) were analysed. (b) Detection summary for early stage NSCLC cohort. Patients are grouped by stage and ctDNA detection. Sensitivity is calculated across samples with >20,000 IR. (c) Summary table of patient characteristics for the stage II-III resected melanoma cohort (n=38). (d) In the stage II-III resected melanoma cohort, patients with detected ctDNA had a significantly poorer overall survival (P=0.02, Cox proportional hazards model). The median survival for patients with detected ctDNA was 2.6 years (95% CI 1.1-5.3) vs. median not reached (95% CI 3.1-median not reached). (e) We estimated the detection rates of ctDNA for different levels of IR (Supplementary Methods). We observe a linear relationship ($R^{2=0.95}$) between the number of IR and detection rate in the baseline samples of the stage IV melanoma cohort (blue). ctDNA was detected in 100% of baseline samples with $10^5$ IR, whereas following the initiation of treatment, $10^6$-$10^7$ IR are needed to detect all longitudinal samples, reflecting the lower levels of ctDNA.

Figure 39:
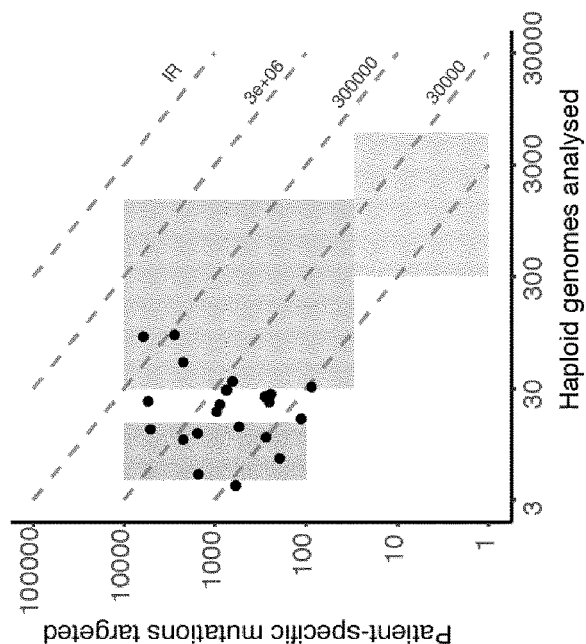
Figure 39:
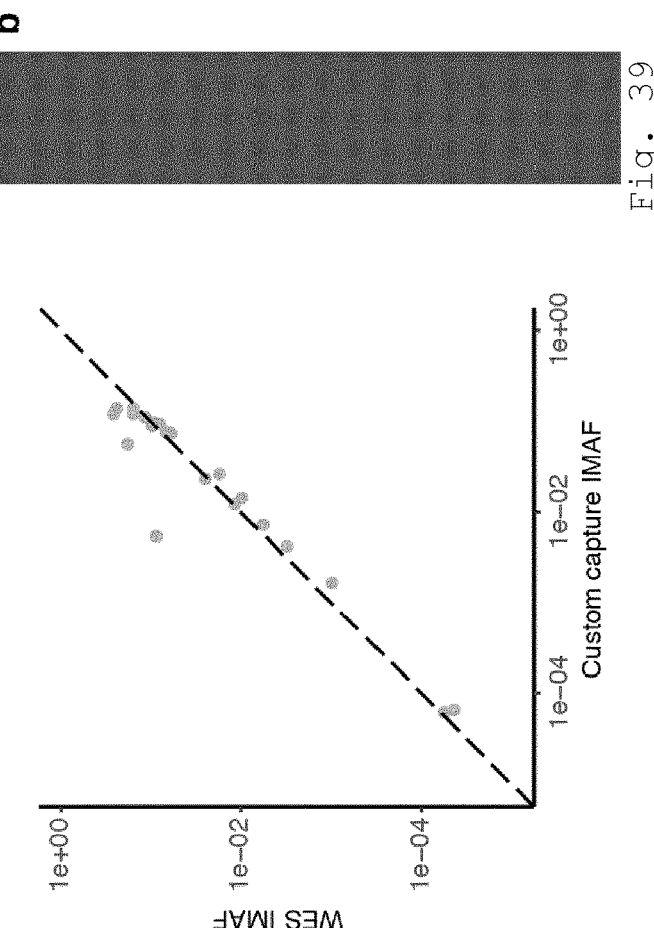

FIG. 39—Application of INVAR to whole exome sequencing data. (a) IMAFs obtained from plasma WES were compared to the IMAF obtained from the custom capture approach of matched samples, showing a correlation of 0.95. (b) Number of hGA (indicating depth of unique coverage after read collapsing) and mutations targeted by plasma WES. Compared to the custom capture approach, the WES samples had fewer hGA and occupy a space further to the left in the two-dimensional space, indicating that INVAR can detect ctDNA from limited data and few genome copies sequenced in a library.

Figure 40:
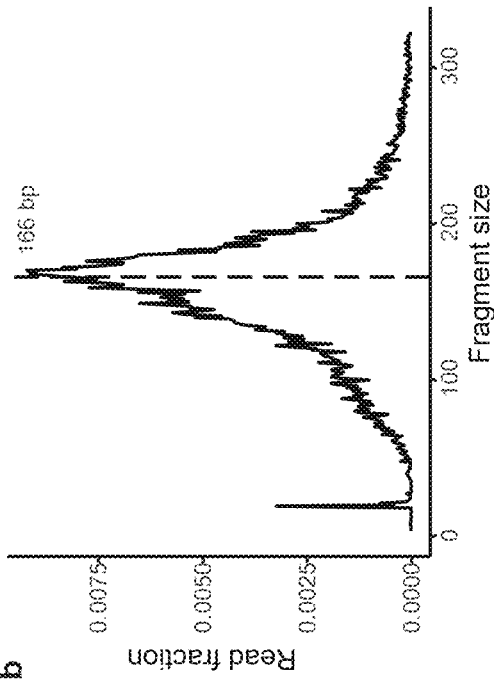
Figure 40:
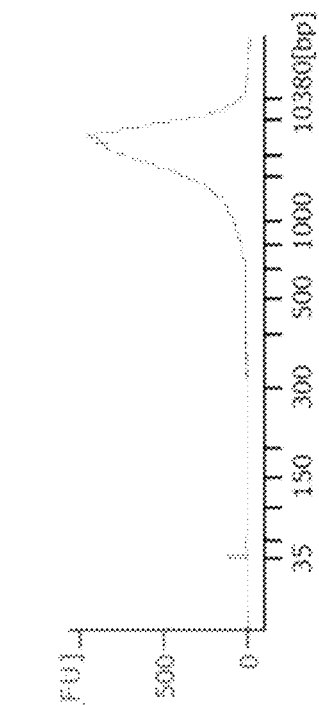
Figure 40:
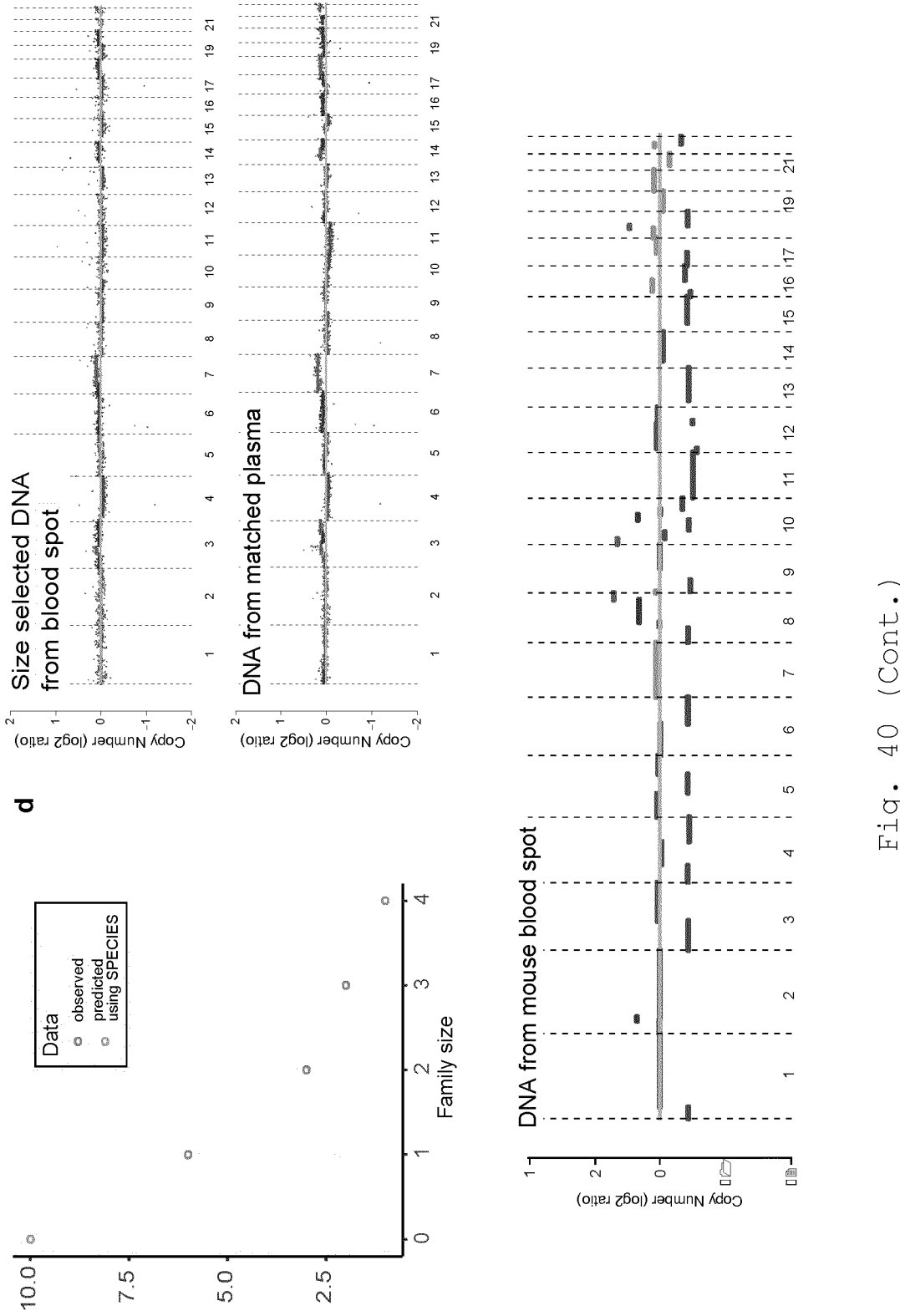

FIG. 40—ctDNA detection from dried blood spots. (a) Bioanalyser trace of a human 50 μL dried blood spot eluate showing a high level of genomic DNA contamination, necessitating a right-sided bead selection in order to isolate cfDNA. No short fragments between 50~300 bp are indicated at this stage. (b) Size profile of library generated from size selected blood spot DNA. The overall size profile is comparable to that of cfDNA, with a peak at ~166 bp. (c) Estimation of the number of cfDNA genome copies from a 50 μL dried blood spot using a statistical method for diversity estimation[8]. (d) Copy number profiles from sWGS of a library generated from a blood spot, and from the matched plasma sample from the same individual. (e) Copy number profile from a 50 μL dried blood spot from a mouse ovarian xenograft model (Methods).

Figure 41:
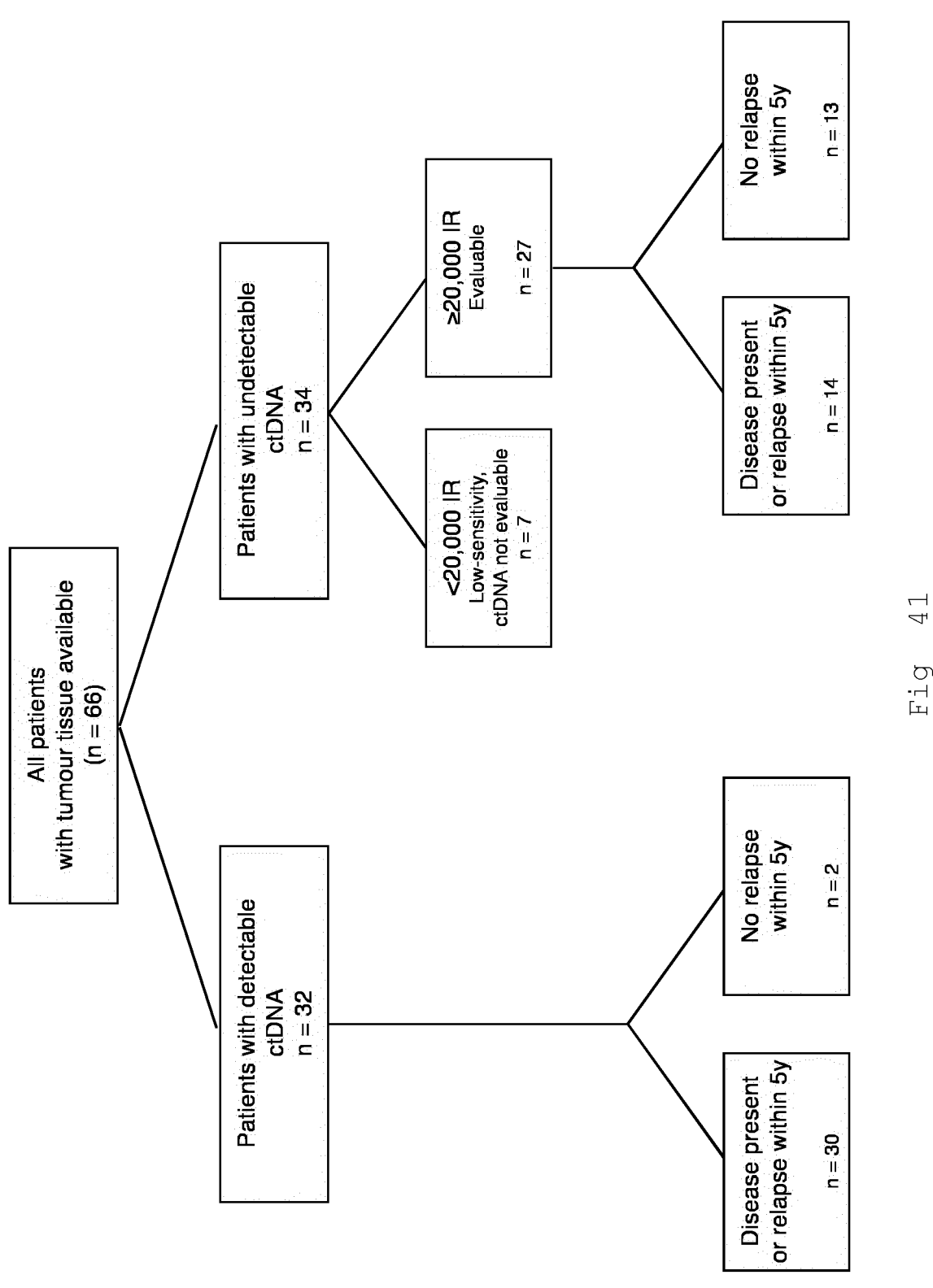

FIG. 41—REMARK flowchart. The number of patients analysed in this study is shown. Patients are categorised based on detection of ctDNA and the number of informative reads (IR) generated for each. All cohorts (stages II-III melanoma post-surgery, stages I-IIIA NSCLC and stage IV melanoma) were combined in this flowchart.

Figure 42:

FIG. 42—Integrated mutant allele fraction (IMAFs) (y-axis) are plotted for each sample in all cohorts (X-axis). From left to right the cohorts are: lung cancer (plasma) and breast cancer (plasma).

Figure 43:

FIG. 43—Integrated mutant allele fraction (IMAFs) (y-axis) are plotted for each sample in all cohorts (X-axis). From left to right the cohorts are: glioblastoma (CSF), glioblastoma (plasma), renal cancer (plasma) and renal cancer (urine).

Figure 44:

FIG. 44—INVAR scores (y-axis) are plotted for each sample classified as evaluable. From left to right the cohorts are: lung cancer (plasma) and breast cancer (plasma).

Figure 45:
Figure 45:
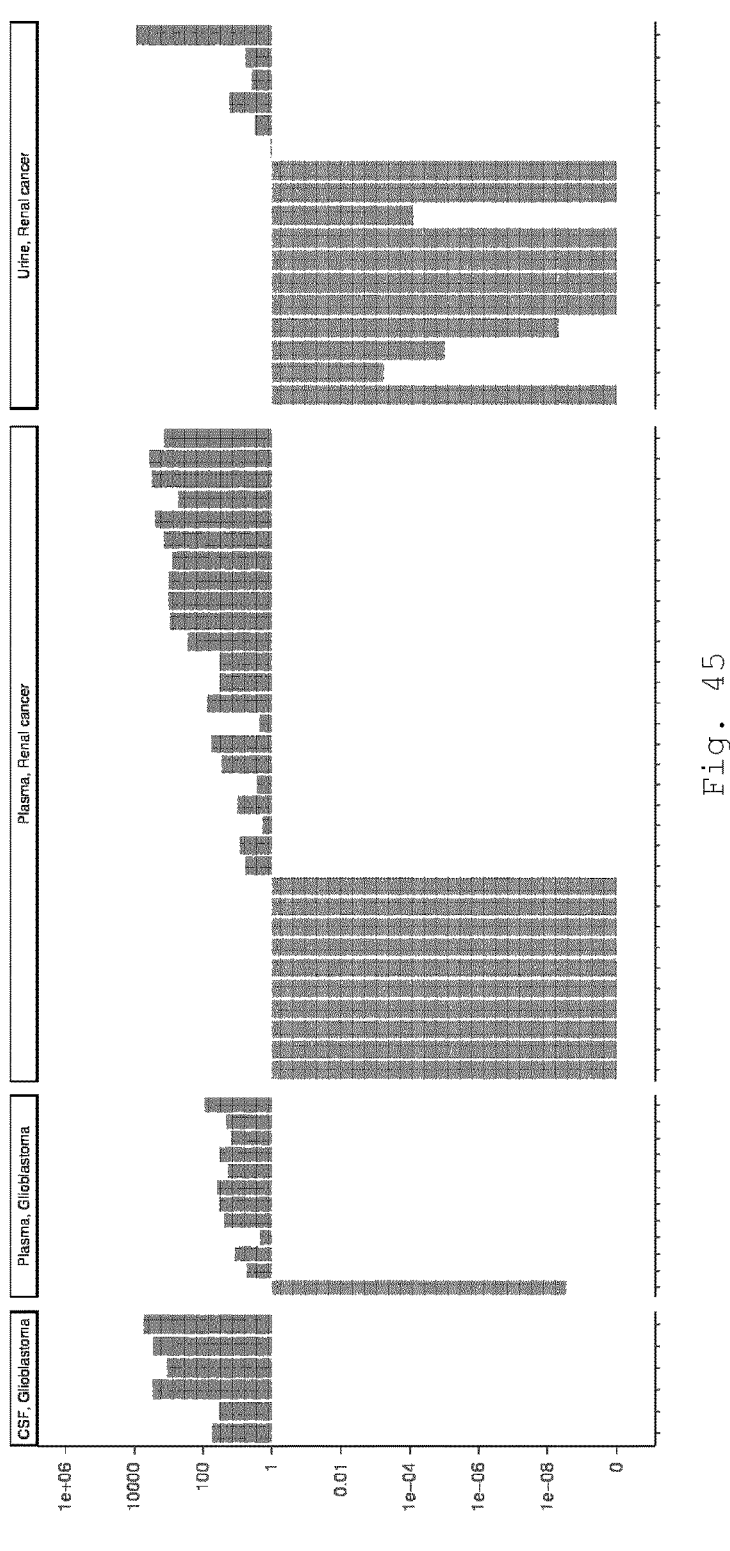

FIG. 45—INVAR scores (y-axis) are plotted for each sample classified as evaluable. From left to right the cohorts are: glioblastoma (CSF), glioblastoma (plasma), renal cancer (plasma) and renal cancer (urine).

DETAILED DESCRIPTION OF THE INVENTION

In describing the present invention, the following terms will be employed, and are intended to be defined as indicated below.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Computer-implemented method" where used herein is to be taken as meaning a method whose implementation involves the use of a computer, computer network or other programmable apparatus, wherein one or more features of the method are realised wholly or partly by means of a computer program.

"Patient" as used herein in accordance with any aspect of the present invention is intended to be equivalent to "subject" and specifically includes both healthy individuals and individuals having a disease or disorder (e.g. a proliferative disorder such as a cancer). The patient may be a human, a companion animal (e.g. a dog or cat), a laboratory animal (e.g. a mouse, rat, rabbit, pig or non-human primate), an animal having a xenografted or xenotransplanted tumour or tumour tissue (e.g. from a human tumour), a domestic or farm animal (e.g. a pig, cow, horse or sheep). Preferably, the patient is a human patient. In some cases, the patient is a human patient who has been diagnosed with, is suspected of having or has been classified as at risk of developing, a cancer.

A "sample" as used herein may be a biological sample, such as a cell-free DNA sample, a cell (including a circulating tumour cell) or tissue sample (e.g. a biopsy), a biological fluid, an extract (e.g. a protein or DNA extract obtained from the subject). In particular, the sample may be a tumour sample, a biological fluid sample containing DNA, a blood sample (including plasma or serum sample), a urine sample, a cervical smear, a cerebrospinal fluid (CSF) sample, or a non-tumour tissue sample. It has been found that urine and cervical smears contains cells, and so may provide a suitable sample for use in accordance with the present invention. Other sample types suitable for use in accordance with the present invention include fine needle aspirates, lymph nodes, surgical margins, bone marrow or other tissue from a tumour microenvironment, where traces of tumour DNA may be found or expected to be found. The sample may be one which has been freshly obtained from the subject (e.g. a blood draw) or may be one which has been processed and/or stored prior to making a determination (e.g. frozen, fixed or subjected to one or more purification, enrichment or extractions steps, including centrifugation). The sample may be derived from one or more of the above biological samples via a process of enrichment or amplification. For example, the sample may comprise a DNA library generated from the biological sample and may optionally be a barcoded or otherwise tagged DNA library. A plurality of samples may be taken from a single patient, e.g. serially during a course of treatment. Moreover, a plurality of samples may be taken from a plurality of patients. Sample preparation may be as described in the Materials and Methods section herein. Moreover, the methods of the present invention have been demonstrated to detect tumour-derived mutant DNA in urine samples (data not shown). Accordingly, use of blood or urine samples as a source of patient DNA potentially containing mutant tumour DNA to be detected is specifically contemplated herein. For forensic applications, the sample may be any fluid or tissue or item having or suspected of having a mixed DNA or RNA (e.g. target and background, such as perpetrator DNA or RNA and victim DNA or RNA). For the analysis of contamination, the sample may be any fluid, organism, item, foodstuff or plant having or suspect of having mixed DNA or RNA (e.g. target and background, such as contamination source (e.g. pathogen) DNA or RNA and non-contamination source DNA or RNA).

"Right-sided size selection" as used herein in some embodiments employ AMPure beads as described at research.fhcrc.org/content/dam/stripe/hahn/methods/mol-_biol/SPRIsele ct%20User%20Guide.pdf (the entire contents of which is incorporate herein by reference). In particular, a 1× selection step as used in some embodiments implies a cut-off in-between the curves for 1.2× and 0.95×, so is estimated at around 200-300 bp.

"Blood spot" as used herein may in some embodiments be a dried blood spot sample. Typically, blood samples are blotted and dried on filter paper. Dried blood spot specimens may be collected by applying one or a few drops of blood (e.g. around 50 µl), drawn by lancet from the finger, heel or toe, onto specially manufactured absorbent filter paper. The blood may be allowed to thoroughly saturate the paper and may typically be air dried for several hours. Specimens may be stored in low gas-permeability plastic bag with desiccant added to reduce humidity, and may be kept at ambient temperature.

Determination of Patient-Specific Loci

In accordance with some embodiments of the present invention, loci that carry mutations that are specific to the tumour of the patient may be identified. In some cases tumour DNA is sequenced so as to give an average 8 Gb of unique mapped reads per sample with an average of 80% of base pairs covered by >20 reads. In some cases, single nucleotide variants (SNVs) (versus a germline sequence, e.g., from a buffy coat sample) may be selected from the sequence data obtained from the tumour sample. In some cases, patient-specific loci are those which display SNVs with ≥1 mutant read and ≥10 total reads as determined from tumour sequencing. In some cases loci may be excluded if they show 1 forward (F) and 1 reverse (R) non-reference read (following read de-duplication) in the germline sequence (e.g. a buffy coat sample). Optionally, loci may be excluded if they are SNPs identified in common SNP databases, such as the 1000 Genomes database.

Providing Sequence Reads

The sequence reads data may be provided or obtained directly, e.g., by sequencing the cfDNA sample or library or by obtaining or being provided with sequencing data that has already been generated, for example by retrieving sequence read data from a non-volatile or volatile computer memory, data store or network location. Where the sequence reads are obtained by sequencing a sample, the median mass of input DNA may in some cases be in the range 1-100 ng, e.g., 2-50 ng or 3-10 ng. The DNA may be amplified to obtain a library having, e.g. 100-1000 ng of DNA. The median sequencing depth of sequence reads (e.g. quality-filtered sequence reads) at each patient-specific loci may be in the range 500×-2000×, e.g., 750×-1500× or even 1200×-1400×. The sequence reads may be in a suitable data format, such as FASTQ.

Sequence Data Processing and Error Suppression

The sequence read data, e.g., FASTQ files, may be subjected to one or more processing or clean-up steps prior to or as part of the step of reads collapsing into read families. For example, the sequence data files may be processed using one or more tools selected from as FastQC v0.11.5, a tool to remove adaptor sequences (e.g. cutadapt v1.9.1). The sequence reads (e.g. trimmed sequence reads) may be aligned to an appropriate reference genome, for example, the human genome hg19.

As used herein "read" or "sequencing read" may be taken to mean the sequence that has been read from one molecule and read once. Each molecule can be read any number of times, depending on the sequencing performed.

As used herein, "read family" may be taken to mean multiple sequencing reads arising from the same molecule (hence replicates). Because they are from the same starting molecule, each read will have the same start and end position in the human genome following alignment of the read. In addition, when molecular barcodes are ligated to starting molecules prior to PCR and sequencing, each read family will also have the same molecular barcode. The process of error suppression by molecular barcodes is described at: github.com/umich-brcf-bioinf/Connor/blob/master/doc/METHODS.rst (the contents of which as shown in 5 Mar. 2018 are expressly incorporated herein by reference).

As used herein "collapsing" or "reads collapsing" may be taken to mean that, given a read family (set of replicate reads), error-suppression for PCR and sequencing errors may be performed by generating a consensus sequence across the family for every base position. Thus, a family of N (number of) reads is 'collapsed' into a consensus sequence of one read, which consensus sequence can be expected to contain fewer errors.

Reads collapsing may be performed based on fragment start and end position and custom inline barcodes. A suitable tool is CONNOR described at github.com/umich-brcf-bioinf/Connor/blob/master/doc/METHODS.rst (the entire contents of which as shown in 5 Mar. 2018 are expressly incorporated herein by reference). CONNOR may be used with a consensus frequency threshold -f set to 8.8, 0.85, 0.9 or 0.95. CONNOR may be used with a minimum family size threshold-s set as 2, 3, 4, 5, 6, 7, 8, 9, or 10. Preferably, the consensus frequency threshold is 0.9 and the minimum family size threshold is 5.

Quality filters may be applied in the process of determining the number of mutant and wild-type reads/read families, as described in the Materials and Methods section herein.

In some cases, one or more MRD-filters are applied to focus on tumour-derived MRD read families. In particular, the MRD-filter step may comprise one or both of:

(i) excluding those loci with >2 mutant molecules; and (ii) selecting (i.e. including) only those fragments which have been sequenced in both forward (F) and reverse (R) direction.

As used herein "barcode" or "molecular barcode" may be taken to mean a unique string of bases, generally but not necessarily of length <10 bp, e.g. a molecular barcode employed by the invention may be 6, 7, 8, 9, or 10 bp in length), that may be ligated to one or more DNA molecules as the first step during library preparation. As a result, read families (from above) may be uniquely identified, and thus linked to their starting molecule. This allows error-suppression via 'reads collapsing', as described above.

Determining Background Sequencing Error Rates

In some cases, a region either side of each patient-specific loci (e.g. 20, 15, 10 or 5 bp either side) may be employed to determine the error rate for each mutation class. In some cases, non-reference bases are only accepted if found to be present in both the forward F and reverse R read. In some cases if a locus displays mutant error-suppressed families in ≥3 separate libraries, it may be filtered out ("blacklisted") on the basis of having a higher locus-specific error rate.

The sequencing error analysis may be carried out to determine the background error rates regardless of mutation class, and by separating data by mutation class. The error rate may be determined by taking the ratio between the sum of mutant reads in a class and the total number of reads in a class. In some cases, this ratio data may be resampled 100 times with replacement to obtain 95% confidence intervals of the error rate.

Integration of Variant Reads (INVAR)

In accordance with some embodiments of the present invention a variant read for a particular patient-specific loci may be accepted only where the observed variant (e.g. SNV) matches the mutation determined in the tumour sequence at that loci. For example, if a C>T mutation was expected based on tumour sequencing/genotyping, but a C>A is observed in the mutant reads, then the mutant reads may ignored and may be excluded from the patient-specific signal. Alternatively or additionally, loci may be only considered as contributing to signal if there are at least ≥1 F and ≥1 R read family at that position. This has two advantages: to reduce single-stranded artefacts from sequencing, and to bias detection towards short fragments which have greater overlap between F and R reads in certain sequencing platforms, e.g. PE150 sequencing.

For each sample, the mutant allele fraction may be calculated across all patient-specific loci as follows:

$$\frac{\sum_{loci} (\text{mutant reads})_{patient\ specific}}{\sum_{loci} (\text{total reads})_{patient\ specific}}$$

In certain cases, the mutant allele fraction may be calculated by trinucleotide context. The mutant allele fraction by context may be based on tumour-weighted read families according to the formula:

$$AF_{context} = \frac{\sum_{MRD\text{-}like\ loci} \text{mutant families} \div (1 - \text{tumour } AF)}{\sum_{MRD\text{-}like\ loci} \text{total families} \div (1 - \text{tumour } AF)}$$

wherein:

$AF_{context}$ is the allele frequency of a given (e.g. trinucleotide) context; tumourAF is the allele frequency of the locus as determined by sequencing DNA obtained directly from the tumour; and MRD-like loci are the mutation-containing loci determined from the tumour of the patient and which have been filtered to select for minimal residual disease signal.

The significance of the observed number of mutant reads may be determined using a one-sided Fisher's exact test, given a contingency table with the number of mutant reads and total reads for both the sample of interest, and from the background error rate.

Mutant allele fraction determination split by mutation class In some embodiments of the present invention each sample may be split into a plurality of mutation classes (e.g. 2, 3, 4, 5, 6, 7, 8, 9, 10, 11 or all 12 of the following SNV classes: C>G, G>C, T>G, A>C, C>A, G>T, T>C, A>G, T>A, A>T, C>T and T>C) based on the mutation class expected at that locus from tumour sequencing. Variant reads may be integrated for each class, as above. Multiple one-sided Fisher's exact tests may be used to determine the significance of the number of mutant read families observed given the background error rate for that mutation class. This method will generate 12 P-values per sample, which may then be combined using the Empirical Brown's method. If a sample had no data in a class, that class may be treated as having zero mutant reads and thus a P-value of 1.

To improve specificity further, in some embodiments, the method of the present invention may require samples to have mutant reads in ≥2 separate classes; this ensures that detection is based on signal being present in multiple loci subject to different types of error processes.

Statistical Significance Determination

The significance threshold for combined P-values obtained by INVAR may in some cases be determined using Receiver Operating Characteristic analysis on patient-specific (test) and non-patient-specific (control) samples. For example, the analysis may employ the OptimalCutpoints package in R, with the 'MaxEfficiency' method, which maximises classification accuracy.

Background Subtraction

In some cases, background error rates may be subtracted from the observed allele fraction. This can be performed with or without taking into account differences in error rate by class. If the observed mutant allele fraction is less than the background error rate, then the background-subtracted allele fraction may be set at zero. For background subtraction by mutation class for a sample, the error rate of each of the classes may be subtracted from the mutant allele fraction of that class. A mean allele fraction may then be calculated from each of the individual background-subtracted allele fractions, weighted by the total number of read families observed in that class.

The following is presented by way of example and is not to be construed as a limitation to the scope of the claims.

EXAMPLES

Materials and Methods

Sample and Data Collection

MelResist (REC number 11/NE/0312) is a translational study of response and resistance mechanisms to systemic therapies of melanoma, including BRAF targeted therapy and immunotherapy. For each patient in this cohort, fresh frozen metastatic tumour biopsies and plasma samples were collected before the initiation of treatment and plasma was collected at varying time points during treatment. Patients may have received multiple lines of treatment over time. Demographics and clinical outcomes are collected prospectively. The study was coordinated by the Cambridge Cancer Trials Unit-Cancer Theme.

Peripheral blood samples were collected longitudinally at each clinic visit in S-Monovette 9 mL EDTA tubes. For this study, up to 8 samples per patient were analysed from their serially-collected samples. One aliquot of whole blood at baseline was stored at −80° C. for germline DNA. For plasma collection, samples were centrifuged at 1600 g for 10 minutes within an hour of the blood draw, and then an additional centrifugation of 20,000 g for 10 minutes was carried out. Plasma aliquots were stored at −80° C.

Extraction of DNA from Fresh Frozen Tissue and Plasma

Up to 30 mg of each fresh frozen tissue biopsy sample was combined with 600 μL RLT buffer (QIAGEN), then placed in a Precellys CD14 tube (Bertin Technologies) and homogenised at 6,500 rpm for two bursts of 20 seconds separated by 5 seconds. DNA was then extracted using the AllPrep extraction kit (Qiagen) as per the manufacturer's protocol.

Genomic DNA was extracted from 10 mL whole blood using the Gentra Puregene Blood Kit (Qiagen) as per the manufacturer's protocol. Eluted DNA concentration was quantified using Qubit (ThermoFisher Scientific).

Plasma samples were extracted using the QIAsymphony instrument (Qiagen) using a 2 mL QIAamp protocol. For each QIAsymphony batch, 24 samples were extracted, which included a healthy individual control sample (Seralab). Plasma samples were eluted in 90 ul water and stored at −80° C.

Imaging

CT imaging was acquired as part of the standard of care for each patient and were examined retrospectively. The slice thickness was 5 mm in all cases. All lesions with a largest diameter greater than ~5 mm were outlined slice by slice on the CT images by an experienced operator, under the guidance of a radiologist, using custom software written in MATLAB (Mathworks, Natick, MA). The outlines were subsequently imported into the LIFEx software application[25] in NifTI format for processing. Tumour volume was then reported by LIFEx as an output parameter from its texture based processing module.

Cell-Free DNA Quantification

To quantify the cfDNA concentration of each sample, digital PCR was carried out using a Biomark HD (Fluidigm) using Taq-man probes for the housekeeping gene RPP30 (Sigma Aldrich), and a unique XenT locus, labelled with ROX and FAM, respectively. 55 PCR cycles were used. The RPP30 assay was 65 bp in length. The estimated number of RPP30 DNA copies per μl of eluate was used to determine the cfDNA concentration in the original sample.

Exome and Targeted Sequencing

Tumour and buffy coat (germline) library preparation, sequencing and variant calling were performed as described by Varela et al.[26], using the SureSelectXT Human All Exon 50 Mb (Agilent) bait set or a custom targeted sequencing bait set. Eight samples were multiplexed per pool and each pool loaded on to two lanes of a HiSeq 2000 (Illumina), giving an average 8 Gb of unique mapped reads per sample with an average of 80% of base pairs covered by >20 reads. Targeted sequencing was carried out using the Sanger CGP Cancer Genes V3 panel for 365 genes relevant to cancer, as described previously[27]. For this exploratory analysis, all mutation calls from tumour sequencing were included in the TAPAS panel design (see Results). Loci were excluded if they showed 1 forward (F) and 1 reverse (R) non-reference read (following read de-duplication) in the buffy coat sample.

Tailored Panel Sequencing Library Preparation

TAPAS libraries from 10 patients were prepared in duplicate using the Rubicon ThruPLEX Tag-seq kit. The median input mass was 4.4 ng for plasma DNA libraries (IQR 3.2-10.0 ng). In order to compare error rates between molecularly barcoded libraries and non-molecularly barcoded libraries, additional plasma libraries were prepared using the Rubicon ThruPLEX Plasma-seq kit. cfDNA samples were vacuum concentrated at 30° C. using a Speed-Vac (ThemoFisher) prior to library preparation where required.

Based on the starting concentration of DNA in each sample, the number of PCR amplification cycles during the ThruPLEX protocol was varied between 7~15 cycles as recommended by the manufacturer[28]. Following amplification and sample barcoding, libraries were purified using Ampure XT beads (Beckman Coulter) at a 1:1 ratio. Library concentration was determined using the Illumina/ROX low Library Quantification kit (Roche) with two sample dilutions, in triplicate. 1:10 diluted libraries were run on Bioanalyser HS chip (Agilent) to determine library fragment size.

333-750 ng of each library was captured using the Agilent SureSelectXT protocol, with the addition of i5 and i7 blocking oligos (IDT) as recommended by the manufacturer[29]. Libraries were pooled for capture between 1 to 3-plex pools up to a maximum capture input of 1000 ng. 13 cycles were used for post-capture amplification. Post-capture libraries were purified with Ampure XT beads at a 1:1.8 ratio, then were quantified and library fragment size was determined as before. A median of 9 TAPAS libraries were pooled per lane of HiSeq 4000.

Sequence Data Processing and Error Suppression

FastQC v0.11.5 was run on all FASTQ files, then cutadapt v1.9.1 was used to remove known 5' and 3' adaptor sequences specified in a separate FASTA of adaptor sequences. Trimmed FASTQ files were aligned to the hg19 genome using BWA-mem v0.7.13 with a seed length of 19. Duplicates were marked using Picardtools v2.2.4 MarkDuplicates. BAM files were indexed using Samtools v1.3.1. Local realignment for known indels and base quality recalibration were carried out using GATK v3.7. Next, regions to be disregarded on the basis of having a high level of sequencing noise (also known as "blacklisted regions") identified by the ENCODE consortia were removed from BAM files.

Error Suppression

Error suppression was carried out on ThruPLEX Tag-seq library BAM files using Connor[30], which generates a consensus sequence between replicate sequencing reads based on fragment start and end position, and custom inline molecular barcodes. The consensus frequency threshold -f was set as 0.9, and the minimum family size threshold -s was set as 5 following analysis of error rates vs. proportion of data retained; read families below these thresholds were discarded. ThruPLEX Plasma-seq libraries were also used as input for Connor with the same settings using a custom shell script. This script adds a false barcode and stem to the appropriate end of each read, and modifies the CIGAR string.

Quality Filters

Samtools mpileup v1.3.1 was used at patient-specific loci to determine the number of mutant and wild-type reads/read-families for raw and error-suppressed data. The following settings were used: -d 10000 (maximum depth threshold) --ff UNMAP (exclude unmapped reads) -q 13 (minimum Phred mapping quality score) -Q 13 (minimum Phred base quality score) -x (ignore overlaps) -f ucsc.hg19.fasta. VCF Parser[31] v1.6--split was used to separate multi-allelic calls, and SnpSift extractFields was used to extract the columns of interest. For analysis of non-error-suppressed TAPAS data, a minimum of 5 reads were required at a locus; the threshold for error-suppressed data was a minimum of 1 read family (consisting of 5 members). Individual data points (i.e. a single locus in a single sample) were filtered if the mapping quality/strand bias (MQSB) at that locus, as determined by Samtools mpileup, was <0.01.

TAPAS Baseline Plasma Mutation Calling

TAPAS was applied to patients' first plasma time point in order to call variants in either the genes of interest that were tiled across, or in the bait regions either side of the patient-specific variants, that may have been missed from tumour exome sequencing alone. Mutect2 (GATK) was used for initial mutation calling, and was given the hg19 COSMIC database VCF, the dbSNP database VCF, the baitset BED file (including resistance loci and genes of interest). The matched buffy coat exome BAM was used as the germline sample.

Determination of Background Error Rates

To learn the background error rates, off-target bases from TAPAS data were used. Sequencing data from patients was used for this purpose, since germline events could be removed based on exome sequencing of buffy coats, and known tumour loci could be excluded. Thus, 10 bp either side of each patient-specific variant was used to determine the error rate for each class of SNV. We specified that non-reference bases had to be present in both the F and R read. To avoid possible biological contamination of error-rates, loci were excluded if they had ≥1 overlapping mutations in COSMIC. In addition, following error suppression, each locus was assessed individually in all the samples belonging to the same patient, and if a locus showed mutant error-suppressed families in ≥3 separate libraries, it was disregarded from further analysis. Given a background error rate per read family of ~6×10⁻⁵, the probability of observing mutant read families at a single locus in ≥3 samples (out of a median of 6 samples per patient) from the same individual by chance, with an average of 200 read families per locus, gives a binomial probability of ~1×10⁻¹².

This analysis was carried out to determine the background error rates regardless of mutation class, and by splitting data by mutation class. The error rate was determined by taking the ratio between the sum of mutant reads in a class and the total number of reads in a class. This data was resampled 100 times with replacement to obtain 95% confidence intervals of the error rate.

Integration of Variant Reads

Detection of ctDNA was carried out for patient-specific loci only, i.e. if a C>T mutation was expected based on tumour genotyping, but a C>A was observed, then the mutant reads were ignored and did not contribute to the patient-specific signal. Furthermore, loci were only considered as contributing to signal if there was at least ≥1 F and ≥1 R read family at that position. This has two advantages: to reduce single-stranded artefacts from sequencing, and to bias detection towards short fragments which have greater overlap between F and R reads using PE150 sequencing.

For each sample, the mutant allele fraction was calculated across all patient-specific loci as follows:

$$\frac{\sum_{loci} (\text{mutant reads})_{patient\ specific}}{\sum_{loci} (\text{total reads})_{patient\ specific}}$$

The significance of the observed number of mutant reads was determined using a one-sided Fisher's exact test, given a contingency table with the number of mutant reads and total reads for both the sample of interest, and from the background error rate.

Detection by Class

Since differences in error rates were observed between SNV classes, each sample was split into 12 based on the mutation class expected at that locus from tumour sequencing. Variant reads were integrated for each class, as above. Multiple one-sided Fisher's exact tests were used to determine the significance of the number of mutant read families observed given the background error rate for that mutation class. This generated 12 P-values per sample, which were then combined using the Empirical Brown's method, which is an extension of Fisher's method that can be used to combine dependent P-values[16]. If a sample had no data in a class, that class was treated as having zero mutant reads and thus a P-value of 1. To improve specificity of this approach further, we required samples to have mutant reads in ≥2 separate classes; this was in order to ensure that detection was based on signal being present in multiple loci subject to different types of error processes.

Significance Threshold Determination

All patients were sequenced with the same sequencing panel, and since 99.9% of the variants were private to each patient (i.e. unique to that individual only), all other patients could be used to determine the false positive for ctDNA detection and thus set the P-value threshold for the cohort. This approach leverages the redundant sequencing performed, and utilises the multiple samples sequenced from each individual to exclude germline variants. As such, TAPAS data was split into patient-specific and non-patient-specific based on whether each locus was mutated in the patient's tumour. Non-patient-specific data was used for determining significance thresholds.

To use patients as controls, the technical noise should be separated from any true biological signal that may be detected in plasma but was missed in the tumour. Therefore, using error-suppressed non-patient-specific data, loci were disregarded from further analysis ("blacklisted") if they contained mutant read families in ≥3 separate libraries from the same individual, which we calculated to be sufficiently unlikely to be observed to warrant ignoring these loci (P=1×10⁻¹², see Determination of background error rates). As a result, 44 loci out of 12,558 (0.35%) were disregarded from further analysis ("blacklisted"). Although imperfect tumour and buffy coat genotyping of patients may result in residual biological signal in control samples, this was preferable to the cost of sequencing many control samples with the same panel and discarding non-patient-specific data.

The significance threshold for combined P-values obtained by INVAR was determined using Receiver Operating Characteristic analysis on patient-specific (test) and non-patient-specific (control) samples using the Optimal-Cutpoints package in R, with the 'MaxEfficiency' method, which maximises classification accuracy.

Experimental Spike-In Dilution for Sensitivity
3.7 ng Spike-In Dilution Experiment Plasma cfDNA was obtained from one healthy individual (Seralab), and mutant cfDNA was obtained from one patient at a high tumour burden time point (MR1004; 2,746 patient-specific mutations). The cfDNA concentrations of the eluates were equalised using water, then the patient's sample was serially diluted by healthy cfDNA in a 1:5 ratio to give a final 15,625× dilution of the original cfDNA eluate. Library preparation was carried out in duplicate using the ThruPLEX Plasma-seq kit with 3.7 ng input for all libraries.
50 ng Spike-In Dilution Experiment Equal masses of plasma cfDNA from 6 patients were pooled to produce a hypothetical patient with a total of 9,636 patient-specific variants. A pool of plasma cfDNA was generated from 11 healthy individuals (Seralab). The cfDNA concentrations of the patient sample and healthy pool were equalised using water, then the patient sample was serially diluted by healthy cfDNA in a 1:10 ratio to give a 100,000× dilution of the original 1× pooled sample. Library preparation was carried out with the ThruPLEX Tag-seq kit, in duplicate, with input amounts of up to 50 ng per library. For libraries with an expected allele fraction greater than the limit of detection of TAPAS without error suppression, we reduced the input material into library preparation to conserve patient plasma DNA where it was certain to be detected.
In Silico Downsampling of Mutations To test the limit of detection of INVAR-TAPAS with varying numbers of mutations, both the patient-specific mixture experiment and all non-patient-specific data were downsampled to between 50-5,000 mutations. BRAF was always included in each set of sampled mutations to simulate a panel design for BRAF$^{mut}$ patients. Mutations were sampled iteratively 100 times, and detection of ctDNA was tested using INVAR.
Background-Subtraction for ctDNA Quantification To accurately determine mutant allele fractions down to parts per million, background error rates were subtracted from the observed allele fraction. This can be performed with or without taking into account differences in error rate by class. If the observed mutant allele fraction was less than the background error rate, then the background-subtracted allele fraction was set at zero.

For background subtraction by mutation class for a sample, the error rate of each of the 12 classes was subtracted from the mutant allele fraction of that class. A mean allele fraction was then calculated from each of the individual background-subtracted allele fractions, weighted by the total number of read families observed in that class.
De Novo Mutation Detection Variants removed by blacklisting (i.e. filtered out on the basis of having a higher locus-specific error rate as described above) were previously excluded on the basis of showing evidence for being biological signal. We attempted to call mutations from this blacklist for variants that were known mutations. Therefore, the data were intersected with the COSMIC database for known driver mutations (number of overlapping mutations ≥5). For each mutation locus, the background error rate for that locus was determined using non-patient-specific data (i.e. patients whose tumours had been genotyped as negative for that mutation). A one-tailed Fisher's exact test was used to test the significance of the number of mutant reads in the sample given the total depth in that sample, and the mutant reads and total depth in the background. The P-value threshold was set as 0.05 and corrected for multiple hypotheses by the Bonferroni method.

Individual mutation calls were confirmed by aggregating mutant reads across multiple, temporally-separated samples.

Example 1—Identification of Patient-Specific Mutations from Tumour And Plasma

Figure 7:
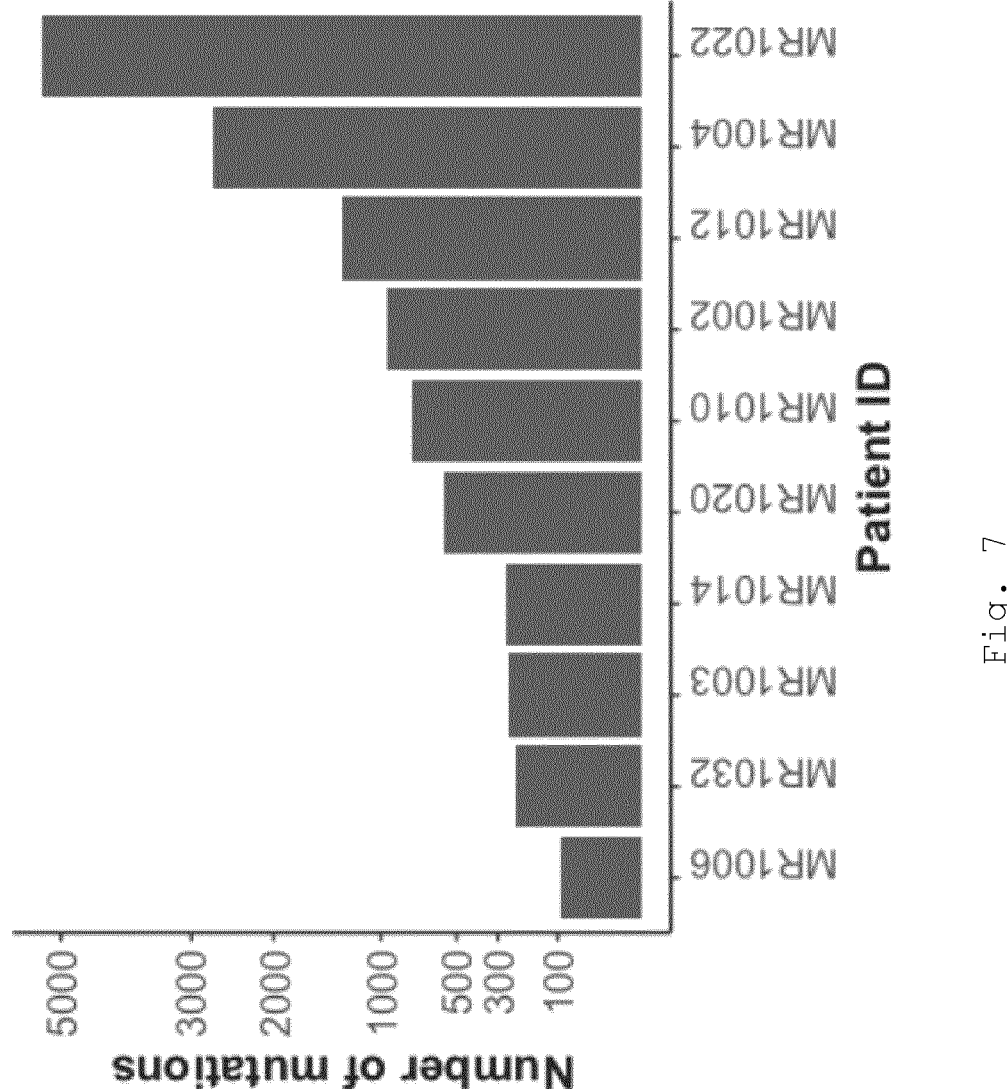
FIG. 7 shows integration of signal across multiple mutations. (a) The number of mutations identified per exome per patient is shown. (b) For one example plasma sample with high levels of ctDNA, the allele fraction of each patient-specific locus is shown. The y-axis has been limited to 100. Mutant reads can be aggregated across all loci to give a depth-weighted average mutant allele fraction; this integrated mutant allele fraction is indicated with a vertical dashed line in red (labelled "Average").
Figure 7:
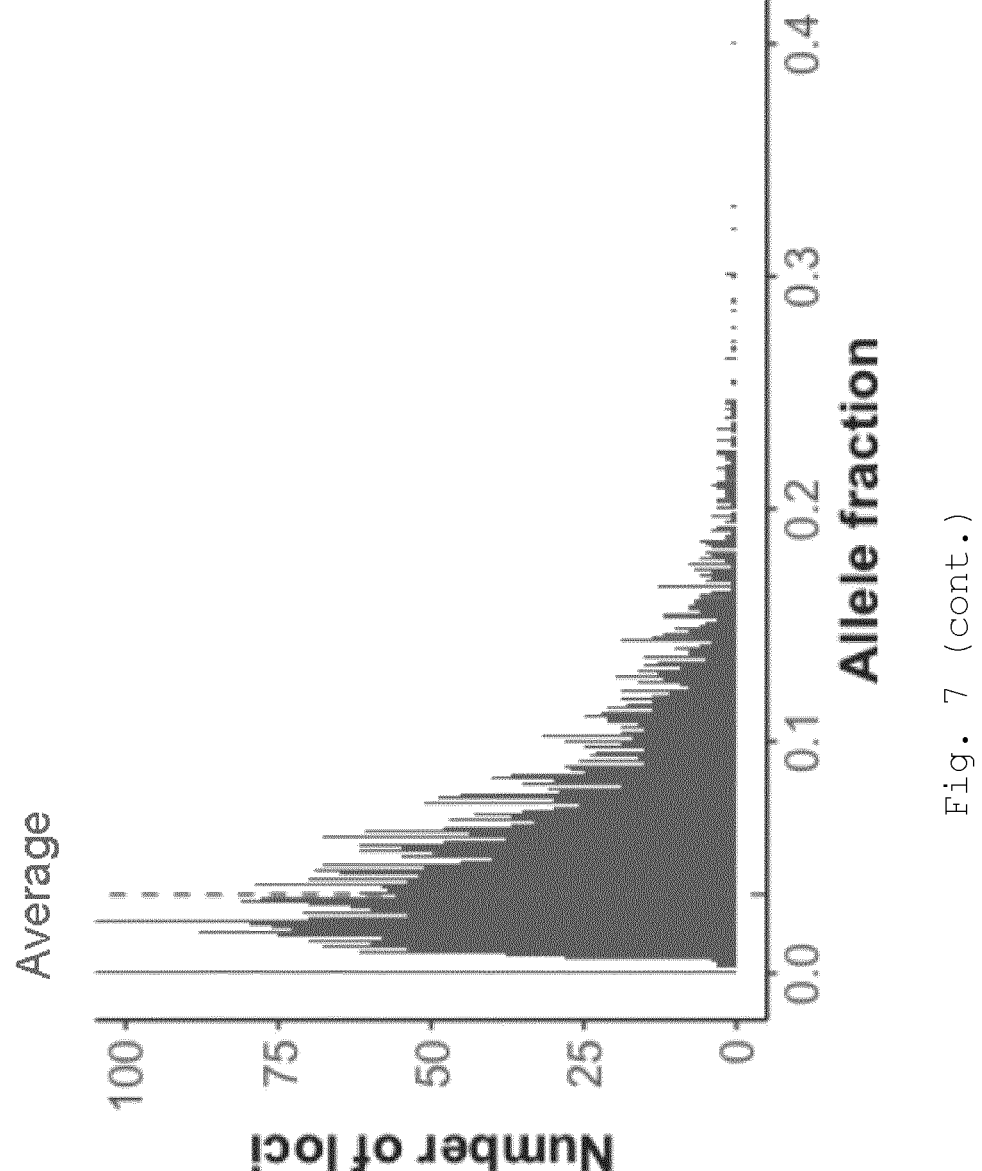

To achieve high sequencing depth at defined loci that were mutated in the patients' tumours, a tailored hybrid-capture sequencing panel was designed based on single nucleotide variants (SNVs) identified in sequencing of tumour biopsies. SNVs with ≥1 mutant read and ≥10 total reads were selected from exome sequencing (9 patients) or targeted sequencing (1 patient) of a baseline metastatic biopsy. The median number of SNVs identified per patient was 673 (IQR 250-1,209; FIG. 7a). Patient-specific variants were determined (not shown). In addition, in order to allow de novo identification of mutations in plasma, coding sequences and untranslated regions of the following genes were included in the panel design: ARID2, BRAF, CDKN2A, NF1, PTEN and TP53, as well as hotspot loci in 37 additional genes commonly mutated in melanoma (not shown). The final panel design covered 1.527 Mbp.

The finalised bait set was applied to libraries generated in duplicate from serially collected plasma cfDNA samples, collected over two years (maximum 8 samples per patient). DNA was extracted from 2 mL of plasma, and the median input mass was 4.4 ng for plasma DNA libraries (IQR 3.2-10.0 ng). A median of 9 TAPAS libraries (IQR 8-12) were pooled per lane of HiSeq 4000 (PE150). For each of the patient-specific loci, the median depth of quality-filtered reads (Methods) was 1,367× for each sample (IQR 761-1, 886×).

To identify additional mutations covered by the panel that may have been missed by tumour sequencing, an additional mutation calling step was performed on the first plasma time point, pre- or on starting drug treatment, when ctDNA levels were expected to be higher. Plasma mutation calling added a median of 19 SNVs mutations per patient (IQR 9-22; not shown) for subsequent analysis, giving a total of 12,558 patient-specific SNVs across the cohort. The observed rate of de novo identification of SNVs in our cohort was in line with the estimate of 14.4 coding mutations per Mb in melanoma (IQR=8.0-24.9) reported previouslyl0. The BRAF V600E mutation was found in 9 out of 10 patients, and a further 18 mutations were shared between any two patients. Overall, 99.9% of the targeted mutated loci were unique to an individual patient.

Example 2—Characterisation of Background Error Rates

We sought to learn the background error rates (i.e. the rate of observing a mutant base that was not expected) with and without error suppression in TAPAS sequencing data. Bases either side of patient-specific variants were studied as they would have a comparable sequencing depth to patient-specific variants, and would be subject to the same technical biases. In order to leverage this off-target sequencing of patient samples, germline events and potential biological signals were excluded if they occurred multiple times in samples from the same individual (Methods); these loci were set aside for subsequent de novo mutation calling.

Figure 2:
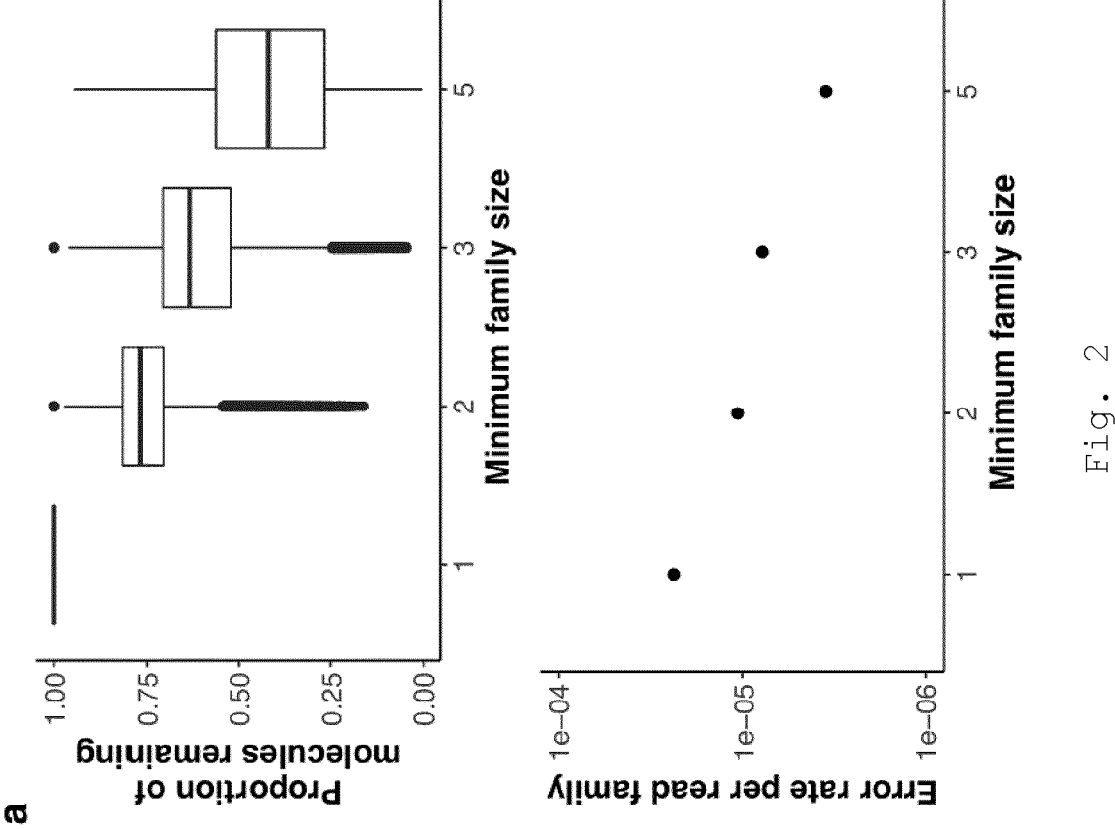
FIG. 2 shows observed error rates following error suppression. (a) Box plots showing the proportion of molecules remaining following error suppression by read-collapsing read families with a minimum family size requirement of between 1 and 5 read families (upper panel). For each family size threshold, the error rate per read family is shown (lower panel). Off-target (but on-bait) sequencing reads 10 bp either side of targeted variants were used to determine the error rate. (b) Non-error-suppressed (blue; upper) and error-suppressed (red; lower) error rates, with minimum family size of 5, for sequence alterations split into 12 mutation classes. In order to characterise the spread of the data around the medians shown, the data were resampled, or "bootstrapped", whereby multiple samples are repeatedly taken from the data to characterise it. In this case, data were bootstrapped 100 times, and 95% confidence intervals are shown.
Figure 2:
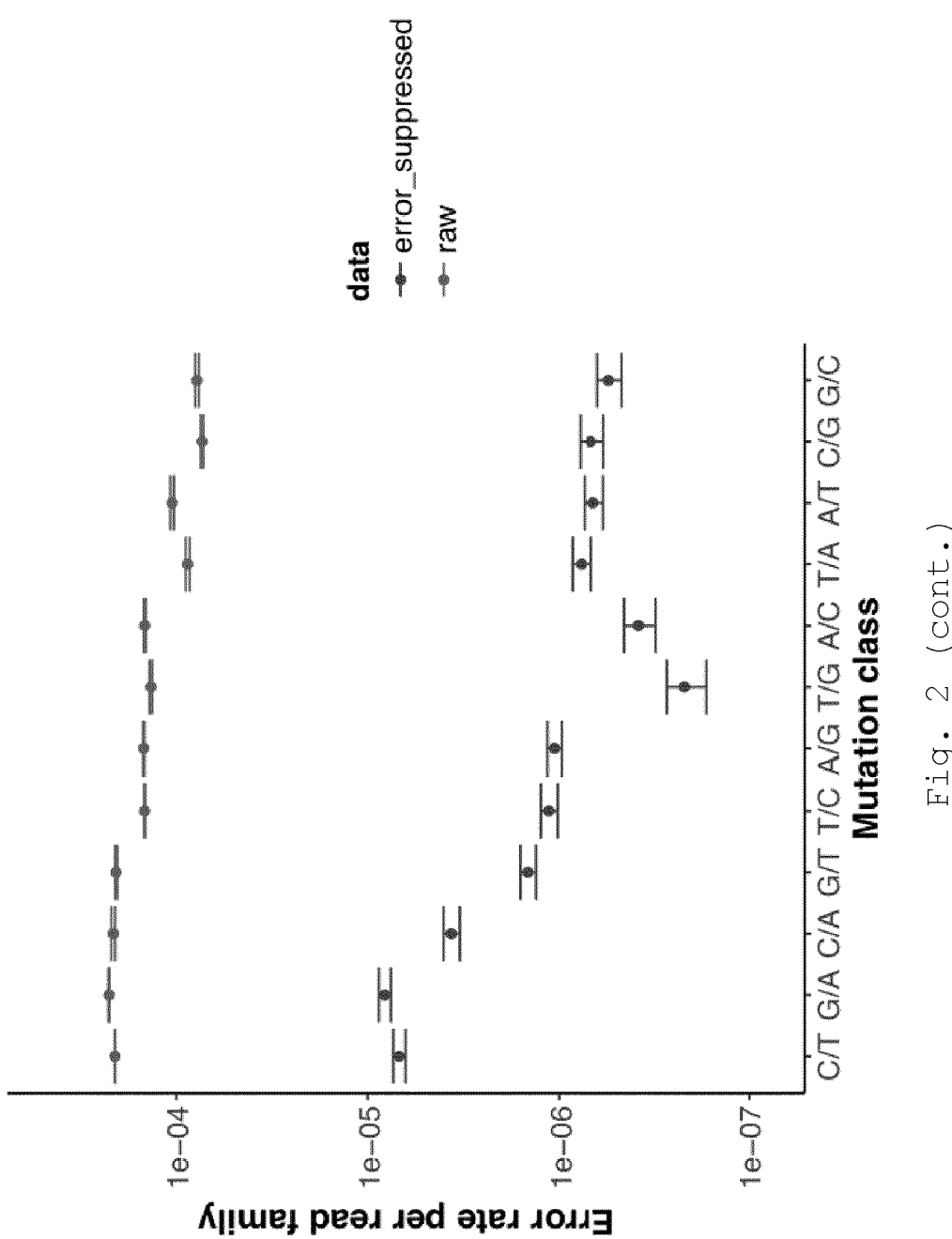

Error suppression can be achieved by determining the consensus sequence across a read family using read collapsing. To achieve this, duplicate reads were grouped into 'read families' based on both start and end fragment positions, previously termed 'endogenous barcodes'[11,12], and molecular barcodes. Read families were collapsed, and a minimum requirement was set at ≥90% consensus between all family members for a base to be called. Without error suppression, the average background error rate was $2 \times 10^{-4}$. Prior to applying error suppression, we determined the optimal minimum number of duplicates per read family ('family size'). The proportion of read families retained and corresponding error rates for data with minimum family size requirements of 1, 2, 3 and 5 are shown in FIG. 2a. A minimum family size threshold of 1, which contains read-collapsed families of size >1 plus families of size=1 that were not collapsed, reduced the error rate to $2.3 \times 10^{-5}$. A minimum family size requirement of 5 was selected, which reduced the background error rate further to $5.9 \times 10^{-6}$ while retaining 42% of read families. Less stringent criteria on family size would retain more reads, but with increased sequencing noise.

Example 3—Integration of Variant Reads (INVAR)

Using a stringent level of error suppression (consensus required in 90% of family members, with a minimum family size of 5), with a median of 4.4 ng input, we obtained a median of $3.2 \times 10^5$ read families at each time point (IQR $8.7 \times 10^4 - 6.2 \times 10^5$), each of which cover a locus that is mutated in that patient's cancer. Under the assumption that each such read family corresponds to a single molecule, we were thus able to probe for each sample hundreds of thousands of target molecules even though the starting material contained only ~1300 copies of the genome.

Figure 1:
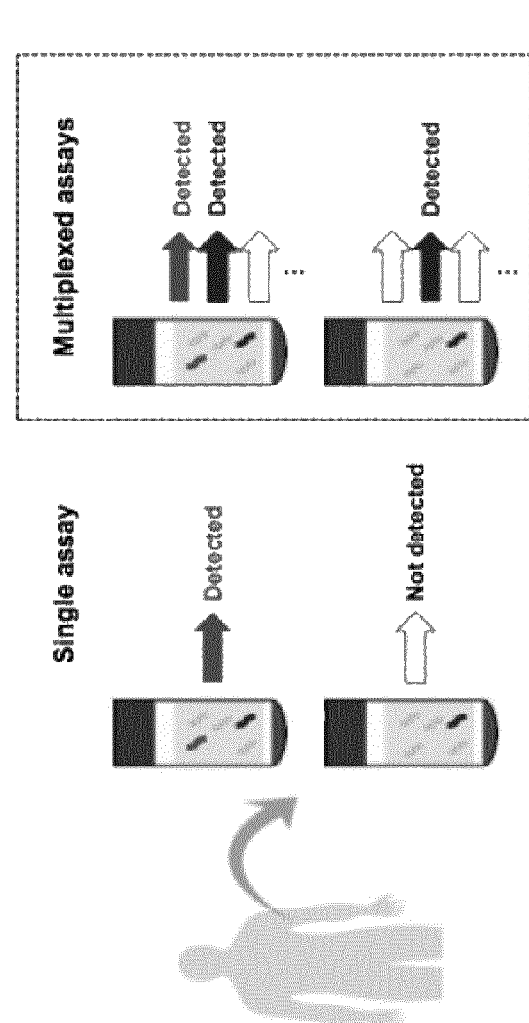
FIG. 1 depicts the rationale and outline of INtegration of VAriant Reads and TAilored PAnel Sequencing. (a) Even with perfect analytical performance, a single-locus assay can fail to detect low ctDNA levels due to random sampling. This can be overcome by using multiplexed assays on the same samples. The table indicates the number of fragments interrogated with varying levels of input material and mutations targeted: 1,000 mutation loci interrogated in 1,000 input genomes leads to $10^6$ molecules that are sampled. (b) To overcome sampling error, we integrate signal across hundreds to thousands of mutations, and classify samples (rather than mutations) as significantly positive for ctDNA, or non-detected. Sequencing reads in plasma overlying known tumour-genotyped loci are termed 'patient-specific' reads, whereas adjacent loci as well as the same loci assessed in other patients can be used to estimate the background noise rate. (c) As described herein, tumour sequencing was first carried out, enabling the design of patient-specific hybrid-capture baits. These were used to capture cell-free DNA and sequence a median of 673 loci in plasma (range 90-5,312), achieving a median quality-filtered depth of 1,367× per SNV locus in each sample (IQR 761-1,886x).
Figure 1:
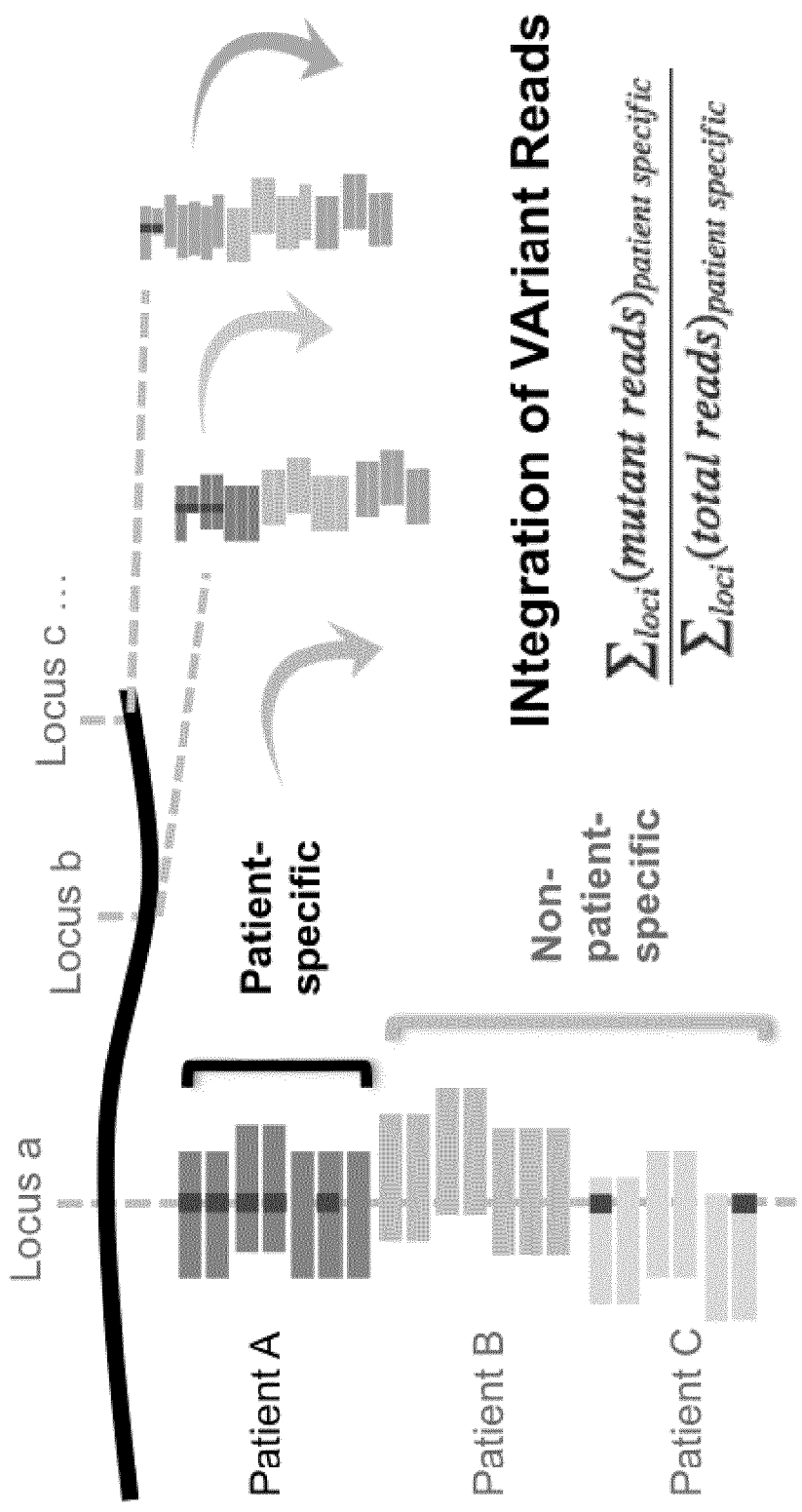
Figure 1:
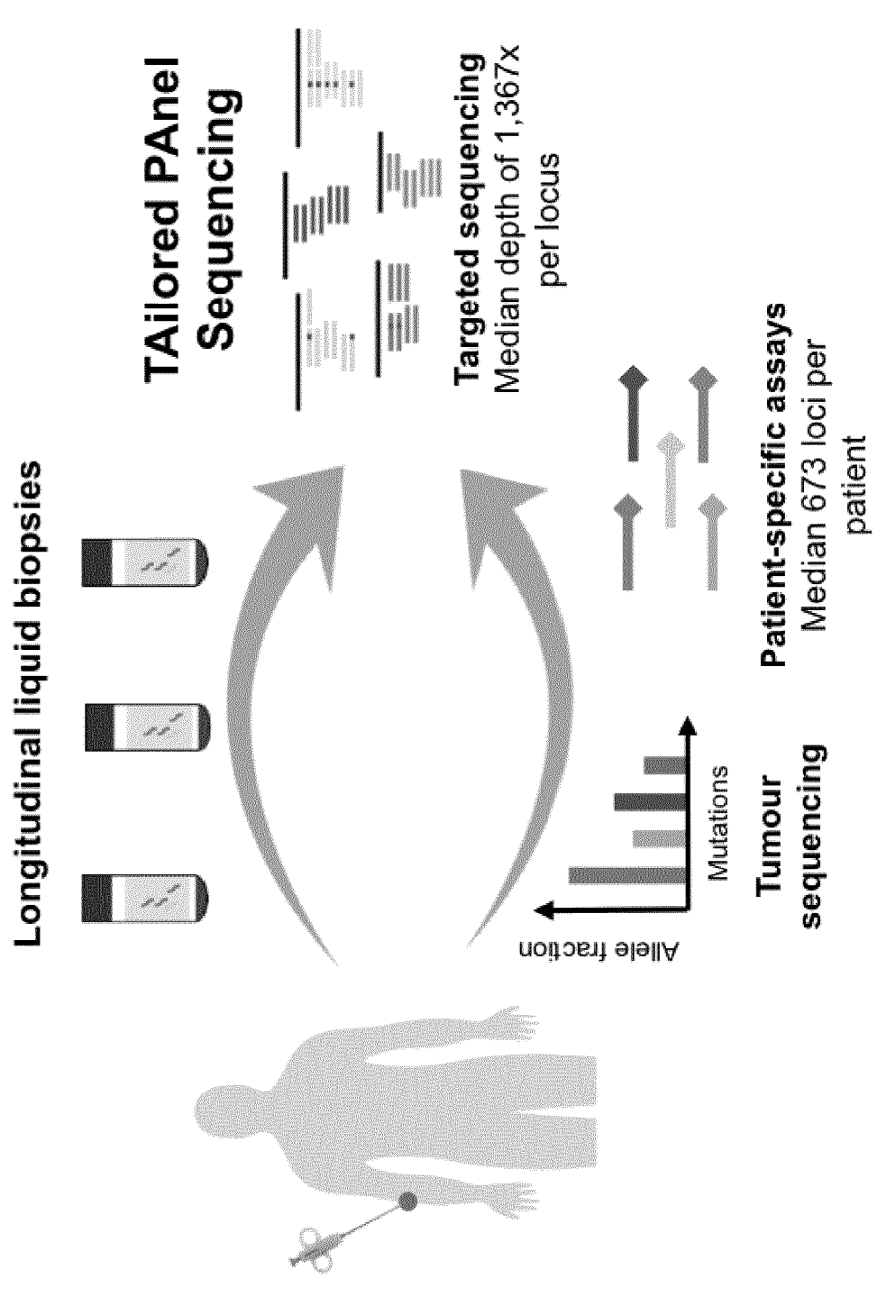

When ctDNA levels are low, many patient-specific loci will have no mutant DNA fragments at that position (FIG. 7b). Therefore, to overcome sampling error, all patient-specific read-families were aggregated and analysed together using INVAR (FIG. 1b). For each sample, a 'global' mutant allele fraction was calculated across all patient-specific loci as follows:

$$\frac{\sum_{loci} (\text{mutant reads})_{patient\ specific}}{\sum_{loci} (\text{total reads})_{patient\ specific}}$$

The significance of the observed number of mutant reads was determined using a one-sided Fisher's exact test, given a contingency table with the number of mutant reads and total reads for both the sample of interest, and from the background error rate. Mutant reads were only considered as contributing to signal at a locus if there was at least one forward (F) and one reverse (R) read from PE150 sequencing data; this may suppresses sequencing artefacts, and also biases towards data from short cfDNA fragments (covered by reads in both direction) which are enriched in ctDNA[13-15].

Based on known differences in error rate between base substitutions in hybrid-capture sequencing[7], we assessed error rates in TAPAS data by mutation class using INVAR. Data were split into 12 classes (C>G, G>C, T>G, A>C, C>A, G>T, T>C, A>G, T>A, A>T, C>T, T>C), which showed differences in error rate by class both before and after error suppression (FIG. 2b). We identified nearly 40-fold difference in error rate between the noisiest and least noisy classes. These data suggested the possibility of utilising low-error rate mutation classes to overcome technical noise and improve sensitivity for low levels of ctDNA.

We developed an algorithm to detect ctDNA based on splitting the read families from each sample into the 12 classes; a P-value was derived for each error class separately using Fisher's Exact Test, and P-values were combined using the Empirical Brown's method, an extension of Fisher's method that can be used to combine dependent P-values[16] (Methods). To increase specificity of this approach further, we specified that mutant signal must be present in at least two mutation classes, thereby reducing the reliance of detection on an individual noisy locus or class.

All patients were sequenced with the same sequencing panel, and since 99.9% of the variants were unique to each patient, all other patients could be used to determine the false positive for ctDNA detection and thus set the P-value threshold for the cohort for each detection algorithm. This approach leverages the redundant sequencing performed that would otherwise be discarded, and utilises the multiple samples sequenced from each individual to exclude germline variants (Methods). As such, sequencing data was split into 'patient-specific' and 'non-patient-specific' based on whether the locus was mutated in the patient's tumour. Significance thresholds for detection were determined empirically, using Receiver Operating Characteristic (ROC) analysis on patient-specific (test) and non-patient-specific (controls) samples using the OptimalCutpoints package in R, which maximises classification accuracy. In accordance with the present invention, either ROC analysis can be used to identify an optimal threshold based on maximising both sensitivity and specificity, or specificity can be fixed at a certain level, e.g. 99.5%, and the sensitivity interrogated.

Example 4—Sensitivity Analysis of INVAR-TAPAS

Figure 8:
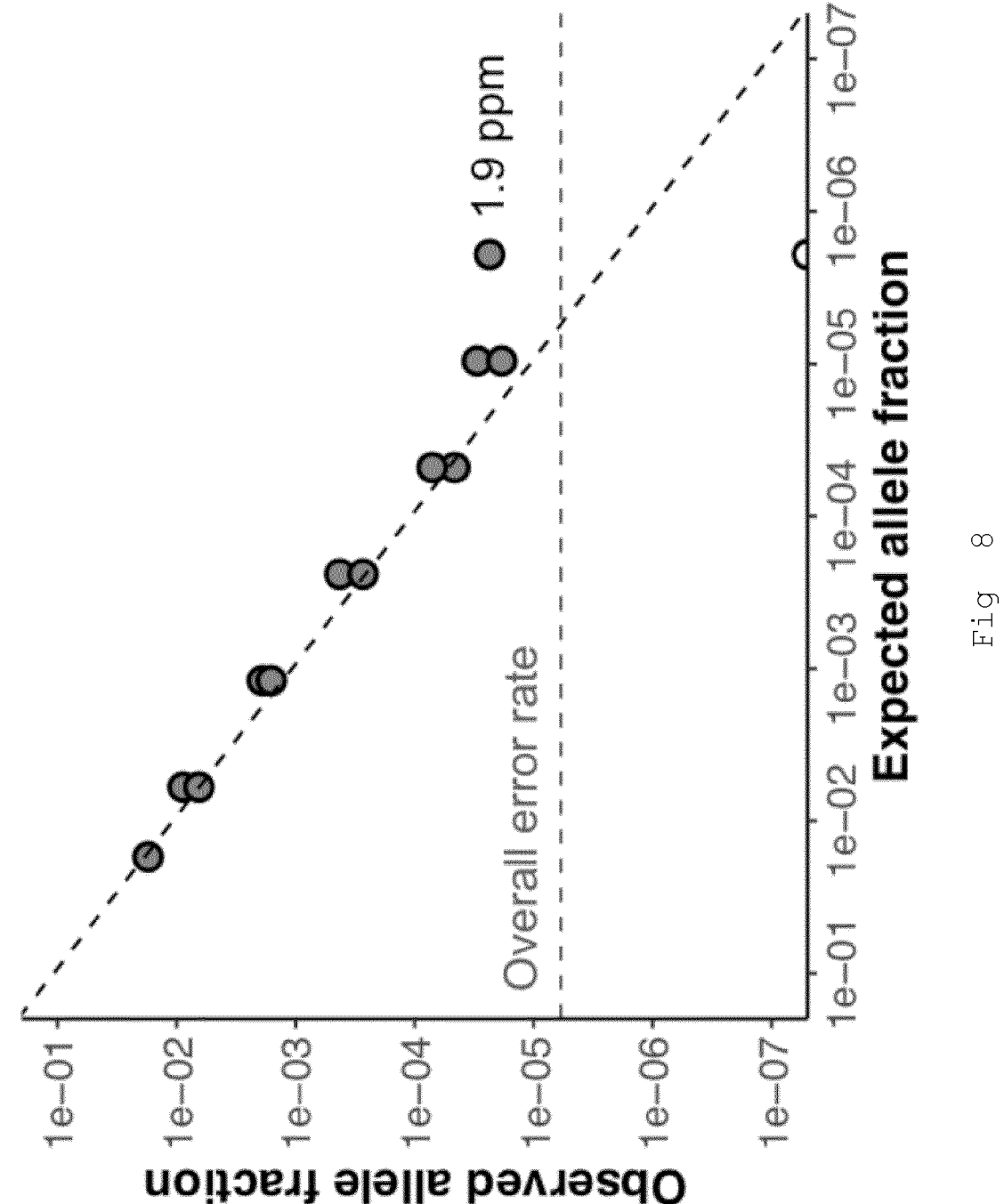
FIG. 8 shows a plot of expected vs. observed allele fraction for an empirical spike-in dilution experiment with error suppression (3.7 ng input), without splitting data into mutation classes. Filled circles indicate significant detection of ctDNA using INVAR. The overall background error rate for error suppressed data is shown (red horizontal line, dashed).

To assess the sensitivity of INVAR-TAPAS, a spike-in dilution experiment was generated in duplicate with 3.7 ng per library using plasma DNA from a patient for whom 2,743 mutations were covered in the TAPAS panel. Using error suppression with endogenous barcodes, we first applied INVAR without splitting reads into mutation classes, and detected a sample with an expected mutant allele fraction of $1.9 \times 10^{-6}$ (FIG. 8). Thus, detection of individual parts per million (ppm) was achieved. A perfect single-locus assay with this same input (approximately 1, 100 haploid genomes) would have a limit of detection (with 95% sensitivity) of $2.7 \times 10^{-3}$ mutant allele fraction, three orders of magnitude higher. The detected sample that had an expected mutant allele fraction of 1.9 ppm had an observed mutant allele fraction of 27 ppm. Since observed allele fractions are composed of background error rate (6 ppm) plus true signal, the background error rate was subtracted from the observed allele fraction, giving a 'background-subtracted' allele fraction of 22 ppm, approximately one order of magnitude greater than the expected mutant allele fraction. At low levels of input, both sequencing noise and sampling error can still hamper accurate quantification.

Figure 3:
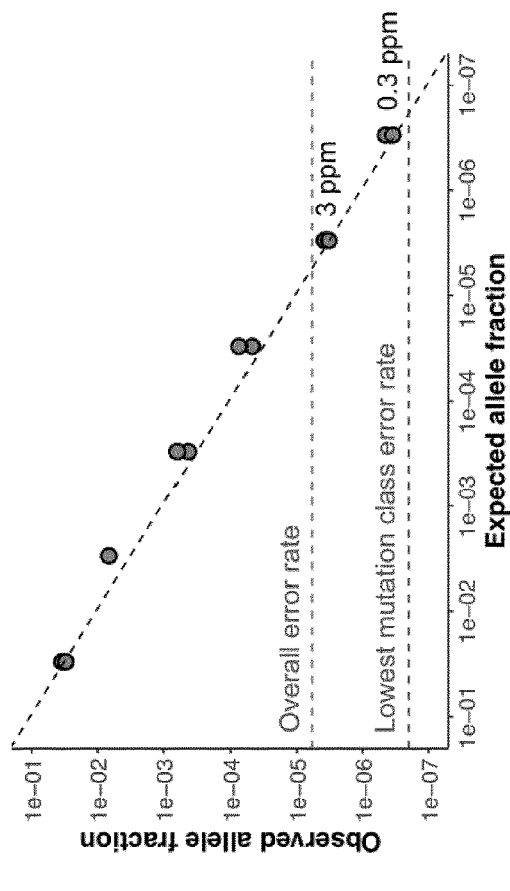
FIG. 3 shows an analysis of sensitivity of INVAR and detection by class (a) Plot of expected vs. observed allele fraction for a spike-in dilution experiment with error suppression (50 ng input), without splitting data into mutation classes. Filled circles indicate significant detection of ctDNA using INVAR. The overall background error rate for error-suppressed data is shown (red horizontal line, dashed). (b) The same spike-in dilution is shown with detection using INVAR and splitting data by mutation class. The overall background error rate and the error rate of the least noisy mutation class are shown (red horizontal lines, dashed). Background subtraction was performed by class. Significant detection was achieved to 0.3 ppm. (c) The number of loci analysed was downsampled in silico, testing between to 50 and 5,000 mutations (methods). The sensitivity is shown for samples with mutant DNA diluted to different levels (indicated). With 2,500 mutations, diluted ctDNA was detected at 0.3 ppm with ~50% sensitivity. (d) The specificity was assessed for different numbers of mutations using non-patient-specific data to assess false positive detection rates. With 2,500 mutations, the false positive rate was less than 1 in 200.
Figure 3:
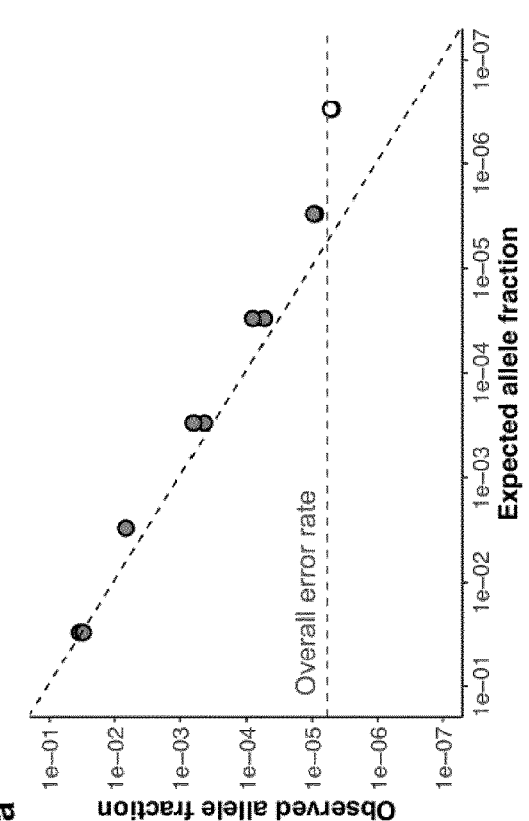
Figure 3:
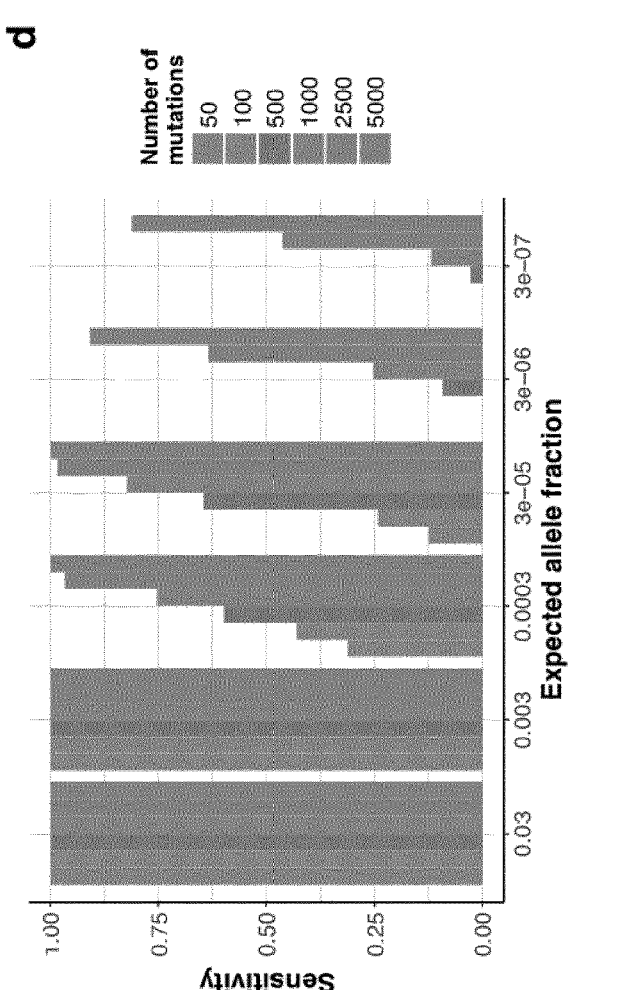

Next, a second spike-in dilution experiment was made in duplicate with up to 50 ng input cfDNA, and molecular barcodes were used. For this experiment, DNA was pooled from 6 patients, and serially diluted in healthy individual DNA (Methods). The patients' cfDNA pool comprised a total of 9,636 patient-specific mutations. 50 ng input DNA corresponds to the cfDNA in 3.0 mL plasma from this cohort (median cfDNA concentration 5,160 copies/mL). Using INVAR without analysis by class, we detected the expected 3 ppm mutant allele fraction spike-in sample, at an observed allele fraction of 9 ppm (FIG. 3a). Following background-subtraction as before, the sample had an observed mutant allele fraction of 3.3 ppm (expected mutant allele fraction of 3.0 ppm). This highlights that for quantification of allele fractions approaching the background error rate, it becomes increasingly important to subtract background error, as the background will comprise an increasing proportion of the signal.

INVAR was then applied by splitting samples into 12 mutation classes, as described above. By leveraging differences in error rate between mutation classes, significant detection was achieved down to 0.3 ppm (FIG. 3b). This detection limit is two orders of magnitude lower than previous capture sequencing methods[1], and also 2-3 orders of magnitude lower than the limit of detection (with 95% sensitivity) for a perfect single-locus assay with the same library input mass (50 ng, equivalent to 15,000 genome copies). As before, background-subtraction was performed, except that subtraction was carried out by class, then combined by taking a depth-weighted average. We observed a background-subtracted allele fraction of 0.4 ppm for the 0.3 ppm expected spike-in dilution, demonstrating a high degree of linearity for ctDNA quantification down to parts per million.

To test the sensitivity of this approach with a smaller panel design, a subset of between 50 and 5,000 mutations were randomly sampled in silico alongside the BRAF V600 locus, and detection of ctDNA using INVAR by mutation class was repeated iteratively (Methods). BRAF V600 was included in each sampled panel to simulate a panel design for BRAF$^{mut}$ patients. The sensitivity achieved for each number of mutations is shown in FIG. 3c; with 2500 mutations, 0.3 ppm could be detected with nearly 50% sensitivity. We empirically determined the specificity of this approach as 99.6% for 2,500 mutations (FIG. 3d).

Example 5—in Silico Size Selection

Figure 9:
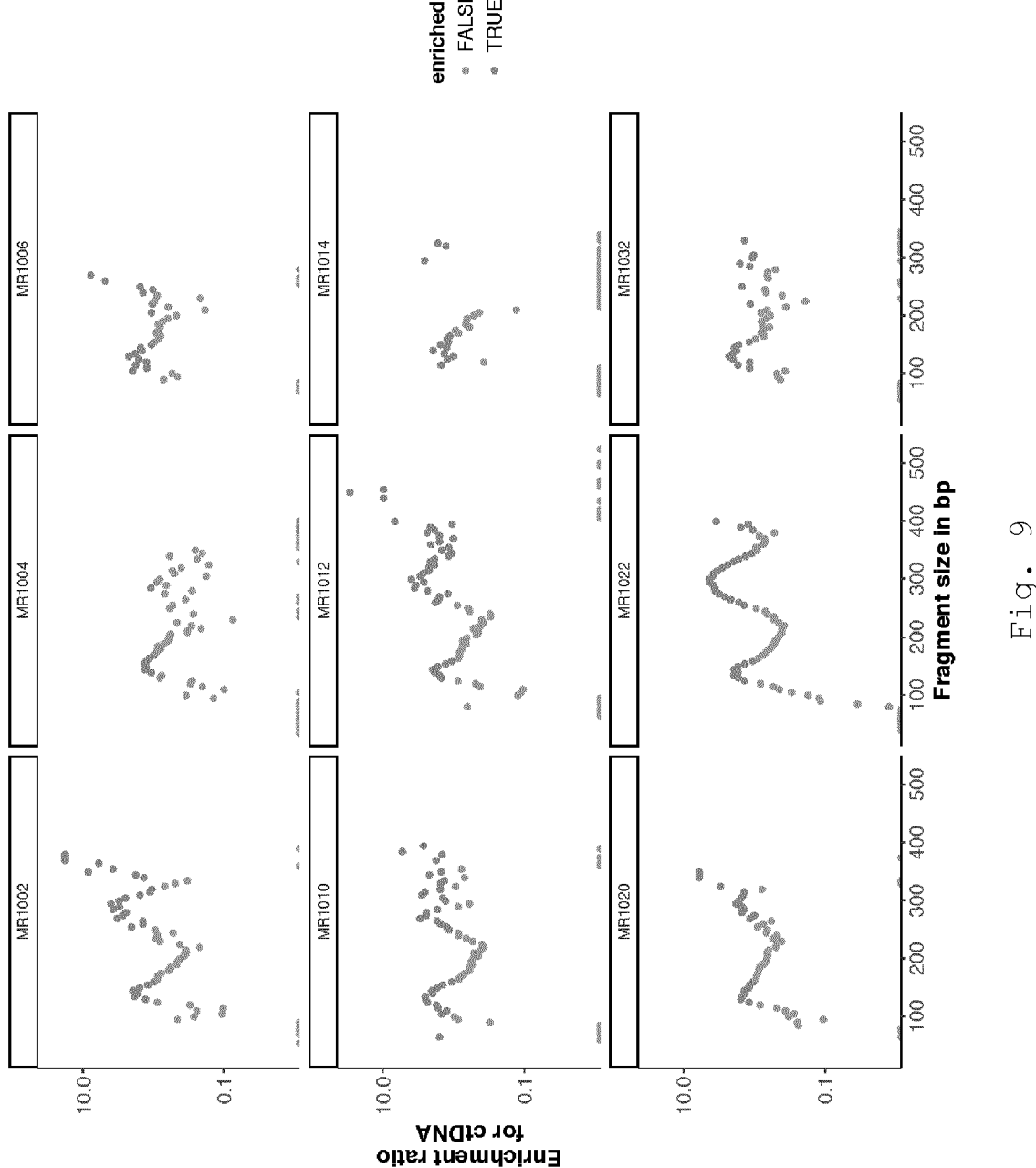
FIG. 9 shows enrichment ratios for ctDNA per patient. For each patient, mutant and wild-type reads were aggregated across all of their plasma samples from error-suppressed data. For each 5 bp bin, the ratio between the proportions of mutant vs. wild-type fragments is shown. Bins with an enrichment ratio >1 are coloured in blue.

The start and end positions of the reads were used to determine fragment size distributions. Error-suppressed data from all plasma samples were combined, and the distribution of fragments was calculated (FIG. 4a). For each 5 bp size bin, the ratio between the proportion of mutant and wild-type was determined (FIG. 4b). Enrichment for ctDNA was observed in fragments ~20-30 bp shorter than nucleosomal DNA sizes (multiples of 166 bp). The magnitude of enrichment was greater in the di-nucleosomal peak than the mono-nucleosomal peak. One patient showed evidence for mutant tri-nucleosomal DNA (FIG. 9). While previous data have demonstrated that mutant fragments are shorter than wild-type fragments[13,14,17], these data indicate that mutant DNA is consistently shorter than mono-, di- and tri-nucleosomal DNA.

Figure 4:
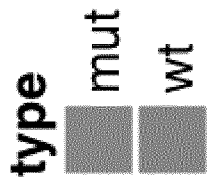
FIG. 4 shows size profiles of tumour-derived and wild-type DNA fragments in plasma. (a) Error-suppressed read families at patient-specific loci were split into mutant and wild-type families. The proportions of mutant reads in bins of 5 bp are shown in red, and wild-type reads are shown in blue. (b) For each bin, the ratio between normalised mutant to wild-type reads was determined as an enrichment ratio. Enrichment maxima were observed at ~140 bp and ~300 bp, approximately corresponding to nucleosomal DNA minus a length of linker DNA. Bins that were enriched are coloured in blue. (c) For each sample that was in silico size-selected based on enriched bins in (b), the percentage enrichment of mutant allele fraction is shown. Samples that were enriched are coloured in blue. An exponential curve was fitted to the data.
Figure 4:
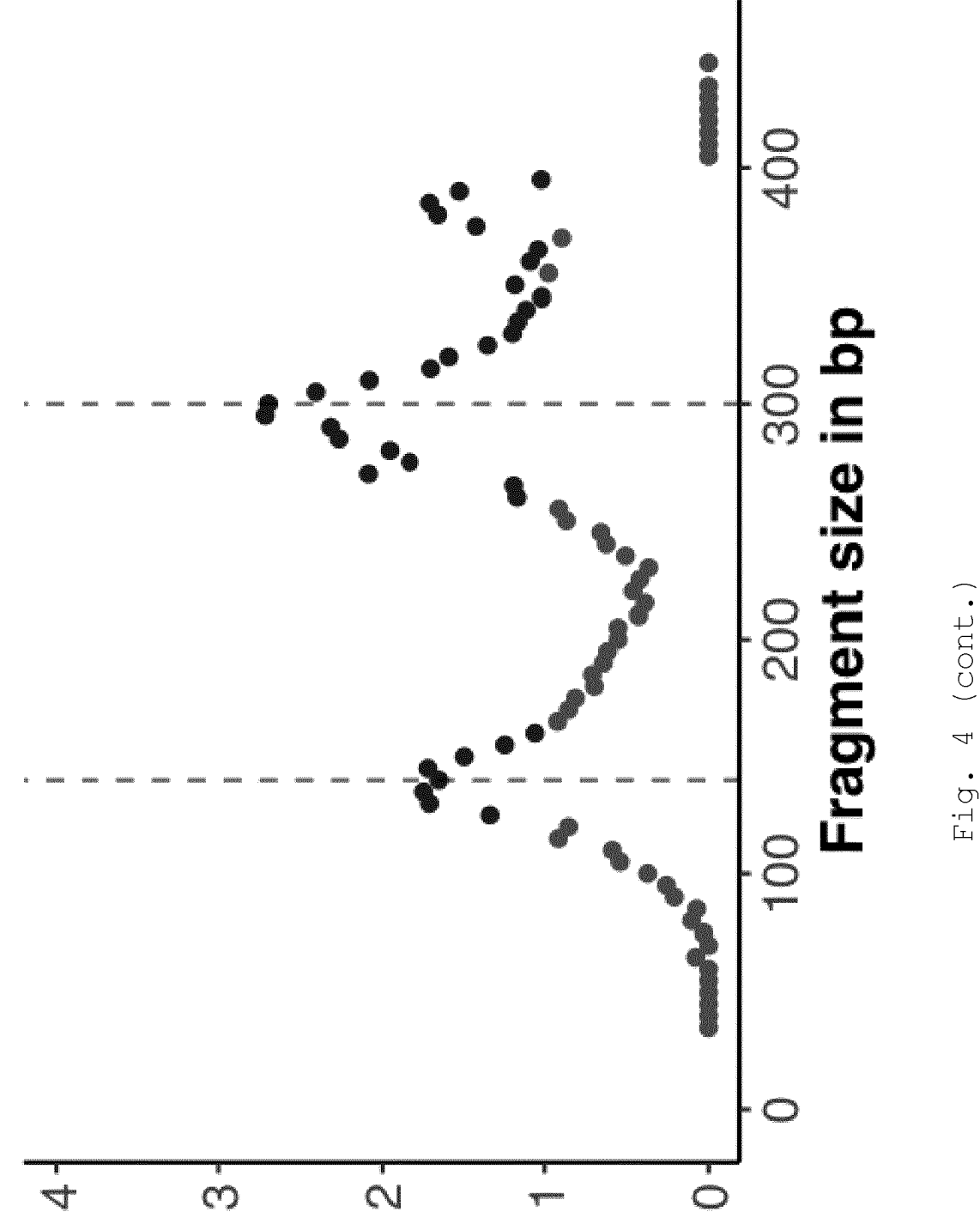
Figure 4:
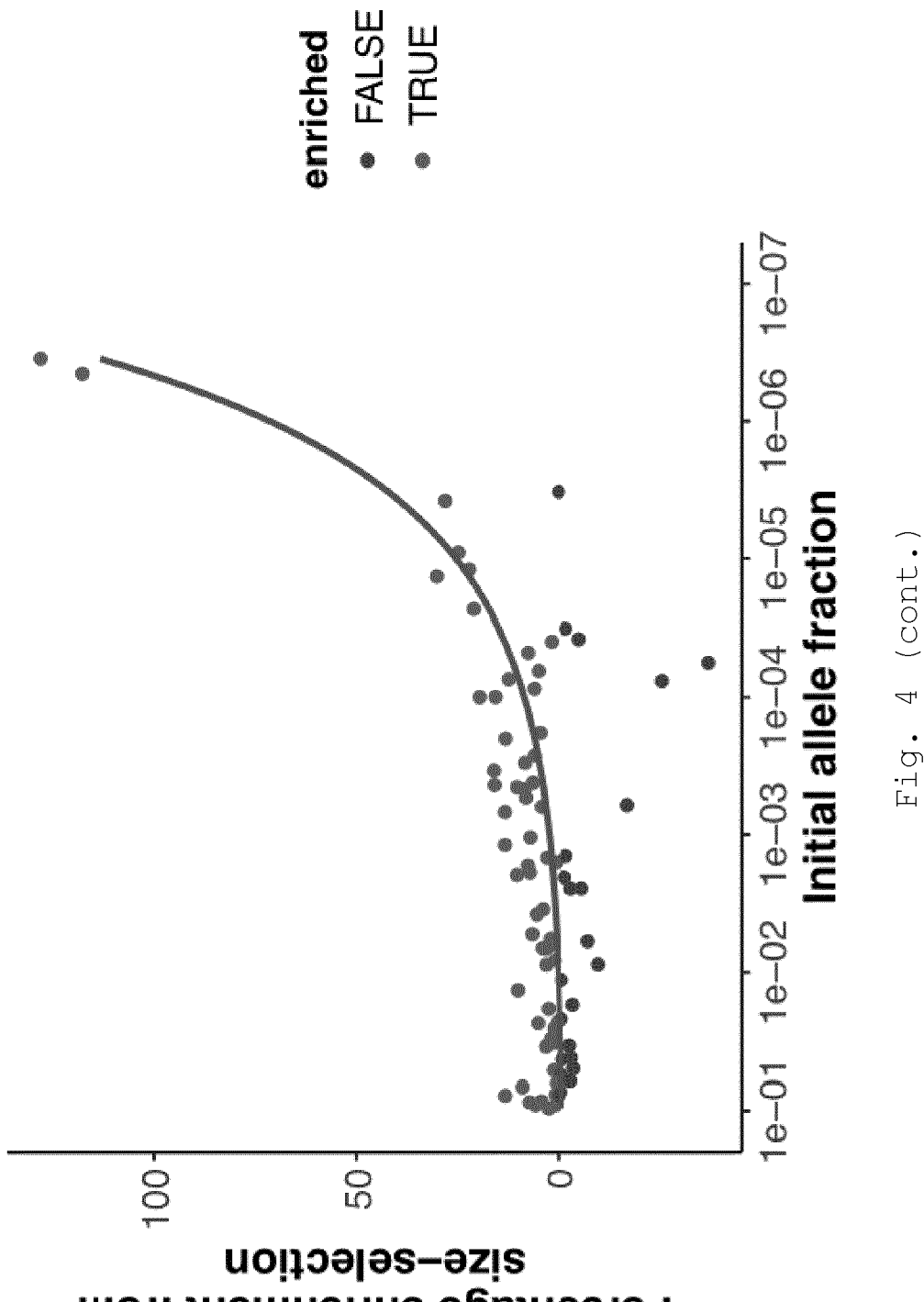
Figure 5:
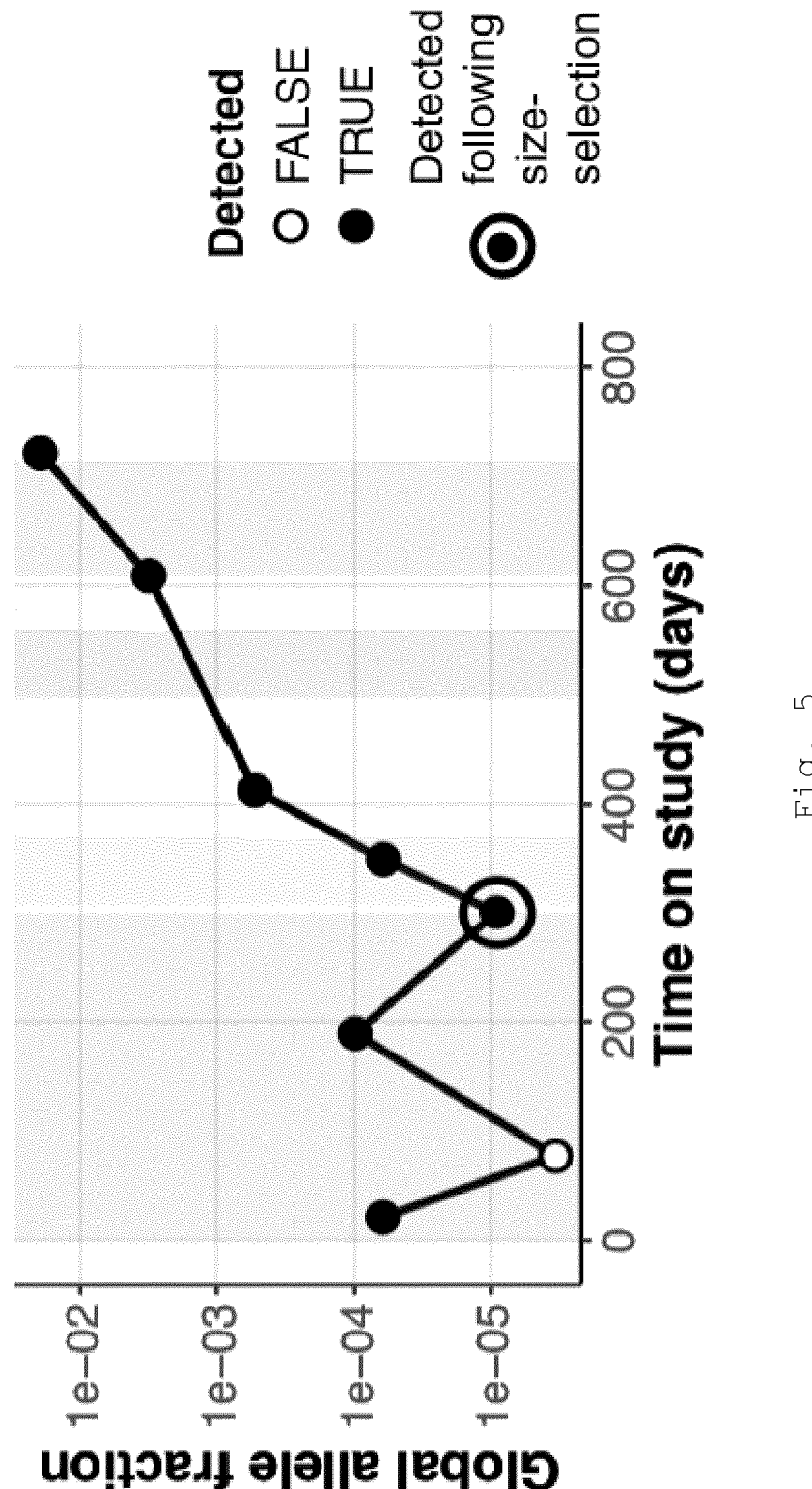
FIG. 5 shows clinical applications of INVAR-TAPAS. (a) ctDNA mutant allele fraction is plotted over time for one patient (MR1004) who underwent multiple therapies in series, indicated by different shaded boxes. Filled circles indicate significant detection of ctDNA. The non-detected time point is plotted at the maximum possible allele fraction based on the total depth achieved. Detection of the fourth time point was achieved following size selection, and is indicated by an additional circle. (b) For the same patient, the total tumour volume over time is shown. (c) Systemic therapies received over time by this patient and RECIST response data are shown. PD=Progressive Disease. (d) Tumour volume from CT imaging is plotted against ctDNA mutant allele fraction for all patients; a Pearson correlation of 0.67 was observed (P=0.0002). (e) Patients (n=10) whose ctDNA levels decreased following treatment initiation to below 10 ppm (red) had 24 months' longer overall survival than patients whose ctDNA levels never dropped below this threshold at any of the time points (light blue; Log-rank test, P=0.009). (f) For each library with significant detection of mutant DNA (Methods), the DNA input mass into the library preparation is plotted against the mutant DNA fraction in that sample determined by INVAR. The blue line indicates where an assay for a single locus would have 95% sensitivity based on the probability of sampling at least one mutant molecule at that locus.
Figure 5:
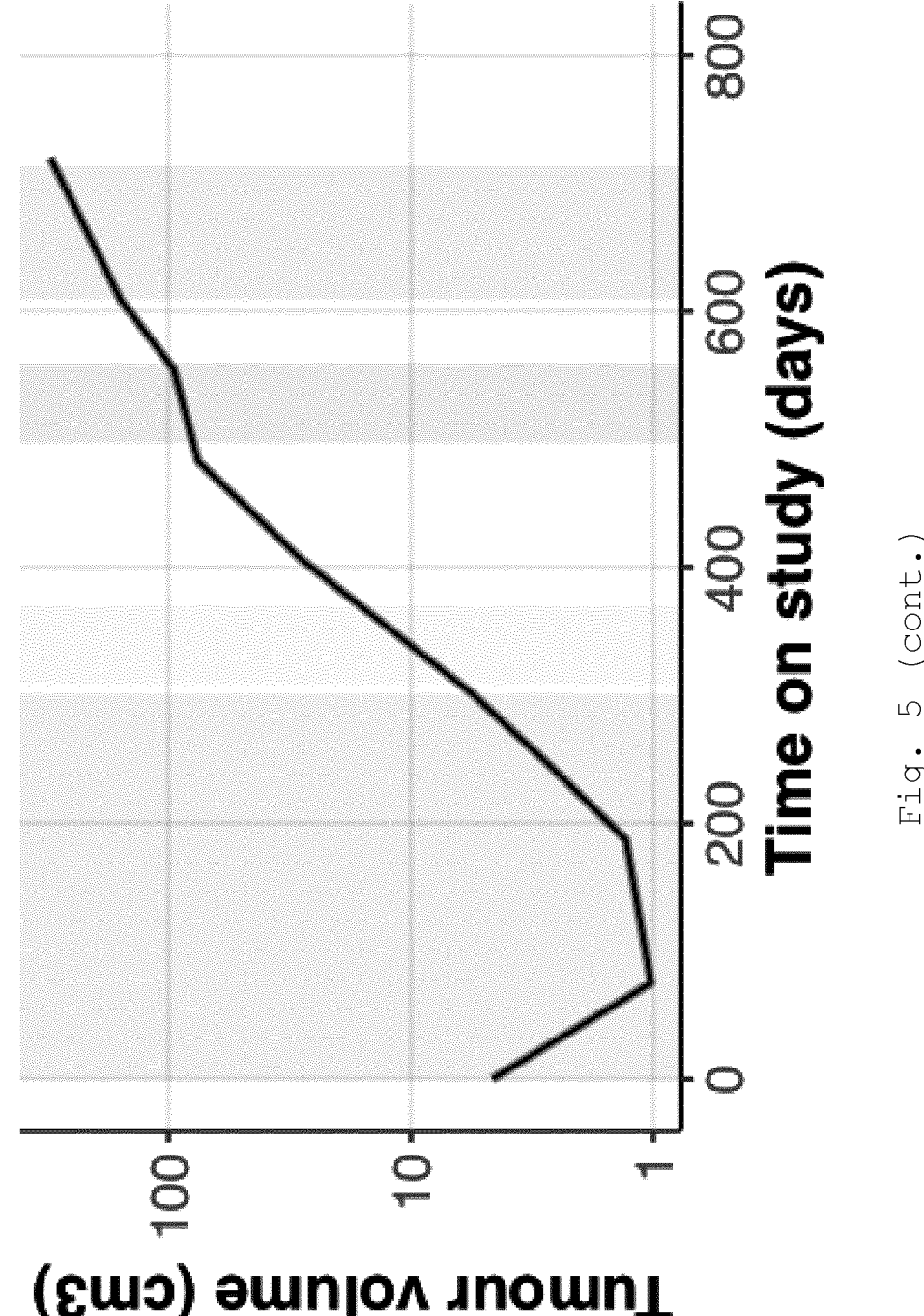
Figure 5:
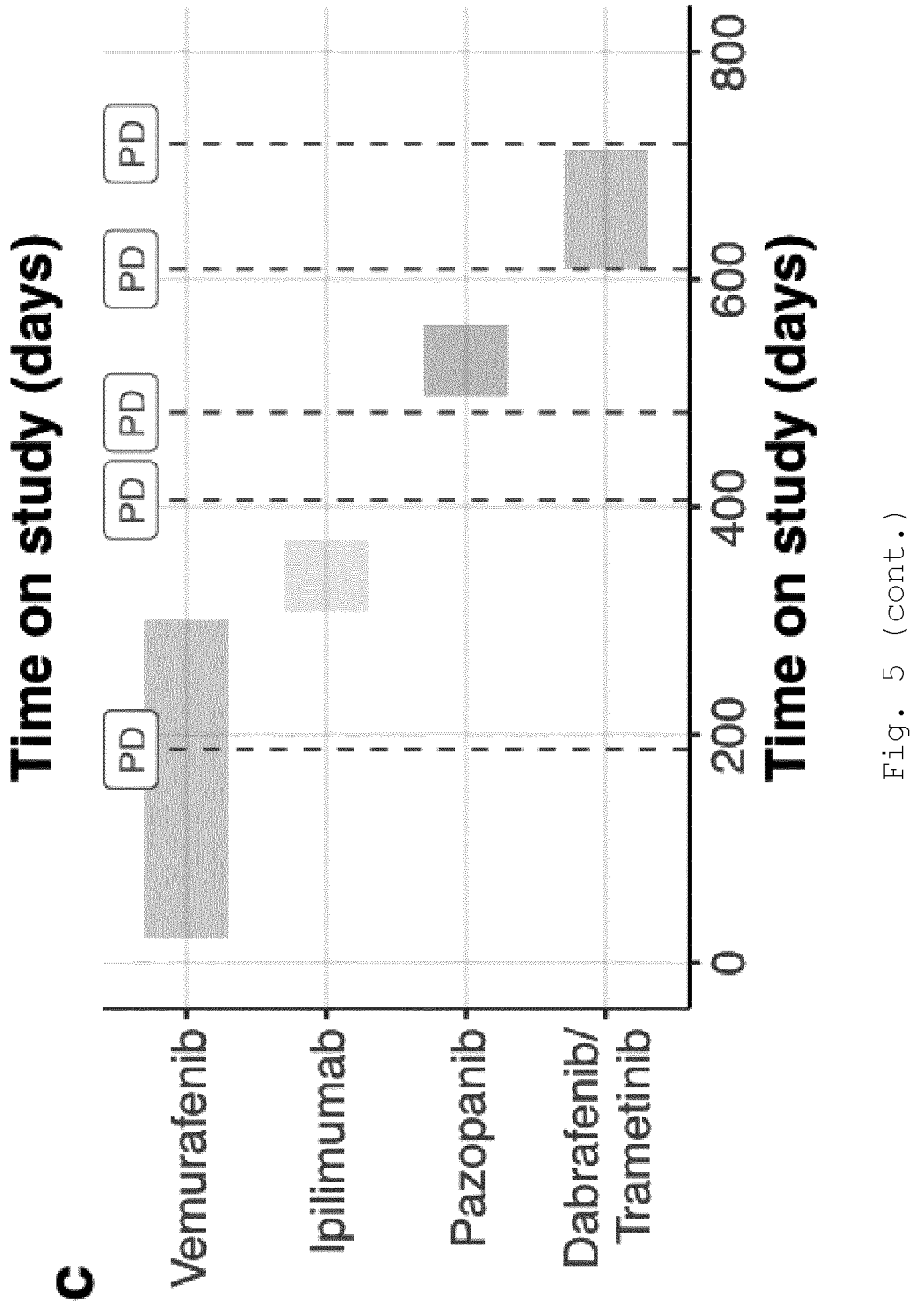
Figure 5:
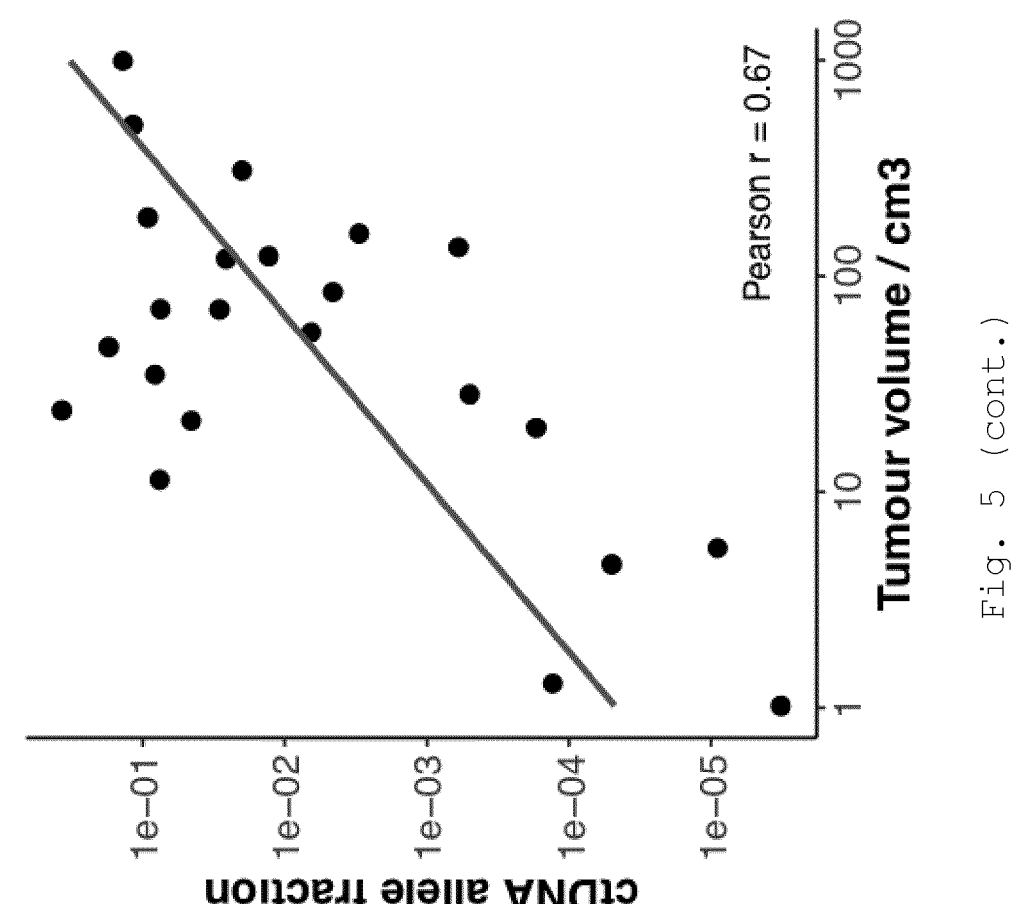
Figure 5:
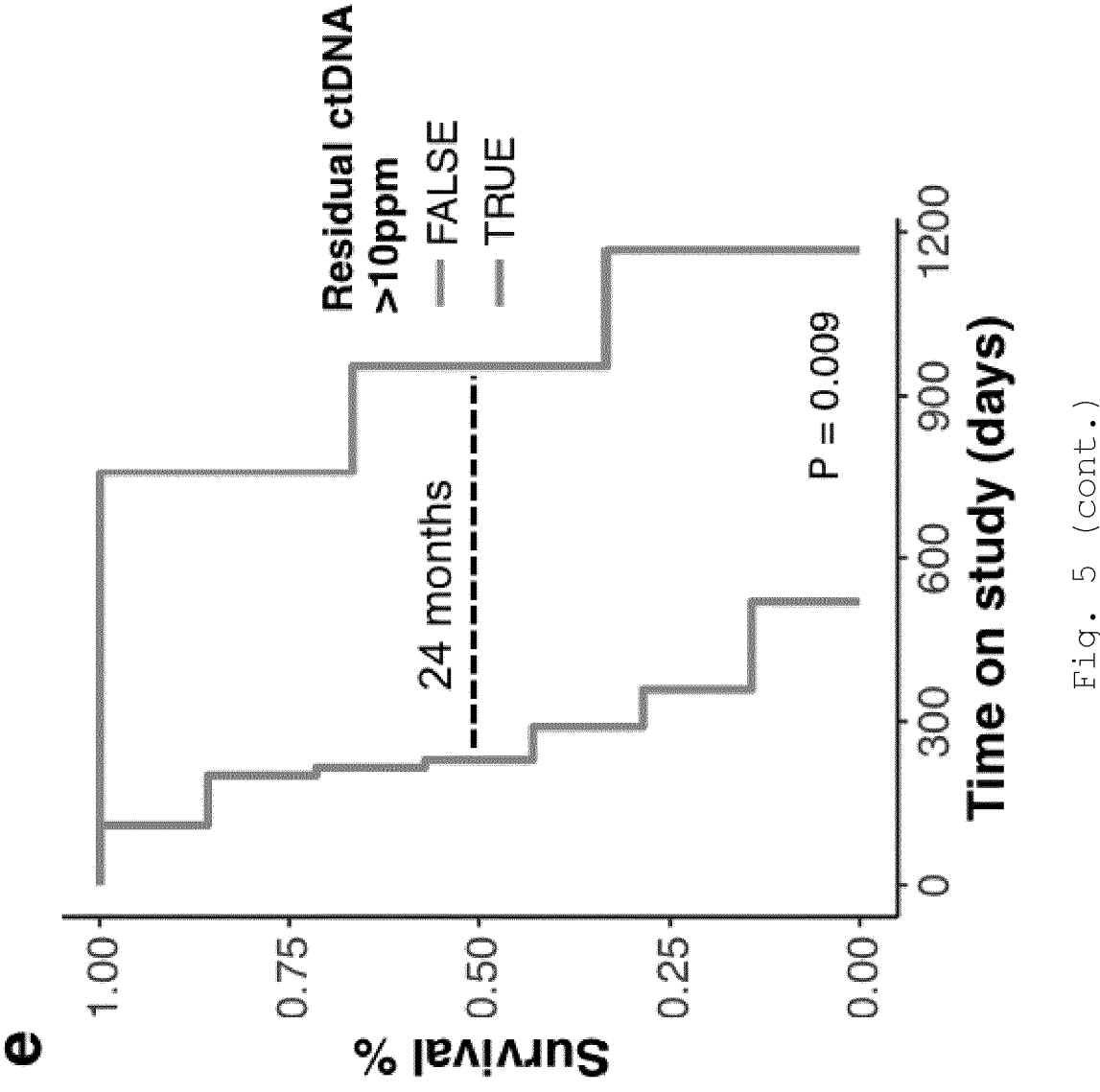
Figure 5:
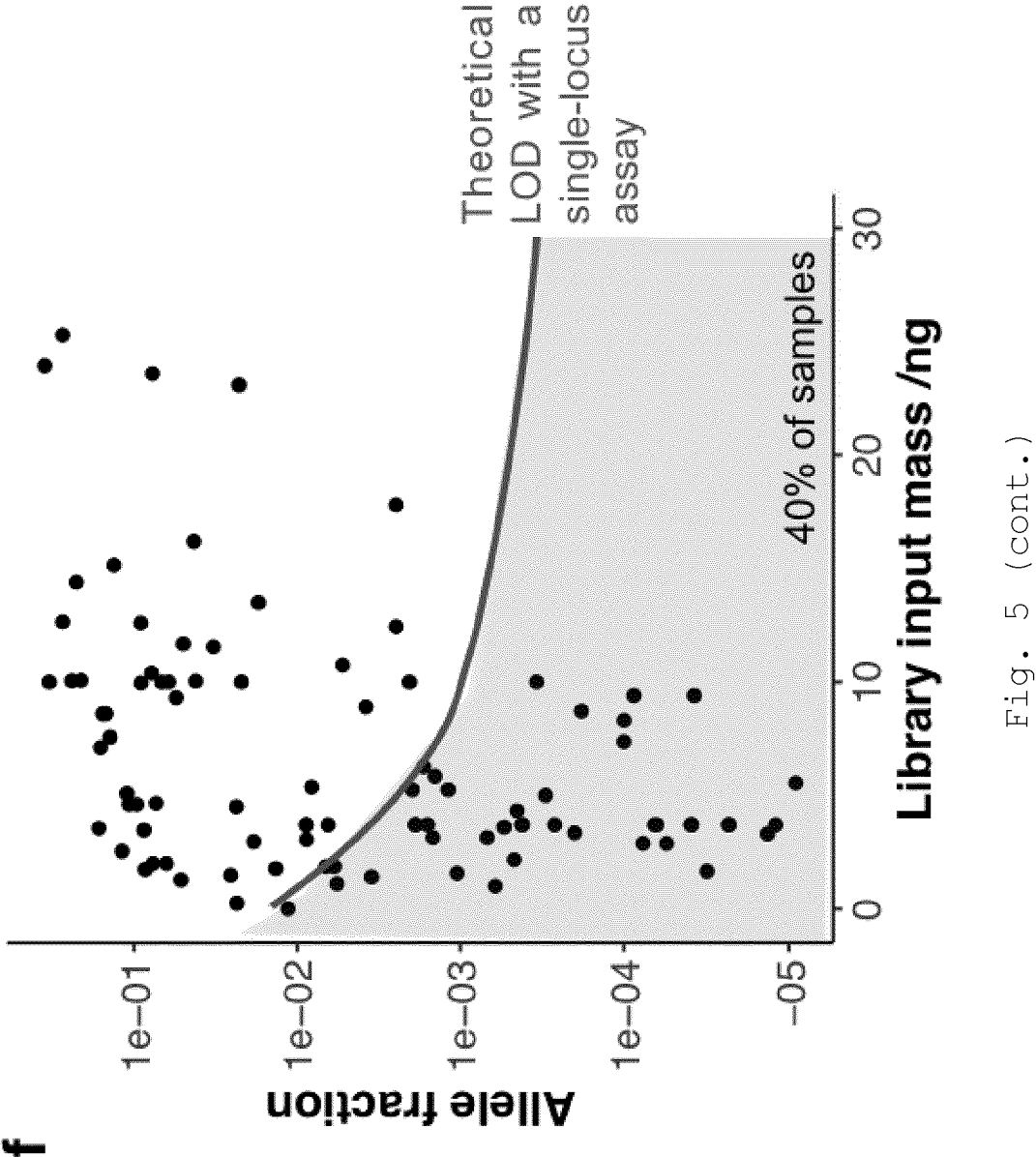

Given these findings, we aimed to enrich for mutant signal through in silico size selection. Based on the size ranges that showed enrichment of ctDNA, data were size-selected in silico for reads within the size ranges of 115-190 bp, 250-400 bp and 440-460 bp. These relatively wide ranges were chosen in order to minimise loss of rare mutant alleles, as the size distributions of mutant and wild-type fragments were mostly overlapping. Overly stringent size selection may result in drop out of rare mutant molecules, which becomes increasingly problematic as ctDNA levels approach parts per million. In principle, with more input DNA and further sequencing, narrower filters may be applied to generate a stronger enrichment factor. When applied to plasma samples and spike-in dilutions, size selection produced a median enrichment of 6.3% in ctDNA relative to wild-type while retaining 93.7% of mutant reads. The extent of enrichment post-size-selection was related to the starting mutant allele fraction of the sample, and followed an exponential relationship with decreasing mutant allele fraction (FIG. 4c). Samples from the 50 ng spike-in experiment with the lowest mutant allele fraction (<1 ppm) showed the greatest extent of enrichment, likely because they had the highest level of contaminating wild-type reads. In one patient (MR1004), size selection enabled detection of previously non-detected mutant signal, with a mutant allele fraction of 9.1 ppm (FIG. 5a). This was observed at a time point when the patient had a total of 1.3 cm³ disease, determined by volumetric CT analysis (FIG. 5a, b). Size selection provided no benefit for patient MR1004's second time point during vemurafenib targeted therapy (FIG. 5a, c) as there were zero mutant read families.

Example 6—Detection of Residual Tumour Volume

Across the cohort, ctDNA mutant allele fractions were compared against volumetric CT imaging data, which showed a Pearson correlation of 0.67 (P=0.0002; FIG. 5d), in agreement with previously published studies[6,8]. One patient (MR1014) was excluded from this comparison because they had low-volume subcutaneous metastases that were non-measurable by international RECIST criteria[18] but may still contribute ctDNA. The maximum possible mutant allele fraction for patient MR1004's non-detected time point (FIG. 5a) was inferred as 3.4 ppm by taking the reciprocal of the number of read families in that sample, adjusted to give a 95% probability of sampling one mutant molecule based on a Poisson distribution and a perfect assay.

Figure 10:
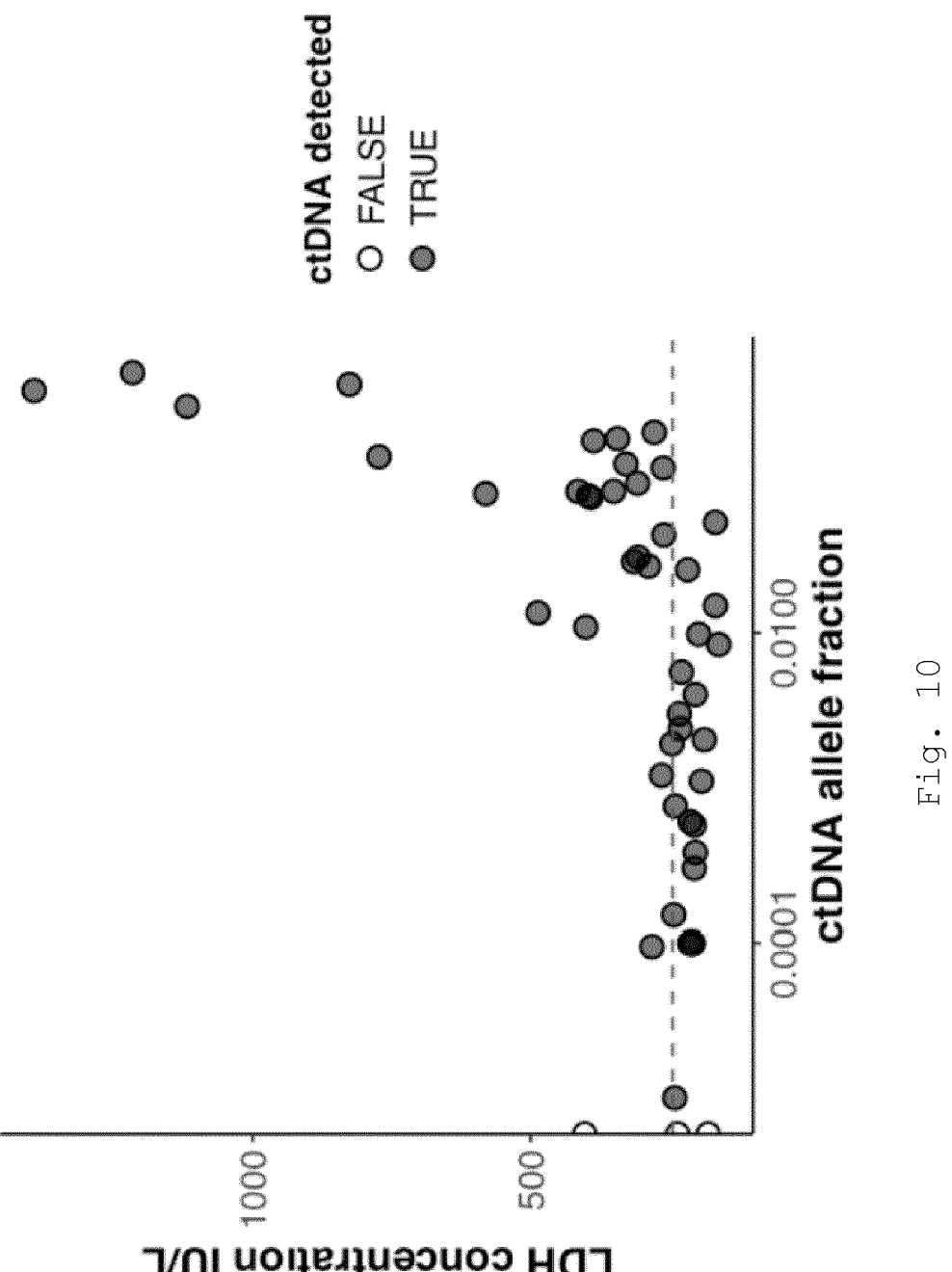
FIG. 10 shows the relationships between plasma ctDNA and clinical parameters. (a) Plasma ctDNA mutant allele fractions are plotted against lactate dehydrogenase (LDH) concentrations at matched time points. Filled circles indicate significant detection of ctDNA. The upper limit of normal for LDH of 245 U/L is shown with a red dashed line. (b) Baseline ctDNA concentration is negatively correlated with overall survival (Pearson r=−0.61; P=0.04).

Across all time points, there was a Pearson correlation of 0.86 between ctDNA and serum lactate dehydrogenase, a prognostic marker used for melanoma patients (P=2.2×10⁻¹⁵; FIG. 10a). At 43% of time points, patients had detected ctDNA but normal LDH, reflecting the low physiological background of ctDNA compared to protein markers. Together, these data indicate that ctDNA can play a prognostic role similar to LDH, and with enhanced sensitivity for residual disease.

Figure 10B:
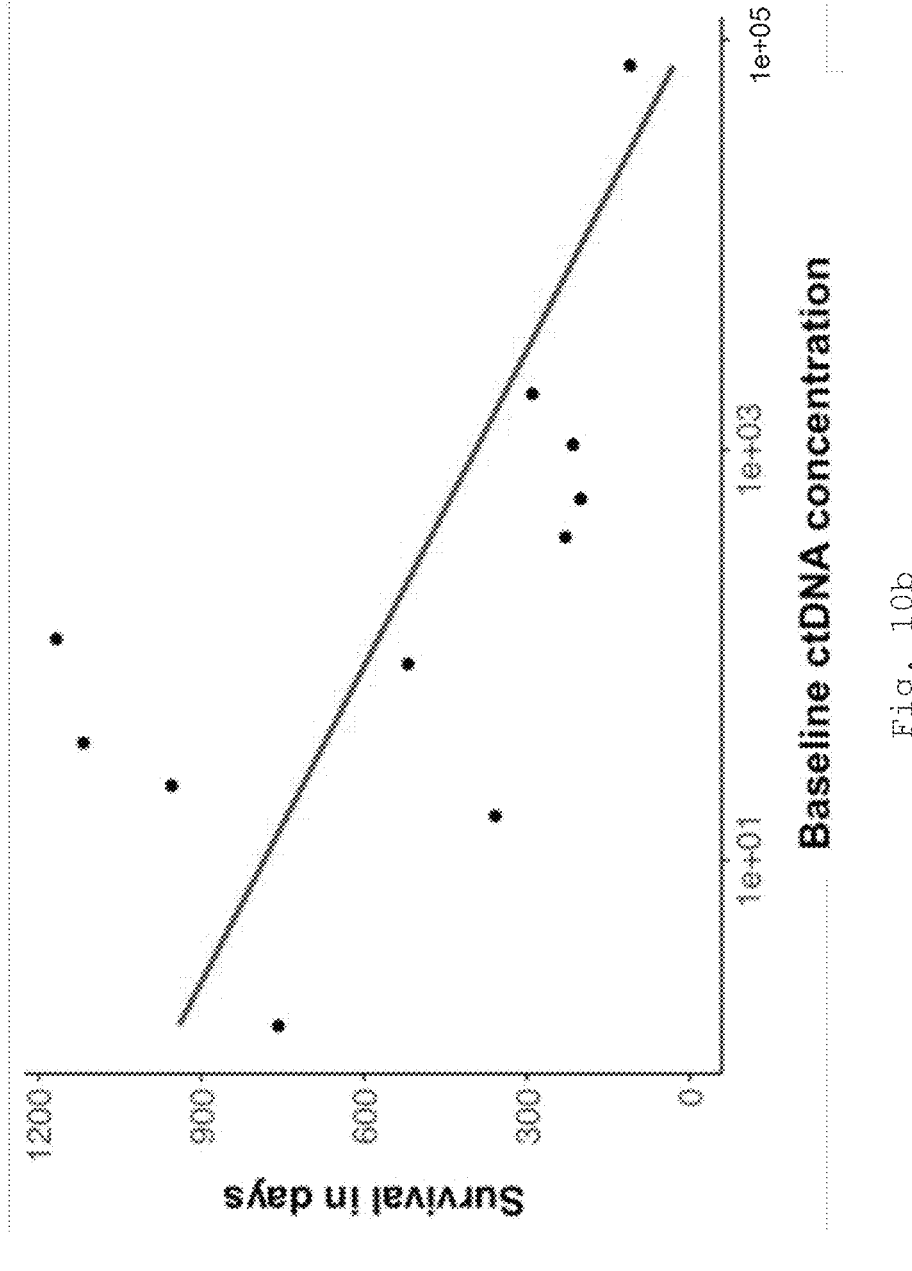

Following initiation of systemic therapy, 3 out of 10 patients' ctDNA declined to levels below 10 ppm. We found that patients whose ctDNA fell to less than 10 ppm had 24 months longer overall survival compared to patients with higher levels of residual ctDNA (median 954 vs. 229 days; log-rank test P=0.009; FIG. 5e). Also, baseline ctDNA levels showed an inverse correlation with overall survival (Pearson r=−0.61, P=0.04; FIG. 10b). Across this cohort, the first rise in ctDNA preceded radiological progression by a median of 54 days (IQR 0-112 days). The lead time was calculated from the time point where the rise was evident; this may be improved further with more frequent plasma sampling than the median time of 55 days between samples analysed (IQR 28-73.5).

Despite the limited DNA input mass used for library preparation (median 4.4 ng per library, 1320 haploid genomes), 40% of plasma samples had significantly-detected allele fractions that were below the theoretical limit of detection (with 95% sensitivity) using a perfect single-locus assay FIG. 5f). Notably, we observed a Pearson correlation of 0.27 between cfDNA concentration and ctDNA mutant allele fraction, indicating that low total cfDNA levels can accompany low ctDNA levels, making detection of low levels of ctDNA even more challenging with assays that rely on individual mutant loci.

Example 7—De Novo Mutation Detection

Figure 6:
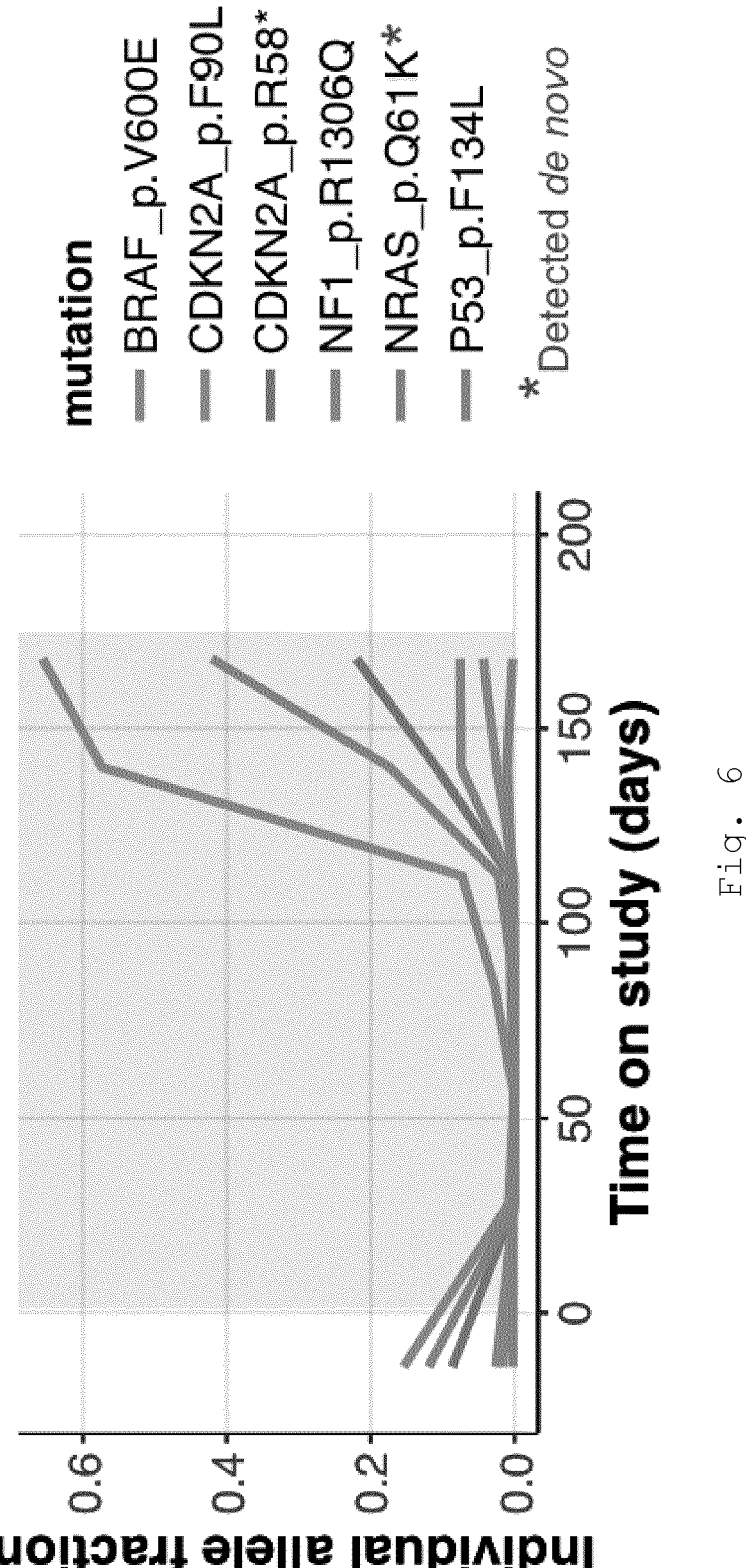
FIG. 6 shows de novo detection of resistance mutations. (a) For patient MR1022, individual mutations that were previously identified in COSMIC are plotted over time during treatment. An NRAS Q61K mutation was identified de novo in three longitudinal plasma time points; this mutation was not previously identified in the patient's tumour. (b) The volumes of multiple tumour lesions over time are shown for the same patient, and total volume in bold. (c) CT imaging showing lesion positions for patient MR1022.
Figure 6:
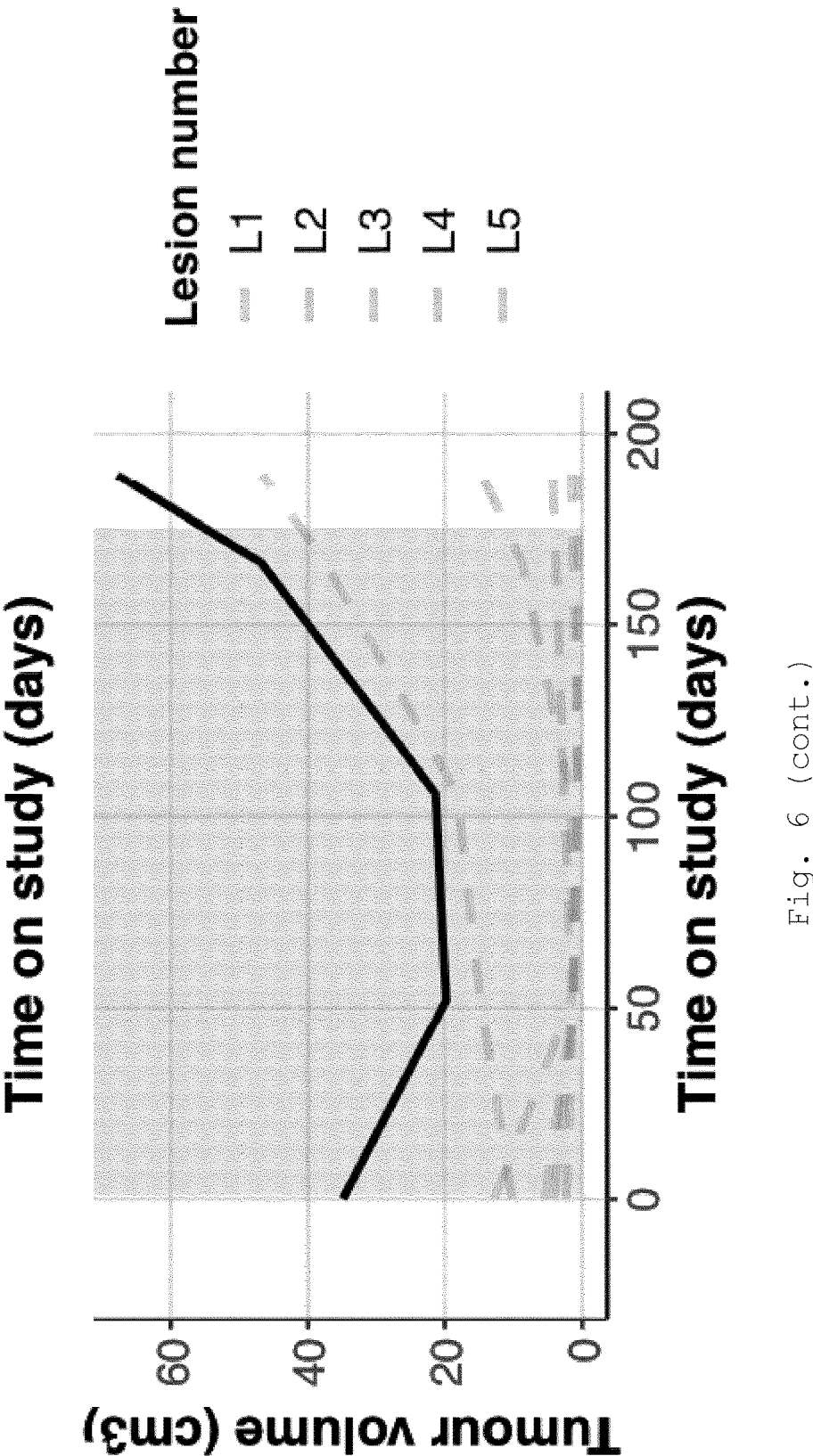
Figure 6:
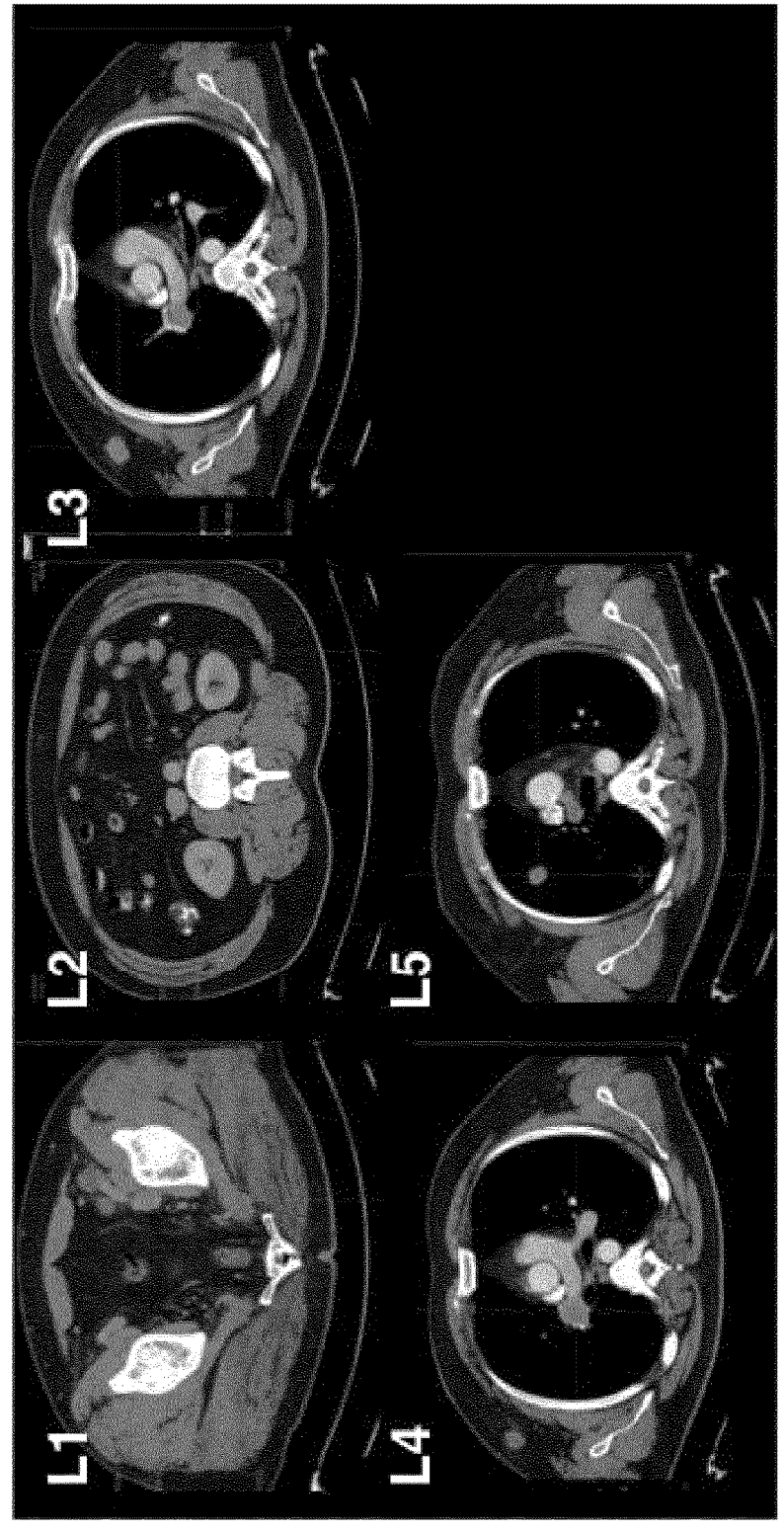

When ctDNA levels are sufficiently high, resistance mutations may be identified de novo, and clonal evolution may be monitored through changes in the allele fractions of mutations[9]. An example from one patient (MR1022) is shown in FIG. 6, indicating allele fractions for individual mutations that had ≥5 occurrences in the COSMIC database[19] (FIG. 6a) alongside individual tumour lesion volumes (FIG. 6b) and tumour lesion positions (FIG. 6c). By testing hotspot mutation loci (Methods), rising NRAS Q61K mutations were significantly detected de novo in plasma samples from two patients in total; these mutations were not identified in these patients' baseline tumour biopsies. For individual mutation calling, detection was carried out on a per-sample basis. In the context of low levels of signal and input material, integrating variant reads from sequential samples, as each sample is collected and sequenced, may enhance sensitivity by allowing multiple samples with below-threshold ctDNA levels to be aggregated.

DISCUSSION

A combination of multiplexed deep sequencing of thousands of tumour-derived mutations and integration of variant reads enabled us to detect ctDNA down to 0.3 ppm. Through the characterisation of error rates and fragmentation patterns from cfDNA sequencing data, we optimised our workflow for hybrid-capture sequencing of cfDNA. In this study, we analysed a large number of mutations for each patient by using all mutations identified by exome or targeted sequencing of baseline tumour biopsies. This enabled sensitive analysis despite limited DNA input amounts into library preparation, approximately 10-fold lower than were used for other high-sensitivity amplicon and hybrid-capture methods[6,8]. Error suppression was used to reduce background sequencing errors, and in silico size selection was used to enhance for mutation signal. By generating a large amount of patient-specific reads overlying known tumour mutations for each patient, TAPAS compensates for small input amounts, and for data losses incurred by error suppression and size selection, while still retaining sufficient mutant reads for highly sensitive detection. As a result, both high sensitivity (below parts per million) and high specificity (>99.5%) were achieved.

INVAR-TAPAS leverages differences in error rates between mutation classes to detect rare mutant alleles while efficiently using the available data. Detection by mutation class, followed by the combination of each test statistic, allowed each class to contribute to the overall signal based on its background error rate. We used a method for combining P-values for correlated datasets[16] to account for dependence between mutation classes. Here we used analysis by 12 mutation classes; a larger dataset might enable analysis based on a greater number of sequence subsets such as by tri-nucleotide context or by individual locus, which may improve resolution into error rates further still.

Using error-suppressed data, size profiles were visualised for both mutant and wild-type reads with minimal confounding error from PCR and/or sequencing. We confirm that ctDNA is enriched in short plasma cfDNA fragments, and provide evidence for enrichment of mutant DNA in di-nucleosomal DNA, which may have contributed to previous findings of longer mutant DNA in the plasma of cancer patients[20,21]. We applied size selection to our data, which was first demonstrated in the field of non-invasive pre-natal testing[22] (where fetal DNA fragments are shorter than maternal fragments[23]), and is beginning to be used experimentally on cancer patient samples[17]. Fan et al.[22] highlight the challenge of retaining mutant molecules with size selection, which we confirm is largely due to highly overlapping size distributions of mutant and wild-type fragments. In the current study, we opted for a relaxed size selection to retain a large fraction of the starting mutant molecules, and demonstrated that a relaxed cut-off can provide benefit, particularly when the mutant fraction is very low (in the range of 1 ppm mutant allele fraction and lower). With greater sequencing depth and DNA input, more stringent filtering can provide further enrichment.

INVAR-TAPAS leverages knowledge of tumour-derived mutations, which requires analysis of an initial sample with high tumour content. This method has potential utility for monitoring disease recurrence post-treatment, particularly after surgery where the tumour tissue DNA can be obtained for sequencing. We showed in one example where this method detected as little as 1.3 cm$^3$ residual disease, with 9.1 ppm ctDNA; this mutant allele fraction observed is consistent with predicted allele fractions for given tumour volumes from a previously described model[6], and indicates that INVAR-TAPAS may theoretically identify lesions at the limit of detection of CT detection. Earlier detection of relapse or disease progression with a high-sensitivity approach may facilitate earlier initiation of adjuvant therapy or change of therapy. For guiding subsequent therapy, we demonstrate that mutations can be identified de novo, though the sensitivity of this is directly proportional to the number of molecules analysed at that locus which can be limiting. Signal may be further integrated across multiple longitudinal samples to enhance identification in the context of limited input DNA. One advantage of the present approach is that low level signal in a previous sample can provide evidence to support mutation detection in a later sample. Thus, each longitudinal sample supports another.

This tailored approach may be carried out using different types of input data from the plasma, and different lists of mutations to inform analysis. Tumour-derived mutations can be identified using exome sequencing as demonstrated here, but also across smaller focused panels or larger scales such as whole genome. In this cohort of 10 melanoma patients, exome sequencing was sufficient to identify hundreds to thousands of mutations per patient. Based on known mutation rates of cancer types[24], exome sequencing would also suffice for many cancer types with relatively high mutation rates, for example: lung, bladder, oesophageal, or colorectal cancers. For cancers with a mutation rate of ~1 per megabase or less[24], whole-genome sequencing of tumours for mutation profiling would be desirable: for ovarian and brain cancers, this would result in thousands of mutations identified per patient.

To generate data for INVAR, we used targeted sequencing with patient-specific panels (e.g. TAPAS), which provided deep sequencing of a large number of mutations, but required development of patient-specific sequencing panels. This is cost-effective for generating data for INVAR from longitudinal samples, as they can be analysed with the same TAPAS panel. In a different implementation, whole-exome or whole-genome sequencing without the design of patient-specific panels may produce similar data suitable for INVAR. While reducing the complexity of the workflow, with this approach much of the sequencing data would not cover tumour-mutated loci (and thus would not be informative for INVAR), resulting in fewer patient-specific read families available for INVAR unless more sequencing is performed. As sequencing costs decrease, and tumour sequencing becomes more frequent with the advent of personalised oncology, we suggest that integration of variant reads from error-suppressed sequencing of plasma cfDNA would provide a highly sensitive means of treatment monitoring, disease surveillance and detection of residual disease.

Example 8—Use of Trinucleotide Contexts

Tumour Sequencing

To achieve high sequencing depth at defined loci that were mutated in the patients' tumours, tailored sequencing panels were designed based on single nucleotide variants (SNVs) identified in sequencing of fresh frozen or FFPE tumour biopsies from 48 patients with Stage II-IV melanoma. Mutation calling was performed on all tumour biopsies, and variant calls were filtered to exclude common SNP sites, repeat regions, and loci with signal in the patient's matched germline DNA (Methods).

Figure 11:
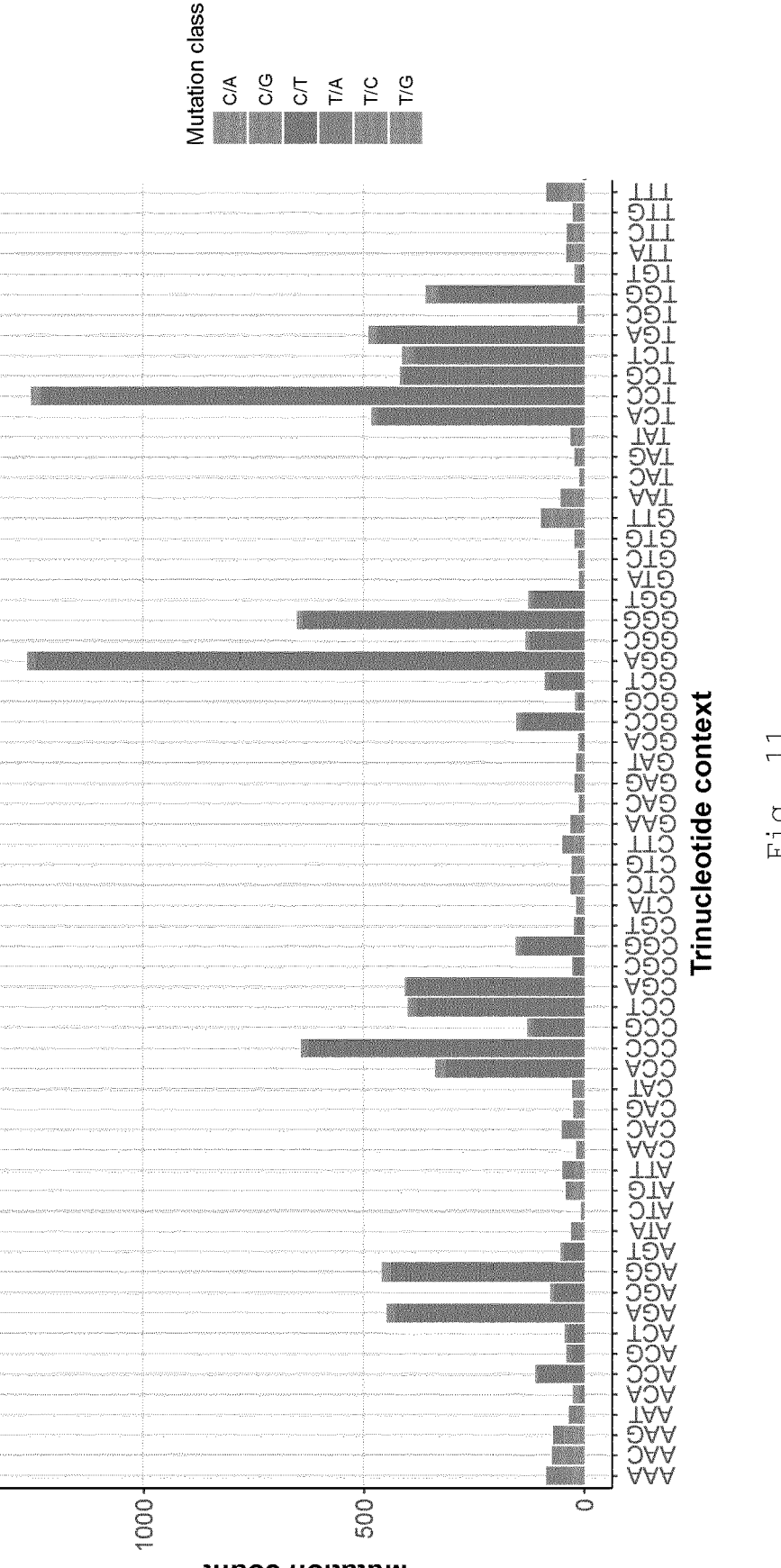
FIG. 11 shows mutation counts split by trinucleotide context and mutation class. Fresh frozen tumour biopsies were sequenced from 10 patients with Stage IV melanoma.
Figure 12:
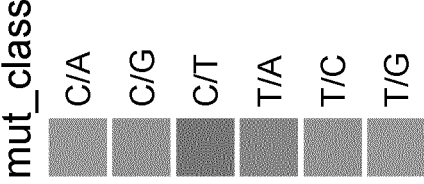
FIG. 12 shows a histogram of tumour mutant allele fractions. Fresh frozen tumour biopsies were sequenced from 10 patients with Stage IV melanoma. The median tumour mutation allele fraction was estimated to be ~25%.
Figure 12:
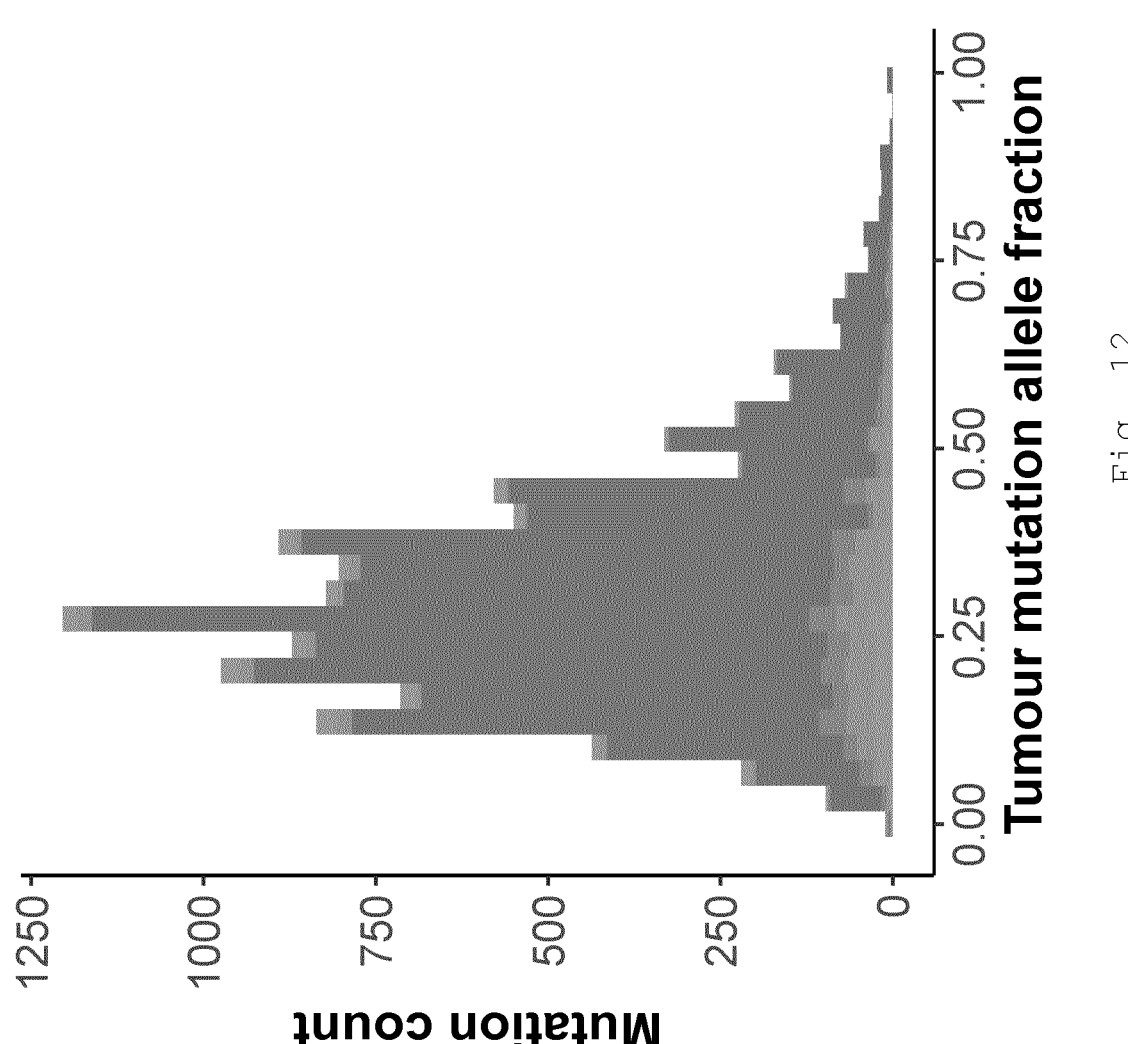

Mutation profiles were assessed in fresh frozen tumour biopsy sequencing (FIGS. 11 and 12), and FFPE biopsy sequencing (data not shown). A majority of mutations were C>T, with GGA and TCC contexts being the most prevalent, reflecting the predominance of the UV signature (FIG. 11). The median mutant allele fraction of tumour mutations was estimated at ~0.25.

Plasma Sequencing

Figure 13:
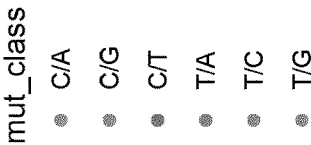
FIG. 13 shows a plot of background error rates by trinucleotide context and mutation class. The error rate was determined as the proportion of total read families that were non-reference in a context. Sequencing was performed using TAPAS on plasma from healthy individuals, and was error-suppressed with a minimum family size threshold of 2. Signal was required in both the F and R read in order to be considered.
Figure 13:
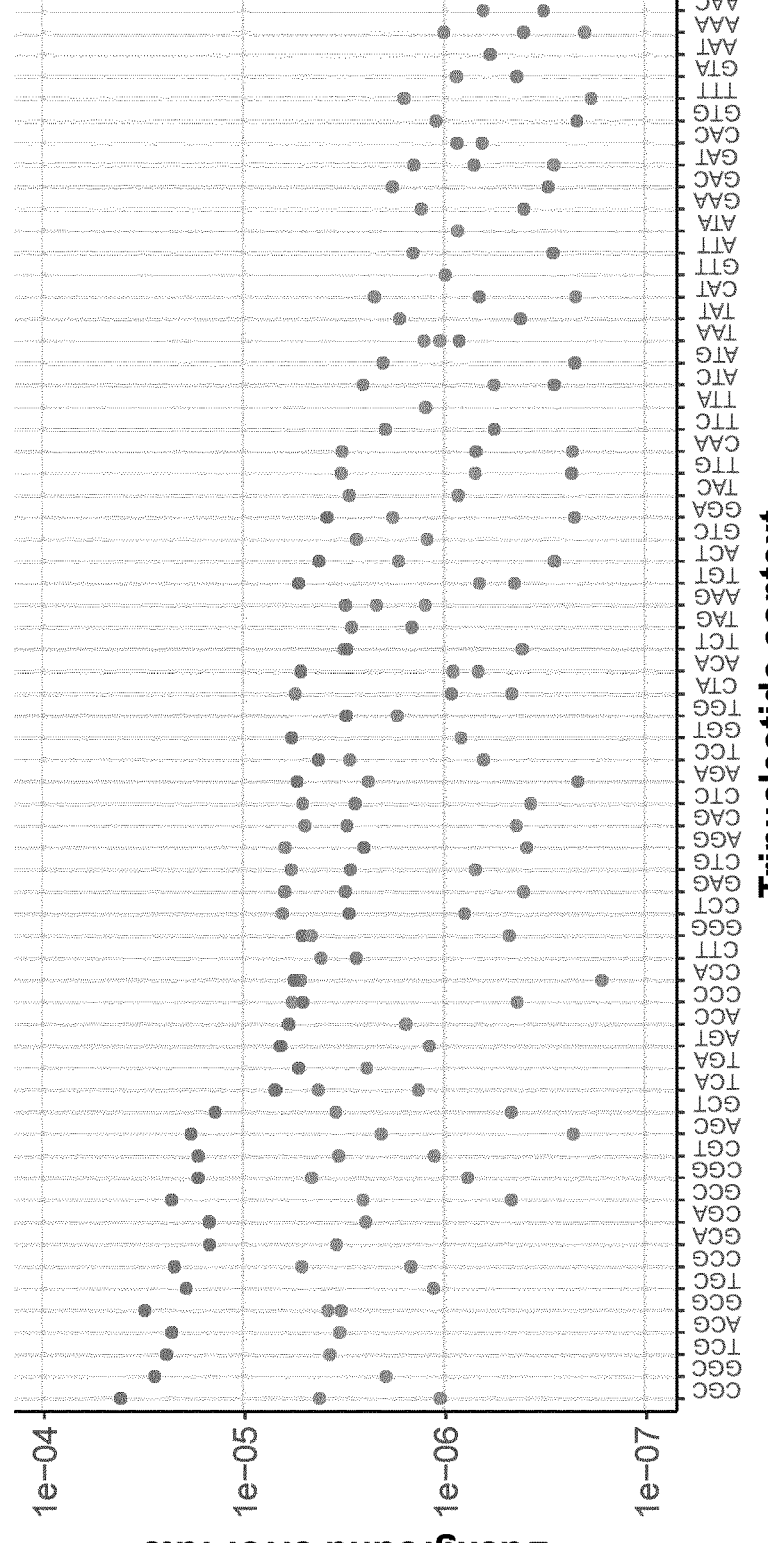

We found that background error rates in plasma from hybrid-capture sequencing varies between trinucleotide context using error-suppressed data with a minimum family size threshold of 2 (FIG. 13). The use of trinucleotide contexts enables the determination of background error rates down to 1 in 10 million through aggregation of read families across contexts; to achieve the same accuracy of background-error estimation on a per-locus level would require a vast number of samples to be sequenced. The use of trinucleotide contexts enables maximum retention of read families following error-suppression (FIG. 2a), while having a range of error rates spanning two orders of magnitude.

Amendments to INVAR to Handle Contexts

When ctDNA levels are low, many patient-specific loci will have no mutant DNA fragments at that position. Therefore, to overcome sampling error, all patient-specific read-families were aggregated and analysed together using INVAR. For each sample, mutant read and total read families were aggregated by trinucleotide context, and the proportion determined:

$$\frac{\sum_{loci} (\text{mutant reads})_{patient\text{-}specific}}{\sum_{loci} (\text{total reads})_{patient\text{-}specific}}.$$

The significance of the observed number of mutant reads was determined using a one-sided Fisher's exact test for each context, generating a vector of P-values for each sample. The length of each P-value vector varied between samples, since the number of contexts represented in each patient differed based on the mutation profile of that patient. In order to account for this, and to take into consideration that in the minimal residual disease (MRD) setting only a small number of molecules would be present, we combined the P-values from the 6 most significant trinucleotide contexts per sample. This was performed on both test samples and control samples, and controls were used to determine a P-value cut-off with 97.5% specificity.

Example 9—Leveraging UV-Derived Dinucleotide Mutations for Melanoma

The high mutation rate in cutaneous melanoma is almost entirely attributable to the abundance of cytidine to thymidine (C>T) transitions, which are characteristic of UV-induced mutations (Hodis et al., 2012). We confirm this mutational signature in our data (FIG. 11). Of the C>T transitions, 1 in 10 mutations are CC>TT (Brash, 2015), which is in keeping with the abundance of mutations in contexts containing CC or GG in our data (FIG. 11).

In melanoma, CC>TT mutations provide an opportunity to achieve ultra-low error rates, since any stochastic PCR/sequencing error would have to occur twice in series. CC>TT mutations can be aggregated as their own mutation class, whereas individual indels each would have a separate error profile. Thus, CC>TT mutations may be sufficiently prevalent in the data to allow the interrogation of a sufficient number of molecules to take advantage of the low noise profile. We are currently generating a script to identify mutant reads with CC>TT in adjacent bases from data error-suppressed with a minimum family size of 2. These mutations can be treated as a separate class with their own error profile for INVAR.

Example 10—INVAR-Integration of Minimal Residual Disease (MRD) Signal

In order to optimise INVAR for detection of residual disease, we generated a spike-in dilution series using a mixture of patient cfDNA and healthy individual cfDNA, and characterised the signal occurring at the lowest dilutions. For this experiment, cfDNA was pooled from 6 patients to create a theoretical patient with a total of 9,636 patient-specific mutations. This pool was then serially diluted in healthy individual DNA (Methods).

Figure 14:
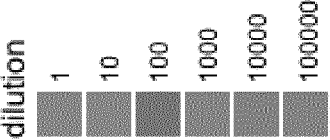
FIG. 14 shows histograms of mutant allele fraction for a spike-in dilution experiment.

Histograms of mutant allele fractions of individual patient-specific mutations for the dilution experiment are shown in FIG. 14. As the sample is diluted further, the histogram of mutant allele fractions shifts to the left, as an increasing proportion of loci are not sampled. Despite this, at low levels of ctDNA, the loci that are observed are seen at low mutant allele fractions (<0.03). This signal represents stochastic sampling of mutant molecules, randomly distributed across the patient-specific loci targeted, shown in FIG. 15.

Figure 15:
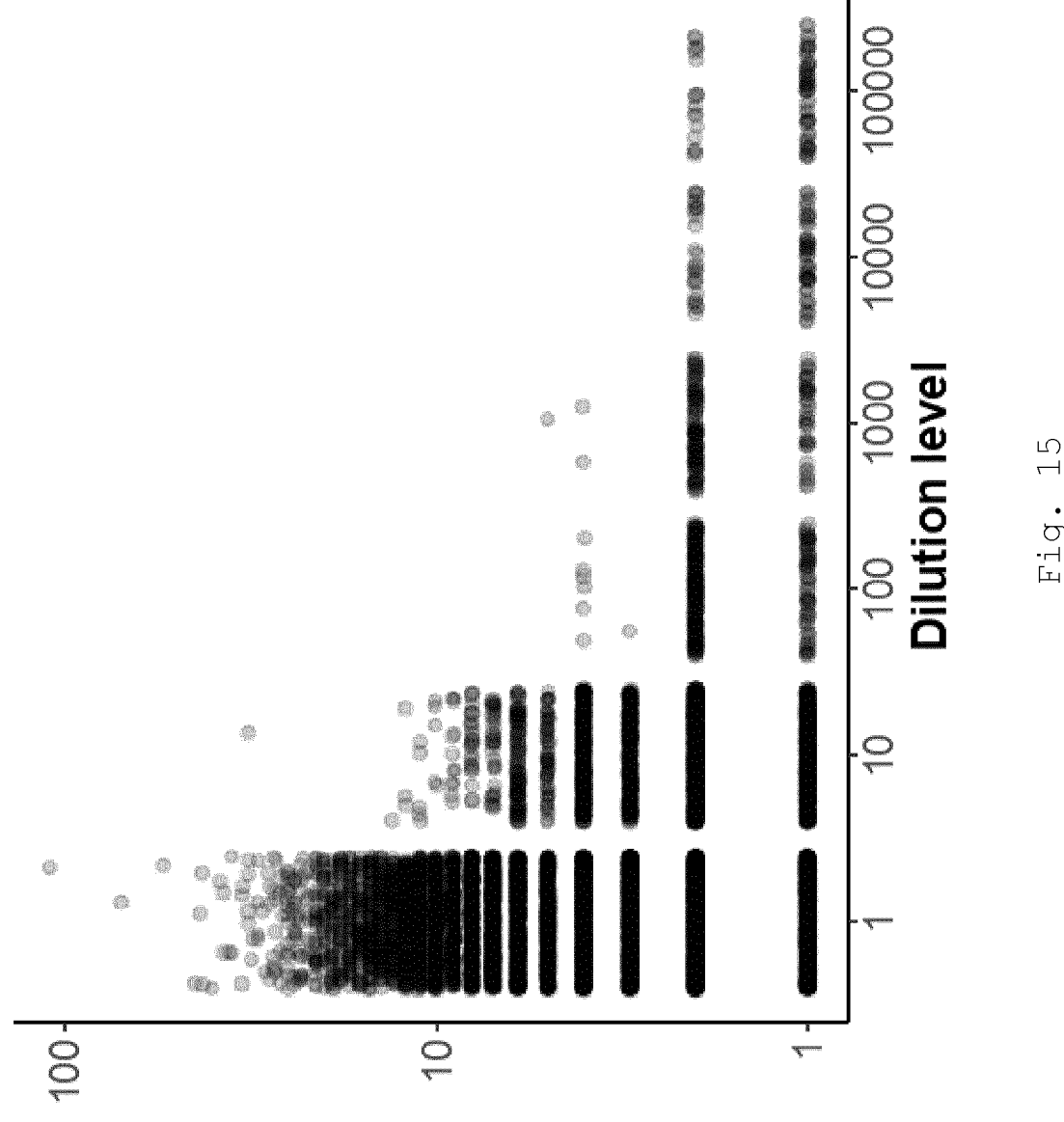
FIG. 15 shows a plot of the number of mutant reads per locus by dilution level of the spike-in experiment. Each point represents one locus. Points with zero mutant reads are not shown. Given that sequencing is performed with PE150, and cfDNA molecules are ~160 bp, an individual mutation sequenced with TAPAS in both the F and R read would have 2 mutant reads at that locus.

At the lowest levels of residual disease, ctDNA would be found in individual mutant molecules at individual loci. It would be highly unlikely for many mutant molecules to be concentrated entirely at one locus without other loci being represented, and this is supported by our data (FIGS. 14 and 15). Loci with an unexpectedly high level of signal relative to the remainder of loci may be SNPs or noisy bases. Therefore, based on this characterisation, we propose an MRD-filter, which deliberately focuses on signal originating from loci with <=4 mutant reads (allowing up to 2 molecules to be present at a locus, read in both F and R reads), and mutant allele fraction <0.03 (requiring sufficiently many total read families to be confident in this signal not being from a SNP).

Using this approach, the probability of mis-genotyping a SNP (expected AF=50%) by focusing on loci with 2 or fewer molecules in 50 total molecules is $1 \times 10^{-12}$ (2 or fewer successes out of 50; p=0.5). This is reduced further by the prior SNP filtering carried out at the tumour sequencing stage, whereby loci are filtered based on common SNP databases (i.e. 1000 Genomes ALL, EUR).

In addition, we also placed a lower limit on the number of mutant reads per locus. Mutant reads were only considered as contributing to signal at a locus if there was at least one F and one R read at a locus. Given that we sequenced with PE150, requiring overlapping F and R mutant read support served a dual purpose of suppressing sequencing artifacts, and selected for mutant reads from short cfDNA fragments (supported by reads in both directions), which are slightly enriched for ctDNA (FIG. 4).

Together, these above parameters focus the INVAR algorithm on aggregating signal from mutant molecules most likely to originate from the tumour that were randomly sampled in the context of MRD.

Example 11—INVAR Tumour Allele Fraction Weighting

Figure 16:
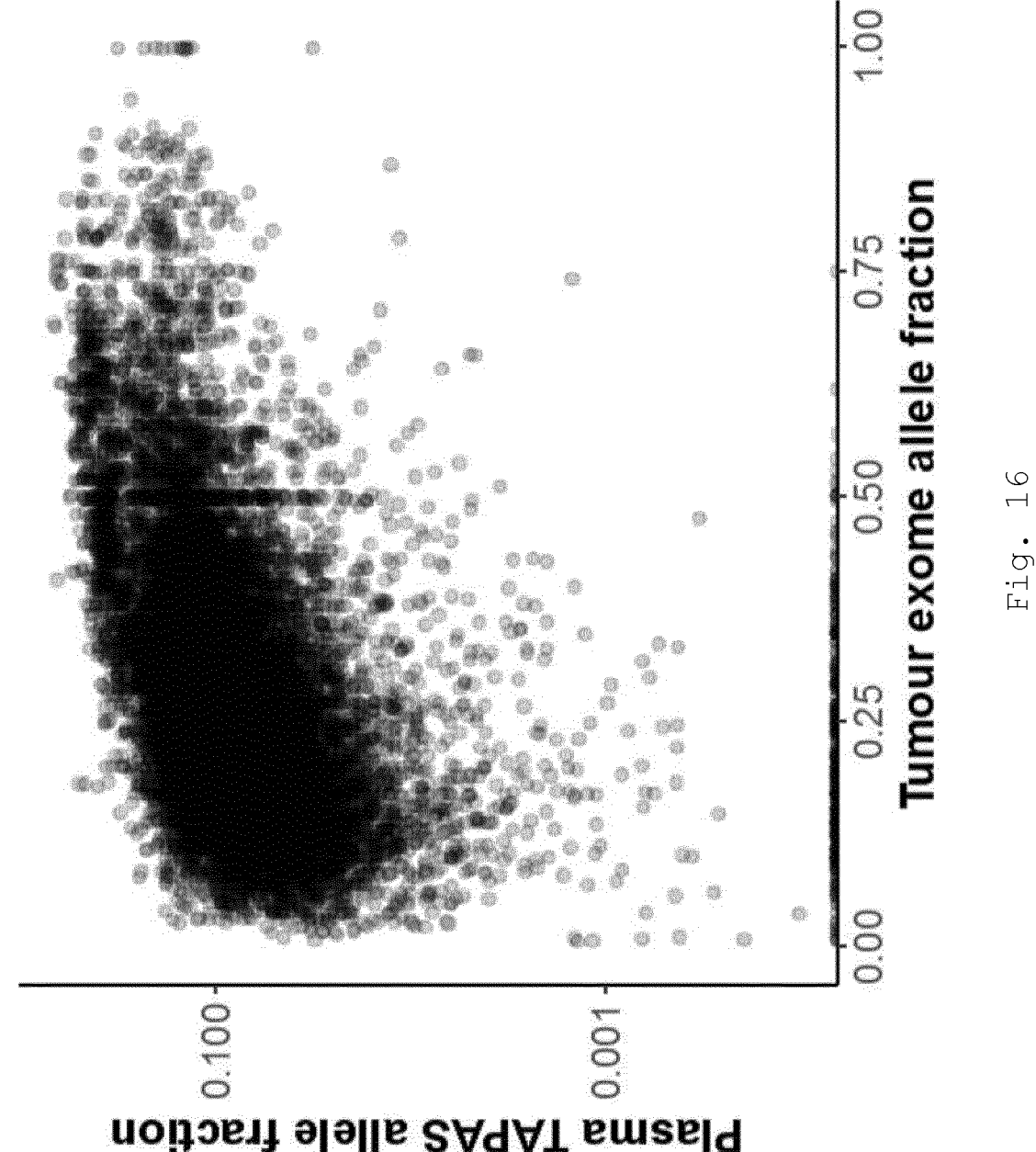
FIG. 16 shows a plot of tumour exome allele fraction versus plasma TAPAS allele fraction. Plasma samples from patients with high levels of ctDNA were used for this analysis of mutation representation.
Figure 17:
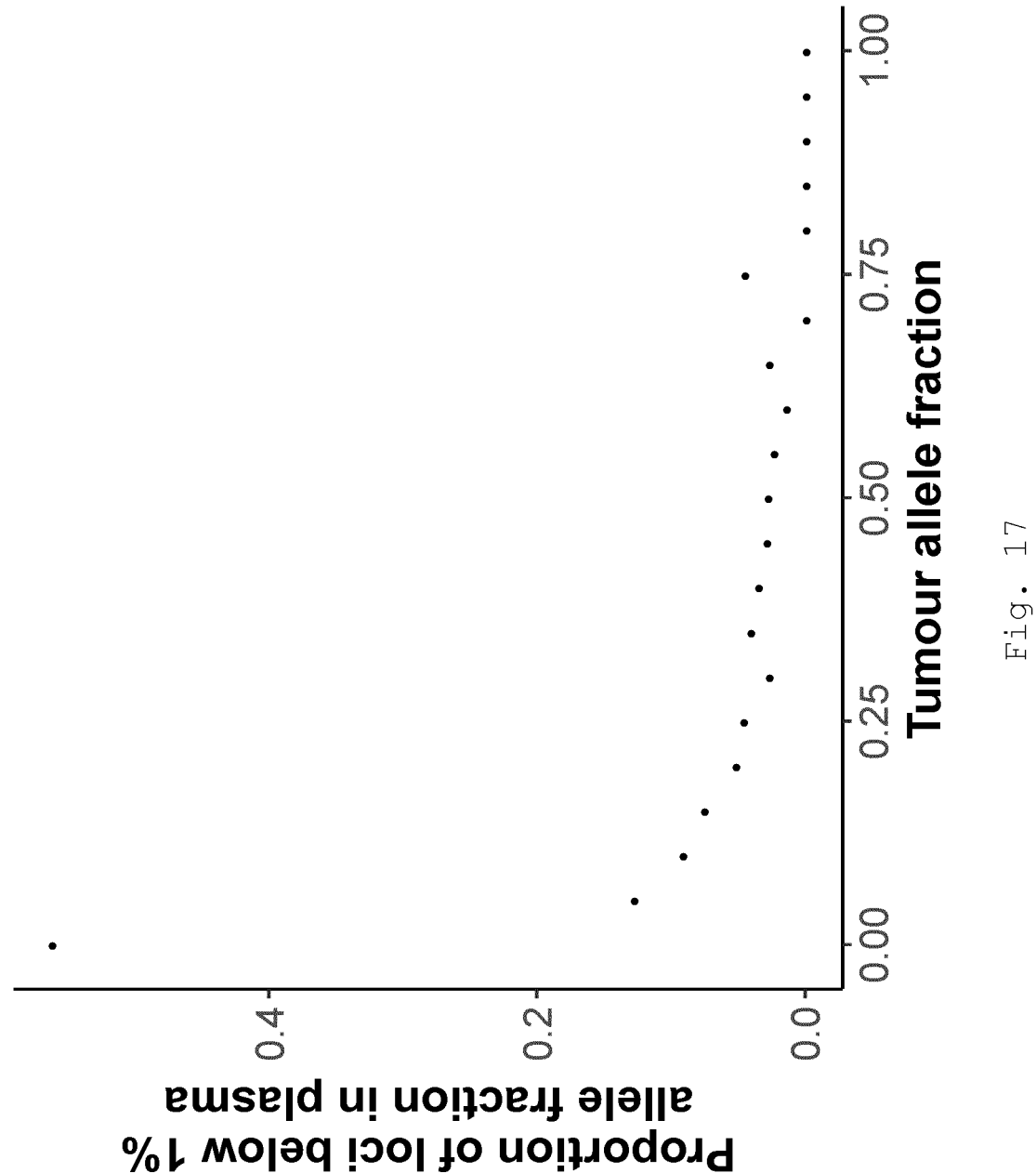
FIG. 17 shows a plot of the proportion of loci below 1% mutant allele fraction in plasma versus tumour allele fraction. The proportion of loci with mutant allele fractions <1% was greatest at tumour mutation loci with low mutant allele fractions.

We assessed the representation of mutations in plasma at time points where ctDNA was high. We found a correlation between tumour exome AF and plasma AF (FIG. 16). Thus, the likelihood of observing a given mutation in plasma is proportional to the tumour AF. This is consistent with work carried out by Jamal-Hanjani et al. (2016).

Patient-specific sequencing provides an opportunity to leverage such tumour prior information. As such, INVAR signal per locus was weighted by the tumour AF prior to aggregation of signal by mutation context. This was performed by dividing both the number of mutant read families and total read families at that locus by 1-tumour allele fraction. This places greater weight on loci more likely to contain true signal in plasma.

Figure 18:
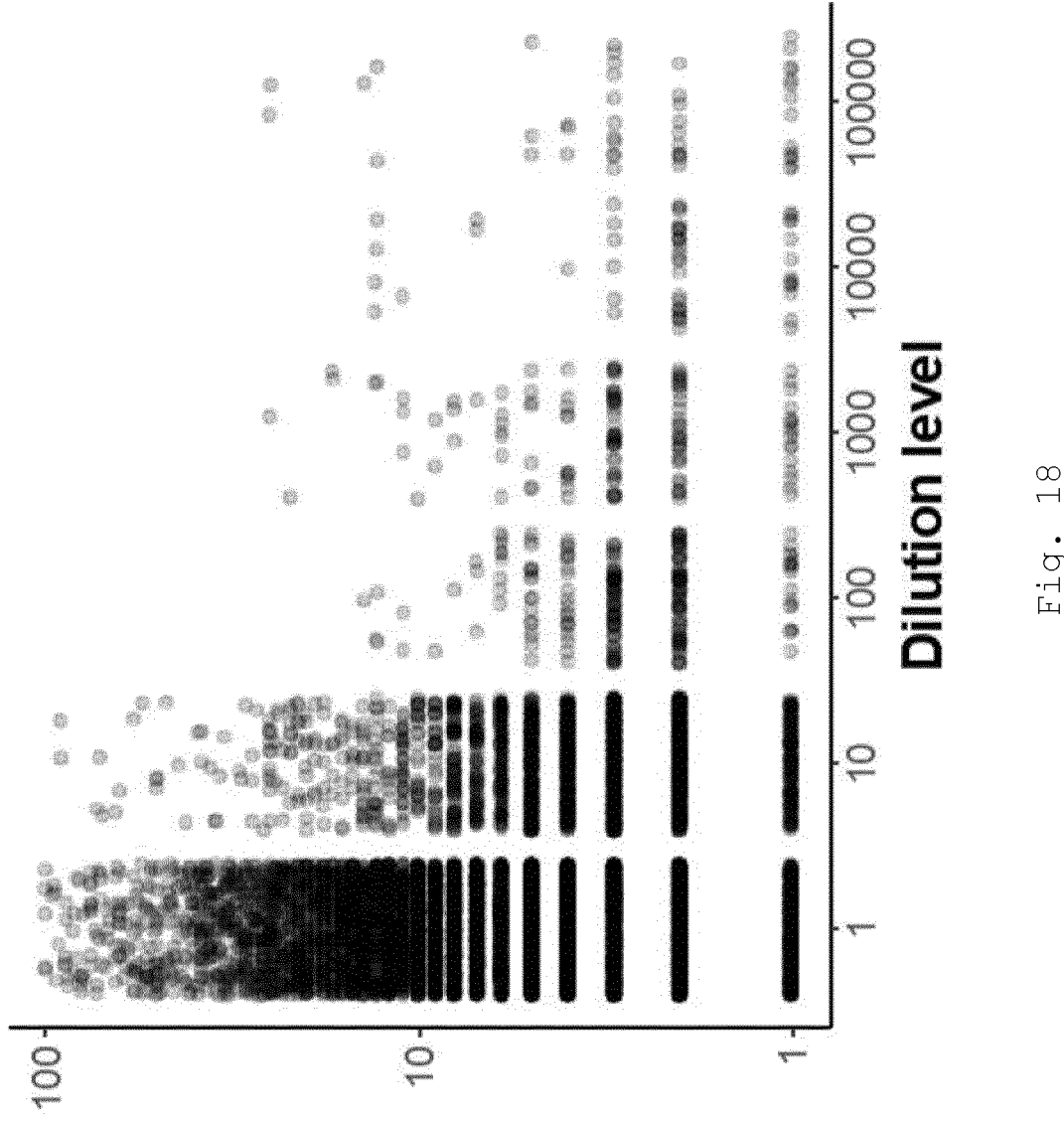
FIG. 18 shows spike-in dilution experiment mutant read families per locus, weighted by tumour allele fraction (1-tumour AF). The same dilution experiment was used as in FIG. 15.
Figure 19:
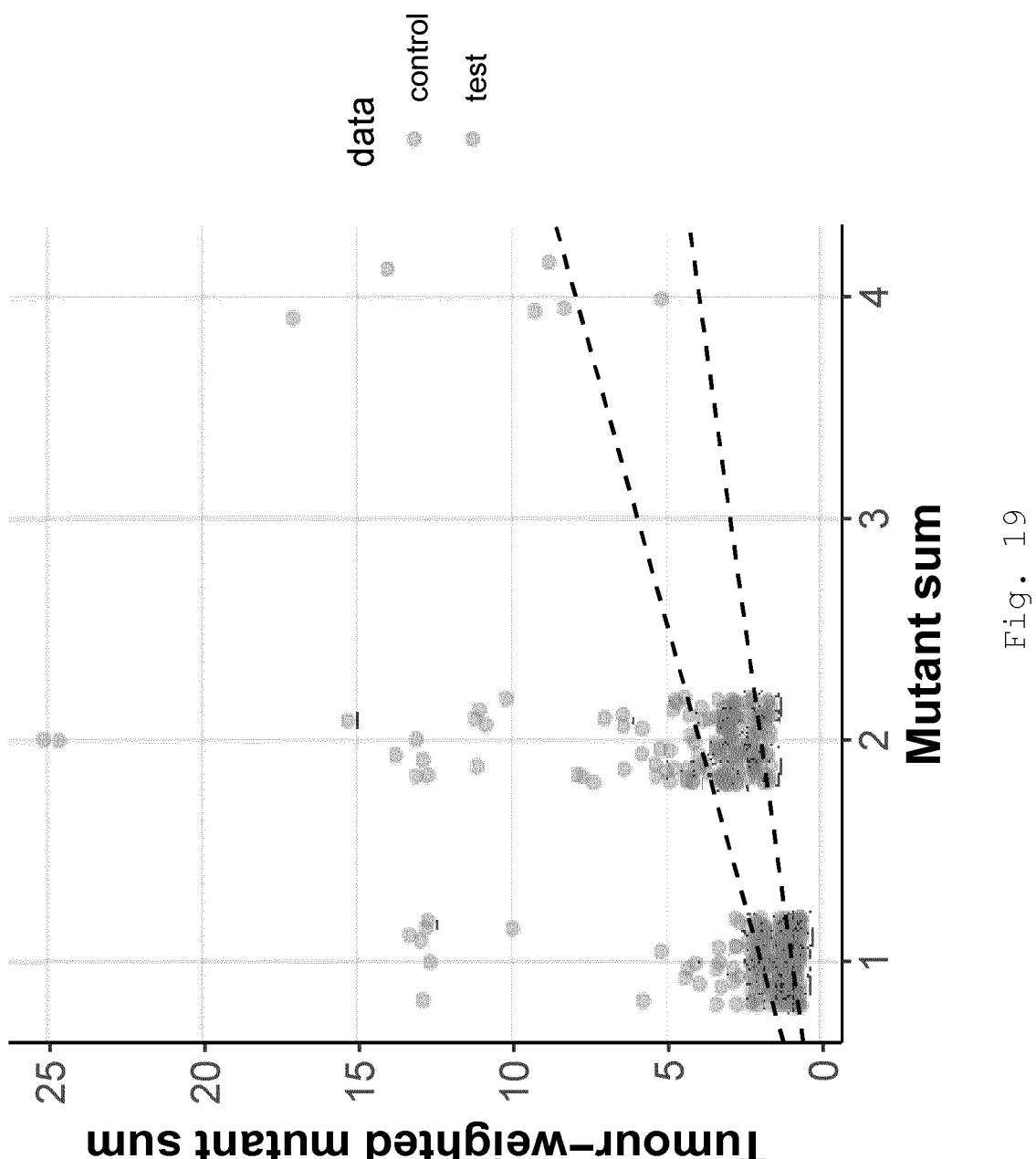
FIG. 19 shows mutant sum before and after tumour AF weighting for test and control samples. Only loci with a mutant sum <=4 are shown.

The raw number of mutant families per locus is shown in FIG. 15. FIG. 18 shows the same data following tumour weighting. The mutant sum per locus is shown before and after weighting in FIG. 19 for the dilution experiment and 7 healthy control samples, down-sampled to the same number of mutant reads between tests and controls. This shows differential enrichment of mutant signal between test and control samples due to weighting.

Example 12—Application of INVAR to Exome Sequencing Data

Next, we applied INVAR to exome sequencing data to demonstrate its generalisability to non-individualised sequencing data. Plasma exome sequencing was carried out on a subset of samples from patients with Stage IV disease.

For exome sequencing data, we did not use molecular barcodes in order to demonstrate that INVAR may be applied to existing exome data, where the use of molecular barcodes is less frequent. Given that INVAR aims to target many loci, the families of interest are spread across multiple genomic regions, and thus the likelihood of clashing endogenous barcodes is reduced. This probability is further reduced by the reduced number of families per locus obtained by exome sequencing. We pooled 3-6 exome libraries per lane of HiSeq 4000 (60-100M reads per sample).

The number of mutant reads at MRD-filtered loci pre- and post-tumour weighting are shown in FIG. 20, highlighting both the utility of requiring 2 mutant reads (1F and 1R), and the extent of weighting between mutant read families from test and control samples. Detection was achieved in all plasma samples following tumour-specific weighting, enabling quantification of ctDNA in one patient down to ~5×10$^{-5}$ AF (FIG. 21). Thus, INVAR can be applied to sequencing data without the prior design of an individualised sequencing panel.

Example 13—Untargeted INVAR

The aggregation of signal across trinucleotide contexts as opposed to calling individual loci enables INVAR to potentially be generalised to plasma sequencing data without a priori tumour knowledge. This may have applicability in patients without tumour sequencing available, though the trade-off would be expected to be a lower sensitivity and reduced ability to quantify ctDNA levels due to the abundance of loci that would never contribute any true mutant signal.

Initially, we used TAPAS data and applied error-suppression with a minimum family size of 2, as before. Next, all bases with >=50 read families in the data were identified, and the mutant signal at each was determined at each position.

In order to focus on mutant signal arising only from ctDNA, the top 100 frequently mutated genes in public exomes were excluded (Shyr et al., 2014), as was the mitochondrial chromosome and recurrently mutated families of genes identified from Shyr et al. (2014; Supplementary Methods).

INVAR was carried out across all bases with sufficient families on a spike-in dilution experiment. Following locus blacklisting (i.e. filtering out of certain loci on the basis of having a higher locus-specific error rate) and after applying an MRD-filter (for 1F+1R MRD signal only), we show preliminary evidence for the use of INVAR in an untargeted manner (FIG. 22).

Example 14—Monitoring ctDNA in Low Burden Cancer to Parts Per Million by Integration of Variant Reads Across Thousands of Mutated Loci Materials and Methods Patient cohort. Samples were collected from patients enrolled on the MelResist (REC 11/NE/0312), AVAST-M (REC 07/Q1606/15, ISRCTN81261306)[30] and LUCID (REC 14/WM/1072) studies. Consent to enter the studies was taken by a research/specialist nurse or clinician who was fully trained regarding the research. MelResist is a translational study of response and resistance mechanisms to systemic therapies of melanoma, including BRAF targeted therapy and immunotherapy, in patients with stage IV melanoma. AVAST-M is a randomised control trial which assessed the efficacy of bevacizumab in patients with stage IIB-III melanoma at risk of relapse following surgery; only patients from the observation arm were selected for this analysis. LUCID is a prospective and observational study of stage I-IIIB non-small cell lung cancer patients (NSCLC) who are planning to undergo radical treatment (surgery or radiotherapy+/−chemotherapy) with curative intent. The Cambridge Cancer Trials Unit-Cancer Theme coordinated all studies, and demographics and clinical outcomes were collected prospectively. FIG. 41 shows the flow of patients through this study as a REMARK diagram.

Sample collection and processing. Fresh frozen tumour biopsies prior to treatment were collected from patients with stage IV cutaneous melanoma. Formalin-fixed paraffin-embedded (FFPE) tumour tissue was obtained for the AVAST-M and LUCID (from surgery) trials. For patients on the AVAST-M study, plasma samples were collected within 12 weeks of tumour resection, with a subsequent sample after 3 months, where available. Patients on the LUCID study had one plasma and matched buffy coat sample taken pre-surgery. Longitudinal samples were collected during treatment of patients with stage IV melanoma as part of the MelResist study. Peripheral blood samples were collected at each clinic visit in S-Monovette 9 mL EDTA tubes.

For plasma collection, samples were centrifuged at 1600 g for 10 minutes within an hour of the blood draw, and then an additional centrifugation of 20,000 g for 10 minutes was carried out. All aliquots were stored at −80° C.

Tissue and plasma extraction and quantification. FFPE samples were sectioned into up to 8 μm sections, and one H&E stained slide was generated, which was outlined for tumour regions by a histopathologist. Marked tumour regions were macrodissected, and DNA extraction was performed using the QIAamp DNA FFPE Tissue Kit using the standard protocol, except with incubation at 56° C. overnight and 500 rpm agitation on a heat block. DNA was eluted twice using 20 μL ATE buffer each time with centrifugation at full speed. Following extraction, DNA repair was performed using the NEBNext® FFPE DNA Repair Mix as per the manufacturer's protocol. Fresh frozen tissue biopsies were first homogenised prior to DNA extraction, which was performed as follows: up to 30 mg of each fresh frozen tissue biopsy sample was combined with 600 μL RLT buffer, then placed in a Precellys CD14 tube (Bertin Technologies) and homogenised at 6,500 rpm for two bursts of 20 seconds separated by 5 seconds.

Subsequently, the Qiagen AllPrep extraction kit as per the manufacturer's protocol.

Genomic DNA was extracted from up to 1 mL whole blood or buffy coat using the Gentra Puregene Blood Kit (Qiagen) as per the manufacturer's protocol. Samples were eluted in two rounds of 70 μL buffer AE and incubated for 3 minutes before centrifugation. Up to 4 mL of plasma was extracted using the QIAsymphony (Qiagen) with a QIAamp protocol. DNA was eluted in 90 μl elution buffer and stored at −80° C. Plasma samples were extracted using the QIAsymphony instrument (Qiagen) using the 2-4 mL QIAamp protocol. For each QIAsymphony batch, 24 samples were extracted, which included a positive and negative control.

Following extraction of fresh frozen, FFPE and genomic DNA, eluted DNA concentration was quantified using a Qubit fluorimeter with a dsDNA broad range assay (ThermoFisher Scientific). To quantify cell-free DNA concentration of plasma DNA eluates, digital PCR was carried out using a Biomark HD (Fluidigm) with a Taq-man probe for the housekeeping gene RPP30 (Sigma Aldrich). 55 PCR cycles were used. The RPP30 assay was 65 bp in length. The estimated number of RPP30 DNA copies per μl of eluate was used to determine the cell-free DNA concentration in the original sample.

Tumour library preparation. FFPE tumour tissue DNA samples (up to 150 ng) and buffy coat DNA samples (75 ng) were sheared to a length of 150 bp, using the Covaris LE 220 (Covaris, Massachusetts, USA).

The standard Covaris protocol for a final fragment length of 150 bp and an input volume of 15 μl using the 8 microTUBE-15 AFA Beads Strip V2 was used. After the shearing, the fragmentation pattern was verified using a Bioanalyser (Agilent).

Sequencing libraries were prepared using the ThruPLEX DNA-seq kit (Rubicon). 100 ng and 50 ng sheared tumour and buffy coat DNA, respectively, were used and the protocol was carried out according to the manufacturer's instructions. The number of amplification cycles was varied during library preparation according to the manufacturer's recommendations. Library concentration was determined using qPCR with the Illumina/ROX low Library Quantification kit (Roche). Library fragment sizes were determined using a Bioanalyser (Agilent). After library preparation, exome capture was performed with The TruSeq Exome Library Kit (Illumina), using a 45 Mbp exome baitset. Three libraries were multiplexed in one capture reaction and 250 ng of each library was used as input. For compatibility with ThruPLEX libraries, the protocol was altered by adding 1 μl of i5 and i7 TruSeq HT xGen universal blocking oligos (IDT) during each hybridisation step. To compensate for the increased hybridisation volume, the volume of CT3 buffer was adjusted to 51 μl. Two rounds of hybridisations were carried out, each lasting for 24 hours. Library QC was performed using qPCR and Bioanalyser, as above. Samples were multiplexed and sequenced with a HiSeq 4000 (Illumina). Fresh frozen tumour biopsies and matched buffy coat library preparation was performed as described by Varela et al. 31 using the SureSelectXT Human All Exon 50 Mb (Agilent) bait set. Samples were multiplexed and sequenced with a HiSeq 2000 (Illumina).

Tumour mutation calling. For fresh frozen tumour biopsies, mutation calling was performed as described by Varela et al.[31]. For FFPE tumour biopsies, mutation calling was performed with Mutect2 with the default settings: --cosmic v77/cosmic. vcf and --dbsnp v147/dbsnp.vcf. To maximise the number of mutations retained, variants achieving Mutect2 pass (LUCID and AVAST-M samples) OR tumour LOD>5.3 were retained (AVAST-M samples). Mutation calls were filtered as follows:

1. Buffy coat mutant allele fraction equals zero
2. Mutation not in homologous region
3. Mutation not at a multiallelic locus
4. 1000 Genomes ALL and EUR frequency equals zero
5. A minimum unique tumour depth of 5.

In addition, for FFPE data in the melanoma cohort, the filter for C/A errors proposed by Costello et al. 32 was applied to suppress C/A artefacts. As a result, we generated patient-specific mutation lists for 64 patients with stage II-IV melanoma and stage I-IIIA lung cancer. A median of 625 (IQR 411-1076) and 388 (IQR 230-600) patient-specific mutations were identified per patient with melanoma and lung cancer, respectively (FIG. 31). These mutation lists were used both to design custom capture sequencing panels, and as input for the INVAR method.

Plasma library preparation. Cell-free DNA samples were vacuum concentrated at 30° C. using a SpeedVac (ThemoFisher) prior to library preparation where required. The median input into the library was 1652 haploid genomes (IQR 900-3013). Whole genome library preparation for plasma cell-free DNA was performed using the Rubicon ThruPLEX Tag-Seq kit. The number of PCR amplification cycles during the ThruPLEX protocol was varied between 7-15 cycles, as recommended by the manufacturer. Following amplification and sample barcoding, libraries were purified using AMPure XP beads (Beckman Coulter) at a 1:1 ratio. Library concentration was determined using the Illumina/ROX low Library Quantification kit (Roche). Library fragment sizes were determined using a Bioanalyser (Agilent). For the stage IV melanoma cohort, library preparation and sequencing was run in duplicate to assess the technical reproducibility of the experimental and computational method, showing a correlation between IMAF values generated by the INVAR pipeline of 0.97 (Pearson's r, p-value <2.2×10⁻¹⁶). For the early-stage cohorts, input cell-free DNA material was not split and was instead prepared and sequenced as a single sample per time point.

Custom hybrid-capture panel design and plasma sequencing. Following mutation calling, custom hybrid-capture sequencing panels were designed using Agilent SureDesign software. Between 5 and 20 patients were grouped together per panel in this implementation. Baits were designed with 4-5× density and balanced boosting for melanoma patients and 1× density and balanced boosting for lung cancer patients. 95.5% of the variants had baits successfully designed; bait design was not reattempted for loci that had failed. Custom panels ranged in size between 1.26-2.14 Mb with 120 bp RNA baits. For each panel, mutation classes and tumour allele fractions are shown in FIG. 31.

Libraries were captured either in single or 3-plex (to a total of 1000 ng capture input) using the Agilent SureSelectXT protocol, with the addition of i5 and i7 blocking oligos (IDT) as recommended by the manufacturer for compatibility with ThruPLEX libraries[33]. Custom Agilent SureSelectXT baits were used, with 13 cycles of post-capture amplification. Post-capture libraries were purified with AMPure XP beads at a 1:1.8 ratio, then were quantified and library fragment size was determined using a Bioanalyser (Agilent).

Exome capture sequencing of plasma. For exome sequencing of plasma, the Illumina TruSeq Exome capture protocol was followed. Libraries generated using the Rubicon ThruPLEX protocol (as above) were pooled in 3-plex, with 250 ng input for each library. Libraries underwent two rounds of hybridisation and capture in accordance with the protocol, with the addition of i5 and i7 blocking oligos (IDT) as recommended by the manufacturer for compatibility with ThruPLEX libraries. Following target enrichment, products were amplified with 8 rounds of PCR and purified using AMPure XP beads prior to QC.

Plasma sequencing data processing. Cutadapt v1.9.1 was used to remove known 5' and 3' adaptor sequences specified in a separate FASTA of adaptor sequences. Trimmed FASTQ files were aligned to the UCSC hg19 genome using BWA-mem v0.7.13 with a seed length of 19. Error-suppression was carried out on ThruPLEX Tag-seq library BAM files using CONNOR[34]. The consensus frequency threshold -f was set as 0.9 (90%), and the minimum family size threshold -s was varied between 2 and 5 for characterisation of error rates. For custom capture and exome sequencing data, a minimum family size of 2 was used. For sWGS and blood-spot analysis, a minimum family size of 1 was used.

To leverage signal across multiple time points, error-suppressed BAM files could be combined using 'samtools view-ubs-|samtools sort -' prior to further data processing. In the early-stage melanoma cohort (AVAST-M), where samples were available at both 3 and 6 month time points post-surgery, BAM files were merged prior to analysis.

Low-depth whole-genome sequencing of plasma. For WGS, 30 libraries were sequenced per lane of HiSeq 4000, achieving a median of 0.6× deduplicated coverage per sample. For these libraries, since the number of informative reads (IR) would limit sensitivity before background errors would become limiting, we used error-suppression with family size 1 for this particular setting. Error rates per trinucleotide were compared between WGS and custom hybrid-capture sequencing data for family size 1, showing a Pearson r of 0.91. WGS data underwent data processing (Supplementary Methods) except the minimum depth at a locus was set to 1, and patient-specific outlier-suppression (Supplementary Methods) was not used because loci with signal vs. loci without signal would only give allele fractions of 0 or 1 given a depth of 0.6x.

Cell-free DNA extraction from dried blood spots. 50 µl fresh (or thawed frozen) whole blood was collected from patients on the MelResist study on to Whatman™ FTA™ Classic Cards, and was allowed to air dry. 50 µl fresh whole blood was obtained from an ovarian cancer xenograft mouse model immediately following its sacrifice, and similarly applied Whatman™ FTA™ Classic Cards, and allowed to air dry. Blood spot card samples were stored at room temperature inside a re-sealable plastic bag. DNA was extracted from the card using the QIAamp DNA Investigator kit, using the manufacturer's recommended extraction protocol for FTA and Guthrie cards, which is conventionally used for assessment for inherited genetic conditions in neonates from gDNA. Three 3 mm punches were made from the blood spot, and carrier RNA was added to Buffer AL as per the manufacturer's recommendation. Blood spot DNA (which we hypothesised contained both cell-free DNA and gDNA) was eluted in 25 µl water, which was reapplied to the membrane and re-eluted.

Size-selection and library preparation of blood spot cell-free DNA. Blood spot DNA eluates contain a low concentration of cell-free DNA, among a large background of gDNA (FIG. 40a). cell-free DNA library preparation cannot be effectively performed from such a sample since the abundance of long fragments reduces the likelihood of any cell-free DNA fragments successfully being ligated with adaptor molecules and amplifying. Based on our characterisation of gDNA length of >1-10 kb (FIG. 40a), and the fact that cell-free DNA is ~166 bp[35], we opted to perform a size-selection in order to remove contaminating gDNA fragments.

A right-sided size-selection was performed on DNA eluates prior to library preparation using AMPure XP beads (Beckman Coulter) in order to remove long gDNA fragments. For this purpose, we adapted a published protocol for right sided size selection that is conventionally used for DNA library size-selection prior to Next Generation Sequencing[36]. Following optimisation of bead: sample ratios for cell-free DNA fragment sizes, we used a bead: sample ratio of 1:1 to remove contaminating gDNA. The supernatant was retained as part of the right-sided selection protocol. A second size-selection step used a 3:1 bead: sample ratio to capture all remaining fragments, and the size-selected DNA was eluted in 20 µl water. Blood spot eluates were concentrated to 10 ul volume using a vacuum concentrator (SpeedVac). Next, Rubicon Tag-Seq library preparation was carried out, and libraries underwent QC using Bioanalyser (Agilent) and qPCR (as described above). Libraries were submitted for whole-genome sequencing on a HiSeq4000 (Illumina) and the INVAR analysis pipeline was used (Supplementary Methods).

Survival analysis for resected stage II-III melanoma cohort. Disease-free interval (DFI), and overall survival were calculated from the date of randomisation of the AVAST-M trial to the date of first recurrence or date of death, respectively[9]. Kaplan-Meier analysis was used to generate survival curves for differences between DFI and OS in patients with detected ctDNA vs. non-detected levels and compared using a Cox proportional hazards model to obtain hazard ratios and 95% CIs.

Imaging. CT imaging was acquired as part of the standard of care from each patient of the stage IV melanoma cohort and was examined retrospectively. Slice thickness was 5 mm in all cases. All lesions with a largest diameter greater than ~5 mm were outlined slice by slice on the CT images by an experienced operator, under the guidance of a radiologist, using custom software written in MATLAB (Mathworks, Natick, MA). The outlines were subsequently imported into the LIFEx software[37] in NifTI format for processing. Tumour volume was then reported by LIFEx as an output parameter from its texture based processing module.

Results

Circulating tumour DNA (ctDNA) can be robustly detected in plasma when multiple copies are present; however, when samples have few copies of tumour DNA, analysis of individual mutation loci can result in false negatives even if assays have perfect analytical performance due to sampling noise (FIG. 23a). Low amounts of ctDNA in plasma can occur when there is little input material due to sampling limitations, or when there is larger amount of plasma but very low tumour burden in plasma such as patients with early-stage cancer[1], or patients at all stages undergoing treatment[1,2] (FIG. 29). Sequencing errors can further limit detection. To improve sensitivity, studies have analysed larger volumes of plasma from multiple blood tubes[3,4], and/or used sequencing panels covering 18-507 genes (2 kb-2 Mb of the genome). Analysis in plasma of up to 32 patient-specific mutations (identified beforehand via tissue analysis) achieved detection to levels of 1 mutant molecule per 25,000 copies in a patient with non-small cell lung cancer (NSCLC)[5]. ctDNA was detected in <50% of patients with stage I NSCLC[6,7] and in only 19% of lung adenocarcinoma cases[6]. In early-stage patients who underwent surgery and later relapsed, ctDNA was detected after surgery in approximately 50% of breast or colorectal cancer patients[4,8] but only 15% of melanoma patients[9]. However, sensitivity can in principle be further increased to detect lower amounts of ctDNA by increasing the number of mutations analysed.

Detection of ctDNA is limited by the amount of DNA, which we quantify as the number of haploid genomes analysed (hGA). In terms of sequencing data, hGA is equivalent to the average unique sequencing coverage. In methods such as shallow whole-genome sequencing (sWGS), often <1 hGA of DNA is analysed (less than 1× coverage), and although this is often generated from nanogram (ng) amounts of DNA, it could in principle be generated from picograms of DNA. Other methods generate many thousands-fold sequencing depth, which may represent duplicate reads of the same molecules if DNA input is few ng or less. Another determinant of analytical sensitivity is the number of tumour-mutated loci that are analysed[2,5-7]. Sensitivity for detecting ctDNA is limited by the total number of 'informative reads' (IR), which we define as the sum of all reads covering loci with patient-specific mutations. This is equivalent to the product of the number of mutations and the average unique depth (across the mutated loci). We therefore plot these two variables in a two-dimensional space (FIG. 23b). The same IR may be generated from different combinations of the two dimensions. For example, $10^5$ IR may be obtained from 10,000 hGA and 10 mutated loci (deep sequencing of a panel covering few tumour mutations per patient), or from 10,000 loci analysed in 10 hGA (limited input or sequencing depth). Although some of these mutations are likely to be subclonal or passenger events, we hypothesized that by analysing a large number of them this would compensate for the loss of individual mutation signals. In a sample with a ctDNA fraction of $10^{-5}$, observing a single mutant read across $10^5$ IR would have a probability of 0.63 based on binomial statistics, but this increases to 0.99 with $5 \times 10^5$ IR, highlighting the relationship between molecules sampled and the maximum sensitivity achievable. To obtain information from a large number of mutations per patient, we sequenced plasma DNA using custom capture panels, whole-exome sequencing (WES) or whole-genome sequencing (WGS). In analysing sequencing data, ctDNA detection algorithms have previously relied on identification of individual mutations[3,6,10], which uses limited information inefficiently: any signal that does not pass a mutation calling threshold is discarded and lost. Studies have highlighted the potential advantages of aggregating signal across multiple loci to detect DNA from transplanted organs[11] or diluted tumour DNA[5]. In cancer monitoring, multiple mutations per patient have been previously analysed[3,5,6,12,13], but detection was performed for each mutation separately. To efficiently use sequencing information from plasma we developed INtegration of VAriant Reads (INVAR). INVAR uses prior information from tumour sequencing to guide analysis and aggregate signal across $10^2$-$10^4$ mutated loci in the patient's cancer (FIG. 23c). The mutation lists are patient-specific; therefore, samples from other patients are used to calculate background signal rates, after confirming for each mutation that it is not found in that patient's tumour sequencing data (FIG. 23d). Additional samples from healthy individuals were used as controls and to assess specificity (FIG. 30a). INVAR considers biological and technical features of ctDNA sequencing including trinucleotide error rate, ctDNA fragment length patterns and the allele fraction of each mutation in the patient's tumour (flowchart in FIG. 30b). Since ctDNA is detected in aggregate rather than attempting to call mutations at each locus, INVAR can also detect ctDNA from data with low sequencing depth (<1× unique coverage) and if input material is limited.

To identify patient-specific mutations, we performed tumour sequencing of 45 patients with stage II-IV melanoma and 19 patients with stage I-IIIA NSCLC. After identifying tumour mutations (Methods), we generated patient-specific mutation lists (FIG. 31), consisting of a median of 625 mutations per patient with melanoma (IQR 411-1076) and 388 mutations per patient with stage I-IIIA NSCLC (IQR 230-600). These lists were used as input for INVAR, and were applied to plasma sequencing data generated using custom capture sequencing panels (2,301× mean raw depth), WES (238× depth) and sWGS (0.6× depth).

14.1 Background Noise Reduction and Signal Integration

Increasing the number of informative reads addresses sampling error, by either increasing the input (hGA) or the mutations analysed. To reduce likelihood of false positive detection at high IR, the background error must be lower than the reciprocal of IR. As part of the INVAR workflow (FIG. 24a), we reduced background error rates by read-collapsing based on endogenous or exogenous unique molecular identifiers[14] (UMIs); excluding signal that was not supported by both forward and reverse reads; using bespoke error models that assess error rates for different mutation contexts; suppressing outlier noise at a locus that is not consistent with the remaining distribution of patient-specific mutant signal in that sample, i.e. "outlier suppression" (FIGS. 32-34, Supplementary Methods). This resulted in a background error rate that was reduced by 131-fold on average across different trinucleotide contexts (FIG. 24b, FIG. 24c).

Previous studies have shown relationships between tumour allele fraction and plasma allele fraction[13,15], as well as showing size differences between mutant and wild-type cell-free DNA fragments[16-18]. To effectively use sequencing information, INVAR enriches for ctDNA signal through probability weighting based on ctDNA fragment sizes and the tumour allele fraction of each mutation locus (FIG. 24d, FIG. 35, Methods). This generates a significance level for each of the loci in the patient-specific mutation list, which are combined into an aggregate likelihood function. Sequencing data from plasma DNA of patients using non-matched mutation lists (FIG. 23c) are used as negative controls for receiver operating characteristic (ROC) curve analysis to select a likelihood threshold for ctDNA detection for each cohort (Methods, FIG. 36). Sequencing data from healthy individuals is used to assess false positive detection at this threshold (FIG. 30a). An integrated mutant allele fraction (IMAF) is determined by taking a background-subtracted, depth-weighted mean allele fraction across the patient-specific loci in that sample (Supplementary Methods).

14.2 Analytical Performance in Positive and Negative Controls

We evaluated the analytical performance of INVAR by analysis of sequencing from a custom capture panel, in a dilution series of plasma from one melanoma patient (stage IV), for whom we had identified 5,073 mutations through exome sequencing (Supplementary Methods), diluted into plasma from two healthy control volunteers to expected IMAF as low as $3.6 \times 10^{-7}$, and analysed in replicates. Without error-suppression, the lowest dilution detected with analytical specificity >0.85 (Methods) had an expected ctDNA concentration of $3.6 \times 10^{-5}$. At this concentration, 2/2 replicates were detected at average IMAF of $4.7 \times 10^{-5}$ (FIG. 24e). Following error-suppression and size-weighting, all samples but one were detected with an analytical specificity >0.95. Both replicates diluted to an expected IMAF of $3.6 \times 10^{-6}$ (3.6 parts per million, ppm) were detected, with IMAF values of 4.3 and 5.2 ppm. Of the 3 replicates diluted to an expected $3.6 \times 10^{-7}$, two were detected, with measured IMAF values of 3.9 ppm and 1.3 ppm (with $3.16 \times 10^{6}$ and $2.44 \times 10^{6}$ IR respectively). The third sample had low IR (370, 381) and no mutant reads were observed, highlighting that many IR are needed to detect low ctDNA concentrations. In contrast, ctDNA detected close to the limit of detection with few mutant reads (such as examples above) may show artificially inflated IMAF due to success bias.

The correlation between IMAF and the expected mutant fraction was 0.98 (Pearson's r, $p < 2.2 \times 10^{-16}$, FIG. 24e). Without spiked-in DNA from the cancer patient, no mutant reads were observed across 11 replicates of the DNA from these healthy individuals, in a total of 6,328,410 IR (FIG. 24e). In the same sequencing data analysed without error-suppression and size-weighting, false-positive detection of ctDNA was observed in 3 samples without spiked-in DNA (FIG. 24e). We downsampled the sequencing data in silico to include only subsets of the patient-specific mutation list, confirming that more mutations resulted in larger IR and correspondingly higher ctDNA detection rates (FIG. 24f, Supplementary Methods).

We defined the analytical specificity using sequencing data from plasma DNA of patients, using non-matched mutation lists (FIG. 23c). This gave a median specificity of 98.0% (FIG. 36). To confirm this, we ran custom capture sequencing and INVAR analysis on samples from healthy individuals using each of the patient-specific mutation lists (FIG. 30a). Across 4 analyses of plasma DNA from 26 healthy individuals, a median specificity value of 97.05% was obtained, matching the expected analytical specificity (FIG. 36).

14.3 Application of INVAR to Detect ctDNA in Plasma of Cancer Patients

We applied INVAR to sequencing data generated using custom capture panels from 125 plasma samples from 47 stage II-IV melanoma patients, and 19 plasma samples from 19 stage I-IIIA NSCLC patients. We analysed a median of 625 mutations per patient with melanoma and 388 mutations per patient with stage I-IIIA NSCLC, resulting in up to $2.9 \times 10^{6}$ IR per sample (median $1.7 \times 10^{5}$ IR), thus analysing orders of magnitude more cell-free DNA fragments compared to methods that analyse individual or few loci (FIG. 25a). Using the same input DNA and sequencing data, analysis of the 20 mutation loci with highest depth would result in less than 20,000 IR for nearly all samples, whereas the use of large mutation lists generated between 20,000 and $10^{6}$ IR for most samples (FIG. 25b).

A small number of samples had <20,000 IR, thus not achieving the high sensitivity that INVAR can in principle produce. When implementing INVAR in future practice, we suggest that such cases where ctDNA is not detected with a low IR be defined as technical failures and would be either repeated with larger DNA input/more sequencing, or by re-analysis of the tumour and normal DNA from that patient by wider-scale sequencing such as WGS (FIG. 25c). In our study, 6 of 144 samples had no ctDNA detected with <20,000 IR (FIG. 25d), and are indicated as technical fails in detection statistics described below. If greater sensitivity is desired, higher thresholds for IR can be selected: a further 11 samples had no ctDNA detected with <66,666 IR (FIG. 25d). In the current implementation of INVAR, positive detection requires at least two mutant reads (across all IR); thus, 95.8% of samples had ctDNA detected, or determined to be lower than 0.01% (less than 2 mutant reads across >20,000 IR). 88.2% had ctDNA detected or determined to be lower than 0.003% (less than 2 mutant reads across >66,666 IR).

In contrast, a small number of cases achieved >$10^{6}$ IR, affording unparalleled sensitivity and detection of ctDNA at levels of 2.9 and 6.5 ppm (FIG. 25d). If patient-specific mutation lists would be generated by WGS rather than WES of tumour and normal DNA samples from each patient, we expect that this level of sensitivity would be reached for the large majority of these cases of melanoma or NSCLC (FIG. 25b).

14.4 ctDNA Monitoring to Parts Per Million and Fractions of a Cellular Genome

We detected ctDNA and quantified its levels, as indicated by IMAF values, ranging from $2.5 \times 10^{-6}$ to 0.25 (FIGS. 25d and 25e). This confirmed a dynamic range of 5 orders of magnitude and detection of trace levels of ctDNA in plasma samples from cancer patients to the few ppm range (FIG. 26a), from a median input material of 1638 copies of the genome (5.46 ng of DNA). In a total of 17 of the 144 plasma samples analysed, ctDNA was detected with signal in <1% of the loci known to be mutated for that patient's tumour, indicating that these samples contained only small fractions of the genome of a single tumour cell (FIG. 26b). The lowest fraction of detected mutations was 1/714, the equivalent of <5 femtograms of tumour DNA. Given the limited input, the low ctDNA levels detected would be below the 95% limit of detection for a perfect single-locus assay in 48% of the cases (FIG. 26b, FIG. 37a).

In patients with metastatic melanoma, IMAF showed a correlation of 0.8 with imaging (Pearson's r, $P = 6.7 \times 10^{-10}$, FIG. 37b), and a correlation of 0.53 with serum lactate dehydrogenase (LDH, Pearson's r, $P = 2.8 \times 10^{-4}$, FIG. 37c). INVAR analysis was used to monitor ctDNA dynamics in response to treatment (FIG. 37d). In one patient treated serially with targeted therapies and immunotherapy for melanoma, ctDNA was detected at an IMAF of 2.5 ppm, with a tumour volume of 1.3 cm$^3$ at that time point (FIG. 25e). Compared to other studies[6,19], INVAR showed a steeper gradient between tumour volume and IMAF, which may reflect the lower detectable IMAF with INVAR (FIG. 37b).

14.5 ctDNA Detection in Early-Stage NSCLC

We tested ctDNA detection by INVAR in plasma samples collected pre-treatment from 19 patients with newly diagnosed stage I-IIIA NSCLC (consisting of 11, 6 and 2 patients with stage I/II/IIIA, respectively). In two samples, ctDNA was not detected, but fewer than 20,000 IR were analysed (FIG. 25*d*) due to a small number of mutations identified in WES of matched tissue (59 and 93 in each case). Excluding these two patients (see FIG. 25*c*), the median number of informative reads was $7.2 \times 10^4$ (IQR $3.9$-$10.3 \times 10^4$). ctDNA was detected (with analytical specificity >0.98, FIG. 36) in 12 out of 17 patients (FIG. 26*a*, FIG. 26*c*), including 1/5 patients with stage IA, 4/5 patients with stage IB, 5/5 patients with stage II and 2/2 patients with stage III disease (FIGS. 38*a* and 38*b*). 9 out of of the stage IA and IB patients had a histological subtype of adenocarcinoma, which were previously difficult to detect using other methods[6]. Across the cohort, ROC analysis was applied to the likelihood ratios generated by INVAR (Supplementary Methods), giving area under the curve (AUC) values of 0.73, 0.82 and 0.93 for stage I only, stage I-IIIA, and stages II-IIIA only, respectively (FIG. 26*d*). Excluding patients where sensitivity of 0.003% was not reached (<66,666 IR, FIG. 25*d*), ctDNA was detected in 12 of 14 samples including 1/2 patients with stage IA, 4/5 patients with stage IB, 5/5 patients with stage II and 2/2 patients with stage III disease.

14.6 Detection of Minimal Residual Disease by INVAR

To test INVAR in the residual disease setting, we analysed samples from 38 patients with resected stage II-III melanoma recruited in the UK AVAST-M trial (FIG. 38*c*), collected up to 6 months after surgery with curative intent. We interrogated a median of $3.6 \times 10^5$ IR (IQR $0.64 \times 10^5$ to $4.03 \times 10^5$) and detected ctDNA (with analytical specificity >0.98, FIG. 36) to a minimum IMAF of 2.85 ppm. Five patients had undetected ctDNA and <20,000 IR, and were excluded (FIG. 25*d*). Of the 33 evaluable patients, ctDNA was detected in 50% of patients who later recurred, and was associated with a significantly shorter disease-free interval (4.5 months vs. median not reached with 5 years' follow-up; Hazard ratio (HR)=3.69; 95% CI 1.44-9.46, P=0.007; FIG. 26*d*) and overall survival (2.6 years vs. median not reached, FIG. 38*d*). In a previous analysis using a single-locus digital PCR assay of plasma DNA from 161 patients with resected BRAF or NRAS mutant melanoma from the same trial, ctDNA was detected in only 15.6% of patients who later relapsed[9].

14.7 Assessing Detection Rates with Varying IR

Using IMAF values from the clinical samples, we estimated the expected detection rates for different cohorts of patients with limited numbers of IRs, and fitted a linear model ($R^2$=0.95) to predict the IRs that would be required to achieve different detection rates. In stage IV melanoma patients at baseline time points, ctDNA was detected in 100% of cases using $10^5$ IR (FIG. 26*e*). In patients with stage IV melanoma undergoing treatment, where ctDNA levels are lower, an extrapolation of the linear fit predicted that $10^6$-$10^7$ IR would enable detection of ctDNA in nearly all samples (FIG. 38*e*). In patients with early-stage NSCLC, we suggest that it may be possible to detect ctDNA in nearly all patients if $10^7$ IR were sequenced for each sample. Reaching >$10^7$ IR per sample becomes limiting in terms of both sequencing costs, the amount of input DNA required and the number of mutations needed to be targeted. For stage II-III melanoma patients who underwent surgery, our data suggests that even analysis of $10^7$ IR would result in detection of ctDNA within 6 months of surgery in only 66.7% of patients who would relapse (FIG. 26*e*).

14.8 Sensitive Detection of ctDNA from WES and WGS

Patient-specific capture panels allow deep sequencing of patient-specific mutation lists at lower sequencing costs, but adds a time-consuming step. We hypothesised that INVAR can be leveraged to achieve increased sensitivity by aggregating informative reads also when applied to standardised workflows such as whole exome or genome sequencing. This can allow sequencing of tumour-normal material to occur in parallel to plasma sequencing, and the resulting tumour-normal data can be used for INVAR analysis on sequencing data generated from plasma cell-free DNA (FIG. 27*a*). To test the generalisability of INVAR, we utilised commercially available exome capture kits to sequence plasma DNA (median depth 238×) in a subset of samples where ctDNA was detected by patient-specific capture panels spanning a range of IMAF from $4.5 \times 10^{-5}$ to 0.16 (FIG. 39*a*). Depending on the number of mutations detected in the tumour exome and the depth of sequencing for each case, we obtained between 1,565 and 473,300 IR (FIG. 27*b*), despite the modest depth of sequencing using a commercial platform. We detected ctDNA in 21 of 21 samples, to an IMAF of $4.34 \times 10^{-5}$ (FIG. 27*c*), demonstrating that ctDNA can be detected by INVAR with high sensitivity using patient-specific mutation lists without need for designing a custom sequencing panel. These IMAF values showed a correlation of 0.96 with custom capture data on the same samples (Pearson's r, P=$8.5 \times 10^{-12}$, FIG. 39*a*). In comparison to custom capture panels, which allowed deep sequencing of plasma DNA and generated information from an equivalent of $10^2$-$10^3$ hGA (FIG. 25*a*), the lower depth obtained by exome sequencing yielded data from only a few dozen hGA (FIG. 39*b*).

We hypothesised that ctDNA could be detected and quantified with INVAR from even smaller amounts of input data. We performed whole-genome sequencing on libraries from cell-free DNA from longitudinal plasma samples from a subset of six patients with stage IV melanoma to a mean depth of 0.6× (FIG. 27*d*). We used patient-specific mutation lists generated by WES from each patient's tumour and normal DNA, which generated >500 patient-specific mutations for each of those patients. This resulted in between 226 and 7, 696 IR per sample (median 861, IQR 471-1,559; FIG. 27*b*). We analysed this data by INVAR, detecting in some samples fractional levels of ctDNA as low as $1.1 \times 10^{-3}$. In samples where ctDNA was not detected, we calculated the maximum possible ctDNA fraction of that sample with 95% confidence based on the number of IR sampled (FIG. 27*d*, Methods).

These results demonstrated detection of ctDNA from untargeted sequencing data with <1 hGA and suggest that with a sufficiently large number of tumour-specific mutations, INVAR may yield high sensitivity for ctDNA detection even with minute amounts of DNA input.

14.9 Detection of ctDNA from Dried Blood Spots

We next hypothesised that by integrating mutant reads across the genome, ctDNA could be detected from limited sequencing data generated from few copies of the genome, extracted from a dried blood spot (from a single drop of blood with volume of 50 μL). Real-time PCR has previously been used to carry out fetal RHD genotyping and HIV detection using maternal dried blood spots[20,21], though NGS of cell-free DNA from blood spots has not been previously described. Generating a cell-free DNA sequencing library from a blood spot is challenging due to the low number of cell-free DNA copies present, and due to the abundance of long genomic DNA (gDNA) fragments released by blood cells (FIG. 40*a*). To determine whether ctDNA could be detected from a blood-spot, we developed a workflow to generate sequencing libraries from the limited cell-free DNA molecules present (Methods). To remove contaminating gDNA fragments, we applied size-selection to DNA extracted from a dried blood-spot collected from a patient with melanoma. Next, we generated a sequencing library from this size-selected DNA, which revealed multiple copy number alterations using sWGS (FIG. 28a), consistent with copy number alterations found in the matched plasma sample from the same patient isolated by traditional methods (FIG. 40b). When INVAR was applied to this data, ctDNA was detected with an IMAF of 0.039, from 6 hGA of sequencing data. We used a statistical method, SPECIES[22], to estimate the total number of haploid genomes in the sequencing library as 10 hGA (FIG. 40c, Supplementary Methods), which may be reached with greater sequencing depth from this library. This therefore demonstrated detection of ctDNA equivalent to a fraction of a single genome of a cancer cell in a dried blood spot.

The size distribution of the DNA fragments sequenced from the blood-spot was similar to that obtained from cell-free DNA of plasma samples[2,16,18] (FIG. 40d). Fragment sizes were evaluated separately for reads which had either reference sequence or tumour-specific mutations at the loci in the patient-specific mutation list. This showed that the tumour-derived fragments were shorter, with a peak around 145 bp, whereas the non-mutated reads had a peak at around 166 bp (FIG. 28b); this recapitulates results recently observed by analysis of plasma samples from cancer patients[2,16,18] Aside from clinical utility in humans, analysis of minute amounts of blood may facilitate longitudinal ctDNA monitoring from other organisms or models, such as rodents[23]. Using an orthotopically xenografted ovarian tumour mouse model, 50 μL of whole blood was sampled using a dried blood spot card, and a sequencing library prepared and sequenced with sWGS (Methods). Upon alignment of sequencing reads, both human genome (tumour-derived) and mouse genome (wild-type) reads were observed, with characteristic fragmentation patterns of mutant and wild-type cell-free DNA (FIG. 28c). Multiple copy number variations were observed in the human sequence (FIG. 40e).

We estimate the potential sensitivity of ctDNA in dried blood spots (50 μL volume) using known mutation rates for different cancer types[24]. If patient-specific mutation lists were generated from WGS of tumour and normal DNA from each patient (rather than WES as was used in this study), larger mutations lists for every patient would be generated. This would allow WGS data from blood spots to generate 1-2 orders of magnitude greater IR per sample, and correspondingly lower limits for ctDNA detection (FIG. 28e), compared to the detection limits we observed. In melanomas, for example, with 0.1× WGS coverage, the detection limit for ctDNA is predicted to have a median of 0.007 (inter-quartile range, $4.4\times10^{-4}$-$1.5\times10^{-3}$). With 10× WGS coverage, the predicted detection limit for different cancer types ranges from <1 ppm for some cancers with high mutation rates, to approximately $10^{-4}$ for cancers with low mutations rates such as breast and prostate cancers.

Discussion of Example 14

Integration of variant reads provides a method to overcome the inherent limitations of sampling noise to detect ctDNA in samples that contain much fewer than one copy of the cancer genome, by combining signal across multiple mutations that have been identified in the patient's tumour (FIG. 23). We showed that by aggregating signal across $10^2$-$10^4$ mutated loci it is possible to detect <0.01 copies of a cancer genome, even when this represents few parts per million of the cell-free DNA in plasma, 1-2 orders of magnitude lower than previous studies[3,5]. This level of sensitivity can only be achieved by targeting a large number of mutations to maximise the number of informative reads (IR); increasing input mass to this extent would not be feasible in practice (FIG. 23b). The number of mutations obtained from tumour sequencing depends on the cancer type and the breadth of sequencing. In this first application of this method, we used exome sequencing to identify cancer mutations, and in several cases had to exclude samples from analysis due to few informative reads. By evaluating samples with sensitivity of at least 0.01%, we detected ctDNA in 67% of stage I-II NSCLC patients pre-surgery. This increased to 83% if a more stringent IR threshold was used, effectively requiring a minimum sensitivity of 0.003% (30 ppm). Following surgery, ctDNA was detected within 6 months in 50% of patients with stage II-III melanoma who later relapsed. This finding reflects the challenge of detection of ctDNA post-surgery, in a clinical setting where patients may relapse as many years after initial treatment[25]. Further increases in IR through additional mutations and input material may further boost the sensitivity of ctDNA for detection of minimal residual disease (FIG. 27e).

A recent trial for early detection of nasopharyngeal cancers leveraged the multiple copies of the Epstein-Barr virus (EBV) in each cancerous cell to detect the presence of cancer in blood samples from asymptomatic individuals[26]. The authors estimated that this was possible because each cancer cell contains approximately 500 copies of the viral DNA sequence that their assay targeted, and suggested that multiplexed analysis of ~500 targets might enable early detection in other cancers[26]. The INVAR method in its current implementation requires prior knowledge of the tumour mutations, and therefore could not be applied as a screening assay for early detection of cancer; however it can leverage the principle of highly multiplexed analysis to detect ctDNA in the majority of patients with early-stage cancers (FIG. 26). INVAR leverages features of cell-free DNA outside of specific sequence alterations, such as fragment sizes and tumour allele fractions of each mutation; in future, additional non-mutation features such as fragment ends[27] could be incorporated to attribute greater weight to cancer-derived fragments.

We showed that INVAR can be applied flexibly to NGS data generated using patient-specific capture panels (FIG. 26), commercial exome sequencing panels, or WGS (FIG. 27). Although these latter methods generated fewer IR, the limited sequencing input allowed detection at ctDNA fractional levels below 50 ppm with WES, and at ~0.1% with SWGS (more than an order of magnitude lower than previously-described methods based on copy-number analysis from WGS[28,29]). Based on these findings, we then leveraged INVAR to detect ctDNA from limited DNA input, including from a dried blood spot collected from a cancer patient. We describe how future implementation of INVAR with mutation lists generated across the entire genome might allow detection of ctDNA to levels of 1-100 ppm from the cell-free DNA in a dried blood spot of 50 μL. This creates the possibility of future tests for cancer monitoring for residual disease or disease relapse based on self-sampling with dried blood spots.

REFERENCES FOR EXAMPLE 14

1. Bettegowda, C. et al. Detection of circulating tumor DNA in early- and late-stage human malignancies. *Sci. Transl. Med.* 6, 224ra24 (2014).

2. Wan, J. C. M. et al. Liquid biopsies come of age: towards implementation of circulating tumour DNA. *Nat Rev Cancer* 17, 223-238 (2017).

3. Cohen, J. D. et al. Detection and localization of surgically resectable cancers with a multi-analyte blood test. *Science* (80-.). (2018).

4. Tie, J. et al. Circulating tumor DNA analysis detects minimal residual disease and predicts recurrence in patients with stage II colon cancer. *Sci. Transl. Med.* 8, 346ra92 (2016).

5. Newman, A. M. et al. Integrated digital error suppression for improved detection of circulating tumor DNA. *Nat Biotechnol* 34, 547-55 (2016).

6. Abbosh, C. et al. Phylogenetic ctDNA analysis depicts early-stage lung cancer evolution. *Nature* 545, 446-451 (2017).

7. Abbosh, C., Birkbak, N. J. & Swanton, C. Early stage NSCLC-challenges to implementing ctDNA-based screening and MRD detection. *Nature Reviews Clinical Oncology* 1-10 (2018). doi:10.1038/s41571-018-0058-3

8. Garcia-Murillas, I. et al. Mutation tracking in circulating tumor DNA predicts relapse in early breast cancer. *Sci. Transl. Med.* 7, (2015).

9. Lee, R. J. et al. Circulating tumor DNA predicts survival in patients with resected high risk stage II/III melanoma. (2017). doi: 10.1093/annonc/mdx717/4589598

10. Phallen, J. et al. Direct detection of early-stage cancers using circulating tumor DNA. *Sci. Transl. Med.* 9, (2017).

11. De Vlaminck, I. et al. Circulating cell-free DNA enables noninvasive diagnosis of heart transplant rejection. *Sci. Transl. Med.* 6, 241ra77 (2014).

12. Forshew, T. et al. Noninvasive Identification and Monitoring of Cancer Mutations by Targeted Deep Sequencing of Plasma DNA. *Sci. Transl. Med.* 4, 136ra68-136ra68 (2012).

13. Murtaza, M. et al. Multifocal clonal evolution characterized using circulating tumour DNA in a case of metastatic breast cancer. Nat. Commun. 6, 8760 (2015).

14. Kinde, I., Wu, J., Papadopoulos, N., Kinzler, K. W. & Vogelstein, B. Detection and quantification of rare mutations with massively parallel sequencing. *Proc. Natl. Acad. Sci. U.S.A* 108, 9530-5 (2011).

15. Jamal-Hanjani, M. et al. Detection of ubiquitous and heterogeneous mutations in cell-free DNA from patients with early-stage non-small-cell lung cancer. *Ann. Oncol.* 27, 862-867 (2016).

16. Mouliere, F. et al. High Fragmentation Characterizes Tumour-Derived Circulating DNA. *PLoS One* 6, e23418 (2011).

17. Underhill, H. R. et al. Fragment Length of Circulating Tumor DNA. *PLoS Genet.* 12, 426-37 (2016).

18. Mouliere, F. et al. Enhanced detection of circulating tumor DNA by fragment size analysis. *Sci. Transl. Med.* 4921, 1-14 (2018).

19. Newman, A. M. et al. An ultrasensitive method for quantitating circulating tumor DNA with broad patient coverage. *Nat. Med.* 20, 548-54 (2014).

20. Xiong, Y., Jeronis, S., Hoffman, B., Liebermann, D. A. & Geifman-Holtzman, O. First trimester noninvasive fetal RHD genotyping using maternal dried blood spots. *Prenat. Diagn.* 37, 311-317 (2017).

21. Luo, W., Yang, H., Rathbun, K., Pau, C. P. & Ou, C. Y. Detection of human immunodeficiency virus type 1 DNA in dried blood spots by a duplex real-time PCR assay. *J. Clin. Microbiol.* 43, 1851-1857 (2005).

22. Wang, J.-P. SPECIES: An R Package for Species Richness Estimation. *J. Stat. Softw.* 40, 1-15 (2011).

23. Rago, C. et al. Serial Assessment of Human Tumor Burdens in Mice by the Analysis of Circulating DNA. *Cancer Res.* 67, 9364-9370 (2007).

24. Lawrence, M. S. et al. Mutational heterogeneity in cancer and the search for new cancer-associated genes. *Nature* 499, 214-218 (2013).

25. Corrie, P. G. et al. Adjuvant bevacizumab for melanoma patients at high risk of recurrence: survival analysis of the AVAST-M trial. *Ann. Oncol.* 29, 1843-1852 (2018).

26. Chan, K. C. A. et al. Analysis of Plasma Epstein-Barr Virus DNA to Screen for Nasopharyngeal Cancer. *N. Engl. J. Med.* 377, 513-522 (2017).

27. Jiang, P. et al. Preferred end coordinates and somatic variants as signatures of circulating tumor DNA associated with hepatocellular carcinoma. *Proc. Natl. Acad. Sci. U.S.A* 201814616 (2018). doi: 10.1073/pnas. 1814616115

28. Adalsteinsson, V. A. et al. Scalable whole-exome sequencing of cell-free DNA reveals high concordance with metastatic tumors. *Nat. Commun.* 8, 1324 (2017).

29. Belic, J. et al. Rapid Identification of Plasma DNA Samples with Increased ctDNA Levels by a Modified FAST-SeqS Approach. *Clin. Chem.* 61, 838-849 (2015).

30. Corrie, P. G. et al. Adjuvant bevacizumab in patients with melanoma at high risk of recurrence (AVAST-M): Preplanned interim results from a multicentre, open-label, randomised controlled phase 3 study. *Lancet Oncol.* 15, 620-630 (2014).

31. Varela, I. et al. Exome sequencing identifies frequent mutation of the SWI/SNF complex gene PBRM1 in renal carcinoma. *Nature* 469, 539-542 (2011).

32. Costello, M. et al. Discovery and characterization of artifactual mutations in deep coverage targeted capture sequencing data due to oxidative DNA damage during sample preparation. *Nucleic Acids Res.* 41, 1-12 (2013).

33. Rubicon Genomics. Targeted Capture of ThruPLEX® Libraries with Agilent SureSelect®XT Target Enrichment System. at rubicongenomics.com/wp-content/uploads/2016/11/RDM-152-002-SureSelectXT.pdf 34. University of Michigan. Connor-METHODS. (2016). at github.com/umich-brcf-bioinf/Connor/blob/master/doc/METHODS.rst 35. Schwarzenbach, H., Hoon, D. S. B. & Pantel, K. Cell-free nucleic acids as biomarkers in cancer patients. *Nat. Rev. Cancer* 11, 426-437 (2011).

36. Beckman Coulter. SPRIselect User Guide. *Beckman* 1-30 (2012).

37. Nioche, C. et al. A freeware for tumor heterogeneity characterization in PET, SPECT, CT, MRI and US to accelerate advances in radiomics. *J. Nucl. Med.* 58, 1316 (2017).

Supplementary Methods for Example 14

Overview of INVAR Pipeline

The INVAR pipeline takes error-suppressed BAM files, a BED file of patient-specific loci, and a CSV file indicating the tumour allele fraction of each mutation and which patient it belongs to. It is optimised for a cluster running Slurm. The workflow is shown in FIG. 30. Briefly, the pipeline assesses wild-type and mutant reads at patient-specific loci in all samples, and this data is annotated with trinucleotide error rate, locus error rate, which patient the mutation belongs to, tumour allele fraction, fragment size, presence in both F and R reads, and whether the signal at that locus is an outlier relative to all other patient-specific loci in that sample. Following data annotation, signal is aggregated across all patient-specific loci in that sample to generate both a likelihood ratio, which is used to define specificity. An integrated mutant allele fraction (IMAF) is calculated separately.

INVAR Data Processing

SAMtools mpileup 1.3.1 was used at patient-specific loci based on a BED file of mutations, with the following settings: --ff UNMAP, -q 40 (mapping quality), -Q 20 (base quality), -x, --d 10,000, then multiallelic calls were split using BCFtools 1.3.1. Next, all TSV files were annotated with 1,000 Genomes SNP data, COSMIC data, and trinucleotide context using a custom Python script. Output files were then concatenated, compressed, and read into R. First, based on prior knowledge from tumour sequencing data, all loci were annotated per patient with being either: patient-specific (present in patient's tumour) or non-patient-specific (not present in patient's tumour, or individual does not have cancer). Since each non-patient-specific sample contains the loci from multiple patients, every non-patient-specific sample may control for all other patients analysed with the same sequencing panel or method (excluding loci that are shared between individuals).

INVAR Data Filters I

The following filters were applied to INVAR data on a per locus basis:
1. Loci were excluded if MOSB<0.01 (mapping quality/strand bias).
2. Multi-allelic loci were identified, and blacklisted if 3 different alternate alleles were observed in the dataset with error-suppressed read families. Loci with 2 separate alternate alleles observed in the dataset were only excluded if there were more than 2 error-suppressed reads of the minor alternate allele.
3. Loci that showed mutant signal in >10% of the non-patient-specific (patient-control) samples or showed an average mutant allele fraction per locus of >1%, were blacklisted. The proportion of loci that were blacklisted with this filter ranged from 0.21%-3.53% (FIG. 33). Patient samples may be used to characterise the noise per locus (at loci that did not belong to them), since 99.8% of mutations were private to each patient.
4. Mutation signal had to be represented in both the F and R read of that read pair (FIG. 33). This both serves to reduce sequencing error and causes a size-selection for fragments, retaining fragments <300 bp as PE150 sequencing was performed (only mutant signal in the overlapping region of the F and R read can be retained). The resulting error-suppression is analogous to tools that merge paired-end reads[1].

INVAR Data Annotation

After data filtering, data was annotated with both locus noise filter and trinucleotide error rate. Since the locus noise filter is limited by the number of control samples and cfDNA molecules at that locus, we also assessed trinucleotide error rate. Trinucleotide error rates were determined from the region up to 10 bp either side of every patient-specific locus (excluding patient-specific locus itself), and data was pooled by trinucleotide context. After pooling data in this manner, a median of $3.0 \times 10^8$ informative reads (or deduplicated reads) per trinucleotide context were analysed.

Trinucleotide error rate was calculated as a mismatch rate for each specific mutation context. If a trinucleotide context had zero mutant deduplicated reads, the error rate was set to the reciprocal of the number of IR/deduplicated reads in that context.

In addition, each data point was annotated with the cfDNA fragment size of that read using a custom Python script. Then, to eliminate outlier signal that was not consistent with the remainder of that patient's loci, we performed patient-specific outlier suppression (FIG. 34). The data is now error-suppressed (both by read-collapsing and bespoke methods for patient-specific sequencing data) and annotated with parameters required for signal-enrichment (by features of ctDNA sequencing) for the INVAR method.

INVAR Data Filters II-Patient-Specific Outlier-Suppression

Patient-specific sequencing data consists of informative reads at multiple known patient-specific loci, providing the opportunity to compare mutant allele fractions across loci as a means of error-suppression. The distribution of signal across loci potentially allows for the identification of noisy loci not consistent with the overall signal distribution. Each locus was tested for the probability of having observed mutant reads given the average signal across all loci (FIG. 34). A locus observed with significantly greater signal than the remainder of the loci might be attributed due to noise at that locus, contamination, or a mis-genotyped SNP locus. The possibility of a mis-genotyped SNP becomes increasingly likely when a large number of mutation loci are targeted by INVAR. For each sample, the IMAF was determined across all loci passing pre-INVAR data processing filters with mutant allele fraction at that locus of <0.25. Loci with signal >0.25 mutant allele fraction were not included in the calculation because (i) in the residual disease setting, loci would not be expected to have such high mutant allele fractions (unless they are mis-genotyped SNPs), and (ii) if the true IMAF of a sample is >0.25, when a large number of loci are tested, they will show a distribution of allele fractions such that detection is supported by having many low allele fraction loci with signal.

Based on the ctDNA level of the sample, the binomial probability of observing each individual locus given the IMAF of that sample was calculated. Loci with a Bonferroni corrected P-value <0.05 (corrected for the number of loci interrogated) were excluded in that sample, thereby suppressing outliers. As a result of outlier-suppression, background noise was reduced to 33% control samples, while retaining 96.1% of signal in patient samples (FIG. 34). By correcting the P-value threshold for the number of loci tested, this filter can be applied to data with a variable number of mutations targeted per patient, enabling analysis of samples from patients with cancer types with both high and low mutation rates.

Statistical Detection Method for INVAR

We developed a statistical method to model the number of mutant reads at multiple patient-specific loci, incorporating prior information available from patient-specific sequencing, such as the background error of the trinucleotide context, the tumour allele fraction at the locus, and fragment length. This approach aggregates signal across multiple patient-specific mutations following error-suppression. For each locus, we test the significance of the number of mutant reads given the trinucleotide error rate of that context. Trinucleotide error rates were used instead of locus-specific error rates in order to determine a more accurate estimation of background error rates to $10^{-7}$ (FIG. 24c).

Tumour allele fractions and trinucleotide error rates were considered as follows: Denote $AF_i$ as the tumour mutant allele fraction at locus i, $e_i$ as the background error in the context of locus i, and let p be an estimate of ctDNA content in that sample for the INVAR algorithm. A random read at locus i can be observed to be mutant either if it arose from a mutant molecule, or an incorrectly sequenced wild type DNA molecule. This occurs with probability $q_i$:

$$q_i = AF_i \cdot (1 - e_i) \cdot p + (1 - AF_i) \cdot e_i \cdot p + e_i \cdot (1 - p) \qquad (1)$$

Testing for the presence of ctDNA is now equivalent to testing the statistical hypothesis $H_0$: $p=0$. Assuming the number of observed mutant reads is independent between loci, the following likelihood function can be produced:

$$L(p; M, AF, e) = \prod_{i=1}^{n} \prod_{j=1}^{R_i} q_i^{M_{ij}} (1 - q_i)^{1-M_{ij}} \tag{2}$$

where $M_{ij}$ is the indicator for a mutation in read j of locus i, and $R_1$ is the number of reads in locus i. The above method allows weighting of signal by tumour allele fraction, which we confirm influences plasma mutation representation in patient samples with early stage and advanced disease (FIG. 35a), and in the spike-in dilution series from one patient (FIG. 35b).

Each sequencing read provides fragment size information (FIG. 35c), which may be used to separate mutant from wild-type molecules and produce an enrichment in ctDNA (FIG. 24d). Probability weighing was preferred over size selection to avoid allelic loss at ultra-low allele fractions, suggested by Fan et al.[2] in the non-invasive prenatal testing setting. Therefore, read length information can also be incorporated into the likelihood. The method for read length distribution of mutant and wild-type fragments estimation is given in the section Estimation of read length distribution for INVAR. This approach is in contrast to size-selection and may be considered as a size-weighting step alongside tumour AF weighting that was performed above. Fragment sizes for each sequencing read may be incorporated to the INVAR method. To do so, let $L_{ji}$ be the length of read j at locus i. The likelihood can be written as:

$$L(p; M, L, AF, e) = \prod_{i=1}^{n} \prod_{j=1}^{R_i} P(m_{ij}, l_{ij} \mid e, AF, p) \tag{3}$$

Assuming that given the read length and mutation status are independent given the source of the read (mutant or wild-type DNA), we can factor the likelihood as follows:

$$
\begin{aligned}
L(p; M, L, AF, e) &= \prod_{i=1}^{n} \prod_{j=1}^{R_i} P(m_{ij}, l_{ij} \mid z_{ij} = 0) \cdot \\
&\quad P(z_{ij} = 0) + P(m_{ij}, l_{ij} \mid z_{ij} = 1) \cdot P(z_{ij} = 1) \\
&= \prod_{i=1}^{n} \prod_{j=1}^{R_i} P(m_{ij} \mid z_{ij} = 0) \cdot p^0(l_{ij}) \cdot \\
&\quad (1 - p) + P(m_{ij} \mid z_{ij} = 1) \cdot p^1(l_{ij}) \cdot p \\
&= \prod_{i=1}^{n} \prod_{j=1}^{R_i} e_i^{m_{ij}} \cdot (1 - e_i)^{1-m_{ij}} \cdot p^0(l_{ij}) \cdot \\
&\quad (1 - p) + g_i^{m_{ij}} \cdot (1 - g_i)^{1-m_{ij}} \cdot p^1(l_{ij}) \cdot p
\end{aligned}
\tag{4}
$$

where $z_{ij}$ is the indicator that read j of locus i came from ctDNA, $p^k$ $(l_{ij}) = P(l_{ij} \mid z_{ij}=k)$, and $g_i = AF_i \cdot (1-e_i) + (1-AF_i) \cdot e_i$. The above method weights the signal based on both fragment length of mutant and wild-type reads, though in this implementation of INVAR, we set the weight of all wild-type size bins to be equal, thereby neglecting size information from wild-type reads.

Lastly, a score is generated for each sample through aggregation of signal across all patient-specific loci in that sample using the Generalized Likelihood Ratio test (GLRT). The GLRT directly compares the likelihood under the null hypothesis against the likelihood under the maximum likelihood estimate of p:

$$\lambda(p_0) = \frac{L(p_0; M, L, AF, e)}{L(\hat{p}; M, L, AF, e)} \tag{5}$$

The higher the value of the likelihood ratio, the greater evidence for ctDNA presence in a sample. Classification of samples was performed based on comparison of likelihood ratios between patient and control samples.

Likelihood Ratio Threshold Determination

Other patients were used to control for one another at non-shared loci (FIG. 23c). Only samples run on the same sequencing panel (i.e. same custom sequencing panel design), with the same error-suppression setting and targeting the same mutation list were used to control for one another.

In order to determine a threshold for the likelihood ratio (LR) based on controls accurately, reads from each control sample were iteratively resampled with replacement 10 times, and the GLRT script was run. To minimise the risk of any patient-specific contamination of signal at non-patient-specific control loci (through de novo mutations overlapping with patient-specific sites), only samples with patient-specific IMAF <1% were used as controls for determination of the cut-point. Based on the LR distribution in patient controls and patient samples, the cut-off for LR was determined for each cohort using the 'OptimalCutpoints' package in R[3], maximising sensitivity and specificity using the 'MaxSnSp' setting. Based on the LRs per cohort, an analytical specificity was determined for each cohort (FIG. 36).

Assessment of Specificity in Healthy Individuals 26 healthy individuals' cfDNA from plasma were analysed using the stage IV melanoma and stage I-IIIA NSCLC custom capture panels. These samples were treated as 'patient' samples, and so had no influence on the filters in the pipeline, and were not used for the determination of LR thresholds. After determination of the LR thresholds (described above), the LRs from healthy individuals' samples were assessed for false positive detection of ctDNA. For each of these cohorts, the clinical specificity values in healthy individuals were determined (FIG. 36).

Estimation of ctDNA Content Per Sample for Likelihood Ratio Determination

In this section we derive an Expectation Maximization (EM) algorithm to estimate p as part of the INVAR method. If we treat the tumour of origin $z_{ij}$ as a latent variable, and assume that it is known, the joint likelihood of Z, M ($m_{ij}$ is the indicator for a mutation in read j of locus i), L ($l_{ij}$ is the length of read i of locus j), AF ($AF_i$ is the tumour allele fraction at locus i), e ($e_i$ is the background error in the context of locus i) can be written as:

$$
\begin{aligned}
L(p; Z, M, L, AF, e) &= \prod_{i=1}^{n} \prod_{j=1}^{R_i} \left[ e_i^{m_{ij}} \cdot (1 - e_i)^{1-m_{ij}} \cdot p^0(l_{ij}) \cdot (1 - p) \right]^{1-z_{ij}} \cdot \\
&\quad \left[ g_i^{m_{ij}} \cdot (1 - g_i)^{1-m_{ij}} \cdot p^1(l_{ij}) \cdot p \right]^{z_{ij}}
\end{aligned}
$$

Where $g_i = AF_i \cdot (1-e_i) + (1-AF_i) \cdot e_i$. The log-likelihood is linear in $z_{ij}$, so taking the expectation of the likelihood amounts simply to replacing the $z_{ij}$ with their expectation at stage 1, $$z_{ij}^l = E(z_{ij} \mid m_{ij}, l_{ij}, p_l),$$

where $p_l$ is the best estimate of p at iteration l. We can thus use EM to find a maximum likelihood estimate for p, by iteratively maximizing the likelihood with respect to p, and taking the expectation of the likelihood with respect to $z_{ij}$. An estimate for $p_l$ is obtained by taking the derivative with respect to $p_l$ and equating it to zero:

$$p_l = \frac{\sum_{i=1}^{n} \sum_{j=1}^{R_t} z_{ij}^l}{\sum_{i=1}^{n} R_i}$$

The above is simply the expected proportion of reads from ctDNA at stage l. Bayes' theorem can be used to compute $$z_{ij}^l:$$

$$z_{ij}^l = P(z_{ij} = 1 \mid m_{ij}, l_{ij}, p_l) = \frac{P(m_{ij} \mid z_{ij} = 1) \cdot p^1(l_{ij}) \cdot p}{P(m_{ij} \mid z_{ij} = 1) \cdot p^1(l_{ij}) \cdot} \newline p + P(m_{ij} \mid z_{ij} = 0) \cdot p^0(l_{ij}) \cdot (1-p)$$

By substituting the respective probabilities we obtain:

$$z_{ij}^l = \frac{g_i^{m_{ij}} (1-g_i)^{1-m_{ij}} p^1(l_{ij}) p}{g_i^{m_{ij}} (1-g_i)^{1-m_{ij}} p^1(l_{ij}) p + e_i^{m_{ij}} (1-e_i)^{1-m_{ij}} p^0(l_{ij})(1-p)}$$

The algorithm proceeds by alternating the maximization of p, and the expectation of the $z_{ij}$.

Estimation of Read Length Distribution for INVAR

Size-weighting with INVAR depends on first having a known distribution of sizes of mutant and wild-type reads against which to perform weighting. In order to estimate the read length distribution with the greatest accuracy, we used all wild type and mutant reads from all samples in that cohort, leaving out the one sample being tested, and we used kernel density estimation to smooth the respective probabilities.

The size distributions from each of the studied cohorts are shown in FIG. 35, and the enrichment ratios for each size range are shown in FIG. 24d. We demonstrated that the early stage cohorts were not significantly different in size profile, whereas the advanced melanoma cohort had a significantly greater proportion of di-nucleosomal fragments despite downsampling of data to a similar number of reads (FIG. 35d). Thus, data from both early stage cohorts were pooled to generate a prior distribution of the size of mutant and wild-type fragments, and data was smoothed with a Gaussian kernel with a default setting of 0.25 (FIG. 35e).

To estimate the probability that a read is of length l, given that the cell of origin of wild type, P(L=l|z=0), we used all of the wild-type reads from each pooled dataset. For both of the data sets, we used the R function "density", with a Gaussian kernel, to smooth the estimated probabilities, and obtained a density estimate $\hat{f}(l|Z=z)$. Finally, to estimate P(L=l|z=z), we integrated the respective density:

$$P(L = l \mid Z = z) = \int_{l=0.5}^{l+0.5} \hat{f}(t \mid Z = z) dt$$

Smoothing the size distribution estimates is important in datasets where data is sparse to avoid assigning too large a weight to any given mutant fragment.

Calculation of Informative Reads (IR)

The number of informative reads (IR) for a sample is the product of the number of mutations targeted (i.e. length of the mutation list) and the number of haploid genomes analysed by sequencing (hGA, equivalent to the deduplicated coverage following read-collapsing). Thus, the limit of detection for every sample can be calculated based on 1/IR (with adjustment for sampling mutant molecules based on binomial probabilities). For non-detected samples, the 1/IR value provides an estimate for the upper limit of ctDNA in that sample; this allows quantification of samples even if no mutant molecules are present, and is utilised in FIG. 27d to define the upper confidence limits to $\sim 10^{-4}$ using sWGS data. Also, samples with limited sensitivity can be identified and classified as a 'low-sensitivity' or 'non-evaluable' group, where the INVAR method is limited by the number of IR (FIG. 25). In this study, we aimed to quantify ctDNA with sensitivity greater than other methods, and classified samples with non-detected ctDNA with <20,000 IR as low-sensitivity and thus non-evaluable. Across the cohorts in this study, 6 patients were non-evaluable with these criteria.

Calculation of Integrated Mutant Allele Fraction (IMAF)

To quantify ctDNA across multiple mutation loci, we calculated an 'integrated mutant allele fraction', as follows:
  a) For each trinucleotide context in a sample, the deduplicated depth-weighted mean allele fraction across all patient-specific loci was calculated
  b) The background error rate per trinucleotide context in control data was subtracted from the mean allele fraction calculated in (a). Trinucleotide contexts with negative mutant allele fraction after subtraction were set to zero.
  c) The mean background-subtracted allele fraction was taken across the trinucleotide contexts, weighted by the deduplicated depth in each trinucleotide context.

Experimental Spike-In Dilution Series

Plasma DNA from one patient with a total of 5,073 patient-specific variants was serially diluted 10-fold each step in a pool of plasma cfDNA from 11 healthy individuals (Seralab) to give a dilution series spanning 1-100,000×. Library preparation was performed, as described in Methods, with 50 ng input per dilution. In order to interrogate a sufficiently large number of molecules in the dilution series to assess sensitivity, the lowest dilution (100,000×) was generated in triplicate. The healthy control cfDNA pools were included as control samples for the determination of locus error rate to identify and exclude potential SNP loci (FIG. 24e). Given the relationship between tumour allele fraction and plasma mutation representation (FIG. 35b), any smaller panel for INVAR should be based on clonal mutations with highest priority, with lower allele fractions included only if plasma sequencing data is sufficiently broad. Thus, we iteratively sampled the data with replacement from each of the dilution series sequencing libraries (with 50 iterations), and then selected the top N mutations (spanning 1 to 5,000 mutations). The locus with the highest mutant allele fraction was the BRAF V600E mutation. After downsampling the number of loci, outlier-suppression was repeated on all samples except for the single BRAF V600E locus data.

Estimated Detection Rates with Fewer Informative Reads

Based on the IMAFs of detected samples, detection rates can be estimated where fewer IR were achieved with a perfectly sensitive assay. For a given number of IR (r), the 95% limit of detection for ctDNA (p) can be determined as follows:

$$p = 1 - e^{log(1-0.95)/r}$$

Thus, for each entry in a vector of IR values ($10^2$, $10^3$ ... $10^7$), the detection rates for cancer were calculated per cohort, and are plotted in FIG. 26e. The maximum value of the vector of IR values was set to be larger than the maximum number of IR per sample in that cohort, rounded to the nearest order of magnitude. For the stage II-III melanoma patients, detection was defined as the sensitivity for patients who relapsed within 5 years. Linear regression was used to calculate $R^2$ values for each cohort.

REFERENCES FOR THE SUPPLEMENTARY METHODS TO EXAMPLE 14

1. Zhang, J., Kobert, K., Flouri, T. & Stamatakis, A. PEAR: A fast and accurate Illumina Paired-End reAd mergeR. *Bioinformatics* 30, 614-620 (2014).
2. Fan, H. C., Blumenfeld, Y. J., Chitkara, U., Hudgins, L. & Quake, S. R. Analysis of the size distributions of fetal and maternal cell-free DNA by paired-end sequencing. *Clin. Chem.* 56, 1279-1286 (2010).
3. López-Ratón, M., Rodríguez-Álvarez, M. X., Suárez, C. C. & Sampedro, F. G. OptimalCutpoints: An R Package for Selecting Optimal Cutpoints in Diagnostic Tests. *J. Stat. Softw.* 61, 1-36 (2014).
4. University of Michigan. Connor-METHODS. (2016). at github.com/umich-brcf-bioinf/Connor/blob/master/doc/METHODS.rst
5. Forshew, T. et al. Noninvasive Identification and Monitoring of Cancer Mutations by Targeted Deep Sequencing of Plasma DNA. *Sci. Transl. Med.* 4, 136ra68-136ra68 (2012).
6. Newman, A. M. et al. An ultrasensitive method for quantitating circulating tumor DNA with broad patient coverage. *Nat. Med.* 20, 548-54 (2014).
7. Abbosh, C. et al. Phylogenetic ctDNA analysis depicts early stage lung cancer evolution. *Nature* 22364, 1-25 (2017).
8. Wang, J.-P. SPECIES: An R Package for Species Richness Estimation. *J. Stat. Softw.* 40, 1-15 (2011).

Example 15—Application of INVAR to Further Cancer Types

For all cohorts outlined below we applied an INVAR score threshold of 0.1 for ctDNA detection. Samples below that threshold are shown as not detected (ND). Samples with an INVAR score lower than 0.1 and a total IR of less than 20,000 were classified as not evaluable (not shown in the plot).

70

TABLE 1

Summary of INVAR application to other cohorts. Samples are split by cancer type and body fluid. Samples are called detected if their INVAR score was greater than 0.1. Samples were classified as not evaluable when their INVAR score was less than 0.1 and their total number of Informative Reads was below 20,000.

| Fluid | Cancer type | De-tected | Not de-tected | Total | De-tection rate | Not evalu-able | Total cohort size |
|---|---|---|---|---|---|---|---|
| CSF | Glioblastoma | 6 | 0 | 6 | 1.00 | 2 | 8 |
| Plasma | Glioblastoma | 11 | 1 | 12 | 0.92 | 0 | 12 |
| Plasma | Lung cancer | 60 | 26 | 86 | 0.70 | 4 | 90 |
| Plasma | Breast cancer | 34 | 1 | 35 | 0.97 | 0 | 35 |
| Plasma | Renal cancer | 22 | 10 | 32 | 0.69 | 7 | 39 |
| Urine | Renal cancer | 6 | 11 | 17 | 0.35 | 6 | 23 |

Lung Cancer

A total of 90 samples was analysed with INVAR. 4 cases were classified as "not evaluable" (not shown) as they did not yield enough informative reads. Out of the remaining 86 samples, ctDNA was detected in 60 samples, yielding to a total detection rate of 70%. Currently we are still blinded to the stage of these patients but the cohort is heavily biased towards early stage patients where 60% are stage I patients (33% with stage IA and 27% with stage IB).

Renal Cancer

INVAR was applied to 39 plasma samples, of which seven were not evaluable (not shown). Of the remaining 32 samples, 22 reached an INVAR score greater than 0.1 (69%). INVAR was also applied to urine samples. Of the 23 analysed samples, six were not evaluable (not shown). Of the remaining 17 samples, six reached an INVAR score greater than 0.1 (35%). Samples stem from different disease subtypes.

Urine Sample Preparation:

Urine samples were collected prior to surgery (mean 8.6, range 0-35 days pre-surgery). From the same urine sample, we isolated both urine supernatant (USN) and urine cell pellet (UCP), as described below.

30-50 ml urine was collected in a 50 ml falcon tube, and 0.5 M EDTA was added within an hour of collection (pH 8.0; 600 µl for 30 ml, final concentration 10 mM. For larger volumes of urine, the volume of EDTA was adjusted accordingly). After gentle inversion, the sample was spun at 2,400 g for 10 minutes. Subsequently, ~3.6 ml aliquots of supernatant were transferred into a separate cryotube. An additional 1 ml of supernatant was transferred to a separate microfuge tube and then returned to the original falcon tube containing the urine cell pellet (UCP). The tube was agitated and the remaining liquid was transferred to a sterile 2 ml microfuge tube, which was spun at 13,300 rpm for 10 minutes and the supernatant was discarded leaving a dry UCP for storage.

Urines samples were extracted using the QIAsymphony platform (Qiagen, Germany). Up to 4 ml of urine were extracted and eluted in 60 µL.

Glioblastoma

Detection of plasma and cerebrospinal fluid (CSF) in glioblastoma patients using INVAR. In CSF samples, 2 samples were excluded from analysis due to insufficient number of informative reads (not shown). All remaining 6 samples were detected at INVAR scores greater than 0.1. In plasma 11 out of 12 samples reached this INVAR threshold (92%).

CSF Sample Preparation:

Lumbar puncture was performed immediately prior to craniotomy for tumour debulking. After sterile field preparation, the thecal sac was cannulated between the L3 and L5 intervertebral spaces using a 0.61 mm gauge lumbar puncture needle, and 10 ml of CSF was removed. After collection, CSF samples were immediately placed on ice and then rapidly transferred to a pre-chilled centrifuge for processing. Samples were centrifuged at 1500 g at 4C for 10 minutes, the supernatant was removed and further centrifuged at 20,000 g for 10 minutes, and aliquoted into 2 mL microtubes for storage at −80° C. (Sarstedt, Germany).

Fluids were extracted using the QIAsymphony platform (Qiagen, Germany). Up to 8 mL of CSF was used for the extraction. DNA from CSF samples was eluted in 90 μL, and further concentrated down to 30 μL using a Speed-Vac concentrator (Eppendorf). The sample then followed the normal library preparation protocol that was also used for the plasma samples.

Breast Cancer

INVAR was applied to breast cancer samples. 34 out of 35 samples reached an INVAR score of 0.1 or greater and were classified as detected (97%). Tumour mutations in this study were identified across the entire genome rather than just the exonic regions. Samples were taken longitudinally from 7 patients and fluctuations in ctDNA concentration across time courses likely represent response to treatment.

The results are shown in FIGS. 42-45. Integrated mutant allele fraction (IMAFs) (y-axis) are shown for all cohorts (samples X-axis) in FIGS. 42 and 43.

FIGS. 44 and 45 show the INVAR scores for all samples classified as evaluable.

REFERENCES

1. Wan J C M, Massie C, Garcia-Corbacho J, et al. Liquid biopsies come of age: towards implementation of circulating tumour DNA. Nat Rev Cancer 2017; 17:223-38.
2. Siravegna G, Marsoni S, Siena S, Bardelli A. Integrating liquid biopsies into the management of cancer. Nat Rev Clin Oncol 2017;
3. Bettegowda C, Sausen M, Leary R J, et al. Detection of circulating tumor DNA in early- and late-stage human malignancies. Sci Transl Med 2014; 6(224):224ra24.
4. Diehl F, Li M, Dressman D, et al. Detection and quantification of mutations in the plasma of patients with colorectal tumors. Proc Natl Acad Sci USA 2005; 102 (45):16368-73.
5. Forshew T, Murtaza M, Parkinson C, et al. Noninvasive Identification and Monitoring of Cancer Mutations by Targeted Deep Sequencing of Plasma DNA. Sci Transl Med 2012; 4(136):136ra68-136ra68.
6. Abbosh C, Birkbak N J, Wilson G A, et al. Phylogenetic ctDNA analysis depicts early stage lung cancer evolution. Nature 2017; 22364:1-25.
7. Newman A M, Lovejoy A F, Klass D M, et al. Integrated digital error suppression for improved detection of circulating tumor DNA. Nat Biotechnol 2016; 34(5):547-55.
8. Newman A M, Bratman S V, To J, et al. An ultrasensitive method for quantitating circulating tumor DNA with broad patient coverage. Nat Med 2014; 20(5):548-54.
9. Murtaza M, Dawson S-J, Tsui D W Y, et al. Non-invasive analysis of acquired resistance to cancer therapy by sequencing of plasma DNA. Nature 2013; 497(7447): 108-12.
10. Hodis E, Watson I R, Kryukov G V., et al. A Landscape of Driver Mutations in Melanoma. Cell 2013; 150(2):251-63.
11. Kinde I, Wu J, Papadopoulos N, Kinzler K W, Vogelstein B. Detection and quantification of rare mutations with massively parallel sequencing. Proc Natl Acad Sci 2011; 108(23):9530-5.
12. Hoang M L, Kinde I, Tomasetti C, et al. Genome-wide quantification of rare somatic mutations in normal human tissues using massively parallel sequencing. Proc Natl Acad Sci 2016; 113(35):9846-51.
13. Underhill H R, Kitzman J O, Hellwig S, et al. Fragment Length of Circulating Tumor DNA. PLOS Genet 2016; 12(7):426-37.
14. Mouliere F, Rosenfeld N. Circulating tumor-derived DNA is shorter than somatic DNA in plasma. Proc Natl Acad Sci 2015; 112(11):201501321.
15. Thierry A R, Mouliere F, Gongora C, et al. Origin and quantification of circulating DNA in mice with human colorectal cancer xenografts. Nucleic Acids Res 2010; 38(18):6159-75.
16. Poole W, Gibbs D L, Shmulevich I, Bernard B, Knijnenburg T A. Combining dependent P-values with an empirical adaptation of Brown's method. Bioinformatics 2016; 32(17):1430-6.
17. Mouliere F, Piskorz A M, Chandrananda D, et al. Selecting Short DNA Fragments In Plasma Improves Detection Of Circulating Tumour DNA. biorxiv 2017;
18. Eisenhauer E A, Therasse P, Bogaerts J, et al. New response evaluation criteria in solid tumours: Revised RECIST guideline (version 1.1). Eur J Cancer 2009; 45(2):228-47.
19. Forbes S A, Beare D, Gunasekaran P, et al. COSMIC: Exploring the world's knowledge of somatic mutations in human cancer. Nucleic Acids Res 2015; 43(D1):D805-11.
20. Jiang P, Chan C W M, Chan K C A, et al. Lengthening and shortening of plasma DNA in hepatocellular carcinoma patients. Proc Natl Acad Sci 2015; 112(11):E1317-25.
21. Jiang P, Lo Y M D. The Long and Short of Circulating Cell-Free DNA and the Ins and Outs of Molecular Diagnostics. Trends Genet 2016; 32(6):360-71.
22. Fan H C, Blumenfeld Y J, Chitkara U, Hudgins L, Quake S R. Analysis of the size distributions of fetal and maternal cell-free DNA by paired-end sequencing. Clin Chem 2010; 56(8):1279-86.
23. Chan K C A, Zhang J, Hui A B Y, et al. Size Distributions of Maternal and Fetal DNA in Maternal Plasma. Clin Chem 2004; 50(1):88-92.
24. Alexandrov L B, Jones P H, Wedge D C, Sale J E, Peter J. Clock-like mutational processes in human somatic cells. Nat Publ Gr 2015; 47(12):1402-7.
25. Nioche C, Orlhac F, Boughdad S, et al. A freeware for tumor heterogeneity characterization in PET, SPECT, CT, MRI and US to accelerate advances in radiomics. J Nucl Med 2017; 58(supplement 1):1316.
26. Varela I, Tarpey P, Raine K, et al. Exome sequencing identifies frequent mutation of the SWI/SNF complex gene PBRM1 in renal carcinoma. Nature 2011; 469 (7331):539-42.
27. Manson-Bahr D, Ball R, Gundem G, et al. Mutation detection in formalin-fixed prostate cancer biopsies taken at the time of diagnosis using next-generation DNA sequencing. J Clin Pathol 2015; 68(3):212-7.
28. Rubicon Genomics. ThruPLEX® Tag-seq Kit Instruction Manual [Internet]. 2016; Available from: rubicongenomics.com/wp-content/uploads/2016/08/QAM-328-001-ThruPLEX-Tag-seq-Kit-Instruction-Manual.pdf 29. Rubicon Genomics. Targeted Capture of ThruPLEX® Libraries with Agilent SureSelect®XT Target Enrichment System [Internet]. Available from: rubicongenomics.com/wp-content/uploads/2016/11/RDM-152-002-SureSelectXT.pdf 30. University of Michigan. Connor-METHODS [Internet]. 2016 [cited 2017 Mar. 27]; Available from: github.com/umich-brcf-bioinf/Connor/blob/master/doc/METH-ODS.rst 31. moonso. VCF Parser [Internet]. 2016 [cited 2017 May 8]; Available from: github.com/moonso/vcf_parser Brash D E. UV Signature Mutations. Photochemistry and photobiology. 2015; 91 (1): 15-26. doi: 10.1111/php.12377.

Hodis E, Watson I R, Kryukov G V, et al. A Landscape of Driver Mutations in Melanoma. Cell. 2012; 150 (2): 251-263. doi: 10.1016/j.cell.2012.06.024.

Jamal-Hanjani G A et al. Detection of ubiquitous and heterogeneous mutations in cell-free DNA from patients with early-stage non-small-cell lung cancer, *Annals of Oncology*, Volume 27, Issue 5, 1 May 2016, Pages 862-867, doi.org/10.1093/annonc/mdw037

Shyr C, Tarailo-Graovac M, Gottlieb M, Lee J J, van Karnebeek C, Wasserman W W. FLAGS, frequently mutated genes in public exomes. BMC Medical Genomics. 2014; 7:64. doi: 10.1186/s12920-014-0064-y.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A method comprising:
detecting circulating tumour DNA (ctDNA) in a cell-free DNA (cfDNA)-containing sample obtained from a patient, the detecting comprising performing computer-implemented steps of:
(a) providing a list of patient-specific loci of interest comprising at least 2, 3, 4, 5, 6, 7, 8, 9, 10, 50, 100, 500, 1000, 2500 or at least 5000 mutation-containing loci obtained by sequencing a tumour sample of the patient or sequencing DNA obtained from a liquid sample from the patient at a time of high tumour disease burden;
(b) receiving sequence data comprising sequence reads of a plurality of DNA fragments from a cfDNA-containing sample from the patient, wherein said sequence reads span said at least 2, 3, 4, 5, 6, 7, 8, 9, 10, 50, 100, 500, 1000, 2500 or 5000 mutation-containing loci of the list of patient-specific loci of interest;
(c) calculating a mutant allele fraction across all of said at least 2, 3, 4, 5, 6, 7, 8, 9, 10, 50, 100, 500, 1000, 2500 or 5000 patient-specific loci that aggregates across said patient-specific loci: a number of mutant reads at a patient-specific locus and a total number of reads at the patient-specific locus, wherein the mutant allele fraction is calculated by determining a ratio of two quantities: a number of mutant reads aggregated across the patient-specific loci and a total number of reads aggregated across the patient-specific loci;

(d) determining that the mutant allele fraction is statistically significantly greater than a background sequencing error rate;
(e) classifying the tumour or the liquid sample as containing ctDNA based on the determination in step (d); and
(f) treating the patient with an anti-cancer therapy, wherein the anti-cancer therapy comprises chemotherapy, immunotherapy, and/or radiotherapy.

2. The method according to claim 1, wherein the computation of the statistical significance of the mutant allele fraction comprises carrying out a one-sided Fisher's exact test, given a contingency table comprising: the number of mutant reads from the sample, the total number of reads from the sample, and the number of mutant reads expected from the background sequencing error rate.

3. The method according to claim 2, wherein the background sequencing error rate has been determined for each class in a plurality of classes of base substitution ("mutation classes") represented in said at least 2, 3, 4, 5, 6, 7, 8, 9, or 10 patient-specific loci, by trinucleotide context,
and wherein the mutant allele fraction calculation in step (c) is performed for each mutation class, optionally wherein the mutation classes comprise at least 5, 6, 7, 8, 9, 10, 11 or all 12 of the following mutation classes: C>G, G>C, T>G, A>C, C>A, G>T, T>C, A>G, T>A, A>T, C>T and T>C,
and wherein the mutant allele statistical significance computation comprises computing the statistical significance for each mutation class taking into account the background sequencing error rate of that mutation class and combining the computed statistical significance of each mutation class to provide a measure of statistical significance for a global mutant allele fraction of the sample.

4. The method according to claim 3, wherein the mutant allele statistical significance computation comprises carrying out multiple one-sided Fisher's exact tests to determine the statistical significance of the number of mutant reads observed given the background sequencing error rate for that mutation class, thereby generating a p-value for each mutation class, and combining the p-values using the Empirical Brown's method to provide a global measure of statistical significance for the mutant allele fraction of the sample.

5. The method according to claim 1, wherein the sequence data comprising sequence reads obtained in step (b) represent:
(i) Tailored Panel Sequencing (TAPAS) sequence reads, focussed-exome sequence reads, whole-exome sequence reads or whole-genome sequence reads; or
(ii) sequence reads of a plurality of DNA fragments from a sample obtained from the patient after the patient has begun a course of treatment of the tumour and/or after the patient has had surgical resection of the tumour.

6. The method according to claim 1, wherein the patient has, or has had, melanoma, lung cancer, bladder cancer, oesophageal cancer, colorectal cancer, ovarian cancer brain cancer, and/or breast cancer.

7. The method according to claim 1, further comprising:
performing reads collapsing to group the sequence reads into read families, wherein performing the reads collapsing comprises grouping reads into read families based on fragment start and end position and at least one molecular barcode,
and wherein a minimum 60%, 70%, 80% or 90% consensus between all family members is required, and wherein a minimum family size of 2, 3, 4 or 5 is required.

8. The method according to claim 1, wherein the analysis of the sample includes a size-selection step which separates out different fragment sizes of DNA.

9. The method according to claim 8, wherein the size selection step is carried out prior to sequencing library preparation or after sequencing library preparation, and/or wherein the size selection step is a right-sided size selection employing bead-based capture of gDNA fragments.

10. The method of claim 8, wherein the sequence reads are size-selected in silico for reads within the size ranges 115-160 bp, 115-190 bp, 250-400 bp and 440-460 bp in order to enrich for those reads representing ctDNA, or wherein the sample being analysed is subjected to a size-selection step in which genomic DNA (gDNA) fragments of >200 bp, >300 bp, >500 bp, >700 bp, >1000 bp, >1200 bp, >1500 bp or >2000 bp are filtered-out, depleted or removed from the sample prior to analysis, optionally prior to DNA sequencing, to generate a size-selected sample.

11. The method according to claim 1, further comprising:

performing reads collapsing to group the sequence reads into read families, wherein said performing reads collapsing further comprises applying at least one minimal residual disease (MRD) filter selected from the group consisting of:

(i) excluding those loci with >2 mutant molecules; and (ii) selecting only those fragments which have been sequenced in both forward (F) and reverse (R) direction.

12. The method according to claim 11, wherein the mutant allele fraction per locus is weighted by tumour allele fraction or wherein the number of mutant alleles per locus is weighted by tumour fraction.

13. The method according to claim 12, wherein the mutant allele fraction per locus is weighted by tumour allele fraction according to the formula:

$$AF_{context} = \frac{\Sigma_{MRD-likeloci} \text{ mutant families} \div (1 - \text{tumour } AF)}{\Sigma_{MRD-likeloci} \text{ total families} \div (1 - \text{tumour } AF)}$$

wherein:

$AF_{context}$ is the allele frequency of a given context; tumourAF is the allele frequency of the locus as determined by sequencing DNA obtained directly from the tumour; and MRD-like loci are the mutation-containing loci determined from the tumour of the patient and to which said MRD filter has subsequently been applied, optionally wherein said context is the trinucleotide context.

14. The method according to claim 13, wherein said context is the trinucleotide context and only the 6 trinucleotide contexts having the most significant p-values are combined, optionally wherein the n most significant trinucleotide context p-values are combined according to the formula:

$$\text{Combined } p - \text{value} = -2 \sum_{i=1}^{n} \ln(p_i),$$

wherein n=1, 2, 3, 4, 5, 6, 8, 10 or 12.

15. The method according to claim 12, wherein the allele fraction is determined according to the formula:

$$AF_{global} = \frac{\Sigma \max(AF_{context} - E_{context}, 0) \times \text{total } familes_{context}}{\Sigma \text{ total families}}.$$

16. The method of claim 1, wherein the patient has previously undergone tumour resection, the method further comprising:

(i) sequencing a cfDNA-containing sample that has been obtained from the patient in order to obtain sequence data comprising sequence reads of a plurality of DNA fragments from the sample, wherein said sequence reads span at least 2, 3, 4, 5, 6, 7, 8, 9, 10, 50, 100, 500, 1000, 2500 or at least 5000 loci that have been determined to be mutation-carrying loci in cancer cells of the patient;

(ii) carrying out the detecting of circulating tumour DNA (ctDNA) in a cell-free DNA (cfDNA)-containing sample obtained from the patient using the sequence reads obtained in step (i), wherein the method further comprises determining the recurrence of the cancer in the patient based on at least the classification of the sample in step (d) as containing cfDNA or based on the mutant allele fraction calculated in step (c).

17. The method according to claim 1, wherein the sample obtained from the patient is:

(a) a limited volume sample comprising less than one tumour-derived haploid genome or wherein the sequencing data from the sample represents sequencing coverage or depth of less than 1, 2, 3, 4, 10 or 20 haploid genomes; or (b) a dried blood spot sample; a pin-prick blood sample; an archival blood, serum or plasma sample that is less than 500 μl and that has been stored for greater than 1 day, for at least one month, for at least 1 year, and/or for at least 10 years after collection from the patient; or (c) a limited volume sample selected from the group consisting of:

(i) a blood, serum or plasma sample of less than 500 μl, less than 400, less than 200, less than 100 μl or less than 75 μl;

(ii) a fine needle aspirate (FNA);

(iii) a lymph node biopsy;

(iv) a urine, cerebrospinal fluid, sputum, bronchial lavage, cervical smear or a cytological sample;

(v) a sample that has been stored for more than 1 year, 2 years, 3 years, 5 years or 10 years from the time of collection from the patient; and (vi) a sample that has been previously processed and failed quality metrics for DNA or sequencing quality, or a sample that belongs to a set of samples from which other samples have been previously processed and failed quality metrics for DNA or sequencing quality.

18. The method of claim 1, wherein the mutant allele fraction is calculated according to the formula:

$$\frac{\sum_{loci} (\text{mutant reads})_{patient-specific}}{\sum_{loci} (\text{total reads})_{patient-specific}}$$

wherein (mutant reads)$_{patient\text{-}specific}$ is the number of mutant reads at a patient-specific locus and (total reads)$_{patient\text{-}specific}$ is the total number of reads at the patient-specific locus.

19. A method comprising:

detecting circulating tumour DNA (ctDNA) in a cell-free DNA (cfDNA)-containing sample obtained from a patient who has previously undergone treatment for cancer, in order to detect recurrence of said cancer, the detecting comprising performing computer-implemented steps of:

(a) providing a list of patient-specific loci of interest comprising at least 2, 3, 4, 5, 6, 7, 8, 9, 10, 50, 100, 500, 1000, 2500 or at least 5000 mutation-containing loci representative of a tumour of the patient;

(b) providing sequence data comprising sequence reads of a plurality of DNA fragments from a cell free DNA-containing sample from the patient, wherein said sequence reads span said at least 2, 3, 4, 5, 6, 7, 8, 9, 10, 50, 100, 500, 1000, 2500 or 5000 mutation-containing loci of the list of patient-specific loci of interest;

(c) performing reads collapsing to group the sequence reads into read families, wherein said performing read collapsing comprises applying at least one minimum residual disease filter selected from the group consisting of: excluding those loci with >2 mutant molecules, and selecting only those fragments which have been sequenced in both forward and reverse direction;

(d) calculating a mutant allele fraction across all of said at least 2, 3, 4, 5, 6, 7, 8, 9, 10, 50, 100, 500, 1000, 2500 or 5000 patient-specific loci, wherein the mutant allele fraction is calculated by aggregating across said patient-specific loci: a number of mutant reads at a patient-specific locus and a total number of reads at the patient-specific locus, and wherein the mutant allele fraction is calculated by determining a ratio of two quantities: a number of mutant reads aggregated across the patient-specific loci and a total number of reads aggregated across the patient-specific loci;

(e) classifying the sample (i) as containing ctDNA when the mutant allele fraction is found to be statistically significantly greater than a background sequencing error rate, or (ii) as not containing ctDNA or having unknown ctDNA status when the mutant allele fraction is not found to be statistically significantly greater than the background sequencing error rate; and (f) determining the recurrence of the cancer in the patient based at least on the classification of the sample in step (e) as containing ctDNA; and wherein the patient is determined to have a recurrence of the cancer in step (f) and the method further comprises treating the patient with an anti-cancer therapy, wherein the anti-cancer therapy comprises chemotherapy, immunotherapy, and/or radiotherapy.

\* \* \* \* \*